US009776997B2

(12) United States Patent
Vakalopoulos et al.

(10) Patent No.: US 9,776,997 B2
(45) Date of Patent: Oct. 3, 2017

(54) 3-ARYL-SUBSTITUTED IMIDAZO[1,2-A]PYRIDINES AND THEIR USE

(71) Applicant: Bayer Pharma Aktiengesellschaft, Berlin (DE)

(72) Inventors: Alexandros Vakalopoulos, Hilden (DE); Markus Follmann, Köln (DE); Ingo Hartung, Berlin (DE); Philipp Buchgraber, Berlin (DE); Alexey Gromov, Erkrath (DE); Niels Lindner, Wuppertal (DE); Frank Wunder, Wuppertal (DE); Johannes-Peter Stasch, Solingen (DE); Gorden Redlich, Bochum (DE); Volkhart Min-Jian Li, Velbert (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/895,809

(22) PCT Filed: Jun. 4, 2014

(86) PCT No.: PCT/EP2014/061523
§ 371 (c)(1),
(2) Date: Dec. 3, 2015

(87) PCT Pub. No.: WO2014/195333
PCT Pub. Date: Dec. 11, 2014

(65) Prior Publication Data
US 2016/0122341 A1    May 5, 2016

(30) Foreign Application Priority Data
Jun. 4, 2013  (EP) .................................. 13170371

(51) Int. Cl.
| A61K 31/437 | (2006.01) |
| C07D 471/04 | (2006.01) |
| A61K 31/506 | (2006.01) |
| A61K 31/444 | (2006.01) |
| A61K 31/4545 | (2006.01) |
| A61K 31/4709 | (2006.01) |
| A61K 31/496 | (2006.01) |
| A61K 31/497 | (2006.01) |
| A61K 31/5377 | (2006.01) |
| A61K 31/541 | (2006.01) |
| A61K 45/06 | (2006.01) |

(52) U.S. Cl.
CPC .......... *C07D 471/04* (2013.01); *A61K 31/437* (2013.01); *A61K 31/444* (2013.01); *A61K 31/4545* (2013.01); *A61K 31/4709* (2013.01); *A61K 31/496* (2013.01); *A61K 31/497* (2013.01); *A61K 31/506* (2013.01); *A61K 31/5377* (2013.01); *A61K 31/541* (2013.01); *A61K 45/06* (2013.01)

(58) Field of Classification Search
CPC ..................................................... C07D 471/04
USPC ......................................................... 546/113
See application file for complete search history.

(56) References Cited

U.S. PATENT DOCUMENTS

| 5,593,993 A | 1/1997 | Morin, Jr. et al. |
| 5,691,336 A | 11/1997 | Dorn et al. |
| 5,698,704 A | 12/1997 | Jackson |
| 6,180,656 B1 | 1/2001 | Fürster et al. |
| 6,403,588 B1 * | 6/2002 | Hayakawa ............ A61K 31/435 514/249 |
| 7,173,037 B2 | 2/2007 | Alonso-Alija et al. |
| 8,129,423 B2 | 3/2012 | Ackermann et al. |
| 8,198,449 B2 | 6/2012 | Pracitto et al. |
| 8,212,041 B2 | 7/2012 | Albrecht et al. |
| 8,536,338 B2 | 9/2013 | Pracitto et al. |
| 8,673,903 B2 | 3/2014 | Hübsch et al. |
| 8,765,769 B2 | 7/2014 | Follmann et al. |
| 8,778,964 B2 | 7/2014 | Vakalopoulos et al. |
| 8,796,305 B2 | 8/2014 | Vakalopoulos et al. |
| 8,859,569 B2 | 10/2014 | Follmann et al. |
| 8,865,734 B2 | 10/2014 | No et al. |
| 8,946,215 B2 | 2/2015 | Vakalopoulos et al. |
| 8,969,045 B2 | 3/2015 | Burkhardt et al. |
| 9,029,389 B2 | 5/2015 | No et al. |
| 9,126,998 B2 | 9/2015 | Vakalopoulos et al. |
| 2004/0176396 A1 * | 9/2004 | Biftu .................... A61K 31/429 514/259.1 |
| 2005/0228004 A1 * | 10/2005 | Gudmundsson ..... C07D 471/04 514/269 |
| 2006/0135517 A1 * | 6/2006 | Lee ...................... C07D 471/02 514/234.5 |

(Continued)

FOREIGN PATENT DOCUMENTS

| DE | 196 42 255 A1 * | 4/1998 |
| EP | 0 266 890 A1 | 5/1988 |

(Continued)

OTHER PUBLICATIONS

Gheorghiade; Heart Fail Rev (2013) 18, 123-134.*

(Continued)

*Primary Examiner* — Noble Jarrell
*Assistant Examiner* — Daniel Carcanague
(74) *Attorney, Agent, or Firm* — Buchanan Ingersoll & Rooney PC

(57) ABSTRACT

The present application relates to novel 3-aryl-substituted imidazo[1,2-a]pyridines, to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of cardiovascular disorders.

8 Claims, No Drawings

(56) References Cited

U.S. PATENT DOCUMENTS

| | | | |
|---|---|---|---|
| 2008/0051409 A1 | 2/2008 | Gmeiner et al. | |
| 2009/0181941 A1 | 7/2009 | Leblanc et al. | |
| 2010/0298314 A1 | 11/2010 | Reddy et al. | |
| 2011/0306618 A1* | 12/2011 | Buettelmann | C07D 471/04 514/252.18 |
| 2012/0029002 A1 | 2/2012 | Straub et al. | |
| 2014/0088080 A1 | 3/2014 | Koga et al. | |
| 2014/0100229 A1 | 4/2014 | Follmann et al. | |
| 2014/0171434 A1 | 6/2014 | Follmann et al. | |
| 2014/0179672 A1 | 6/2014 | Vakalopoulos et al. | |
| 2014/0350020 A1 | 11/2014 | Follmann et al. | |
| 2014/0357637 A1 | 12/2014 | Follmann et al. | |
| 2015/0274719 A1* | 10/2015 | Vakalopoulos et al. | |

FOREIGN PATENT DOCUMENTS

| | | | |
|---|---|---|---|
| EP | 1 277 754 A1 | | 1/2003 |
| EP | 2 716 642 A1 | | 4/2014 |
| JP | H01-258674 A | | 10/1989 |
| JP | 2003313126 | * | 11/2003 |
| WO | 89/03833 A1 | | 5/1989 |
| WO | 96/34866 A1 | | 11/1996 |
| WO | 98/16223 A1 | | 4/1998 |
| WO | 01/96335 A1 | | 12/2001 |
| WO | 03/095451 A1 | | 11/2003 |
| WO | 2005/058325 A1 | | 6/2005 |
| WO | 2005/073205 A1 | | 8/2005 |
| WO | 2005/090358 A2 | | 9/2005 |
| WO | 2006/015737 A1 | | 2/2006 |
| WO | 2006/135667 A1 | | 12/2006 |
| WO | 2007/002181 A2 | | 1/2007 |
| WO | 2008/008539 A2 | | 1/2008 |
| WO | 2008/032191 A2 | | 3/2008 |
| WO | 2008/082490 A2 | | 7/2008 |
| WO | 2008/134553 A1 | | 11/2008 |
| WO | 2008/148867 A2 | | 12/2008 |
| WO | 2009/155527 A2 | | 12/2009 |
| WO | 2010/030538 A2 | | 3/2010 |
| WO | 2010/065275 A1 | | 6/2010 |
| WO | 2010/079120 A1 | | 7/2010 |
| WO | 2010/101949 A1 | | 9/2010 |
| WO | 2010/125102 A1 | | 11/2010 |
| WO | 2010/136971 A1 | | 12/2010 |
| WO | 2011/088045 A1 | | 7/2011 |
| WO | 2011/113606 A1 | | 9/2011 |
| WO | 2011/141409 A1 | * | 11/2011 |
| WO | 2011/149921 A1 | | 12/2011 |
| WO | 2012/004258 A1 | | 1/2012 |
| WO | 2012/004259 A1 | | 1/2012 |
| WO | 2012/006760 A1 | | 1/2012 |
| WO | 2012/143510 A1 | | 10/2012 |
| WO | 2012/143796 A2 | * | 10/2012 |
| WO | 2012/152629 A1 | | 11/2012 |
| WO | 2012/165399 A1 | | 12/2012 |
| WO | WO2012165399 | * | 12/2012 |
| WO | 2013/030288 A1 | | 3/2013 |
| WO | 2013/104703 A1 | | 7/2013 |
| WO | 2014/068099 A1 | | 5/2014 |
| WO | WO2015124544 | * | 8/2015 |

OTHER PUBLICATIONS

Hamill et al., "Improved Patch-Clamp Techniques for High-Resolution Current Recording from Cells and Cell-Free Membrane Patches," Pflügers Archiv, (Aug. 1981), vol. 391, Issue 2, pp. 85-100.

Himmel et al., "Suitability of Commonly used Excipients for Electrophysiological in-vitro Safety Pharmacology Assessment of Effects on hERG Potassium Current and on Rabbit Purkinje Fiber Action Potential," Journal of Pharmacological and Toxicological Methods, (Sep.-Oct. 2007), vol. 56, Issue 2, pp. 145-158.

Scheel et al. "Introduction of a Modular Automated Voltage-Clamp Platform and Its Correlation with Manual Human Ether-à-go-go Related Gene Voltage-Clamp Data," Assay and Drug Development Technologies, (Dec. 2011), vol. 9, Issue 6, pp. 600-607.

Zhou et al., "Properties of HERG Channels Stably Expressed in HEK 293 Cells Studied at Physiological Temperature," Biophysical Journal, (Jan. 1998), vol. 74, Issue 1, pp. 230-241.

Written Opinion of the International Searching Authority mailed on Jul. 3, 2014, by the European Patent Office as the International Searching Authority for International Application No. PCT/EP2014/061523.

Cui et al., "Structure Based Drug Design of Crizotinib (PF-02341066), a Potent and Selective Dual Inhibitor of Mesenchymal-Epithelial Transition Factor (c-MET) Kinase and Anaplastic Lymphoma Kinase (ALK)," J.Med.Chem., 2011, 54:6342-6363.

Palmer et al., "Synthesis and Evaluation of 7H-8,9-Dihydropyrano[2,3-c]imidazo[1,2-a]pyridines as Potassium—Competitive Acid Blockers," J.Med.Chem., 2007, 50:6240-6264.

Hassan et al., "Aryl-Aryl Bond Formation One Century after the Discovery of the Ullmann Reaction," Chem.Rev., 2002, 102:1359-1469.

Stasch et al., "Pharmacological actions of a novel NO-independent guanylyl cyclase stimulator, BAY 41/8543: in vitro studies," Brit. J.Pharma., 2002, 135:333-343.

Florentin et al., "Etude des pKa et de la protodeboronation des acides furanneboroniques," J.Hetero.Chem., 1976, 13: 1265-1272.

International Search Report (PCT/ISA/210) issued on Jul. 3, 2014, by the European Patent Office as the International Searching Authority for International Application No. PCT/EP2014/061523.

Bodanszky et al., "The Practice of Peptide Synthesis," Springer-Verlag, Berlin, 1984.

Chien-nien et al., "Cyclic Guanosine Monophasphate Signalling Pathway in Pulmonary Arterial Hypertension," Vascular Pharmacology, 2013, 58:211-218.

Dembinski et al., "Recent Advances in the Mitsunobu Reaction: Modified Reagents and the Quest for Chromatography-Free Separation," Eur. J. Org. Chem., 2004, 13:2763-2772.

Deng et al., "Studies on Phosphoroheterocycle Chemistry II: A Simple and New Route to 1,3,2-Diazaphospholidine-4-thione 2-sulfide Derivatives," Synthesis, 2001, 16:2445-2449.

Gensini et al., "3-Azabicyclo[3.1.0]hex-1-ylamines by Ti-Mediated Intramolecular Reductive Cyclopropanation of α-(N-Allylamino)-Substituted N,N-Dialkylcarboxamides and Carbonitriles," Eur. J. Org. Chem., 2002, 15: 2499-2507.

Glass et al., "Stimulation of Human Platelet Guanylate Cyclase by Fatty Acids," J. Biol. Chem., Feb. 1977, 252(4):1279-1285.

Greene et al., Greene's Protective Groups in Organic Synthesis, 4th ed., chapter 1, "The Role of Protective Groups in Organic Synthesis," 2007, Published by John Wiley & Sons, New York.

Hjorringgaard et al., "An Automatic Solid-Phase Synthesis of Peptaibols," J. Org. Chem., 2009, 74:1329-1332.

Hoenicka et al., "Purified Soluble Guanylyl Cyclase Expressed in a Baculovirus/Sf9 System: Stimulation by YC-1, Nitric Oxide, and Carbon Monoxide," J. Mol. Med., 1999, 77:14-23.

Hughes et al., "The Mitsunobu Reaction," Organic Reactions, vol. 42, 1992, Chapter 2, Published by John Wiley & Sons, Inc, pp. 335-395 and 636-656.

Kozo et al., International Review of Experimental Pathololgy, vol. 7, 1969, chapter 2, "Spontaneous Hypertension in Rats," Published by Academic Press, Inc., New York, 227-270.

Lasker et al., "Targeting soluble guanylate cyclase for the treatment of pulmonary hypertension," Expert Rev Respir Med., Apr. 2011, 5(2):153-161.

Maarten van den Buuse, "Circadian Rhythms of Blood Pressure, Heart Rate, and Locomotor Activity in Spontaneously Hypertensive Rats as Measured with Radio-Telemetry," Physiology & Behavior, 1994, 55:(4) 783-787.

McElroy et al., "The Preparation and Properties of Crystalline Firefly Luciferin," Archives of Biochemistry and Biophysics 1957, 72:358-368.

Mülsch et al., "Effect of YC-1, An NO-independent, Superoxide-senstive Stimulator of Soluble Guanylyl Cyclase, On Smooth Muscle Responsiveness to Nitrovasodilators," British Journal Pharmacology 1997, 120:681-689.

(56) References Cited

OTHER PUBLICATIONS

Ogrel et al., "Synthesis of 15N-Labelled D-Isovaline and á-Aminoisobutyric Acid," Eur. J. Org. Chem., 2000, 5:857-859.
Pettibone et al., "A Structurally Novel Stimulator of Guanylate Cyclase With Long-Lasting Hypotensive Activity in the Dog," European Journal of Pharmacology, 1985, 116:307-312.
Soler et al., "Betulinic Acid Derivatives: A New Class of Specific Inhibitors of Human Immunodeficiency Virus Type 1 Entry," Journal Med. Chem., 1996, 39:1069-1083.
Stasch et al., "Cardiovascular actions of a novel NO-independent guanylyl cyclase stimulator, BAY 41-8543: in vivo studies," British Journal of Pharmacology, 2002, 135(2):344-355.
Ko et al., "YC-1, a novel activator of platelet guanylate cyclase," Blood, 1994, 84(12): 4226-4233.
Wunder et al., "A cell-based cGMP assay useful for ultra-high-throughput screening and identification of modulators of the nitric oxide/cGMP pathway," Analytical Biochemistry, 2005, 339:104-112.
Yu et al., "Vasorelaxant Effect of Isoliquiritigenin, A Novel Soluble Guanylate Cyclase Activator, In Rat Aorta," British Journal of Pharmacology, 1995, 114:1587-1594.
Witte et al., "Experimental heart failure in rats: effects on cardiovascular circadian rhythms and on myocardial β-adrenergic signaling," Cardiovascular Research, 2000, 47:350-358.
International Search Report (PCT/ISA/210) mailed on Dec. 13, 2013, by the European Patent Office as the International Searching Authority for International Application No. PCT/EP2013/072891.
Albersen et al., "Synergistic Effects of BAY 60/4552 and Vardenafil on Relaxation of Corpus Cavernosum Tissue of Patients with Erectile Dysfunction and Clinical Phosphodiesterase Type 5 Inhibitor Failure," Journal of Sexual Medicine, (2013), vol. 10, No. 5, pp. 1268-1277.
Daley et al., "The First Complete Identification of a Diastereomeric Catalyst-Substrate (Alkoxide) Species in an Enantioselective Ketone Hydrogenation. Mechanistic Investigations," Journal of the American Chemical Society, (2002), vol. 124, No. 14, pp. 3680-3691.
Evgenov et al., "NO-Independent Stimulators and Activators of Soluble Guanylate Cyclase: Discovery and Therapeutic Potential," Nature Reviews Drug Discovery, (2006), vol. 5, No. 9, pp. 755-768.
Mittendorf et al., "Discovery of Riociguat (BAY 63-2521): A Potent, Oral Stimulator of Soluble Guanylate Cyclase for the Treatment of Pulmonary Hypertension," ChemMedChem, (2009), vol. 4, No. 5, pp. 853-865.
Oudot et al., "Combination of BAY 60-4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, (2011), vol. 60, No. 5, pp. 1020-1026.
Sharkovska et al., "Nitric Oxide-Independent Stimulation of Soluble Guanylate Cyclase Reduces Organ Damage in Experimental Low-Renin and High-Renin Models," Journal of Hypertension, (2010), vol. 28, No. 8, pp. 1666-1675.
Stasch et al., "Soluble Guanylate Cyclase as an Emerging Therapeutic Target in Cardiopulmonary Disease," Circulation, (2011), vol. 123, No. 20, pp. 2263-2273.

* cited by examiner

3-ARYL-SUBSTITUTED IMIDAZO[1,2-A]PYRIDINES AND THEIR USE

The present application relates to novel 3-aryl-substituted imidazo[1,2-a]pyridines, to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem. In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223).

Various imidazo[1,2-a]pyridine derivatives which can be used for treating disorders are described, inter alia, in EP 0 266 890-A1, WO 89/03833-A1, JP 01258674-A [cf. *Chem. Abstr.* 112:178986], WO 96/34866-A1, EP 1 277 754-A1, WO 2001/096335, WO 2006/015737-A1, WO 2006/135667, WO 2008/008539-A2, WO 2008/082490-A2, WO 2008/134553-A1, WO 2010/030538-A2, WO 2011/113606-A1 and WO 2012/165399-A1.

It was an object of the present invention to provide novel substances which act as stimulators of soluble guanylate cyclase and are suitable as such for treatment and/or prophylaxis of diseases.

The present invention provides compounds of the general formula (I)
in which

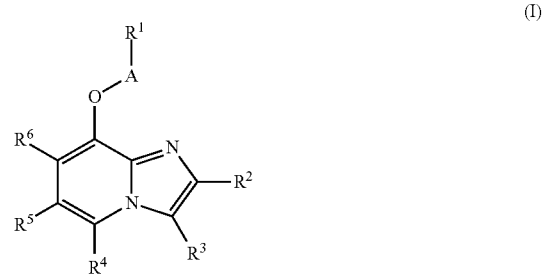

A represents $CH_2$, $CD_2$ or $CH(CH_3)$, $R^1$ represents $(C_3-C_7)$-cycloalkyl, phenyl or pyridyl,
  where $(C_3-C_7)$-cycloalkyl may be substituted by 1 to 4 substituents independently of one another selected from the group consisting of fluorine, trifluoromethyl and $(C_1-C_4)$-alkyl,
  where phenyl may be substituted by 1 to 4 substituents independently selected from the group consisting of halogen, cyano, monofluoromethyl, difluoromethyl, trifluoromethyl, $(C_1-C_4)$-alkyl, $(C_1-C_4)$-alkoxy and difluoromethoxy
  and
  where pyridyl is substituted by 1 or 2 substituents independently of one another selected from the group consisting of halogen, cyano and $(C_1-C_4)$-alkyl, $R^2$ represents $(C_1-C_4)$-alkyl, cyclopropyl, monofluoromethyl, difluoromethyl or trifluoromethyl, $R^3$ represents phenyl or 5- to 10-membered heteroaryl,
  where phenyl may be substituted by 1 to 3 substituents independently of one another selected from the group consisting of halogen, cyano, trifluoromethyl, difluoromethyl, $(C_1-C_6)$-alkyl, $(C_1-C_4)$-alkylcarbonyl, $(C_1-C_4)$-alkoxycarbonyl, hydroxycarbonyl, —(C=O)$NR^7R^8$, $(C_1-C_4)$-alkylsulphonyl, $(C_3-C_6)$-cycloalkylsulphonyl, $(C_1-C_4)$-alkylthio, $(C_1-C_4)$-alkoxy, trifluoromethoxy, difluoromethoxy, phenoxy, hydroxy and $(C_3-C_7)$-cycloalkyl,
  in which $(C_1-C_6)$-alkyl may be substituted by 1 or 2 substituents selected from the group consisting of fluorine, trifluoromethoxy, $(C_1-C_4)$-alkylcarbonyl, —(C=O)$NR^7R^8$, $(C_1-C_4)$-alkoxy, $(C_3-C_6)$-cycloalkyl, morpholinyl, piperidinyl, pyrrolidinyl, piperazinyl, hydroxy and amino,
  in which amino may be substituted by 1 or 2 substituents independently of one another selected from $(C_1-C_6)$-alkyl, $(C_1-C_4)$-alkylcarbonyl, $(C_3-C_6)$-cycloalkylsulphonyl, $(C_1-C_4)$-alkylsulphonyl and methoxy-$(C_1-C_4)$-alkyl, and
in which $(C_3-C_6)$-cycloalkyl may be substituted by amino or hydroxy,
and in which
$R^7$ and $R^8$ each independently of one another represent hydrogen, $(C_1-C_4)$-alkyl or $(C_3-C_7)$-cycloalkyl,
where 5- to 10-membered heteroaryl may be substituted by 1 to 3 substituents independently of one another selected from the group consisting of fluorine, chlorine, cyano, $(C_1-C_6)$-alkyl, $(C_1-C_4)$-alkoxy, amino, $(C_1-C_4)$-alkoxycarbonyl, hydroxycarbonyl, —(C=O)NR$^7$R$^8$, phenyl, pyridyl, pyrimidyl, 1,3-thiazol-5-yl and $(C_3-C_7)$-cycloalkyl,
in which $(C_1-C_6)$-alkyl may be substituted by 1 to 3 substituents selected from the group consisting of halogen, cyano, hydroxy, amino, trifluoromethyl, difluoromethyl, $(C_1-C_4)$-alkylsulphonyl, $(C_1-C_4)$-alkylcarbonyl, $(C_1-C_4)$-alkoxycarbonyl, hydroxycarbonyl, —(C=O)NR$^7$R$^8$, —O(C=O)NR$^7$R$^8$, $(C_1-C_4)$-alkylthio, $(C_1-C_4)$-alkoxy, trifluoromethoxy, difluoromethoxy, phenoxy, phenyl, pyridyl, pyrimidyl, 5-membered heteroaryl, tetrahydrothiophenyl 1,1-dioxide, $(C_3-C_7)$-cycloalkyl, morpholinyl, piperidinyl, pyrrolidinyl, 2-oxopyrrolidin-1-yl, piperazinyl, tetrahydrothiophenyl 1,1-dioxide, thiomorpholinyl 1,1-dioxide and azetidine,
in which 5-membered heteroaryl may be substituted by 1 to 3 substituents selected from the group consisting of halogen, $(C_1-C_4)$-alkyl and $(C_1-C_4)$-alkoxy,
in which piperidinyl may be substituted by 1 to 4 fluorine substituents,
in which phenyl may be substituted by 1 to 3 substituents selected from the group consisting of halogen, $(C_1-C_4)$-alkyl and $(C_1-C_4)$-alkoxy,
in which azetidine may be substituted by hydroxy, and
in which piperazinyl may be substituted by 1 to 3 substituents independently of one another selected from the group consisting of $(C_1-C_4)$-alkyl, $(C_3-C_7)$-cycloalkyl and trifluoromethyl,
in which $(C_3-C_7)$-alkyl may be substituted by 1 or 2 substituents independently of one another selected from the group consisting of halogen, $(C_1-C_6)$-alkyl, $(C_1-C_4)$-alkoxycarbonyl and hydroxycarbonyl,
in which amino may be substituted by $(C_1-C_4)$-alkyl,
in which phenyl, pyridyl, pyrimidyl and 1,3-thiazol-5-yl may be substituted by 1 or 2 substituents selected from the group consisting of methyl, ethyl and fluorine,
in which
$R^7$ and $R^8$ each independently of one another represent hydrogen, $(C_1-C_4)$-alkyl or $(C_3-C_7)$-cycloalkyl,
and
with the proviso that, if 5- to 10-membered heteroaryl represents pyridyl, pyridyl may not be substituted by amino,
$R^4$ represents hydrogen,
$R^5$ represents hydrogen, halogen, cyano, $(C_1-C_4)$-alkyl, $(C_1-C_4)$-alkoxy, $(C_3-C_5)$-cycloalkyl, difluoromethoxy, difluoromethyl, trifluoromethyl, 4- to 7-membered heterocyclyl or 5- or 6-membered heteroaryl,
$R^6$ represents hydrogen or halogen,
and the N-oxides, salts, solvates, salts of the N-oxides and solvates of the N-oxides or salts thereof.
Compounds according to the invention are the compounds of the formula (I) and their salts, solvates and solvates of the salts, the compounds, comprised by formula (I), of the formulae mentioned below and their salts, solvates and solvates of the salts and the compounds, comprised by the formula (I), mentioned below as embodiments and their salts, solvates and solvates of the salts if the compounds, comprised by the formula (I), mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further below and the procedures described in the working examples, by using corresponding isotopic modifications of the respective reagents and/or starting compounds.

In addition, the present invention also encompasses prodrugs of the compounds according to the invention. The term "prodrugs" in this context denotes compounds which may themselves be biologically active or inactive but are converted (for example metabolically or hydrolytically) to compounds according to the invention during their residence time in the body.

In the context of the present invention, unless specified otherwise, the substituents are defined as follows:

Alkyl in the context of the invention represents a straight-chain or branched alkyl radical having the particular number of carbon atoms specified. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Cycloalkyl or carbocycle in the context of the invention represents a monocyclic saturated alkyl radical having the particular number of ring carbon atoms specified. The following may be mentioned by way of example and by way of preference: cyclopropyl, cyclobutyl, cyclopentyl, cyclohexyl and cycloheptyl.

Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Alkoxycarbonyl in the context of the invention represents a straight-chain or branched alkoxy radical having 1 to 4 carbon atoms and a carbonyl group attached to the oxygen atom. The following may be mentioned by way of example and by way of preference: methoxycarbonyl, ethoxycarbonyl, n-propoxycarbonyl, isopropoxycarbonyl and tert-butoxycarbonyl.

Alkylsulphonyl in the context of the invention represents a straight-chain or branched alkyl radical which has 1 to 4 carbon atoms and is attached via a sulphonyl group. Preferred examples include: methylsulphonyl, ethylsulphonyl, n-propylsulphonyl, isopropylsulphonyl, n-butylsulphonyl and tert-butylsulphonyl.

4- to 7-membered heterocyclyl in the context of the invention represents a monocyclic saturated heterocycle which has a total of 4 to 7 ring atoms, contains one or two ring heteroatoms from the group consisting of N, O, S, SO and $SO_2$ and is attached via a ring carbon atom or optionally a ring nitrogen atom. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Heteroaryl in the context of the invention represents a monocyclic aromatic heterocycle (heteroaromatic) which has a total of 5 or 10 ring atoms, contains up to three identical or different ring heteroatoms from the group of N, O and/or S and is attached via a ring carbon atom or optionally via a ring nitrogen atom. The following may be mentioned by way of example and by way of preference: furyl, pyrrolyl, thienyl, 1H-pyrazol-4-yl, 1H-pyrazol-5-yl, imidazolyl, 1,3-thiazol-5-yl, 1,3-thiazol-2-yl, 1,3-oxazol-5-yl, 1,3-oxazol-2-yl, isoxazolyl, isothiazolyl, triazolyl, 1,3,4-oxadiazol-2-yl, 1,2,4-oxadiazol-3-yl, 1,2,4-oxadiazol-5-yl, 1,3,4-thiadiazol-2-yl, 1,2,4-thiadiazol-3-yl, 1,2,4-thiadiazol-5-yl, pyridyl, pyrimidinyl, pyridazinyl, pyrazinyl and triazinyl.

Halogen in the context of the invention includes fluorine, chlorine, bromine and iodine. Preference is given to chlorine or fluorine.

In the formula of the group that $R^3$ or $R^1$ may represent, the end point of the line marked by the symbol *, # or ## does not represent a carbon atom or a $CH_2$ group but is part of the bond to the respective atom to which $R^3$ or $R^1$ is attached.

When radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, preference is given to compounds of the formula (I) in which A represents $CH_2$ or $CD_2$, $R^1$ represents cyclohexyl, phenyl or pyridyl, where phenyl may be substituted by 1 to 4 substituents independently of one another selected from the group consisting of fluorine, bromine, chlorine, cyano and methyl,
and
where pyridyl may be substituted by 1 or 2 substituents independently of one another selected from the group consisting of fluorine, cyano and methyl,
$R^2$ represents $(C_1-C_4)$-alkyl, cyclopropyl or trifluoromethyl,
$R^3$ represents phenyl,
where phenyl may be substituted by 1 to 3 substituents selected from the group consisting of halogen, cyano, trifluoromethyl, difluoromethyl, $(C_1-C_6)$-alkyl, $(C_1-C_4)$-alkylcarbonyl, $(C_1-C_4)$-alkoxycarbonyl, hydroxycarbonyl, —(C=O)NR$^7$R$^8$, $(C_1-C_4)$-alkylsulphonyl, $(C_1-C_4)$-alkylthio, $(C_1-C_4)$-alkoxy, trifluoromethoxy, difluoromethoxy, phenoxy, hydroxy and $(C_3-C_7)$-cycloalkyl,
in which $(C_1-C_6)$-alkyl may be substituted by 1 or 2 substituents selected from the group consisting of trifluoromethoxy, $(C_1-C_4)$-alkylcarbonyl, —(C=O)NR$^7$R$^8$, $(C_1-C_4)$-alkoxy, $(C_3-C_6)$-cycloalkyl, morpholinyl, piperidinyl, pyrrolidinyl, piperazinyl, hydroxy and amino,
in which amino may be substituted by 1 or 2 substituents independently of one another selected from $(C_1-C_6)$-alkyl, $(C_1-C_4)$-alkylcarbonyl, $(C_1-C_4)$-alkylsulphonyl and methoxy-$(C_1-C_4)$-alkyl,
in which $(C_3-C_6)$-cycloalkyl may be substituted by amino or hydroxy,
and in which
$R^7$ and $R^8$ each independently of one another represent hydrogen, $(C_1-C_4)$-alkyl or $(C_3-C_5)$-cycloalkyl,
or
represents 5-membered heteroaryl,
where 5-membered heteroaryl is substituted by 1 or 2 substituents independently of one another selected from the group consisting of chlorine, cyano, $(C_1-C_6)$-alkyl, $(C_1-C_4)$-alkoxy, amino, $(C_1-C_4)$-alkoxycarbonyl, hydroxycarbonyl, —(C=O)NR$^7$R$^8$, phenyl, pyridyl, pyrimidyl, 1,3-thiazol-5-yl and $(C_3-C_6)$-cycloalkyl,
in which $(C_1-C_6)$-alkyl may be substituted by 1 to 3 substituents selected from the group consisting of fluorine, cyano, trifluoromethyl, difluoromethyl, $(C_1-C_4)$-alkylcarbonyl, $(C_1-C_4)$-alkoxycarbonyl, hydroxycarbonyl, —(C=O)NR$^7$R$^8$, —O(C=O)NR$^7$R$^8$, $(C_1-C_4)$-alkylsulphonyl, $(C_1-C_4)$-alkoxy, trifluoromethoxy, difluoromethoxy, phenoxy, phenyl, pyridyl, pyrimidyl, 5-membered heteroaryl, tetrahydrothiophenyl 1,1-dioxide, hydroxy, amino, $(C_3-C_7)$-cycloalkyl, morpholinyl, piperidinyl, pyrrolidinyl, 2-oxopyrrolidin-1-yl, piperazinyl, tetrahydrothiophenyl 1,1-dioxide, thiomorpholinyl 1,1-dioxide and azetidine,
in which 5-membered heteroaryl may be substituted by 1 or 2 methyl or ethyl substituents,
in which piperidinyl may be substituted by 1 to 4 fluorine substituents,
in which phenyl may be substituted by 1 or 2 substituents selected from the group consisting of fluorine, chlorine and methyl,
in which azetidine may be substituted by hydroxy,
in which
$R^7$ and $R^8$ each independently of one another represent hydrogen, $(C_1-C_4)$-alkyl or $(C_3-C_7)$-cycloalkyl,
and in which piperazinyl may be substituted by 1 or 2 methyl or ethyl substituents,
where phenyl, pyridyl, pyrimidyl and 1,3-thiazol-5-yl may be substituted by 1 or 2 substituents selected from the group consisting of methyl, ethyl and fluorine,
where $(C_3-C_6)$-alkyl may be substituted by 1 or 2 substituents independently of one another selected from the group consisting of fluorine, methyl, ethyl, $(C_1-C_4)$-alkoxycarbonyl and hydroxycarbonyl,
and in which
$R^7$ and $R^8$ each independently of one another represent hydrogen, $(C_1-C_4)$-alkyl or $(C_3-C_7)$-cycloalkyl,
$R^4$ represents hydrogen,
$R^5$ represents hydrogen, halogen, cyano, $(C_1-C_4)$-alkyl, methoxy, ethoxy, $(C_3-C_5)$-cycloalkyl or difluoromethyl,
$R^6$ represents hydrogen or fluorine,
and the N-oxides, salts, solvates, salts of the N-oxides and solvates of the N-oxides or salts thereof.
In the context of the present invention, preference is given to compounds of the formula (I) in which
A represents $CH_2$,
$R^1$ represents cyclohexyl or phenyl,
where phenyl is substituted by 1 to 3 fluorine substituents,
or
represents a pyridyl group of the formula
where

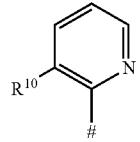

represents the point of attachment to A,
and
$R^{10}$ represents fluorine,
$R^2$ represents methyl or ethyl,
$R^3$ represents phenyl,
where phenyl may be substituted by 1 or 2 substituents selected from the group consisting of fluorine, bromine, chlorine, cyano, trifluoromethyl, difluoromethyl, methyl, ethyl, —(C=O)NR$^7$R$^8$, amino, hydroxycarbonyl, methylsulphonyl, ethylsulphonyl, methoxy, ethoxy, trifluoromethoxy, difluoromethoxy and cyclobutyl,
in which methyl and ethyl may be substituted by 1 or 2 substituents selected from the group consisting of trifluoromethoxy, —(C=O)NR$^7$R$^8$, methoxy, ethoxy, morpholinyl, piperidinyl, pyrrolidinyl, piperazinyl, hydroxy and amino,
in which amino may be substituted by 1 or 2 substituents independently of one another selected from the group consisting of $(C_1-C_4)$-alkyl, methylcarbonyl, ethylcarbonyl, methylsulphonyl, ethylsulphonyl and methoxyethyl,
in which cyclobutyl may be substituted by amino or hydroxy,
in which amino may be substituted by 1 or 2 substituents independently of one another selected from methyl, ethyl, methylcarbonyl, ethylcarbonyl, methylsulphonyl or ethylsulphonyl,
and in which
$R^7$ and $R^8$ independently of one another represent hydrogen, methyl, ethyl or cyclopropyl, or represent a group of the formula (a-1) 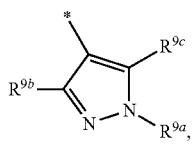

(b-1) 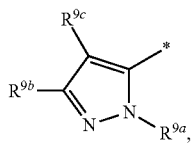

(c-1) 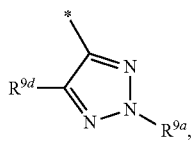

(d-1) 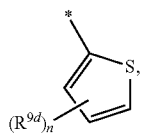

(e-1) 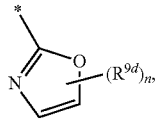

(f-1) 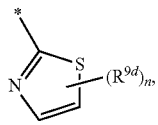

(g-1) 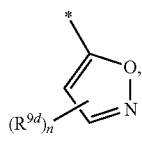

(h-1) 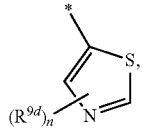

(i-1) 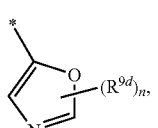

(j-1) 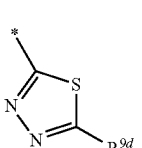

(k-1) 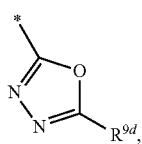

(l-1) 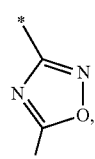

(m1) 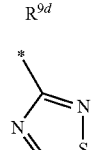

(n-1) 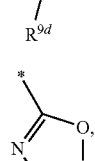

(o-1) 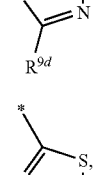

(p-1) 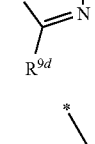

(q-1) 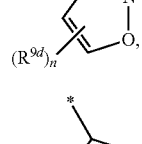

where

* represents the point of attachment to the imidazopyridine, n represents a number 1 or 2, $R^{9a}$ represents $(C_1-C_6)$-alkyl, phenyl, pyridyl or cyclopropyl, where $(C_1-C_6)$-alkyl may be substituted by 1 or 2 substituents selected from the group consisting of fluorine, cyano, trifluoromethyl, difluoromethyl, methylcarbonyl, methoxycarbonyl, ethoxycarbonyl, hydroxycarbonyl, —(C=O)NR$^7$R$^8$, —O(C=O)NR$^7$R$^8$, methylsulphonyl, ethylsulphonyl, methoxy, phenyl, pyridyl, 1H-pyrazolyl, 1H-tetrazolyl, 1,2-oxazolyl, hydroxy, amino, $(C_3-C_5)$-cycloalkyl, morpholinyl, piperidinyl, pyrrolidinyl, piperazinyl, thiomorpholinyl 1,1-dioxide and azetidine, where 1H-pyrazolyl, 1H-tetrazolyl and 1,2-oxazolyl may be substituted by 1 or 2 methyl or ethyl substituents,
where piperidinyl may be substituted by 1 to 2 fluorine substituents,
where azetidine may be substituted by hydroxy, and
in which piperazinyl may be substituted by methyl,
where cyclopropyl may be substituted by 1 or 2 substituents independently selected from the group consisting of methyl, ethyl, methoxycarbonyl, ethoxycarbonyl and hydroxycarbonyl,
where phenyl and pyridyl may be substituted by 1 or 2 fluorine substituents,
and where
$R^7$ and $R^8$ independently of one another represent hydrogen, methyl, ethyl or cyclopropyl,
$R^{9b}$ represents hydrogen or $(C_1-C_4)$-alkyl,
$R^{9c}$ represents hydrogen or $(C_1-C_4)$-alkyl,
$R^{9d}$ represents hydrogen, $(C_1-C_6)$-alkyl, trifluoromethyl, methoxy, ethoxy, amino, methoxycarbonyl, ethoxycarbonyl, hydroxycarbonyl, —(C=O)NR$^7$R$^8$, phenyl, pyridyl, pyrimidyl, 1,3-thiazolyl, tetrahydrothiophenyl 1,1-dioxide or cyclopropyl,
where $(C_1-C_6)$-alkyl may be substituted by 1 or 2 substituents selected from the group consisting of trifluoromethyl, difluoromethyl, $(C_1-C_4)$-alkoxy, 2-oxopyrrolidin-1-yl, phenyl, pyridyl, pyrimidyl, 1H-1,2,4-triazolyl, hydroxy and amino,
in which 1H-1,2,4-triazolyl may be substituted by 1 or 2 methyl or ethyl substituents,
and
in which amino may be substituted by $(C_1-C_4)$-alkyl,
where amino may be substituted by $(C_1-C_4)$-alkyl,
where phenyl, pyridyl, pyrimidyl and 1,3-thiazolyl may each be substituted by 1 or 2 methyl or ethyl substituents,
and in which
$R^7$ and $R^8$ each independently of one another represent hydrogen, methyl, ethyl or cyclopropyl,
$R^4$ represents hydrogen,
$R^5$ represents hydrogen, chlorine, fluorine, methyl, ethyl, difluoromethyl or cyclopropyl,
$R^6$ represents hydrogen,
and the N-oxides, salts, solvates, salts of the N-oxides and solvates of the N-oxides or salts thereof.

Particular preference is given in the context of the present invention to compounds of the formula (I) in which
A represents $CH_2$,
$R^1$ represents cyclohexyl,
or
represents a phenyl group of the formula

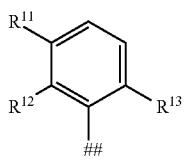

where
represents the point of attachment to A,
and
$R^{11}$, $R^{12}$ and $R^{13}$ independently of one another represent hydrogen or fluorine, with the proviso that at least two of the radicals $R^{11}$, $R^{12}$, $R^{13}$ are different from hydrogen,
or
represents a pyridyl group of the formula

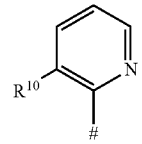

where
represents the point of attachment to A,
and
$R^{10}$ represents fluorine,
$R^2$ represents methyl or ethyl,
$R^3$ represents phenyl,
where phenyl may be substituted by 1 or 2 substituents selected from the group consisting of fluorine, chlorine, cyano, amino, trifluoromethyl, difluoromethyl, methyl, —(C=O)NR$^7$R$^8$, methoxy, piperidinyl and cyclobutyl,
in which methyl may be substituted by 1 or 2 substituents selected from the group consisting of —(C=O)NR$^7$R$^8$, methoxy, morpholinyl, piperidinyl, pyrrolidinyl, piperazinyl, hydroxy and amino,
in which amino may be substituted by 1 or 2 substituents independently of one another selected from methyl, ethyl and methoxyethyl,
in which amino may be substituted by 1 or 2 substituents independently of one another selected from methyl, ethyl, methylcarbonyl, ethylcarbonyl, methylsulphonyl or ethylsulphonyl,
in which cyclobutyl is substituted by amino,
and in which
$R^7$ and $R^8$ each independently of one another represent hydrogen, methyl, ethyl or cyclopropyl,
or
represents a group of the formula

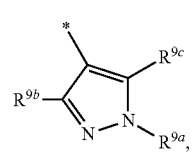

(a-1)

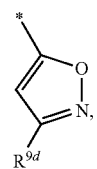

(g-1)

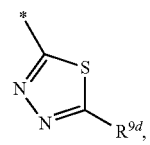

(j-1)

where
* represents the point of attachment to the imidazopyridine,
$R^{9a}$ represents $(C_1-C_6)$-alkyl, phenyl, pyridyl or cyclopropyl, where (C₁-C₆)-alkyl may be substituted by fluorine, cyano, trifluoromethyl, difluoromethyl, methylcarbonyl, methoxycarbonyl, ethoxycarbonyl, hydroxycarbonyl, —(C=O)NR⁷R⁸, —O(C=O)NR⁷R⁸, methylsulphonyl, ethylsulphonyl, methoxy, ethoxy, trifluoromethoxy, difluoromethoxy, phenyl, pyridyl, 1H-pyrazolyl, 1H-tetrazolyl, 1,2-oxazolyl, hydroxy, amino, cyclopropyl, cyclobutyl, morpholinyl, piperidinyl, pyrrolidinyl, piperazinyl, thiomorpholinyl 1,1-dioxide or azetidine,
  in which 1H-pyrazolyl, 1H-tetrazolyl and 1,2-oxazolyl may be substituted by 1 or 2 methyl or ethyl substituents,
  in which piperidinyl may be substituted by 1 to 2 fluorine substituents,
  in which azetidine may be substituted by hydroxyl, and
  in which piperazinyl may be substituted by methyl,
where cyclopropyl may be substituted by methoxycarbonyl, ethoxycarbonyl or hydroxycarbonyl,
where phenyl and pyridyl may be substituted by 1 or 2 fluorine substituents,
and in which
  R⁷ and R⁸ independently of one another represent hydrogen, methyl, ethyl or cyclopropyl,
R⁹ᵇ represents hydrogen or methyl,
R⁹ᶜ represents hydrogen or methyl,
R⁹ᵈ represents hydrogen, (C₁-C₆)-alkyl, trifluoromethyl, methoxy, ethoxy, amino, methoxycarbonyl, ethoxycarbonyl, hydroxycarbonyl, —(C=O)NR⁷R⁸, phenyl, pyridyl, pyrimidyl, 1,3-thiazolyl, tetrahydrothiophenyl 1,1-dioxide or cyclopropyl,
  where (C₁-C₆)-alkyl may be substituted by 1 or 2 substituents selected from the group consisting of trifluoromethyl, difluoromethyl, (C₁-C₄)-alkoxy, 2-oxopyrrolidin-1-yl, phenyl, pyridyl, pyrimidyl, 1H-1,2,4-triazolyl, hydroxy and amino,
    in which 1H-1,2,4-triazolyl may be substituted by 1 or 2 methyl or ethyl substituents,
    and
    where amino may be substituted by (C₁-C₄)-alkyl,
  where amino may be substituted by (C₁-C₄)-alkyl,
  where phenyl, pyridyl, pyrimidyl and 1,3-thiazolyl may each be substituted by 1 or 2 methyl or ethyl substituents,
  and in which
    R⁷ and R⁸ each independently of one another represent hydrogen, methyl, ethyl or cyclopropyl,
R⁴ represents hydrogen,
R⁵ represents hydrogen, chlorine, fluorine, methyl, ethyl, difluoromethyl or cyclopropyl,
R⁶ represents hydrogen,
and the N-oxides, salts, solvates, salts of the N-oxides and solvates of the N-oxides or salts thereof.

In the context of the present invention, particular preference is also given to compounds of the formula (I) in which
A represents CH₂,
R¹ represents cyclohexyl,
  or
  represents a phenyl group of the formula

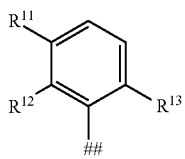

where
represents the point of attachment to A,
and
R¹¹, R¹² and R¹³ independently of one another represent hydrogen or fluorine,
with the proviso that at least two of the radicals R¹¹, R¹², R¹³ are different from hydrogen,
or
represents a pyridyl group of the formula

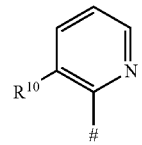

where
represents the point of attachment to A,
and
R¹⁰ represents fluorine,
R² represents methyl,
R³ represents phenyl,
  where phenyl may be substituted by 1 or 2 substituents selected from the group consisting of fluorine, chlorine, cyano, amino, methyl, —(C=O)NR⁷R⁸, methoxy, piperidinyl and cyclobutyl,
    in which methyl may be substituted by 1 or 2 substituents selected from the group consisting of —(C=O)NR⁷R⁸, methoxy, morpholinyl, piperidinyl, pyrrolidinyl, piperazinyl, hydroxy and amino,
      in which amino may be substituted by 1 or 2 substituents independently of one another selected from methyl, ethyl and methoxyethyl,
    in which amino may be substituted by 1 or 2 substituents independently of one another selected from methyl, ethyl, methylcarbonyl, ethylcarbonyl, methylsulphonyl or ethylsulphonyl,
    in which cyclobutyl is substituted by amino,
    and in which
      R⁷ and R⁸ each independently of one another represent hydrogen, methyl or cyclopropyl,
  or
  represent a group of the formula

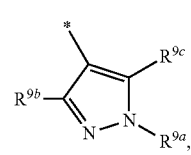
(a-1)

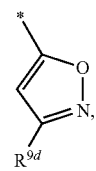
(g-1)

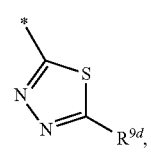
(j-1)

where
* represents the point of attachment to the imidazopyridine,
$R^{9a}$ represents $(C_1-C_4)$-alkyl or cyclopropyl,
  where $(C_1-C_4)$-alkyl may be substituted by fluorine, cyano, methoxycarbonyl, hydroxycarbonyl, —(C=O)NR$^7$R$^8$, —O(C=O)NR$^7$R$^8$, methylsulphonyl, phenyl, 1H-pyrazolyl, 1H-tetrazolyl, 1,2-oxazolyl, hydroxy, amino, cyclopropyl, morpholinyl, piperidinyl, pyrrolidinyl, 2-oxopyrrolidin-1-yl, piperazinyl, thiomorpholinyl 1,1-dioxide or azetidine,
    in which 1H-pyrazolyl, 1H-tetrazolyl and 1,2-oxazolyl may be substituted by 1 or 2 methyl substituents,
    in which piperidinyl may be substituted by 1 or 2 fluorine substituents,
    in which phenyl may be substituted by 1 or 2 fluorine substituents,
    in which azetidine is substituted by hydroxy,
    in which piperazinyl may be substituted by methyl,
    and in which
      $R^7$ and $R^8$ each independently of one another represent hydrogen, methyl or cyclopropyl,
    and
    where cyclopropyl is substituted by methoxycarbonyl or hydroxycarbonyl,
$R^{9b}$ represents hydrogen,
$R^{9c}$ represents hydrogen,
$R^{9d}$ represents $(C_1-C_4)$-alkyl,
  where $(C_1-C_4)$-alkyl is substituted by amino or hydroxy,
$R^4$ represents hydrogen,
$R^5$ represents hydrogen, chlorine or methyl,
$R^6$ represents hydrogen,
and the N-oxides, salts, solvates, salts of the N-oxides and solvates of the N-oxides or salts thereof.

In the context of the present invention, preference is also given to compounds of the formula (I) in which
$R^1$ is a phenyl group of the formula

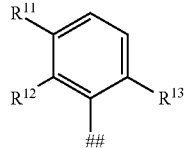

where
represents the point of attachment to A,
and
$R^{11}$, $R^{12}$ and $R^{13}$ independently of one another represent hydrogen or fluorine,
with the proviso that at least two of the radicals $R^{11}$, $R^{12}$, $R^{13}$ are different from hydrogen,
and the N-oxides, salts, solvates, salts of the N-oxides and solvates of the N-oxides or salts thereof.

In the context of the present invention, preference is also given to compounds of the formula (I) in which
$R^1$ represents a pyridyl group of the formula

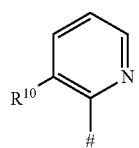

where
# represents the attachment site to A,
and
$R^{10}$ represents fluorine,
and the N-oxides, salts, solvates, salts of the N-oxides and solvates of the N-oxides or salts thereof.

In the context of the present invention, preference is also given to compounds of the formula (I) in which
$R^2$ represents methyl,
and the N-oxides, salts, solvates, salts of the N-oxides and solvates of the N-oxides or salts thereof.

In the context of the present invention, preference is also given to compounds of the formula (I) in which
$R^3$ represents a group of the formula

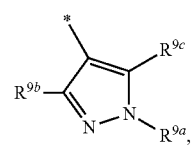

(a-1)

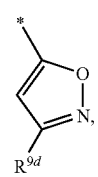

(g-1)

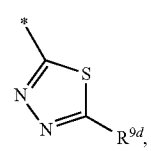

(j-1)

where
* represents the point of attachment to the imidazopyridine,
$R^{9a}$ represents $(C_1-C_4)$-alkyl or cyclopropyl,
  where $(C_1-C_4)$-alkyl may be substituted by fluorine, cyano, methoxycarbonyl, hydroxycarbonyl, —(C=O)NR$^7$R$^8$, —O(C=O)NR$^7$R$^8$, methylsulphonyl, phenyl, 1H-pyrazolyl, 1H-tetrazolyl, 1,2-oxazolyl, hydroxy, amino, cyclopropyl, morpholinyl, piperidinyl, pyrrolidinyl, 2-oxopyrrolidin-1-yl, piperazinyl, thiomorpholinyl 1,1-dioxide or azetidine,
    in which 1H-pyrazolyl, 1H-tetrazolyl and 1,2-oxazolyl may be substituted by 1 or 2 methyl substituents,
    in which piperidinyl may be substituted by 1 or 2 fluorine substituents,
    in which phenyl may be substituted by 1 or 2 fluorine substituents,
    in which azetidine is substituted by hydroxy,
    in which piperazinyl is substituted by methyl,
    and
      $R^7$ and $R^8$ each independently of one another represent hydrogen, methyl or cyclopropyl,
    and
    where cyclopropyl is substituted by methoxycarbonyl or hydroxycarbonyl,
$R^{9b}$ represents hydrogen,
$R^{9c}$ represents hydrogen,
$R^{9d}$ represents hydrogen or $(C_1-C_4)$-alkyl, where (C₁-C₄)-alkyl is substituted by amino or hydroxy,
and the N-oxides, salts, solvates, salts of the N-oxides and solvates of the N-oxides or salts thereof.

In the context of the present invention, preference is also given to compounds of the formula (I) in which
$R^3$ represents a group of the formula

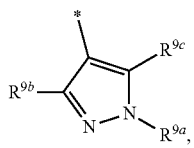
(a-1)

where
* represents the point of attachment to the imidazopyridine,
$R^{9a}$ represents (C₁-C₄)-alkyl,
where (C₁-C₄)-alkyl is substituted by hydroxy or amino,
$R^{9b}$ represents hydrogen,
$R^{9c}$ represents hydrogen,
and the N-oxides, salts, solvates, salts of the N-oxides and solvates of the N-oxides or salts thereof.

In the context of the present invention, preference is also given to compounds of the formula (I) in which
$R^3$ represents a group of the formula

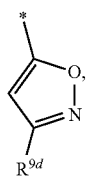
(g-1)

where
* represents the point of attachment to the imidazopyridine,
$R^{9d}$ represents (C₁-C₄)-alkyl,
where (C₁-C₄)-alkyl is substituted by hydroxy or amino,
and the N-oxides, salts, solvates, salts of the N-oxides and solvates of the N-oxides or salts thereof.

In the context of the present invention, preference is also given to compounds of the formula (I) in which
$R^3$ represents a group of the formula

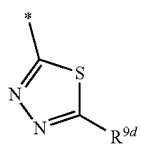
(j-1)

where
* represents the point of attachment to the imidazopyridine,
$R^{9d}$ represents (C₁-C₄)-alkyl,
where (C₁-C₄)-alkyl is substituted by hydroxy or amino, and the N-oxides, salts, solvates, salts of the N-oxides and solvates of the N-oxides or salts thereof.

In the context of the present invention, preference is also given to compounds of the formula (I) in which
$R^5$ represents hydrogen, chlorine, fluorine, methyl, ethyl, difluoromethyl or cyclopropyl,
and the N-oxides, salts, solvates, salts of the N-oxides and solvates of the N-oxides or salts thereof.

In the context of the present invention, preference is also given to compounds of the formula (I) in which
$R^5$ represents hydrogen, chlorine or methyl,
and the N-oxides, salts, solvates, salts of the N-oxides and solvates of the N-oxides or salts thereof.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the compounds according to the invention of the formula (I), characterized in that
[A] a compound of the formula (II)

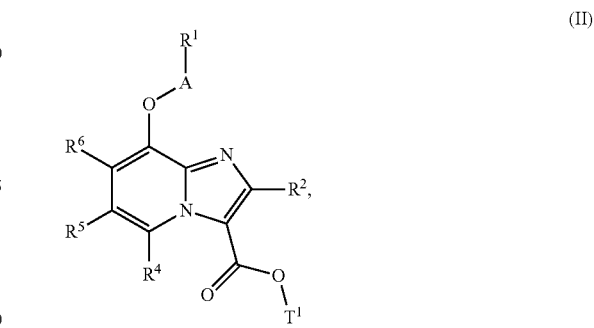
(II)

in which A, $R^1$, $R^2$, $R^4$, $R^5$ and $R^6$ are each as defined above and
$T^1$ represents (C₁-C₄)-alkyl or benzyl,
is converted in an inert solvent in the presence of a suitable base or acid into a carboxylic acid of the formula (III)

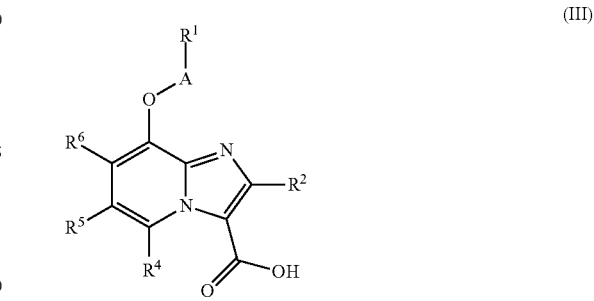
(III)

in which A, $R^1$, $R^2$, $R^4$, $R^5$ and $R^6$ each have the meanings given above,
[A] and these are subsequently converted in the presence of a suitable acid into an imidazo[1,2-a]-pyridine of the formula (IV)

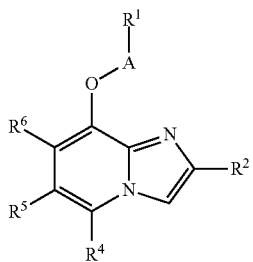

(IV)

in which A, R$^1$, R$^2$, R$^4$, R$^5$ and R$^6$ each have the meanings given above, and this is then converted with a halogen equivalent into a compound of the formula (V)

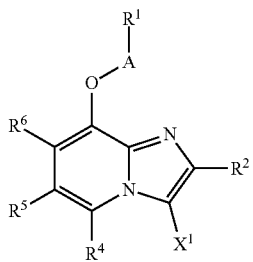

(V)

in which A, R$^1$, R$^2$, R$^4$, R$^5$ and R$^6$ are each as defined above and

X$^1$ represents chlorine, bromine or iodine, and this is subsequently reacted in an inert solvent, in the presence of a suitable transition metal catalyst, with a compound of the formula (VI)

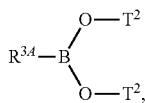

(VI)

in which

R$^{3A}$ has the meanings given above for R$^3$ and

T$^2$ represents hydrogen or (C$_1$-C$_4$)-alkyl, or the two T$^2$ radicals together form a —C(CH$_3$)$_2$—C(CH$_3$)$_2$— bridge, to give a compound of the formula (I-A)

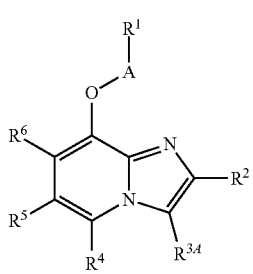

(I-A)

and these compounds are subsequently, if R$^{3A}$ represents

(VII)

reacted in an inert solvent in the presence of a suitable base with a compound of the formula (VIII)

R$^{14}$—X$^1$ (VIII)

in which

X$^1$ represents a suitable leaving group, in particular chlorine, bromine, iodine, mesylate, triflate or tosylate, and R$^{14}$ represents (C$_1$-C$_6$)-alkyl,
where (C$_1$-C$_6$)-alkyl may be substituted by 1 to 3 substituents selected from the group consisting of fluorine, cyano, trifluoromethyl, difluoromethyl, (C$_1$-C$_4$)-alkylcarbonyl, (C$_1$-C$_4$)-alkoxycarbonyl, hydroxycarbonyl, —(C=O)NR$^7$R$^8$, —O(C=O)NR$^7$R$^8$, (C$_1$-C$_4$)-alkylsulphonyl, (C$_1$-C$_4$)-alkoxy, trifluoromethoxy, difluoromethoxy, phenyl, 1H-pyrazolyl, 1H-1,2,4-triazolyl, 1H-tetrazolyl, 1,2-oxazolyl, tetrahydrothiophenyl 1,1-dioxide, hydroxy, amino, (C$_3$-C$_7$)-cycloalkyl, morpholinyl, piperidinyl, pyrrolidinyl, 2-oxopyrrolidin-1-yl, piperazinyl, tetrahydrothiophenyl 1,1-dioxide, thiomorpholinyl 1,1-dioxide and azetidine,
in which 1H-pyrazolyl, 1H-1,2,4-triazolyl, 1H-tetrazolyl and 1,2-oxazolyl may be substituted by 1 or 2 methyl or ethyl substituents,
in which piperidinyl may be substituted by 1 or 2 fluorine substituents,
in which phenyl may be substituted by 1 or 2 fluorine substituents,
in which piperazinyl may be substituted by methyl, and in which
R$^7$ and R$^8$ each independently of one another represent hydrogen, methyl or cyclopropyl,
or
R$^7$ and R$^8$ together with the carbon atom to which they are attached form a 3- to 5-membered carbocycle, to give a compound of the formula (I-B)

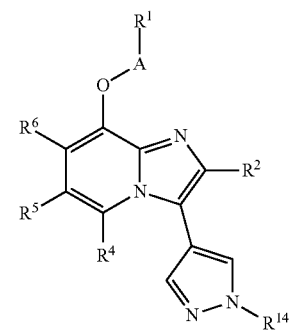

(I-B)

in which A, R$^1$, R$^2$, R$^4$, R$^5$, R$^6$ and R$^{14}$ each have the meanings given above and any protecting groups present are subsequently removed, and the resulting compounds of the formula (I) are optionally converted with the appropriate (i) solvents and/or (ii) acids or bases into the solvates, salts and/or solvates of the salts thereof, or

[B] a compound of the formula (II) is converted in the presence of hydrazine hydrate into a compound of the formula (IX)

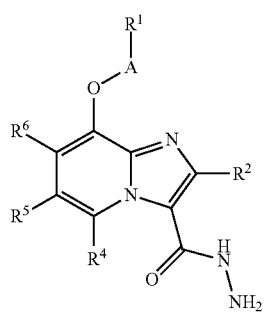
(IX)

in which A, R¹, R², R⁴, R⁵ and R⁶ each have the meanings given above, and these are subsequently reacted in an inert solvent under amide coupling conditions with a carboxylic acid of the formula (X)

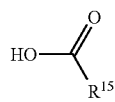
(X)

in which R¹⁵ represents (C₁-C₆)-alkyl, where (C₁-C₆)-alkyl may be substituted by 1 to 3 substituents selected from the group consisting of trifluoromethyl, difluoromethyl, hydroxy and amino, to give a compound of the formula (XI)

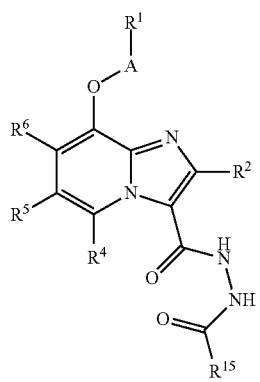
(XI)

in which A, R¹, R², R⁴, R⁵, R⁶ and R¹⁵ each have the meanings given above, and this compound is then converted with 2,4-bis(4-methoxyphenyl)-1,3,2,4-dithiadiphosphetane-2,4-disulphide [Lawesson's reagent] into a compound of the formula (I-C)

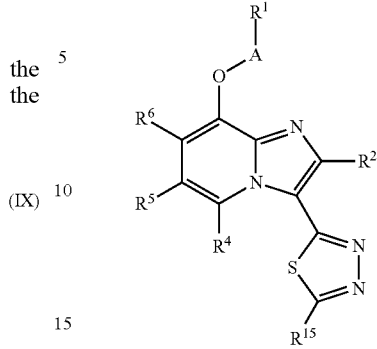
(I-C)

in which A, R¹, R², R⁴, R⁵, R⁶ and R¹⁵ each have the meanings given above, then any protecting groups present are detached, and the resulting compounds of the formula (I) are optionally converted with the appropriate (i) solvents and/or (ii) acids or bases to the solvates, salts and/or solvates of the salts thereof.

The compounds of the formulae (I-A), (I-B) and (I-C) form a subgroup of compounds according to the invention of the formula (I).

The preparation processes described can be illustrated by way of example by the following synthesis schemes (Schemes 1 and 2):

Scheme 1:

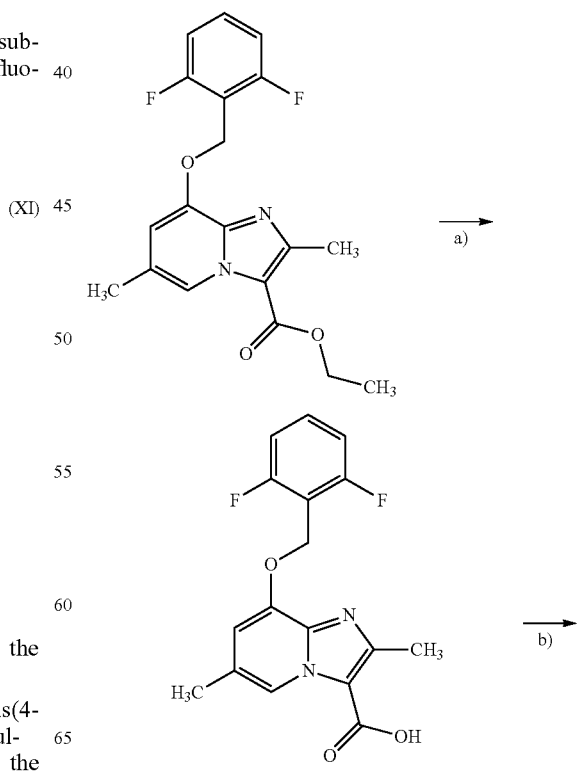

Scheme 2:
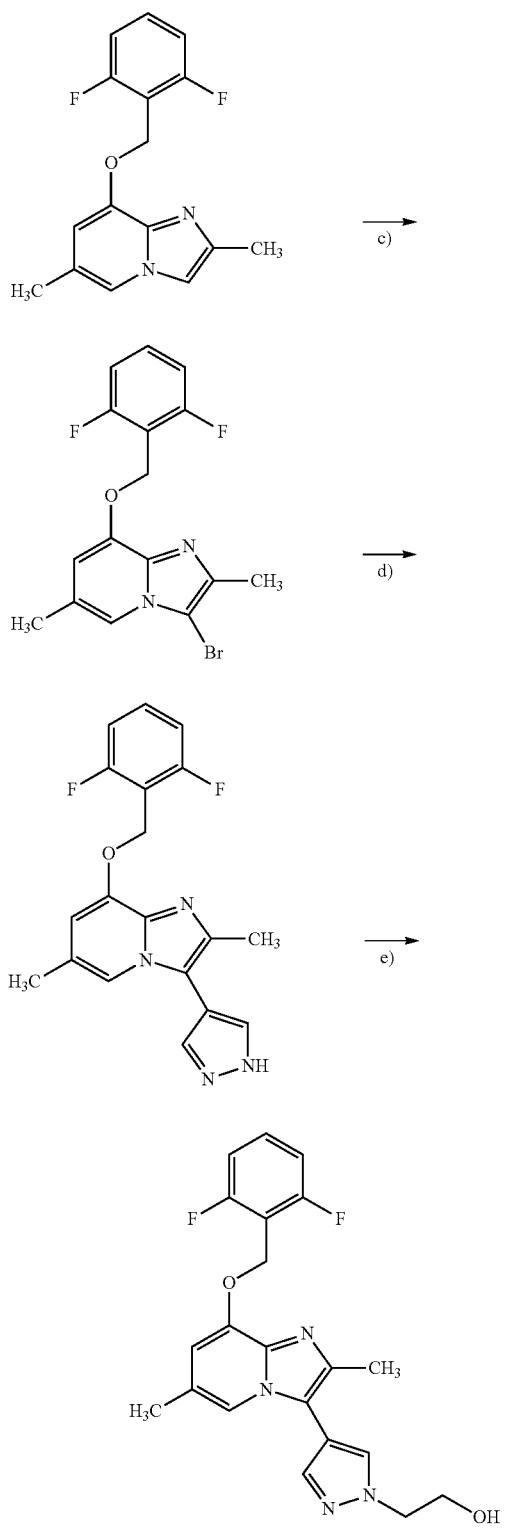
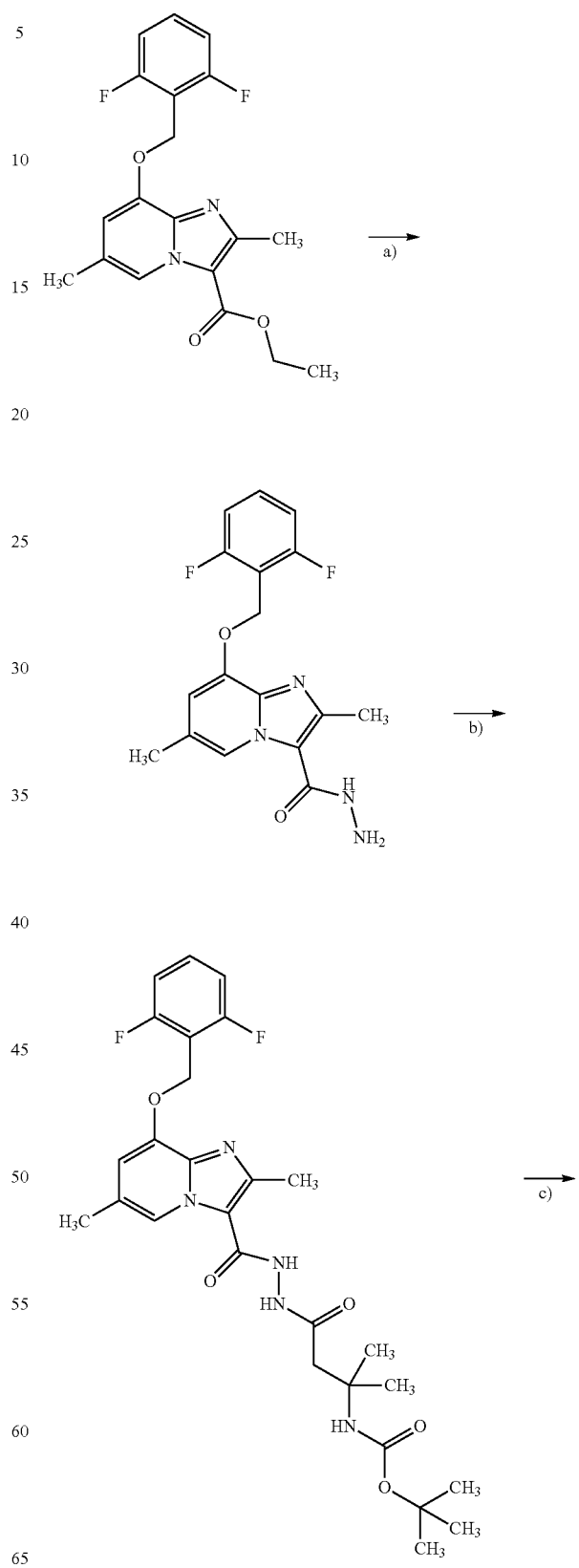
[a]: lithium hydroxide, THF/methanol/H₂O, RT; b): 6N hydrochloric acid, 100° C.; c): N-bromosuccinimide, ethanol, RT; d): 1H-pyrazol-4-ylboronic acid or [1-(tert-butoxycarbonyl)-1H-pyrazol-4-yl]boronic acid, bis(tri-tert-butylphosphine)palladium(0), K₃PO₄, ethanol/water/toluene, 120° C.; e): caesium carbonate, potassium iodide, iodoethanol, DMF, 70° C.].

-continued

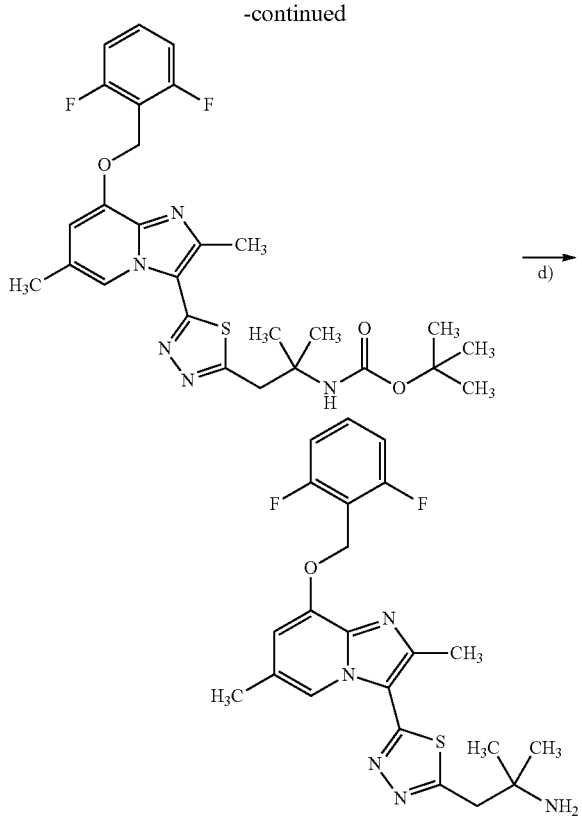

[a]: hydrazine hydrate, ethanol, 80° C.; b): 3-[tert-butoxycarbonyl)amino]-3-methylbutanoic acid, EDCI, HOBT, DMF, RT; c): 2,4-bis(4-methoxyphenyl)-1,3,2,4-dithiadiphosphetane-2,4-disulphide[Lawesson's reagent], THF, 100° C. microwave oven; d): TFA, dichloromethane, RT].

The compounds of the formulae (VI), (VIII) and (X) are commercially available, known from the literature or can be prepared in analogy to literature processes.

The hydrolysis of the ester group $T^1$ in the compounds of the formula (II) is effected by customary methods, by treating the esters in inert solvents with acids or bases, in which latter case the salts formed at first are converted to the free carboxylic acids by treating with acid. In the case of the tert-butyl esters, the ester hydrolysis is preferably effected with acids. In the case of the benzyl esters, the ester hydrolysis is preferably effected by hydrogenolysis with palladium on activated carbon or Raney nickel. Suitable inert solvents for this reaction are water or the organic solvents customary for ester hydrolysis. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester cleavage are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally carried out within a temperature range from 0° C. to +100° C., preferably at +0° C. to +50° C.

These conversions can be performed at atmospheric, elevated or reduced pressure (for example from 0.5 to 5 bar). In general, the reactions are in each case carried out at atmospheric pressure.

A suitable solvent for the process step (III)→(IV) is water.

Suitable acids for the process step (III)→(IV) are hydrogen chloride/hydrochloric acid, hydrogen bromide/hydrobromic acid, sulphuric acid, acetic acid, . . . , or mixtures thereof, optionally with addition of water. Preference is given to using hydrochloric acid.

The decarboxylation (III)→(IV) is generally carried out in a temperature range of from +20° C. to +100° C., preferably at from 75° C. to +100° C. The conversion can be effected under standard, elevated or reduced pressure (for example from 0.5 to 5 bar). In general, the reactions are carried out at atmospheric pressure.

Suitable solvents for process step (IV)→(V) include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulphoxide. It is also possible to use mixtures of the solvents mentioned. Preference is given to using methanol and/or ethanol.

A suitable halogen source for the reaction (IV)→(V) is, for example, N-bromosuccinimide, N-chlorosuccinimide, N-iodosuccinimide, chlorine, bromine or iodine. Preference is given to using N-bromosuccinimide.

The reaction (IV)→(V) is generally carried out in a temperature range of from +20° C. to +100° C., preferably from +20° C. to +80° C. The reaction can be performed at atmospheric, elevated or reduced pressure (for example in the range from 0.5 to 5 bar). Standard pressure is generally employed.

Process step (V)+(VI)→(I-A) is carried out in a solvent which is inert under the reaction conditions. Suitable solvents are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as 1,2-dimethoxyethane (DME), dimethylformamide (DMF), dimethyl sulphoxide (DMSO), N,N'-dimethylpropyleneurea (DMPU), N-methylpyrrolidone (NMP), pyridine, acetonitrile, toluene or else water. It is also possible to use mixtures of the solvents mentioned. Preference is given to methanol, ethanol, toluene and water.

The conversion (V)+(VI)→(I-A) can optionally be carried out in the presence of a suitable palladium and/or copper catalyst. A suitable palladium catalyst is, for example, palladium(II) acetate, tetrakis(triphenylphosphine)palladium(0), bis(tri-tert-butylphosphine)palladium(0), bis(triphenylphosphine)palladium(II) chloride, bis(acetonitrile) palladium(II) chloride and [1,1'-bis(diphenylphosphino)ferrocene]dichloropalladium(II) and the corresponding dichloromethane complex, optionally in conjunction with additional phosphane ligands, for example (2-biphenyl)di-tert-butylphosphine, 2-dicyclohexylphosphino-2',6'-dimethoxybiphenyl (SPHOS), dicyclohexyl[2',4',6'-tris(1-methylethyl)biphenyl-2-yl]phosphane (XPHOS), bis(2-phenylphosphinophenyl) ether (DPEphos) or 4,5-bis(diphenylphosphino)-9,9-dimethylxanthene (Xantphos) [cf., for example, Hassan J. et al., Chem. Rev. 102, 1359-1469 (2002)].

The conversion (V)+(VI)→(I-A) is optionally carried out in the presence of a suitable base. Suitable bases for this conversion are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®) or potassium phosphate. Preference is given to using potassium phosphate.

The reaction (V)+(VI)→(I-A) is generally carried out in a temperature range from 0° C. to +200° C., preferably at from +100° C. to +150° C. The conversion can be effected under standard, elevated or reduced pressure (for example from 0.5 to 5 bar). Standard pressure is generally employed.

Inert solvents for the process step (I-A)+(VIII)→(I-B) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (I-A)+(VIII)→(I-B) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally effected within a temperature range from 0° C. to +120° C., preferably at +20° C. to +80° C., optionally in a microwave. The reaction can be conducted at standard, elevated or reduced pressure (for example from 0.5 to 5 bar).

Suitable solvents for the process step (II)→(IX) are chloroform or alcohols such as methanol, ethanol, n-propanol, isopropanol, n-butanol, n-pentanol or tert-butanol. It is also possible to use mixtures of the solvents mentioned. Preference is given to using ethanol.

A suitable reagent for process step (II)→(IX) is hydrazine or hydrazine hydrate. Preference is given to hydrazine hydrate.

The reaction (II)→(IX) is generally conducted within a temperature range of 0° C. to +200° C., preferably at +70° C. to +100° C. The conversion can be effected under standard, elevated or reduced pressure (for example from 0.5 to 5 bar). Standard pressure is generally employed.

Suitable inert solvents for the process steps (IX)+(X)→(XI) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable condensing agents for the amide formation in the process steps (IX)+(X)→(XI) are carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride (T3P), 1-chloro-N,N,2-trimethylprop-1-en-1-amine, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also, as bases, alkali metal carbonates, for example sodium carbonate or potassium carbonate or sodium hydrogencarbonate or potassium hydrogencarbonate, or organic bases such as trialkylamines, e.g. triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-en-1-amine.

The condensation (IX)+(X)→(XI) is generally conducted within a temperature range of −20° C. to +100° C., preferably at 0° C. to +60° C. The conversion can be carried out under atmospheric, elevated or reduced pressure (for example from 0.5 to 5 bar). Standard pressure is generally employed.

Suitable solvents for process step (XI)→(I-C) are ethers such as diethyl ether, dioxane, tetrahydrofuran, glycol dimethyl ether or diethylene glycol dimethyl ether or other solvents such as acetone, dichloromethane, ethyl acetate, acetonitrile, dimethyl sulphoxide, N,N-dimethylformamide, N,N-dimethylacetamide, N-methylpyrrolidone (NMP), toluene or pyridine. It is also possible to use mixtures of the solvents mentioned. Preference is given to diethyl ether and tetrahydrofuran or mixtures of these solvents.

A suitable reagent for process step (XI)→(I-C) is 2,4-bis (4-methoxyphenyl)-1,3,2,4-dithiadiphosphetane-2,4-disulphide [Lawesson's reagent], diphosphorus pentasulphide or tetraphosphorus decasulphide. Preference is given to 2,4-bis (4-methoxyphenyl)-1,3,2,4-dithiadiphosphetane-2,4-disulphide [Lawesson's reagent].

The reaction (XI)→(I-C) is generally carried out in a temperature range of from 0° C. to +200° C., preferably at from +70° C. to +120° C., optionally in a microwave. The conversion can be effected under standard, elevated or reduced pressure (for example from 0.5 to 5 bar). The reaction is preferably carried out in a microwave oven.

The compounds of the formula (II) are known from the literature or can be prepared by reacting a compound of the formula (XII)

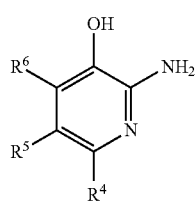

(XII)

in which $R^4$, $R^5$ and $R^6$ have the meaning given above, in an inert solvent in the presence of a suitable base with a compound of the formula (XIII)

(XIII)

in which A and $R^1$ have the meaning given above and $X^1$ represents a suitable leaving group, in particular chlorine, bromine, iodine, mesylate, triflate or tosylate, to give a compound of the formula (XIV)

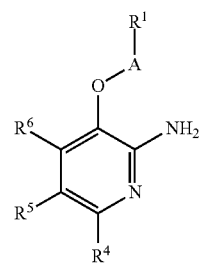

(XIV)

in which $R^1$, $R^4$, $R^5$ and $R^6$ each have the meanings given above, and then reacting this in an inert solvent with a compound of the formula (XV)

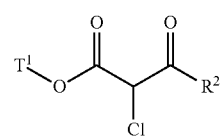

(XV)

in which $R^2$ and $T^1$ each have the meanings given above.

The process described is illustrated in an exemplary manner by the scheme below (Scheme 3):

Scheme 3:

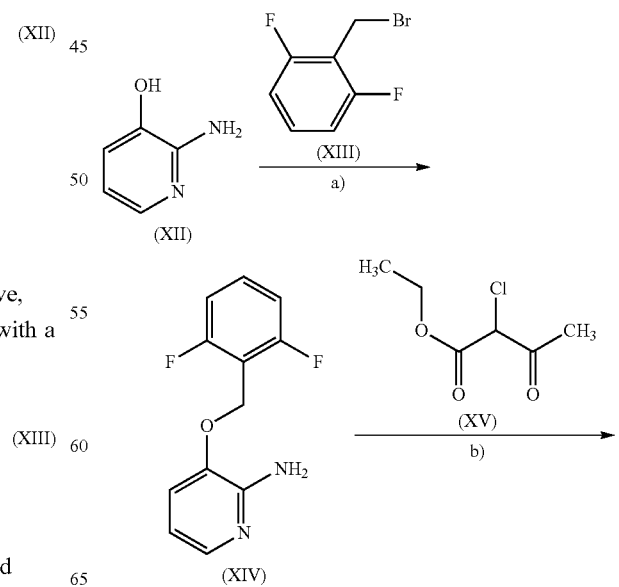

-continued

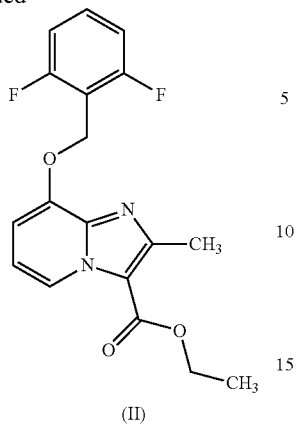

(II)

[a]: i) NaOMe, MeOH, RT; ii) DMSO, RT; b): EtOH, molecular sieve, reflux].

The synthesis sequence shown can be modified such that the respective reaction steps are carried out in a different order. An example of such a modified synthesis sequence is shown in Scheme 4.

Scheme 4:

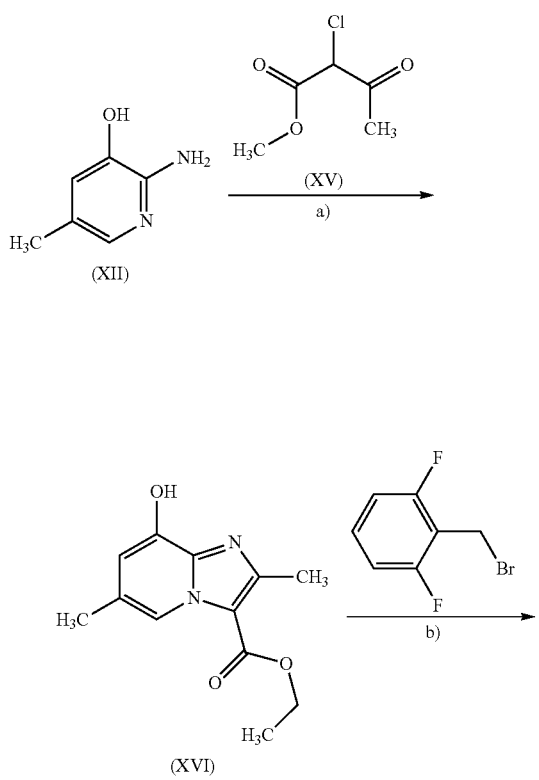

-continued

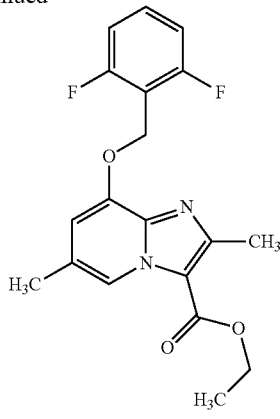

(II)

[a]: EtOH, molecular sieve, reflux; b): b) Cs$_2$CO$_3$, DMF, 50° C.].

Inert solvents for the process step (XII)+(XIII)→(XIV) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, alcohols such as methanol, ethanol, tert-butanol, or other solvents such as acetone, methyl ethyl ketone, ethyl acetate, acetonitrile, N,N-dimethylformamide, dimethyl sulphoxide, N,N'-dimethylpropyleneurea (DMPU), N-methylpyrrolidone (NMP) or pyridine. It is also possible to use mixtures of the solvents mentioned. Preference is given to using methanol, dimethylformamide or dimethyl sulphoxide.

Suitable bases for the process step (XII)+(XIII)→(XIV) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl) amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally effected within a temperature range from 0° C. to +120° C., preferably at +20° C. to +80° C., optionally in a microwave. The reaction can be carried out under atmospheric, elevated or reduced pressure (for example from 0.5 to 5 bar).

Inert solvents for the ring closure to give the imidazo[1,2-a]pyridine base skeleton (XIV)+(XV)→(II) or (XII)+(XV)→(XVI) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulphoxide. It is also possible to use mixtures of the solvents mentioned. Preference is given to using ethanol.

The ring closure is generally effected within a temperature range from +50° C. to +150° C., preferably at +50° C. to +100° C., optionally in a microwave.

The ring closure (XIV)+(XV)→(II) or (XII)+(XV)→(XVI) is optionally carried out in the presence of dehydrating reaction additives, for example in the presence of molecular sieve (pore size 4 Å) or by means of a water separator. The reaction (XIV)+(XV)→(II) or (XII)+(XV)→(XVI) is effected using an excess of the reagent of the formula (XV), for example with 1 to 20 equivalents of the reagent (XV), optionally with addition of bases (for example sodium hydrogencarbonate), in which case the addition of this reagent can be effected all at once or in several portions.

Further inventive compounds can optionally also be prepared by conversions of functional groups of individual substituents, especially those listed for $R^3$, proceeding from compounds of the formula (I) obtained by above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester cleavage, etherification, ether cleavage, formation of carbonamides, and introduction and removal of temporary protective groups.

The compounds according to the invention have valuable pharmacological properties and can be used for prevention and treatment of diseases in humans and animals. The inventive compounds offer a further treatment alternative and thus enlarge the field of pharmacy.

The inventive compounds bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the inventive compounds enhance the action of substances which increase the cGMP level, for example EDRF (endothelium-derived relaxing factor), NO donors, protoporphyrin IX, arachidonic acid or phenylhydrazine derivatives.

The compounds according to the invention are suitable for treatment and/or prophylaxis of cardiovascular, pulmonary, thromboembolic and fibrotic disorders.

The inventive compounds can therefore be used in medicaments for treatment and/or prophylaxis of cardiovascular disorders, for example hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The compounds according to the invention can also be used for treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The inventive compounds are also suitable for treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also comprises the use of the compounds according to the invention for the treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

In addition, the compounds according to the invention are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

In addition, the compounds according to the invention have anti-inflammatory action and can therefore be used as anti-inflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

In addition, the inventive compounds can likewise be used for treatment and/or prophylaxis of autoimmune disorders.

The compounds according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds according to the invention are also suitable for controlling postoperative scarring, for example as a result of glaucoma operations.

The compounds according to the invention can also be used cosmetically for ageing and keratinized skin.

Moreover, the compounds according to the invention are suitable for treatment and/or prophylaxis of hepatitis, neoplasms, osteoporosis, glaucoma and gastroparesis.

The present invention further provides for the use of the compounds according to the invention for treatment and/or prophylaxis of disorders, especially the disorders mentioned above.

The present invention further provides for the use of the compounds according to the invention for treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds according to the invention for use in a method for treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds according to the invention for production of a medicament for treatment and/or prophylaxis of disorders, especially the disorders mentioned above.

The present invention further provides for the use of the compounds according to the invention for preparing a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for treatment and/or prophylaxis of disorders, in particular the disorders mentioned above, using an effective amount of at least one of the compounds according to the invention.

The present invention further provides a method for treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the inventive compounds.

The compounds according to the invention can be used alone or, if required, in combination with other active compounds. The present invention furthermore provides medicaments containing at least one of the compounds according to the invention and one or more further active compounds, in particular for treatment and/or prophylaxis of the abovementioned disorders. Preferred examples of active compounds suitable for combinations include:
- organic nitrates and NO donors, for example sodium nitroprusside, nitroglycerin, isosorbide mononitrate, isosorbide dinitrate, molsidomine or SIN-1, and inhaled NO;
- compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;
- antithrombotic agents, by way of example and with preference from the group of the platelet aggregation inhibitors, the anticoagulants or the profibrinolytic substances;
- hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or
- active compounds which alter lipid metabolism, for example and with preference from the group of thyroid receptor agonists, cholesterol synthesis inhibitors, preferred examples being HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embursatan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference dalcetrapib, BAY 60-5521, anacetrapib or CETP vaccine (CETi-1).

In a preferred embodiment of the invention, the compounds according to the invention are administered in combination with a thyroid receptor agonist, by way of example and with preference D-thyroxin, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, nontoxic, pharmaceutically suitable excipients, and the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary in some cases to deviate from the stated amounts, specifically as a function of the body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

A. EXAMPLES

Abbreviations and Acronyms aq. aqueous solution
calc. calculated
br. broad signal (NMR coupling pattern)
CAS No. Chemical Abstracts Service number
δ shift in the NMR spectrum (stated in)
d doublet (NMR coupling pattern)
TLC thin-layer chromatography
DCI direct chemical ionization (in MS)
DMAP 4-N,N-dimethylaminopyridine
DMF dimethylformamide
DMSO dimethyl sulphoxide
EDCI N-[3-(dimethylamino)propyl]-N'-ethylcarbodiimide
eq. equivalent(s)
ESI electrospray ionization (in MS)
Et ethyl
h hour(s)
HATU N-[(dimethylamino)(3H-[1,2,3]triazolo[4,5-b]-pyridin-3-yloxy)methylene]-N-methylmethanaminium hexafluorophosphate
HOBT 1H-benzotriazol-1-ol
HPLC high-pressure, high-performance liquid chromatography
HRMS high-resolution mass spectrometry
ID internal diameter
conc. concentrated
LC-MS liquid chromatography-coupled mass spectrometry
LiHMDS lithium hexamethyldisilazide
m multiplet
Me methyl
min minute(s)
MS mass spectrometry
NMR nuclear magnetic resonance spectrometry
PDA photodiode array detector
$Pd_2dba_3$ tris(dibenzylideneacetone)dipalladium
Ph phenyl
q quartet (NMR coupling pattern)
quint. quintet (NMR coupling pattern)
$R_F$ retention factor (in thin-layer chromatography)
RT room temperature
$R_t$ retention time (in HPLC)
s singlet (NMR coupling pattern)
t triplet (NMR coupling pattern)
THF tetrahydrofuran
TBTU (benzotriazol-1-yloxy)bisdimethylaminomethylium fluoroborate
UPLC-MS ultra-pressure liquid chromatography-coupled mass spectrometry
UV ultraviolet spectrometry
v/v ratio by volume (of a solution)
Xantphos 4,5-bis(diphenylphosphino)-9,9-dimethylxanthene
XPHOS dicyclohexyl(2',4',6'-triisopropylbiphenyl-2-yl)phosphine Unless stated otherwise, the percentages in the tests and examples which follow are percentages by weight; parts are parts by weight. Solvent ratios, dilution ratios and concentration data for the liquid/liquid solutions are based in each case on volume. Details given for coupling patterns in NMR spectra are of a descriptive nature; coupling patterns of a higher order are not described as such.

LC/MS and HPLC Methods:

Method 1 (LC-MS):
Instrument: Waters ACQUITY SQD UPLC system; column: Waters Acquity UPLC HSS T3 1.8 µ50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):
Instrument: Micromass Quattro Premier with Waters UPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 3 (LC-MS):
MS instrument type: Waters Micromass Quattro Micro; HPLC instrument type: Agilent 1100 series; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):
MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 5 (LC-MS):
MS instrument: Waters ZQ 2000; HPLC instrument: Agilent 1100, 2-column system, autosampler: HTC PAL; column: YMC-ODS-AQ, 50 mm×4.6 mm, 3.0 µm; mobile phase A: water+0.1% formic acid, mobile phase B: acetonitrile+0.1% formic acid; gradient: 0.0 min 100% A—0.2 min 95% A—1.8 min 25% A—1.9 min 10% A—2.0 min 5% A—3.2 min 5% A—3.21 min 100% A—3.35 min 100% A; oven: 40° C.; flow rate: 3.0 ml/min; UV detection: 210 nm.
Method 6 (Preparative HPLC):
Column: Macherey-Nagel VP 50/21 Nucleosil 100-5 C18 Nautilus. Flow rate: 25 ml/min. Gradient: A=acetonitrile, B=water+0.1% formic acid, 0 min 10% A; 2.00 min 10% A; 6.00 min 90% A; 7.00 min 90% A; 7.10 min 10% A; 8 min 10% A; UV detection: 220 nm
Method 7 (Preparative HPLC):
Column: Phenomenex Gemini C18; 110A, AXIA, 5 µm, 21.2×50 mm 5 micron; gradient: A=water+0.1% conc. ammonia, B=acetonitrile, 0 min=10% B, 2 min=10% B, 6 min=90% B, 7 min=90% B, 7.1 min=10% B, 8 min=10% B, flow rate 25 ml/min, UV detection 220 nm.
Method 8 (Preparative HPLC):
Column: Axia Gemini 5µ C18 110 A, 50×21.5 mm, P/NO: 00B-4435-P0-AX, S/NO: 35997-2, gradient: A=water+0.1% conc. aq. ammonia, B=acetonitrile, 0 min=30% B, 2 min=30% B, 6 min=100% B, 7 min=100% B, 7.1 min=30% B, 8 min=30% B, flow rate 25 ml/min, UV detection 220 nm.
Method 9 (Preparative HPLC):
Column: Macherey-Nagel VP 50/21 Nucleosil 100-5 C18 Nautilus. Flow rate: 25 ml/min. Gradient: A=water+0.1% formic acid, B=methanol, 0 min=30% B, 2 min=30% B, 6 min=100% B, 7 min=100% B, 7.1 min=30% B, 8 min=30% B, flow rate 25 ml/min, UV detection 220 nm.
Method 10 (Preparative HPLC):
Column: Macherey-Nagel VP 50/21 Nucleosil 100-5 C18 Nautilus. Flow rate: 25 ml/min. Gradient: A=water+0.1% conc. aq. ammonia, B=methanol, 0 min=30% B, 2 min=30% B, 6 min=100% B, 7 min=100% B, 7.1 min=30% B, 8 min=30% B, flow rate 25 ml/min, UV detection 220 nm.
Method 11 (Preparative HPLC):
MS instrument: Waters; HPLC instrument: Waters (column Waters X-Bridge C18, 18 mm×50 mm, 5 Ξm, mobile phase A: water+0.05% triethylamine, mobile phase B: acetonitrile (ULC)+0.05% triethylamine; gradient: 0.0 min 95% A—0.15 min 95% A—8.0 min 5% A—9.0 min 5% A; flow rate: 40 ml/min; UV detection: DAD; 210-400 nm). and
MS instrument: Waters; HPLC instrument: Waters (column Phenomenex Luna 5µ C18(2) 100A, AXIA Tech. 50×21.2 mm, mobile phase A: water+0.05% formic acid, mobile phase B: acetonitrile (ULC)+0.05% formic acid; gradient: 0.0 min 95% A—0.15 min 95% A—8.0 min 5% A—9.0 min 5% A; flow rate: 40 ml/min; UV detection: DAD; 210-400 nm).
Method 12 (LC-MS):
MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.
When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.
Method 13 (DCI-MS):
Instrument: DSQ II; Thermo Fisher-Scientific; DCI with $NH_3$, flow rate: 1.1 ml/min; source temperature: 200° C.; ionization energy 70 eV; DCI filament heated to 800° C.; mass range 80-900.
Method 14 (GC-MS):
Instrument: Micromass GCT, GC6890; column: Restek RTX-35, 15 m×200 µm×0.33 µm; constant helium flow rate: 0.88 ml/min; oven: 70° C.; inlet: 250° C.; gradient: 70° C., 30° C./min→310° C. (maintained for 3 min).
Method 15 (MS):
Instrument: Waters ZQ; ionization type: ESI (+); mobile phase: acetonitrile/water.
Method 16 (LCMS):
Instrument: Waters ACQUITY SQD UPLC system; column: Waters Acquity UPLC HSS T3 1.8µ 30×2 mm; mobile phase A: 1 l of water+0.25 ml of 99% strength formic acid; mobile phase B: 1 l of acetonitrile+0.25 ml of 99% strength formic acid; gradient: 0.0 min 90% A→1.2 min 5% A→2.0 min 5% A oven: 50° C.; flow rate: 0.60 ml/min; UV detection: 208-400 nm.
Method 17 (LC-MS):
Instrument: Micromass Quattro Premier with Waters UPLC Acquity; column: Thermo Hypersil GOLD 1.9µ 50×1 mm; mobile phase A: 1 l of water+0.5 ml of 50% strength formic acid; mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.
Method 18 (Preparative HPLC):
Chromatorex C18 10µ 250×20 mm gradient: A=water+0.5% formic acid, B=acetonitrile, 0 min=5% B, 3 min=5% B pre-rinse without substance, then injection, 5 min=5% B, 25 min=30% B, 38 min=30% B, 38.1 min=95% B, 43 min=95% B, 43.01 min=5% B, 48.0 min=5% B flow rate 20 ml/min, wavelength 210 nm.
Method 19 (Preparative HPLC):
Chromatorex C18 10µ 250×20 mm gradient: A=water+0./5% formic acid, B=acetonitrile, 0 min=5% B, 3 min=5% B pre-rinse without substance, then injection, 5 min=5% B, 25 min=50% B, 38 min=50% B, 38.1 min=95% B, 43 min=95% B, 43.01 min=5% B, 48.0 min=5% B flow rate 20 ml/min, wavelength 210 nm.
Method 20 (Preparative HPLC):
XBridge Prep. C18 5µ 50×19 mm gradient: A=water+0.5% ammonium hydroxide, B=acetonitrile, 0 min=5% B, 3 min=5% B pre-rinse without substance, then injection, 5 min=5% B, 25 min=50% B, 38 min=50% B, 38.1 min=95% B, 43 min=95% B, 43.01 min=5% B, 48.0 min=5% B flow rate 15 ml/min, wavelength 210 nm.
Method 21 (Preparative HPLC):
Chromatorex 10 Ξ 250×20 mm gradient: A=water, B=acetonitrile, 0 min=5% B, 3 min=5% B pre-rinse without substance, then injection, 5 min=5% B, 25 min=95% B, 38 min=95% B, 38.1 min=5% B, 40 min=5% B, flow rate 20 ml/min, wavelength 210 nm.
Method 22 (LC-MS):
Instrument: Acquity UPLC coupled with Quattro Micro mass spectrometer; column: Acquity UPLC BEH C18 (50 mm×2.1 mm ID, 1.7 Ξm packing diameter); mobile phase A:

10 mM aqueous ammonium bicarbonate solution (adjusted with ammonia to a pH of 10), mobile phase B: acetonitrile; gradient: 0.0 min 97% A, 3% B, flow rate 1 ml/min; 1.5 min 100% B, flow rate 1 ml/min; 1.9 min 100% B, flow rate 1 ml/min; 2.0 min 97% A, 3% B, flow rate 0.05 ml/min; column temperature: 40° C.; UV detection: from 210 nm to 350 nm; MS conditions: ionization mode: alternating scans positive and negative electrospray (ES+/ES−); scan range: 100 to 1000 AMU.

Method 23 (LC-MS):

Instrument: Acquity UPLC coupled with Quattro Micro mass spectrometer; column: Acquity UPLC BEH C18 (50 mm×2.1 mm ID, 1.7 μm packing diameter); mobile phase A: 0.1% formic acid in water, mobile phase B: 0.1% formic acid in acetonitrile; gradient: 0.0 min 97% A, 3% B, flow rate 1 ml/min; 1.5 min 100% B, flow rate 1 ml/min; 1.9 min 100% B, flow rate 1 ml/min; 2.0 min 97% A, 3% B, flow rate 0.05 ml/min; column temperature: 40° C.; UV detection: from 210 nm to 350 nm; MS conditions: ionization mode: alternating scans positive and negative electrospray (ES+/E−); scan range: 100 to 1000 AMU.

Method 24 (LC-MS):

Instrument: Waters 2690, PDA detector Waters 2996 coupled with Quattro Micro mass MS detector; column: Waters SunFire C18 3.5 μm, 2.1×50 mm; mobile phase A: 10 mM aqueous ammonium bicarbonate solution (adjusted with ammonia to a pH of 10), mobile phase B: acetonitrile; gradient: 0.0 min 95% A, 5% B, flow rate 0.5 ml/min; 3.0 min 95% A, 5% B, flow rate 0.5 ml/min; 17.50 min 5% A, 95% B, flow rate 0.5 ml/min; 19.00 min 5% A, 95% B, flow rate 0.5 ml/min; 19.50 min 95% A, 5% B, flow rate 0.5 ml/min; 20.00 min 95% A, 5% B, flow rate 0.5 ml/min; column temperature: 30° C.; UV detection: from 210 nm to 400 nm; MS conditions: ionization mode: scans positive and negative electrospray (ES+/ES−); scan range: 130 to 1100 AMU.

Method 25 (LC-MS):

Instrument: Waters 2690, PDA detector Waters 2996 coupled with Quattro Micro mass MS detector; column: Waters SunFire C18 3.5 μm, 2.1×50 mm; mobile phase A: 0.1% formic acid in water, mobile phase B: 0.1% formic acid in acetonitrile; gradient: 0.0 min 95% A, 5% B, flow rate 0.5 ml/min; 3.0 min 95% A, 5% B, flow rate 0.5 ml/min; 17.50 min 5% A, 95% B, flow rate 0.5 ml/min; 19.00 min 5% A, 95% B, flow rate 0.5 ml/min; 19.50 min 95% A, 5% B, flow rate 0.5 ml/min; 20.00 min 95% A, 5% B, flow rate 0.5 ml/min; column temperature: 30° C.; UV detection: from 210 nm to 400 nm; MS conditions: ionization mode: scans positive and negative electrospray (ES+/ES−); scan range: 130 to 1100 AMU.

Method 26 (prep. HPLC):

Instrument: Waters 2690, PDA detector Waters 2996 coupled with Quattro Micro mass MS detector; column: XBridge Prep. MS C18 OBD (150 mm×30 mm ID 5 μm particle size) at room temperature; mobile phase A: 10 mM $NH_4HCO_3$, adjusted with ammonia to a pH of 10, mobile phase B: acetonitrile; gradient: 0.0 min 97% A, 3% B; 1.0 min 97% A, 3% B; 30 min 0% A, 100% B; 35 min 0% A, 100% B, flow rate 50 ml/min; column temperature: 30° C.; UV detection: from 210 nm to 400 nm; MS conditions: ionization mode: scans positive and negative electrospray (ES+/ES−); scan range: 100 to 1000 AMU.

Starting Materials and Intermediates

Example 1A

3-[(2,6-Difluorobenzyl)oxy]pyridine-2-amine

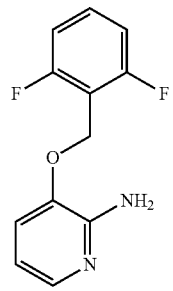 [SMILES: Nc1ncccc1OCc1c(F)cccc1F]

At RT, 51 g of sodium methoxide (953 mmol, 1.05 equivalents) were initially charged in 1000 ml of methanol, 100 g of 2-amino-3-hydroxypyridine (908 mmol, 1 equivalent) were added and the mixture was stirred at RT for 15 min. The reaction mixture was concentrated under reduced pressure, the residue was taken up in 2500 ml of DMSO and 197 g of 2,6-difluorobenzyl bromide (953 mmol, 1.05 equivalents) were added. After 4 h at RT, the reaction mixture was added to 20 l of water, the mixture was stirred for 15 min and the solid was filtered off with suction. The solid was washed with 1 l of water and 100 ml of isopropanol and 500 ml of petroleum ether and dried under high vacuum. This gave 171 g of the title compound (78% of theory).

$^1$H-NMR (400 MHz, DMSO-$d_6$): δ=5.10 (s, 2 H), 5.52 (br. s, 2 H), 6.52 (dd, 1 H), 7.16-7.21 (m, 3 H), 7.49-7.56 (m, 2 H).

Example 2A

Ethyl 8-[(2,6-difluorobenzyl)oxy]-2-methylimidazo[1,2-a]pyridine-3-carboxylate

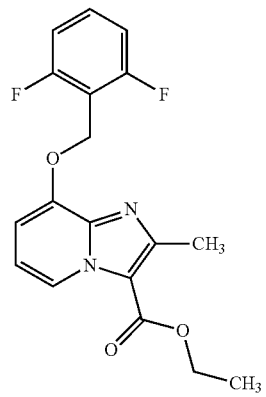 [SMILES: CCOC(=O)c1c(C)nc2c(OCc3c(F)cccc3F)cccn12]

170 g of 3-[(2,6-difluorobenzyl)oxy]pyridine-2-amine (Example 1A; 719 mmol, 1 equivalent) were initially charged in 3800 ml of ethanol, and 151 g of powdered molecular sieve 3 Å and 623 g of ethyl 2-chloroacetoacetate (3.6 mol, 5 equivalents) were added. The reaction mixture was heated at reflux for 24 h and then filtered off through silica gel and concentrated under reduced pressure. The mixture was kept at RT for 48 h and the solid formed was filtered off. The solid was stirred with a little isopropanol and then filtered off three times, and washed with diethyl ether. This gave 60.8 g (23% of theory) of the title compound. The combined filtrates of the filtration steps were concentrated and the residue was chromatographed on silica gel using the mobile phase cyclohexane/diethyl ether. This gave a further 46.5 g (18% of theory, total yield: 41% of theory) of the title compound.

LC-MS (Method 1): $R_t$=1.01 min

MS (ESpos): m/z=347 (M+H)$^+$ $^1$H-NMR (400 MHz, DMSO-d$_6$): δ=1.36 (t, 3 H), 2.54 (s, 3 H; obscured by DMSO signal), 4.36 (q, 2 H), 5.33 (s, 2 H), 7.11 (t, 1 H), 7.18-7.27 (m, 3 H), 7.59 (quint, 1 H), 8.88 (d, 1 H).

Example 3A

8-[(2,6-Difluorobenzyl)oxy]-2-methylimidazo[1,2-a]pyridine-3-carboxylic acid

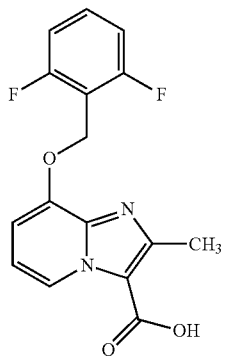 [SMILES: Cc1nc2c(OCc3c(F)cccc3F)cccn2c1C(=O)O]

107 g of ethyl 8-[(2,6-difluorobenzyl)oxy]-2-methylimidazo[1,2-a]pyridine-3-carboxylate (Example 2A; 300 mmol, 1 equivalent) were dissolved in 2.8 l of THF/methanol (1:1), 1.5 l of 1 N aqueous lithium hydroxide solution (1.5 mol, 5 equivalents) were added and the mixture was stirred at RT for 16 h. The organic solvents were removed under reduced pressure and the resulting aqueous solution was, in an ice bath, adjusted to pH 3-4 using 1 N aqueous hydrochloric acid. The resulting solid was filtered off, washed with water and isopropanol and dried under reduced pressure. This gave 92 g (95% of theory) of the title compound.

LC-MS (Method 1): $R_t$=0.62 min

MS (ESpos): m/z=319.1 (M+H)$^+$ $^1$H-NMR (400 MHz, DMSO-d$_6$): δ=2.55 (s, 3 H; superposed by DMSO signal), 5.32 (s, 2 H); 7.01 (t, 1 H), 7.09 (d, 1 H), 7.23 (t, 2 H), 7.59 (quint, 1 H), 9.01 (d, 1 H).

Example 4A 3-(Cyclohexylmethoxy)pyridine-2-amine

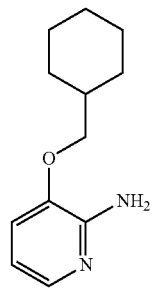 [SMILES: Nc1ncccc1OCC1CCCCC1]

At RT, 96 g of sodium hydroxide, 45% strength in water (1081 mmol, 1 equivalent), were initially charged in 1170 ml of methanol, 119 g of 2-amino-3-hydroxypyridine (1080 mmol, 1 equivalent) were added and the mixture was stirred at RT for another 10 min. The reaction mixture was concentrated under reduced pressure, the residue was taken up in 2900 ml of DMSO and 101 g of cyclohexylmethyl bromide (1135 mmol, 1.05 equivalents) were added. After 16 h at RT, the reaction mixture was slowly added to 6 l of water and the aqueous solution was extracted twice with in each case 2 l of ethyl acetate. The combined organic phases were washed with in each case 1 l of saturated aqueous sodium bicarbonate solution and water, dried, filtered and concentrated. The residue was stirred with 500 ml of n-pentane, filtered and dried under reduced pressure. This gave 130 g (58% of theory) of the title compound.

LC-MS (Method 3): $R_t$=1.41 min

MS (ESpos): m/z=207.1 (M+H)$^+$

Example 5A

Ethyl 8-(cyclohexylmethoxy)-2-methylimidazo[1,2-a]pyridine-3-carboxylate

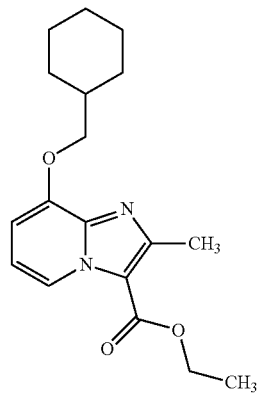 [SMILES: CCOC(=O)c1c(C)nc2c(OCC3CCCCC3)cccn12]

130 g of 3-(cyclohexylmethoxy)pyridine-2-amine (Example 4A; 630 mmol, 1 equivalent) were initially charged in 3950 ml of ethanol, and 436 ml of ethyl 2-chloroacetoacetate (3.2 mol, 5 equivalents) were added. The mixture was heated at reflux for 24 h and then concentrated under reduced pressure. The crude product thus obtained was chromatographed on silica gel using the mobile phase cyclohexane/diethyl ether, giving 66.2 g (33% of theory) of the title compound.

LC-MS (Method 1): $R_t$=1.17 min
MS (ESpos): m/z=317.1 (M+H)$^+$
$^1$H-NMR (400 MHz, DMSO-d$_6$): δ=1.02-1.31 (m, 5 H), 1.36 (t, 3 H), 1.64-1.77 (m, 3 H), 1.79-1.90 (m, 3 H), 2.60 (s, 3 H), 3.97 (d, 2 H), 4.35 (q, 2 H), 6.95 (d, 1 H), 7.03 (t, 1 H), 8.81 (d, 1 H).

Example 6A 8-(Cyclohexylmethoxy)-2-methylimidazo[1,2-a]pyridine-3-carboxylic acid

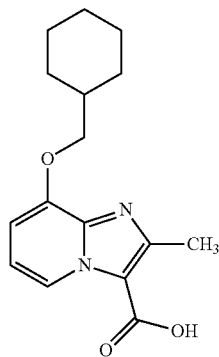 [SMILES: Cc1nc2c(OCC3CCCCC3)cccn2c1C(=O)O]

50 g of ethyl 8-(cyclohexylmethoxy)-2-methylimidazo[1,2-a]pyridine-3-carboxylate (Example 5A; 158 mmol, 1 equivalent) were dissolved in 600 ml of 1,4-dioxane, 790 ml of 2 N aqueous sodium hydroxide solution (1.58 mol, 10 equivalents) were added and the mixture was stirred at RT for 16 h. 316 ml of 6 N aqueous hydrochloric acid were added and the mixture was concentrated to about ⅓ of the total volume. The resulting solid was filtered off, washed with water and tert-butyl methyl ether and dried under reduced pressure. This gave 35 g (74% of theory) of the title compound.

LC-MS (Method 1): $R_t$=0.81 min
MS (ESpos): m/z=289.0 (M+H)$^+$
$^1$H-NMR (400 MHz, DMSO-d$_6$): δ=1.03-1.44 (m, 5 H), 1.64-1.78 (m, 3 H), 1.81-1.92 (m, 3 H), 2.69 (s, 3 H), 4.07 (d, 2 H), 7.30-7.36 (m, 2 H), 9.01 (d, 1 H).

Example 7A

5-Chloro-2-nitropyridin-3-ol

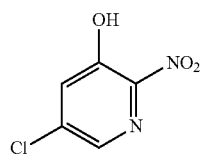 [SMILES: O=[N+]([O-])c1ncc(Cl)cc1O]

With ice cooling, 30 g of 5-chloropyridin-3-ol (232 mmol, 1 equivalent) were dissolved in 228 ml of concentrated sulphuric acid, and 24 ml of concentrated nitric acid were added slowly at 0° C. The mixture was warmed to RT, stirred overnight and then stirred into an ice/water mixture and stirred for another 30 min. The solid was filtered off, washed with cold water and air-dried. This gave 33 g (82% of theory) of the title compound which was used without further purification for the next reaction.

LC-MS (Method 1): $R_t$=0.60 min
MS (ESneg): m/z=172.9/174.9 (M–H)$^-$
$^1$H-NMR (400 MHz, DMSO-d$_6$): δ=7.71 (d, 1 H), 8.10 (d, 1 H), 12.14 (br. 1 H).

Example 8A

5-Chloro-3-[(2,6-difluorobenzyl)oxy]-2-nitropyridine

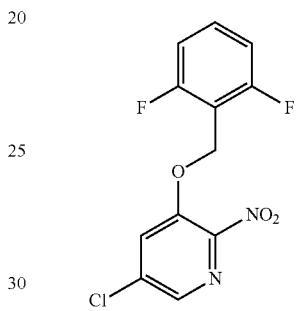

33 g of 5-chloro-2-nitropyridin-3-ol (Example 7A; 189 mmol, 1 equivalent) and 61.6 g of caesium carbonate (189 mmol, 1 equivalent) were initially charged in 528 ml of DMF, 40.4 g of 2,6-difluorobenzyl bromide (189 mmol, 1 equivalent) were added and the mixture was stirred at RT overnight. The reaction mixture was stirred into water/1N aqueous hydrochloric acid. The solid was filtered off, washed with water and air-dried. This gave 54.9 g (97% of theory) of the title compound.

$^1$H-NMR (400 MHz, DMSO-d$_6$): δ=5.46 (s, 2 H), 7.22 (t, 2 H), 7.58 (q, 1 H), 8.28 (d, 1 H), 8.47 (d, 1 H).

Example 9A

5-Chloro-3-[(2,6-difluorobenzyl)oxy]pyridine-2-amine

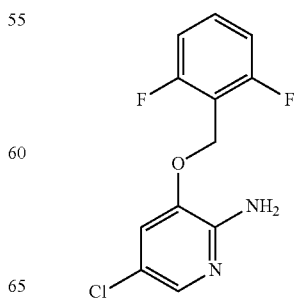

59.7 g of 5-chloro-3-[(2,6-difluorobenzyl)oxy]-2-nitropyridine (Example 8A; 199 mmol, 1 equivalent) were initially charged in 600 ml of ethanol, 34.4 g of iron powder (616 mmol, 3.1 equivalents) were added and the mixture was heated to reflux. 152 ml of concentrated hydrochloric acid were slowly added dropwise, and the mixture was boiled at reflux for a further 30 min. The reaction mixture was cooled and stirred into an ice/water mixture. The resulting mixture was adjusted to pH 5 used sodium acetate. The solid was filtered off, washed with water and air-dried and then dried under reduced pressure at 50° C. This gave 52.7 g (98% of theory) of the title compound.

LC-MS (Method 1): $R_t$=0.93 min

MS (ESpos): m/z=271.1/273.1 (M+H)$^+$ $^1$H-NMR (400 MHz, DMSO-d$_6$): δ=5.14 (s, 2 H), 5.82 (br. s, 2 H); 7.20 (t, 2 H), 7.35 (d, 1 H), 7.55 (q, 1 H), 7.56 (d, 1 H).

Example 10A

Ethyl 6-chloro-8-[(2,6-difluorobenzyl)oxy]-2-methylimidazo[1,2-a]pyridine-3-carboxylate

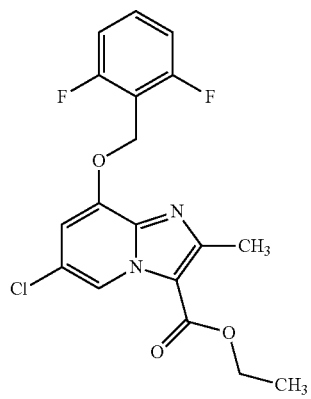 [SMILES: CCOC(=O)c1c(C)nc2c(OCc3c(F)cccc3F)cc(Cl)cn12]

40 g of 5-chloro-3-[(2,6-difluorobenzyl)oxy]pyridine-2-amine (Example 9A; 147.8 mmol, 1 equivalent) were initially charged in 800 ml of ethanol, 30 g of powdered molecular sieve 3 Å and 128 g of ethyl 2-chloroacetoacetate (739 mmol, 5 equivalents) were added and the mixture was heated at reflux overnight. The reaction mixture was concentrated, and the residue was taken up in ethyl acetate and filtered. The ethyl acetate phase was washed with water, dried, filtered and concentrated. This gave 44 g (78% of theory) of the title compound.

LC-MS (Method 1): $R_t$=1.27 min

MS (ESpos): m/z=381.2/383.2 (M+H)$^+$ $^1$H-NMR (400 MHz, DMSO-d$_6$): δ=1.36 (t, 3 H), 2.54 (s, 3 H; obscured by DMSO signal); 4.37 (q, 2 H), 5.36 (s, 2 H), 7.26 (t, 2 H), 7.38 (d, 1 H), 7.62 (q, 1 H), 8.92 (d, 1 H).

Example 11A

6-Chloro-8-[(2,6-difluorobenzyl)oxy]-2-methylimidazo[1,2-a]pyridine-3-carboxylic acid

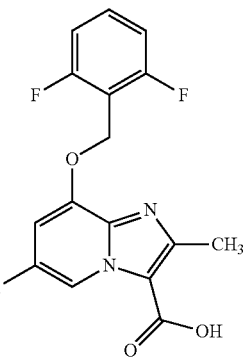

44 g of ethyl 6-chloro-8-[(2,6-difluorobenzyl)oxy]-2-methylimidazo[1,2-a]pyridine-3-carboxylate (Example 10A; 115 mmol, 1 equivalent) were dissolved in 550 ml of THF and 700 ml of methanol, 13.8 g of lithium hydroxide (dissolved in 150 ml of water; 577 mmol, 5 equivalents) were added and the mixture was stirred at RT overnight. 1 N aqueous hydrochloric acid was added and the mixture was concentrated under reduced pressure. The solid obtained was filtered off and washed with water. This gave 34 g of the title compound (84% of theory).

LC-MS (Method 2): $R_t$=1.03 min

MS (ESpos): m/z=353.0/355.0 (M+H)$^+$ $^1$H-NMR (400 MHz, DMSO-d$_6$): δ=2.54 (s, 3 H; superimposed by DMSO signal), 5.36 (s, 2 H), 7.26 (t, 2 H), 7.34 (d, 1 H), 7.61 (q, 1 H), 8.99 (d, 1 H), 13.36 (br. s, 1 H).

Example 12A

5-Bromo-3-[(2,6-difluorobenzyl)oxy]pyridine-2-amine

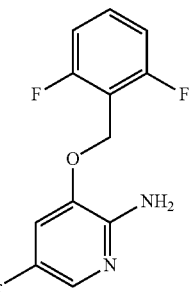

32.6 g of 3-[(2,6-difluorobenzyl)oxy]pyridine-2-amine (Example 1A; 138 mmol, 1 equivalent) were suspended in 552 ml of 10% strength sulphuric acid, and the mixture was cooled to 0° C. 8.5 ml of bromine (165 mmol, 1.2 equivalents) were dissolved in 85 ml of acetic acid and then, over 90 min, added dropwise to the reaction solution, cooled with ice. After the addition had ended, the mixture was stirred at 0° C. for 90 min and then diluted with 600 ml of ethyl acetate, and the aqueous phase was separated off. The aqueous phase was extracted with ethyl acetate. The organic phases were combined, washed with saturated aqueous sodium bicarbonate solution, dried and concentrated. The residue was dissolved in dichloromethane and chromatographed on silica gel (petroleum ether/ethyl acetate gradient as mobile phase). This gave 24 g (55% of theory) of the title compound.

LC-MS (Method 1): $R_t$=0.96 min

MS (ESpos): m/z=315.1/317.1 (M+H)$^+$ $^1$H-NMR (400 MHz, DMSO-d$_6$): δ=5.14 (s, 2 H), 5.83 (br. s, 2 H), 7.20 (t, 2 H), 7.42 (d, 1 H), 7.54 (q, 1 H), 7.62 (d, 1 H).

Example 13A

Ethyl 6-bromo-8-[(2,6-difluorobenzyl)oxy]-2-methylimidazo[1,2-a]pyridine-3-carboxylate

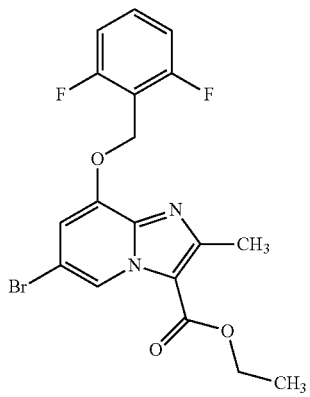

16 g of powdered molecular sieve 3 Å and 52.7 ml of ethyl 2-chloroacetoacetate (380.8 mmol, 5 equivalents) were added to 24 g of 5-bromo-3-[(2,6-difluorobenzyl)oxy]pyridine-2-amine (Example 12A; 76.2 mmol, 1 equivalent) in 400 ml of ethanol, and the mixture was heated at reflux overnight. 8 g of molecular sieve were added and the mixture was heated at reflux for a further 24 h. The reaction mixture was concentrated under reduced pressure, and the residue was taken up in dichloromethane and chromatographed on silica gel (mobile phase: dichloromethane/methanol 20:1). The product-containing fractions were concentrated and the residue was stirred with 100 ml of diethyl ether for 30 min. The solid was then filtered off, washed with a little diethyl ether and dried. This gave 15 g (45% of theory) of the title compound.

LC-MS (Method 2): $R_t$=1.43 min

MS (ESpos): m/z=414.9/416.8 (M+H)$^+$ $^1$H-NMR (400 MHz, DMSO-d$_6$): δ=1.36 (t, 3 H), 2.54 (s, 3H; obscured by DMSO signal), 4.37 (q, 2 H), 5.36 (s, 2 H), 7.25 (t, 2 H), 7.42 (d, 1 H), 7.61 (q, 1 H), 9.00 (d, 1 H).

Example 14A

6-Bromo-8-[(2,6-difluorobenzyl)oxy]-2-methylimidazo[1,2-a]pyridine-3-carboxylic acid

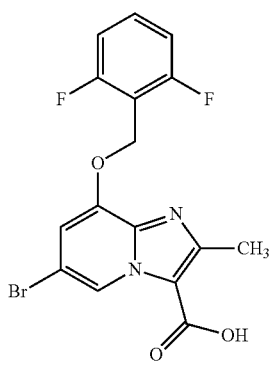 [SMILES: Cc1nc2c(OCc3c(F)cccc3F)cc(Br)cn2c1C(=O)O]

1.5 g of ethyl 6-bromo-8-[(2,6-difluorobenzyl)oxy]-2-methylimidazo[1,2-a]pyridine-3-carboxylate (Example 13A; 3.5 mmol, 1 equivalent) were dissolved in 72 ml of THF/methanol 5:1, 17.6 ml of 1N aqueous lithium hydroxide solution (17.6 mmol, 5 equivalents) were added and the mixture was warmed to 40° C. and stirred at this temperature for 6 h. Using 6 N aqueous hydrochloric acid, the mixture was adjusted to pH 4 and concentrated under reduced pressure. Water was added to the solid formed, the mixture was stirred and the product was filtered off, washed with water and dried under reduced pressure. This gave 1.24 g of the title compound (88% of theory).

LC-MS (Method 1): $R_t$=0.93 min

MS (ESpos): m/z=397.0/399.1 (M+H)$^+$ $^1$H-NMR (400 MHz, DMSO-d$_6$): δ=2.54 (s, 3 H; superimposed by DMSO signal); 5.36 (s, 2 H); 7.25 (t, 2 H); 7.40 (d, 1 H); 7.61 (q, 1 H); 9.06 (d, 1 H); 13.35 (br. s, 1 H).

Example 15A

Ethyl 8-[(2,6-difluorobenzyl)oxy]-2,6-dimethylimidazo[1,2-a]pyridine-3-carboxylate

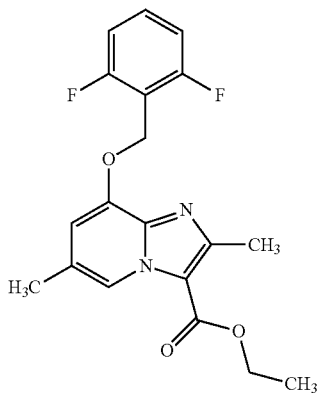 [SMILES: CCOC(=O)c1c(C)nc2c(OCc3c(F)cccc3F)cc(C)cn12]

Method 1:

600 mg of ethyl 6-bromo-8-[(2,6-difluorobenzyl)oxy]-2-methylimidazo[1,2-a]pyridine-3-carboxylate (Example 13A; 1.4 mmol, 1 equivalent) and 230 mg of 1,1'-bis (diphenylphosphino)ferrocenepalladium(II) dichloride/dichloromethane complex (0.282 mmol, 20 mol %) were dissolved in 25 ml of THF, and 0.88 ml (1.76 mmol, 1.2 equivalents) of a 2 M solution of methylzinc chloride in THF was added. In a microwave oven, the reaction mixture was heated at 100° C. for 40 min. The reaction mixture was filtered through Celite and then concentrated under reduced pressure. The residue was chromatographed (Biotage Isolera Four; cyclohexane:ethyl acetate). This gave 225 mg (38% of theory) of the title compound.

Method 2:

20.00 g (85.38 mmol) of ethyl 8-hydroxy-2,6-dimethylimidazo[1,2-a]pyridine-3-carboxylate from Example 20A, 19.44 g (93.91 mmol) of 2,6-difluorobenzyl bromide and 61.20 g (187.83 mmol) of caesium carbonate in 1.18 l of DMF were stirred at 60° C. for 5 h. The reaction mixture was then added to 6.4 l of 10% strength aqueous sodium chloride solution and then twice extracted with ethyl acetate. The combined organic phases were washed with 854 ml of a 10% strength aqueous sodium chloride solution, dried, concentrated and dried at RT under high vacuum overnight. This gave 28.2 g (92% of theory, purity: 90%) of the title compound.

LC-MS (Method 1): $R_t$=1.05 min

MS (ESpos): m/z=361.1 (M+H)$^+$ $^1$H-NMR (400 MHz, DMSO-d$_6$): δ=1.38 (t, 3 H), 2.36 (s, 3 H), 4.35 (q, 2 H), 5.30 (s, 2 H), 7.10 (s, 1 H), 7.23 (t, 2 H), 7.59 (q, 1 H), 8.70 (s, 1 H).

Example 16A

8-[(2,6-Difluorobenzyl)oxy]-2,6-dimethylimidazo[1,2-a]pyridine-3-carboxylic acid

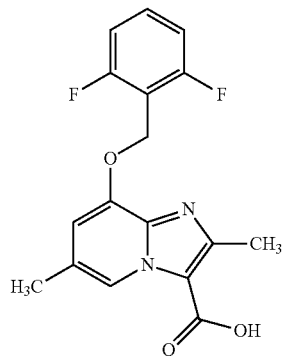

220 mg of ethyl 8-[(2,6-difluorobenzyl)oxy]-2,6-dimethylimidazo[1,2-a]pyridine-3-carboxylate (Example 15A; 0.524 mmol, 1 equivalent) were dissolved in 7 ml of THF/methanol (1:1), 2.6 ml of 1 N aqueous lithium hydroxide solution (2.6 mmol, 5 equivalents) were added and the mixture was stirred at RT for 16 h. The mixture was concentrated under reduced pressure and the residue was acidified with 1N aqueous hydrochloric acid and stirred for 15 min. The solid was filtered off, washed with water and dried under reduced pressure. This gave 120 mg of the title compound (60% of theory).

LC-MS (Method 1): $R_t$=0.68 min

MS (ESpos): m/z=333.1 (M+H)$^+$ $^1$H-NMR (400 MHz, DMSO-d$_6$): δ=2.34 (s, 3 H), 5.28 (s, 2 H), 7.09 (s, 1 H), 7.23 (t, 2 H), 7.58 (q, 1 H), 8.76 (s, 1 H), 13.1 (br. s, 1 H).

Example 17A 3-(Benzyloxy)-5-bromopyridine-2-amine

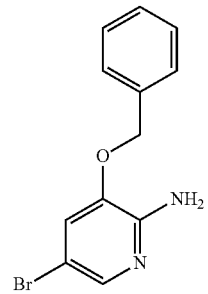 [SMILES: Nc1ncc(Br)cc1OCc1ccccc1]

The target compound is known from the literature and described:

1) Palmer, A. M. et al. J Med. Chem. 2007, 50, 6240-6264.
2) ALTANA WO2005/58325
3) ALTANA WO2005/90358
4) Cui, J. T. et al. J Med. Chem. 2011, 54, 6342-6363

Further Preparation Method:

200 g (1 mol) of 2-amino-3-benzyloxypyridine were initially charged in 4 l of dichloromethane, and at 0° C. a solution of 62 ml (1.2 mol) of bromine in 620 ml of dichloromethane was added over 30 min. After the addition had ended, the reaction solution was stirred at 0° C. for 60 min. About 4 l of saturated aqueous sodium bicarbonate solution were then added to the mixture. The organic phase was removed and concentrated. The residue was purified by silica gel column chromatography (petroleum ether/ethyl acetate 6:4) and the product fractions were concentrated. This gave 214 g (77% of theory) of the title compound.

LC-MS (Method 1): $R_t$=0.92 min

MS (ESpos): m/z=279 (M+H)$^+$ $^1$H-NMR (400 MHz, DMSO-d$_6$): δ=5.16 (s, 2H), 5.94-6.00 (m, 2H), 7.26-7.29 (m, 1H), 7.31-7.36 (m, 1H), 7.37-7.43 (m, 2H), 7.47-7.52 (m, 2H), 7.57-7.59 (m, 1H).

Example 18A

Ethyl 8-(benzyloxy)-6-bromo-2-methylimidazo[1,2-a]pyridine-3-carboxylate

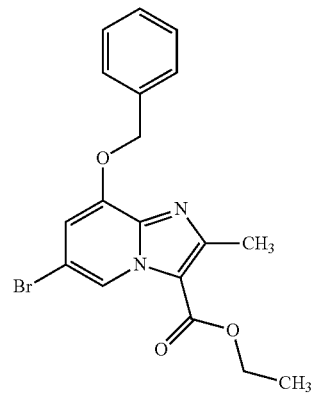

Under argon, 200 g (0.72 mol) of 3-(benzyloxy)-5-bromopyridine-2-amine from Example 17A, 590 g (3.58 mol) of ethyl 2-chloroacetoacetate and 436 g of 3 Å molecular sieve were suspended in 6 l of ethanol, and the suspension was stirred at reflux for 72 h. The reaction mixture was filtered off through silica gel and concentrated. The residue was purified by silica gel chromatography (petroleum ether:ethyl acetate 9:1, then 6:4) and the product fractions were concentrated. This gave 221 g (79% of theory) of the target compound.

LC-MS (Method 16): $R_t$=1.31 min

MS (ESpos): m/z=389 (M+H)$^+$ $^1$H-NMR (400 MHz, DMSO-d$_6$): δ=1.36 (t, 3 H), 2.58 (s, 3 H), 4.32-4.41 (m, 2 H), 5.33 (s, 2 H), 7.28-7.32 (m, 1 H), 7.36-7.47 (m, 3 H), 7.49-7.54 (m, 2 H), 8.98 (d, 1 H).

Example 19A

Ethyl 8-(benzyloxy)-2,6-dimethylimidazo[1,2-a]pyridine-3-carboxylate

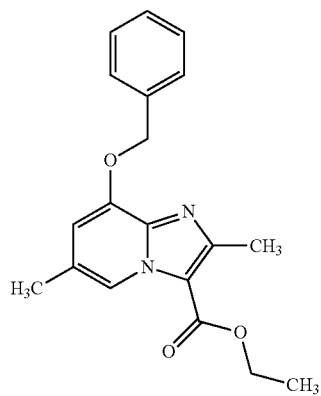 [SMILES: CCOC(=O)c1c(C)nc2c(OCc3ccccc3)cc(C)cn12]

Under argon, 105 g (270 mmol) of ethyl 8-(benzyloxy)-6-bromo-2-methylimidazo[1,2-a]pyridine-3-carboxylate from Example 18A were suspended in 4.2 l of 1,4-dioxane, and 135.4 g (539 mmol, purity 50%) of trimethylboroxine, 31.2 g (27 mmol) of tetrakis(triphenylphosphine)palladium (0) and 78.3 g (566 mmol) of potassium carbonate were added in succession and the mixture was stirred under reflux for 8 h. The reaction mixture was cooled to RT and, using silica gel, freed from the precipitate, and the filtrate was concentrated. The residue was dissolved in dichloromethane and purified by silica gel chromatography (dichloromethane:ethyl acetate=9:1). This gave 74 g (84.6% of theory, purity 100%) of the target compound.

LC-MS (Method 16): $R_t$=1.06 min

MS (ESpos): m/z=325 (M+H)$^+$ $^1$H-NMR (400 MHz, DMSO-d$_6$): δ=1.35 (t, 3 H), 2.34 (br. s, 3 H), 2.56 (s, 3 H), 4.31-4.38 (m, 2 H), 5.28 (br. s, 2 H), 6.99-7.01 (m, 1 H), 7.35-7.47 (m, 3 H), 7.49-7.54 (m, 2 H), 8.68-8.70 (m, 1 H).

Example 20A

Ethyl 8-hydroxy-2,6-dimethylimidazo[1,2-a]pyridine-3-carboxylate

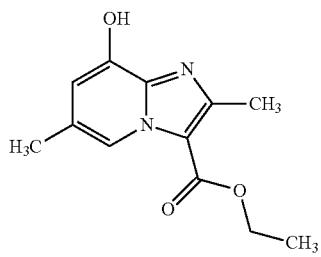 [SMILES: CCOC(=O)c1c(C)nc2c(O)cc(C)cn12]

74 g (228 mmol) of ethyl 8-(benzyloxy)-2,6-dimethylimidazo[1,2-a]pyridine-3-carboxylate from Example 19A were initially charged in 1254 ml of dichloromethane and 251 ml of ethanol, and 20.1 g of 10% strength palladium on activated carbon (moist with water, 50%) were added. Overnight, the reaction mixture was hydrogenated at RT and under atmospheric pressure. The reaction mixture was filtered off through silica gel and concentrated. The crude product was purified by silica gel chromatography (dichloromethane:methanol=95:5). This gave 50.4 g (94% of theory) of the target compound.

DCI-MS: (Method 13) (ESpos): m/z=235.2 (M+H)$^+$ $^1$H-NMR (400 MHz, DMSO-d$_6$): δ=1.35 (t, 3 H), 2.27 (s, 3 H), 2.58 (s, 3 H), 4.30-4.38 (m, 2 H), 6.65 (d, 1 H), 8.59 (s, 1 H), 10.57 (br. s, 1H).

Example 21A

Ethyl 2,6-dimethyl-8-[(2,3,6-trifluorobenzyl)oxy]imidazo[1,2-a]pyridine-3-carboxylate

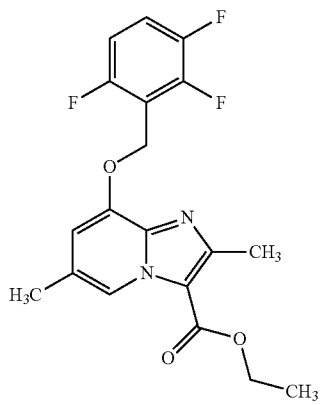 [SMILES: CCOC(=O)c1c(C)nc2c(OCc3c(F)ccc(F)c3F)cc(C)cn12]

3.00 g (12.81 mmol) of ethyl 8-hydroxy-2,6-dimethylimidazo[1,2-a]pyridine-3-carboxylate Example 20A, 3.27 g (14.1 mmol) of 2-(bromomethyl)-1,3,4-trifluorobenzene and 9.18 g (28.17 mmol) of caesium carbonate were initially charged in 183 ml of dry DMF, and the mixture was heated in an oil bath at 60° C. for 30 min. About 1.8 l of water were then added, and the mixture was stirred for 30 min. The solid was filtered off, washed with water and dried under reduced pressure. This gave 5.07 g of the title compound (99% of theory).

LC-MS (Method 1): $R_t$=1.14 min

MS (ESpos): m/z=379 (M+H)$^+$ $^1$H-NMR (400 MHz, DMSO-d$_6$): δ=1.35 (t, 3 H), 2.36 (s, 3 H); 2.55 (s, 3 H; superimposed by DMSO signal), 4.36 (q, 2 H), 5.35 (s, 2 H), 7.09 (s, 1 H), 7.22-7.32 (m, 1 H), 7.60-7.73 (m, 1 H), 8.72 (s, 1 H).

Example 22A 2,6-Dimethyl-8-[(2,3,6-trifluorobenzyl)oxy]imidazo[1,2-a]pyridine-3-carboxylic acid

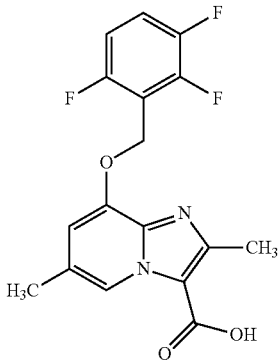

5.07 g (12.87 mmol) of ethyl 2,6-dimethyl-8-[(2,3,6-trifluorobenzyl)oxy]imidazo[1,2-a]pyridine-3-carboxylate Example 21A were dissolved in 275 ml of THF/methanol (5/1), 64.4 ml of 1 N aqueous lithium hydroxide solution were added and the mixture was stirred at 40° C. for 3.5 h. At 0° C., the reaction was brought to a pH of about 4 using 6 N aqueous hydrochloric acid and then concentrated. The solid obtained was filtered off, washed with water and dried under reduced pressure. This gave 4.77 g (98% of theory, purity about 93%) of the title compound.

LC-MS (Method 1): $R_t$=0.72 min

MS (ESpos): m/z=351 (M+H)$^+$ $^1$H-NMR (400 MHz, DMSO-d$_6$): δ=2.37 (s, 3 H), 2.54 (s, 3 H; superimposed by DMSO signal), 5.36 (s, 2 H), 7.11 (s, 1 H), 7.25-7.33 (m, 1 H), 7.61-7.73 (m, 1 H), 8.78 (s, 1 H), 13.10 (br. s, 1 H).

Example 23A

Ethyl 8-[(3-fluoropyridin-2-yl)methoxy]-2,6-dimethylimidazo[1,2-a]pyridine-3-carboxylate

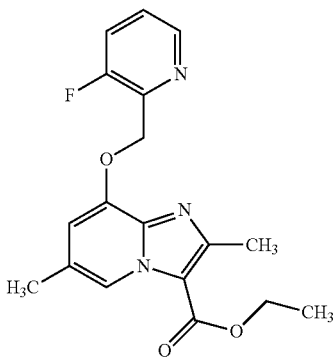 [SMILES: CCOC(=O)c1c(C)nc2c(OCc3ncccc3F)cc(C)cn12]

16.92 g (72.2 mmol) of ethyl 8-hydroxy-2,6-dimethylimidazo[1,2-a]pyridine-3-carboxylate from Example 20A were initially charged in 956 ml of DMF, and 15.78 g (86.7 mmol) of 2-(chloromethyl)-3-fluoropyridine hydrochloride (described in: U.S. Pat. No. 5,593,993 A1, 1997; WO2007/2181 A2, 2007) and 94.06 g (288.9 mmol) of caesium carbonate were added. The reaction mixture was stirred at 60° C. overnight. The reaction mixture, cooled to RT, was filtered, the filter cake was washed with ethyl acetate and the filtrate was concentrated. About 500 ml of water were added to the residue, and the solid was filtered off and dried under high vacuum. This gave 24.1 g (93% of theory) of the target compound.

LC-MS (Method 1): $R_t$=0.84 min

MS (ESpos): m/z=344 (M+H)$^+$ $^1$H-NMR (400 MHz, DMSO-d$_6$): δ=1.35 (t, 3H), 2.35 (s, 3H), 2.54 (s, 3H, obscured by DMSO signal), 4.35 (q, 2H), 5.40 (s, 2H), 7.08 (s, 1H), 7.55-7.62 (m, 1H), 7.82-7.89 (m, 1H), 8.48-8.52 (m, 1H), 8.70 (s, 1H).

Example 24A

8-[(3-Fluoropyridin-2-yl)methoxy]-2,6-dimethylimidazo[1,2-a]pyridine-3-carboxylic acid

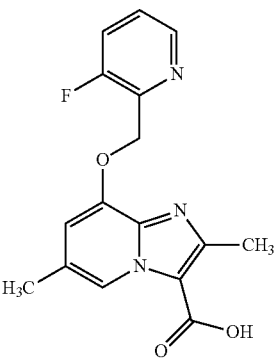

24.06 g (70.1 mmol) of ethyl 8-[(3-fluoropyridin-2-yl)methoxy]-2,6-dimethylimidazo[1,2-a]pyridine-3-carboxylate from Example 23A were initially charged in 1.5 l of THF/methanol (5:1), 350.4 ml (350.4 mmol) of 1 N aqueous lithium hydroxide solution were added and the mixture was stirred at 40° C. for 2.5 h. After cooling, the mixture was adjusted to a pH of about 4 using 1 N aqueous hydrochloric acid, and the solution was freed from THF/methanol under reduced pressure. The residue was cooled and the solid was filtered off and dried under reduced pressure. This gave 22.27 g (100% of theory) of the title compound.

LC-MS (Method 1): $R_t$=0.55 min

MS (ESpos): m/z=316 (M+H)$^+$ $^1$H-NMR (400 MHz, DMSO-d$_6$): δ=2.34 (s, 3H), 2.53 (s, 3H, obscured by DMSO signal), 5.38-5.42 (m, 2H), 7.06 (s, 1H), 7.56-7.62 (m, 1H), 7.82-7.89 (m, 1H), 8.48-8.52 (m, 1H), 8.74 (s, 1H), 13.02 (br. s, 1H).

Example 25A

8-[(2,6-Difluorobenzyl)oxy]-2-methylimidazo[1,2-a]pyridine-3-carbonyl chloride hydrochloride

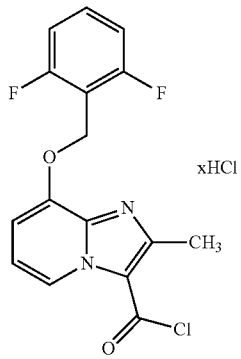 [SMILES: Cc1nc2c(OCc3c(F)cccc3F)cccn2c1C(=O)Cl]

4 drops of DMF and then 3.19 g of oxalyl chloride (25.14 mmol, 4 equivalents) were added dropwise to 2.0 g of 8-[(2,6-difluorobenzyl)oxy]-2-methylimidazo[1,2-a]pyridine-3-carboxylic acid (6.28 mmol, 1 equivalent) from Example 3A in 25 ml of dry THF. The reaction mixture was stirred at RT for 3 h. Another 0.80 g of oxalyl chloride (6.28 mmol, 1 equivalent) was added and the reaction was stirred at RT for a further 4 h. The reaction mixture was concentrated and evaporated three times with toluene, and the residue was dried under high vacuum. This gave 2.43 g of the title compound (103% of theory).

DCI-MS (Method 13): MS (ESpos): m/z=437 (M-HCl+H)$^+$

Example 26A 8-(Cyclohexylmethoxy)-2-methylimidazo[1,2-a]pyridine-3-carbonyl chloride

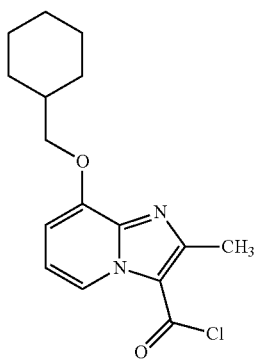 [SMILES: Cc1nc2c(OCC3CCCCC3)cccn2c1C(=O)Cl]

2.8 g of 8-(cyclohexylmethoxy)-2-methylimidazo[1,2-a]pyridine-3-carboxylic acid (Example 6A, 9.6 mmol) were dissolved in 60 ml of thionyl chloride, and the mixture was stirred at 80° C. overnight. The mixture was then concentrated under reduced pressure, dissolved in toluene and concentrated again. The residue was dried under high vacuum. This gave 2.9 g (98% of theory) of the title compound. The crude product obtained was reacted further without purification.

Example 27A

8-[(2,6-Difluorobenzyl)oxy]-2-methylimidazo[1,2-a]pyridine

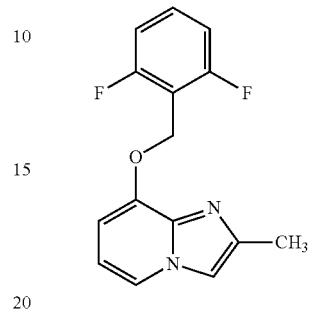

12 g of 3-[(2,6-difluorobenzyl)oxy]pyridine-2-amine (Example 1A, 50.8 mmol, 1 equivalent) and 8 g of 1-chloroacetone (86.4 mmol, 1.7 equivalents) in 90 ml of ethanol were stirred at 80° C. overnight. Silica gel was added and the reaction mixture was concentrated. The residue was purified by silica gel chromatography (mobile phase mixture dichloromethane/ethanol=50:1). The product mixture obtained was then purified by silica gel chromatography (mobile phase mixture dichloromethane/ethanol/diethylamine=50:1:0.1, 40:1:0.5, 30:1:0.5). This gave 6.3 g (45% of theory) of the title compound.

LC-MS (Method 1): R$_t$=0.58 min
MS (ESpos): m/z=274 (M+H)$^+$
$^1$H-NMR (400 MHz, DMSO-d$_6$): δ=2.27 (s, 3 H), 5.27 (s, 2 H), 6.69-6.80 (m, 2 H), 7.23 (s, 2 H), 7.51-7.62 (m, 1 H), 7.65 (s, 1 H), 8.03-8.12 (m, 1 H).

Example 28A

3-Bromo-8-[(2,6-difluorobenzyl)oxy]-2-methylimidazo[1,2-a]pyridine

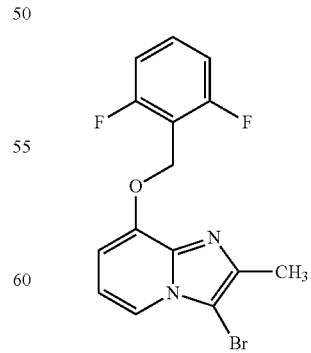

193 g of 8-[(2,6-difluorobenzyl)oxy]-2-methylimidazo[1,2-a]pyridine (Example 27A, 0.7 mmol, 1 equivalent) were initially charged in 2.2 l of ethanol, and 150.3 g of N-bromosuccinimide (0.8 mmol, 1.2 equivalents) were added. After 1.5 h at RT, the mixture was concentrated under reduced pressure at RT. The residue was then diluted with ethyl acetate, and the organic phase was washed with saturated aqueous sodium hydrogencarbonate solution, dried over sodium sulphate, filtered and concentrated by rotary evaporation. The residue was purified by silica gel chromatography (mobile phase mixture cyclohexane/ethyl acetate=98:2, 96:4, 92:8, 9:1, 8:2 and 7:3). The product obtained was stirred with 600 ml of ethyl acetate and decanted off. The residue was dried under reduced pressure. This gave 23.4 g (9% of theory) of the title compound. The filtrate was concentrated under reduced pressure and the residue was stirred with 100 ml of ethyl acetate. The ethyl acetate phase was decanted off and the residue was dried under reduced pressure. This gave a further 6.1 g (2.3% of theory) of the title compound.

LC-MS (Method 1): $R_t$=0.90 min

MS (ESpos): m/z=353 (M+H)$^+$ $^1$H-NMR (400 MHz, DMSO-$d_6$): δ=2.27 (s, 3 H), 5.27 (s, 2 H), 6.70-6.80 (m, 2 H), 7.23 (t, 2 H), 7.52-7.62 (m, 1 H), 7.65 (s, 1 H), 8.09 (d, 1 H).

Example 29A

8-[(2,6-Difluorobenzyl)oxy]-2,6-dimethylimidazo[1,2-a]pyridine

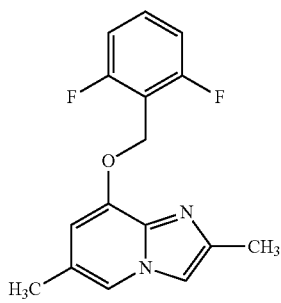

10.0 g (30.09 mmol) of 8-[(2,6-difluorobenzyl)oxy]-2,6-dimethylimidazo[1,2-a]pyridine-3-carboxylic acid from Example 16A were initially charged in 228 ml of dioxane, 25.1 ml of 6 N aqueous hydrochloric acid solution were added and the mixture was stirred at 100° C. for 2 h. After cooling, the dioxane was removed under reduced pressure and the aqueous residue was adjusted to pH 8 using 2 N aqueous sodium hydroxide solution. The solid obtained was filtered off, washed with water and dried under high vacuum. This gave 8.97 g of the target compound (97% of theory, purity 94%).

LC-MS (Method 1): $R_t$=0.70 min

MS (ESpos): m/z=289 (M+H)$^+$ $^1$H-NMR (400 MHz, DMSO-$d_6$): δ=2.22-2.30 (m, 6 H); 5.27 (s, 2 H); 6.67 (s, 1 H); 7.21 (t, 2 H); 7.53-7.63 (m, 2 H); 7.89 (s, 1 H).

Example 30A

3-Bromo-8-[(2,6-difluorobenzyl)oxy]-2,6-dimethylimidazo[1,2-a]pyridine

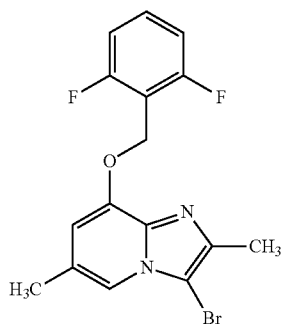

Under argon and with exclusion of light, 3.865 g (13.41 mmol) of 8-[(2,6-difluorobenzyl)oxy]-2,6-dimethylimidazo[1,2-a]pyridine from Example 29A were initially charged in 42 ml of ethanol, 2.625 g (14.75 mmol) of N-bromosuccinimide were added and the mixture was stirred at room temperature for 4 h. The reaction mixture was concentrated. The residue was stirred with about 100 ml of water, and the resulting suspension was then stirred at RT for 30 min. The precipitate formed was filtered off, washed with water and dried under high vacuum. This gave 4.48 g of the target compound (91% of theory, purity 100%).

LC-MS (Method 1): $R_t$=0.93 min

MS (ESpos): m/z=267 (M+H)$^+$ $^1$H-NMR (400 MHz, DMSO-$d_6$): δ=2.28 (s, 3H), 2.33 (s, 3 H); 5.30 (s, 2 H); 6.89 (s, 1 H); 7.22 (t, 2 H); 7.53-7.63 (m, 1 H); 7.75 (s, 1 H).

Example 31A 2,6-Dimethyl-8-[(2,3,6-trifluorobenzyl)oxy]imidazo[1,2-a]pyridine

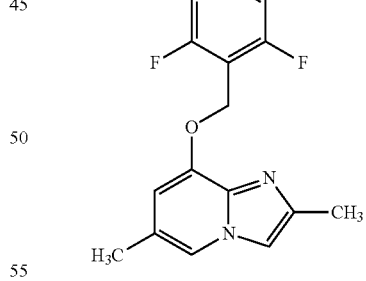

6.48 g (18.50 mmol) of 2,6-dimethyl-8-[(2,3,6-trifluorobenzyl)oxy]imidazo[1,2-a]pyridine-3-carboxylic acid from Example 22A were initially charged in 140 ml of dioxane, 15.4 ml of 6 N aqueous hydrochloric acid solution were added and the mixture was stirred at 100° C. for 4 h. After cooling, the dioxane was removed under reduced pressure and the aqueous residue was adjusted to pH 8 using 1 N aqueous sodium hydroxide solution. The solid formed was filtered off, washed with water and dried under high vacuum. This gave 5.57 g of the target compound (96% of theory).

LC-MS (Method 1): $R_t$=0.65 min
MS (ESpos): m/z=307 (M+H)$^+$
$^1$H-NMR (400 MHz, DMSO-d$_6$): δ=2.20-2.29 (m, 6 H), 5.29 (s, 2 H), 6.69 (s, 1 H), 7.23-7.33 (m, 1 H), 7.57 (s, 1 H), 7.60-7.73 (m, 1 H), 7.91 (s, 1 H).

Example 32A

3-Bromo-2,6-dimethyl-8-[(2,3,6-trifluorobenzyl)oxy]imidazo[1,2-a]pyridine

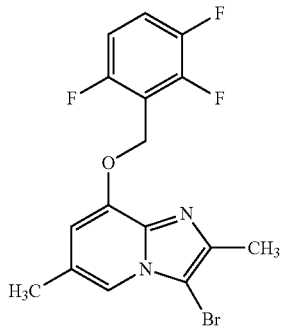

Under argon and with exclusion of light, 2.28 g (7.45 mmol) of 2,6-dimethyl-8-[(2,3,6-trifluorobenzyl)oxy]imidazo[1,2-a]pyridine from Example 31A were initially charged in 23.4 ml of ethanol, 1.46 g (8.20 mmol) of N-bromosuccinimide were added and the mixture was stirred at room temperature for 1.5 h. The reaction mixture was concentrated under reduced pressure. The residue was stirred with 200 ml of water, and the resulting suspension was then stirred at RT for 2 h. The precipitate formed was filtered off, washed with water and dried under high vacuum. 2.47 g of the target compound were obtained (86% of theory).

LC-MS (Method 1): $R_t$=0.97 min
MS (ESpos): m/z=385 (M+H)$^+$
$^1$H-NMR (400 MHz, DMSO-d$_6$): δ=2.28 (s, 3 H), 2.33 (s, 3 H); 5.32 (s, 2 H); 6.87 (s, 1 H); 7.24-7.33 (m, 1 H); 7.62-7.73 (m, 1 H); 7.76 (s, 1 H).

Example 33A

8-[(3-Fluoropyridin-2-yl)methoxy]-2,6-dimethylimidazo[1,2-a]pyridine

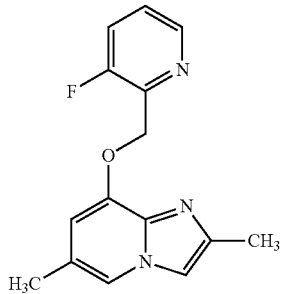

2.30 g (7.29 mmol) of 8-[(3-fluoropyridin-2-yl)methoxy]-2,6-dimethylimidazo[1,2-a]pyridine-3-carboxylic acid from Example 24A were initially charged in 55.2 ml of dioxane, 12.2 ml of 6 N aqueous hydrochloric acid solution were added and the mixture was stirred at 100° C. overnight. After cooling, the dioxane was removed under reduced pressure and the aqueous residue was adjusted to pH 8 using 2 N aqueous sodium hydroxide solution. The solid formed was filtered off, washed well with water and dried under high vacuum. 2.53 g of the target compound were obtained (125% of theory).

LC-MS (Method 1): $R_t$=0.58 min
MS (ESpos): m/z=272 (M+H)$^+$
$^1$H-NMR (400 MHz, DMSO-d$_6$): δ=2.24 (s, 3 H), 2.26 (s, 3 H), 5.40 (s, 2 H), 6.87 (s, 1 H), 7.54-7.70 (m, 2 H), 7.85 (t, 1 H), 7.99 (s, 1 H), 8.47-8.53 (m, 1 H).

Example 34A

3-Bromo-8-[(3-fluoropyridin-2-yl)methoxy]-2,6-dimethylimidazo[1,2-a]pyridine trifluoroacetate

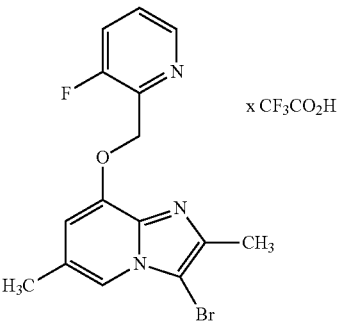

Under argon, 916 mg (3.38 mmol) of 8-[(3-fluoropyridin-2-yl)methoxy]-2,6-dimethylimidazo[1,2-a]pyridine from Example 33A were initially charged in 10.6 ml of dichloromethane, the mixture was cooled to −78° C., 631 mg (3.55 mmol) of N-bromosuccinimide were added and the mixture was stirred at −78° C. for 1 h. The reaction mixture was concentrated under reduced pressure. The residue was taken up in acetonitrile, water/TFA was added and the mixture was purified by preparative HPLC (RP18 column, mobile phase: acetonitrile/water gradient with addition of 0.1% TFA). This gave 508 mg of the target compound (30% of theory, purity 94%).

LC-MS (Method 1): $R_t$=0.71 min
MS (ESpos): m/z=350 (M+H)$^+$
$^1$H-NMR (400 MHz, DMSO-d$_6$): δ=2.29 (s, 3 H), 2.34 (s, 3 H); 5.39 (s, 2 H); 6.85 (s, 1 H); 7.54-7.62 (m, 1 H); 7.72 (s, 1H); 7.85 (t, 1 H), 8.49 (d, 1 H).

Example 35A

8-[(2,6-Difluorobenzyl)oxy]-2-methylimidazo[1,2-a]pyridine-3-carboxamide

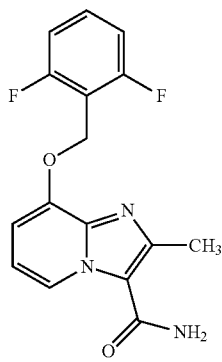

Under argon, 5 g of 8-[(2,6-difluorobenzyl)oxy]-2-methylimidazo[1,2-a]pyridine-3-carboxylic acid (Example 3A, 15.7 mmol, 1 equivalent) were initially charged in 300 ml of dichloromethane, 4.5 g of 1-(3-dimethylaminopropyl)-3-ethylcarbodiimide hydrochloride (23.6 mmol, 1.5 equivalents) and 3.6 g of 1-hydroxy-1H-benzotriazole hydrate (HOBT, 23.6 mmol, 1.5 equivalents) were added successively at RT and the mixture was stirred at RT for 10 min. 4.2 g of ammonium chloride (78.5 mmol, 5 equivalents) and 19.2 ml of N,N-diisopropylethylamine (109.9 mmol, 7 equivalents) were then added, and the mixture was stirred at RT overnight. The mixture was concentrated by rotary evaporation, dichloromethane was added to the residue, the mixture was filtered, the filter cake was washed with dichloromethane and the product was dried under reduced pressure overnight. This gave 5.38 g (108% of theory) of the title compound which was reacted further without purification.

LC-MS (Method 1): $R_t$=0.65 min
MS (ESpos): m/z=318.2 (M+H)$^+$

Example 36A

8-[(2,6-Difluorobenzyl)oxy]-2-methylimidazo[1,2-a]pyridine-3-carbonitrile

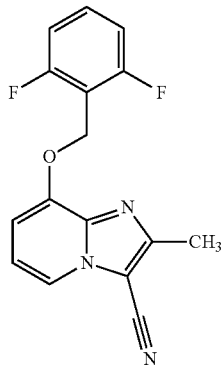 [SMILES: Cc1nc2c(OCc3c(F)cccc3F)cccn2c1C#N]

912 mg of 8-[(2,6-difluorobenzyl)oxy]-2-methylimidazo[1,2-a]pyridine-3-carboxamide (Example 35A, 2.9 mmol, 1 equivalent) were initially charged in 13 ml of THF, and 0.6 ml of pyridine (7.4 mmol, 2.56 equivalents) was added. Subsequently, 1.04 ml (7.4 mmol, 2.56 equivalents) of trifluoroacetic anhydride were added dropwise and the mixture was stirred at RT overnight. Subsequently, the mixture was added to water and extracted three times with ethyl acetate. The combined organic phases were washed once with saturated aqueous sodium bicarbonate solution, once with 1 N aqueous hydrochloric acid and once with saturated sodium chloride solution, dried over sodium sulphate and concentrated on a rotary evaporator. The residue was dried under reduced pressure overnight. This gave 787 mg (91% of theory) of the title compound.

LC-MS (Method 1): $R_t$=0.97 min
MS (ESpos): m/z=300.1 (M+H)$^+$
$^1$H-NMR (400 MHz, DMSO-d$_6$): δ=2.44 (s, 3 H), 5.33 (s, 2 H), 7.10-7.16 (m, 1 H), 7.18-7.28 (m, 3 H), 7.54-7.64 (m, 1 H), 8.22 (d, 1 H).

Example 37A

8-[(2,6-Difluorobenzyl)oxy]-2-methylimidazo[1,2-a]pyridine-3-carboximidamide

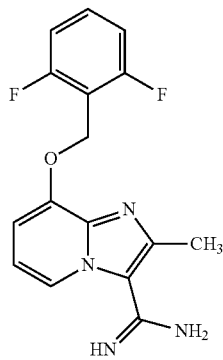 [SMILES: Cc1nc2c(OCc3c(F)cccc3F)cccn2c1C(=N)N]

Under argon, 135 mg (2.5 mmol, 2.52 equivalents) of ammonium chloride were initially charged in 3.9 ml of toluene, and the mixture was cooled to 0° C. At this temperature, 1.26 ml of 2 M trimethylaluminium in toluene (2.5 mmol, 2.52 equivalents) were added, and the solution was stirred at RT for 2 h. In another flask, 300 mg of 8-[(2,6-difluorobenzyl)oxy]-2-methylimidazo[1,2-a]pyridine-3-carbonitrile (Example 36A, 1.0 mmol, 1 equivalent) were initially charged in 3.3 ml of toluene, 2 ml of the solution prepared beforehand were added at RT and the mixture was stirred at 110° C. for 1 h. This procedure was repeated four times. The mixture was then cooled, silica gel and a 1:1 mixture of dichloromethane/methanol were added at RT and the mixture was stirred at RT for 30 min. The silica gel was filtered off over a frit. The silica gel was washed with methanol and the filtrate was concentrated under reduced pressure. The residue was purified by silica gel chromatography (mobile phase: dichloromethane; dichloromethane: methanol=10:2). This gave 137.5 mg (43% of theory) of the title compound.

LC-MS (Method 1): $R_t$=0.51 min
MS (ESpos): m/z=317.1 (M+H)$^+$
$^1$H-NMR (400 MHz, DMSO-d$_6$): δ=2.46 (s, 3 H), 5.32 (s, 2 H), 7.04 (t, 1 H), 7.14 (d, 1 H), 7.24 (t, 2 H), 7.53-7.66 (m, 1 H), 8.17 (d, 1 H), 9.31 (d, 3 H).

Example 38A

8-[(2,6-Difluorobenzyl)oxy]-N-hydroxy-2-methyl-imidazo[1,2-a]pyridine-3-carboximidamide

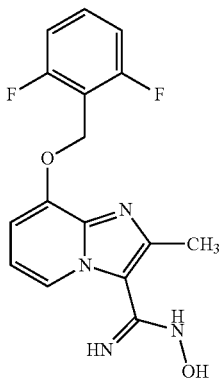 [SMILES: Cc1nc2c(OCc3c(F)cccc3F)cccn2c1C(=N)NO]

50.0 g (148.9 mmol) of 8-[(2,6-difluorobenzyl)oxy]-2-methylimidazo[1,2-a]pyridine-3-carbonitrile from Example 36A were suspended in ethanol (1.5 l), 51.75 g (744.6 mmol) of hydroxylamine hydrochloride and 103.0 ml (744.6 mmol) of triethylamine were added and the mixture was stirred at RT overnight. The mixture was then concentrated under reduced pressure, water (2.0 l) and ethanol (100 ml) were added and the mixture was stirred for 1 h. The solid formed was filtered off, washed with water and dried under high vacuum overnight. This gave 38.5 g (78% of theory) of the title compound.

LC-MS (Method 1): $R_t$=0.56 min

MS (ESpos): m/z=333.2 (M+H)$^+$

Example 39A

8-[(2,6-Difluorobenzyl)oxy]-2-methylimidazo[1,2-a]pyridine-3-carboximidamide hydrochloride

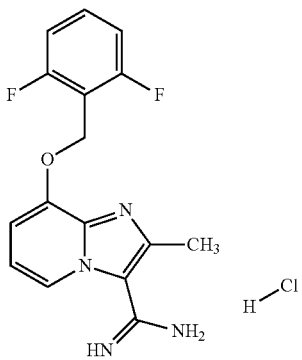 [SMILES: Cc1nc2c(OCc3c(F)cccc3F)cccn2c1C(=N)N ; Cl]

37.5 g (98.4 mmol, purity 87%) of 8-[(2,6-difluorobenzyl)oxy]-N-hydroxy-2-methylimidazo[1,2-a]pyridine-3-carboximidamide from Example 38A were initially charged in acetic acid (1.0 l), and 11.14 ml (118.08 mmol) of acetic anhydride were added. 7.5 g of palladium/carbon (10%, moist) were then added, and the mixture was hydrogenated at atmospheric pressure for 16 h. The mixture was filtered through kieselguhr and washed with ethanol. After concentration, three times in each case 500 ml of toluene were added to the residue, and the mixture was concentrated under reduced pressure. The residue was stirred with 200 ml of ethyl acetate, filtered and dried under high vacuum. This gave 22.0 g (59% of theory) of the title compound.

LC-MS (Method 1): $R_t$=0.51 min

MS (ESpos): m/z=317.2 (M+H)$^+$ $^1$H-NMR (400 MHz, DMSO-$d_6$): δ=1.82 (s, 3H), 2.46 (s, 3 H), 5.31 (s, 2 H), 6.93 (t, 1 H), 7.01 (d, 1 H), 7.21-7.25 (m, 2 H), 7.55-7.63 (m, 1 H), 8.55 (br d, 1 H).

Example 40A

8-[(2,6-Difluorobenzyl)oxy]-2,6-dimethylimidazo[1,2-a]pyridine-3-carboxamide

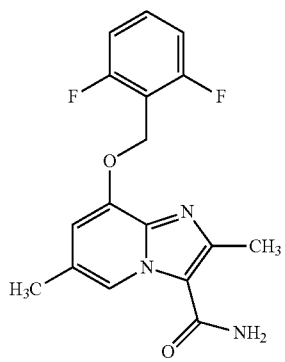

7.0 g (21.07 mmol) of 8-[(2,6-difluorobenzyl)oxy]-2,6-dimethylimidazo[1,2-a]pyridine-3-carboxylic acid from Example 16A were initially charged in 403 ml of dichloromethane, 6.06 g (31.60 mmol) of 1-(3-dimethylaminopropyl)-3-ethylcarbodiimide hydrochloride and 4.27 g (31.60 mmol) of 1-hydroxy-1H-benzotriazole hydrate were added and the mixture was stirred at room temperature for 10 min. Subsequently, 5.63 g (105.32 mmol) of ammonium chloride and 25.68 ml (147.5 mmol) of N,N-diisopropylethylamine were added and the mixture was stirred at room temperature overnight. Water was added to the reaction mixture, and the solid present was filtered off, then stirred with water at 50° C. for 30 min, filtered off again and washed with water. This gave 4.59 g (65% of theory) of the title compound. The combined filtrate fractions (dichloromethane/water) were separated into the phases. The dichloromethane phase was washed in each case once with saturated aqueous sodium bicarbonate solution and saturated aqueous sodium chloride solution. The organic phase was dried over sodium sulphate, filtered and concentrated under reduced pressure. The residue was triturated with a little acetonitrile and filtered off. This gave a further 1.29 g (17% of theory, purity: 93%) of the title compound.

LC-MS (Method 1): $R_t$=0.64 min

MS (ESpos): m/z=332 (M+H)$^+$ $^1$H-NMR (400 MHz, DMSO-$d_6$): δ=2.31 (s, 3H), 2.50 (s, 3 H; hidden under DMSO signal), 5.28 (s, 2 H), 6.92 (s, 1 H), 7.22 (t, 2 H), 7.35 (br. s, 2 H), 7.53-7.63 (m, 1 H); 8.62 (s, 1 H).

Example 41A

8-[(2,6-Difluorobenzyl)oxy]-2,6-dimethylimidazo[1,2-a]pyridine-3-carbonitrile

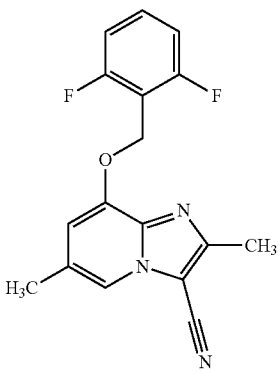

5.7 g (17.20 mol) of 8-[(2,6-difluorobenzyl)oxy]-2,6-dimethylimidazo[1,2-a]pyridine-3-carboxamide Example 40A were initially charged in 77 ml of THF, and 3.56 ml (44.0 mmol) of pyridine were added. At RT, 6.22 ml (44.0 mmol) of trifluoroacetic anhydride were added dropwise, and the reaction mixture was stirred at RT for 3 h. After the reaction had ended, the mixture was added to water and extracted three times with ethyl acetate. The combined organic phases were washed once with saturated aqueous sodium bicarbonate solution, once with 1 N aqueous hydrochloric acid and once with saturated sodium chloride solution, dried over sodium sulphate and concentrated under reduced pressure. The residue was dried under reduced pressure overnight. This gave 5.47 g (90% of theory) of the title compound.

LC-MS (Method 1): $R_t$=1.12 min
MS (ESpos): m/z=314 (M+H)$^+$
$^1$H-NMR (400 MHz, DMSO-d$_6$): δ=2.37 (s, 3 H), 2.41 (s, 3 H), 5.31 (s, 2 H), 7.12 (s, 1 H), 7.23 (t, 2 H), 7.54-7.63 (m, 1 H), 8.09 (s, 1 H).

Example 42A

8-[(2,6-Difluorobenzyl)oxy]-2,6-dimethylimidazo[1,2-a]pyridine-3-carboximidamide

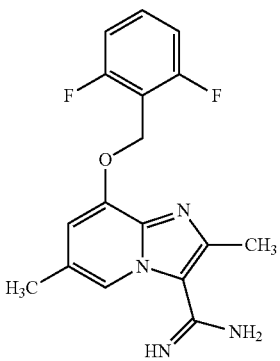

5.47 g (17.46 mmol) of 8-[(2,6-difluorobenzyl)oxy]-2,6-dimethylimidazo[1,2-a]pyridine-3-carbonitrile from Example 41A were reacted analogously to Example 37A. This gave 1.28 g (22% of theory) of the title compound.

LC-MS (Method 1): $R_t$=0.60 min
MS (ESpos): m/z=331.3 (M+H)$^+$
$^1$H-NMR (400 MHz, DMSO-d$_6$): δ=2.35 (s, 3 H), 2.43 (s, 3 H), 5.31 (s, 2 H), 7.06 (s, 1 H), 7.24 (t, 2 H), 7.54-7.65 (m, 1 H), 8.02 (s, 1 H), 9.25 (br. s, 3 H).

Example 43A

8-[(2,6-Difluorobenzyl)oxy]-2,6-dimethylimidazo[1,2-a]pyridine-3-carboximidohydrazide

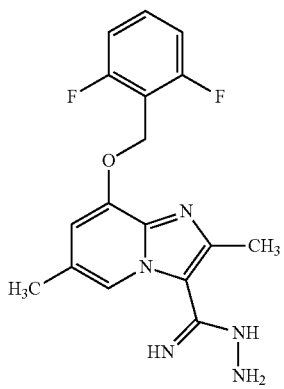

600 mg (1.82 mmol) of 8-[(2,6-difluorobenzyl)oxy]-2,6-dimethylimidazo[1,2-a]pyridine-3-carboximidamide from Example 42A were initially charged in ethanol (15 ml), and 2.025 ml (14.53 mmol) of triethylamine and then 220 µl (3.63 mmol) of hydrazine hydrate (80%) were added. The mixture was stirred at 50° C. overnight and then concentrated under reduced pressure. This gave 681 mg of crude product.

LC-MS (Method 1): $R_t$=0.55 min
MS (ESpos): m/z=346.2 (M+H)$^+$

Example 44A

8-[(2,6-Difluorobenzyl)oxy]-2-methylimidazo[1,2-a]pyridine-3-carbohydrazide

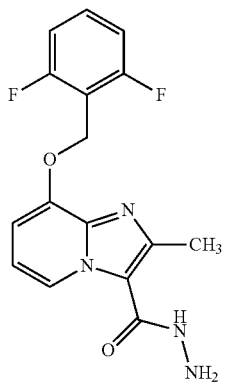 [SMILES: Cc1nc2c(OCc3c(F)cccc3F)cccn2c1C(=O)NN]

At RT, 3 g of 8-[(2,6-difluorobenzyl)oxy]-2-methylimidazo[1,2-a]pyridine-3-carboxylic acid (Example 16A, 9.4 mmol), 5.4 g of N-[3-(dimethylamino)propyl]-N'-ethylcarbodiimide hydrochloride (28.3 mmol, 3 equivalents) and 3.8 g of 1H-benzotriazol-1-ol (28.3 mmol, 3 equivalents) were initially charged in DMF. After 30 min, 1.4 ml of hydrazine hydrate (28.3 mmol, 1.4 g, 3 equivalents) and 3.9 ml of triethylamine (28.3 mmol, 2.9 g, 3 equivalents) were added and the mixture was stirred at RT for 6 h. Water and ethyl acetate were then added to the reaction mixture. The organic phase was separated off, washed with saturated aqueous sodium chloride solution, dried over magnesium sulphate and concentrated under reduced pressure. This gave 3.1 g (85% of theory, purity: 85%) of the title compound.

LC-MS (Method 1): $R_t$=0.58 min

MS (ESpos): m/z=333 (M+H)$^+$

Example 45A

5-{8-[(2,6-Difluorobenzyl)oxy]-2-methylimidazo[1,2-a]pyridin-3-yl}-1,3,4-oxadiazol-2(3H)-one

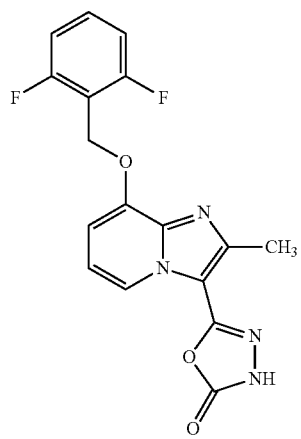 [SMILES: Cc1nc2c(OCc3c(F)cccc3F)cccn2c1-c1n[nH]c(=O)o1]

At RT, 3.1 g of 8-[(2,6-difluorobenzyl)oxy]-2-methylimidazo[1,2-a]pyridine-3-carbohydrazide (Example 44A, 7.9 mmol, 1 equivalent) were initially charged in 23.7 ml of DMF, and 1.35 g of di-1H-imidazol-1-ylmethanone (CDI; 8.3 mmol, 1.05 equivalents) were added. The mixture was stirred at RT overnight, and water was then added. The solid formed was filtered off and dried under reduced pressure. This gave 0.71 g (23% of theory) of the title compound.

LC-MS (Method 2): $R_t$=1.01 min

MS (ESpos): m/z=359 (M+H)$^+$ $^1$H-NMR (400 MHz, DMSO-$d_6$): δ=2.55 (s, 3 H; obscured by DMSO signal), 5.32 (s, 2 H), 7.09-7.15 (m, 2 H), 7.24 (t, 2 H), 7.54-7.64 (m, 1 H), 8.60 (d, 1 H), 12.61 (br. s, 1 H).

Example 46A

6-Chloro-8-[(2,6-difluorobenzyl)oxy]-N-[(2R)-1-hydroxyhexan-2-yl]-2-methylimidazo[1,2-a]pyridine-3-carboxamide

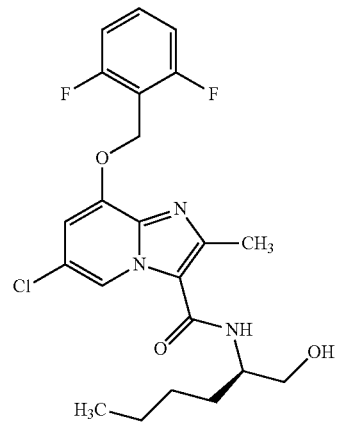 [SMILES: CCCC[C@H](CO)NC(=O)c1c(C)nc2c(OCc3c(F)cccc3F)cc(Cl)cn12]

Successively, 37.2 mg of (2R)-2-aminohexan-1-ol (0.32 mmol, 1.4 equivalents), 112 mg HATU (0.3 mmol, 1.3 equivalents) and 0.112 ml of N,N-diisopropylethylamine (0.68 mmol, 3 equivalents) were added to 80 mg of 6-chloro-8-[(2,6-difluorobenzyl)oxy]-2-methylimidazo[1,2-a]pyridine-3-carboxylic acid (Example 11A, 0.23 mmol, 1 equivalent) in 0.72 ml of DMF, and the mixture was stirred at RT overnight. The solid formed was filtered off, washed with water and dried under reduced pressure. This gave 88 mg (82% of theory) of the title compound.

LC-MS (Method 1): $R_t$=1.05 min

MS (ESpos): m/z=452.1 (M+H)$^+$ $^1$H-NMR (400 MHz, DMSO-$d_6$): δ=0.88 (s, 3 H), 1.25-1.40 (m, 4 H), 1.42-1.53 (m, 1 H), 1.54-1.67 (m, 1 H), 3.39-3.56 (m, 2 H), 3.92-4.04 (m, 1 H), 4.67-4.79 (m, 1 H), 5.35 (s, 2 H), 7.13-7.32 (m, 3 H), 7.53-7.66 (m, 2 H), 8.59-8.67 (m, 1 H), [further signals hidden under the solvent peaks].

Example 47A

6-Chloro-N-[(2R)-1-chlorohexan-2-yl]-8-[(2,6-difluorobenzyl)oxy]-2-methylimidazo[1,2-a]pyridine-3-carboxamide hydrochloride

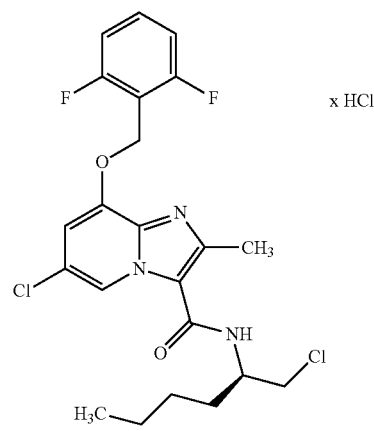 [SMILES: CCCC[C@H](CCl)NC(=O)c1c(C)nc2c(OCc3c(F)cccc3F)cc(Cl)cn12]

270 mg of 6-chloro-8-[(2,6-difluorobenzyl)oxy]-N-[(2R)-1-hydroxyhexan-2-yl]-2-methylimidazo[1,2-a]pyridine-3-carboxamide (Example 46A, 0.6 mmol, 1 equivalent) were initially charged in 2.5 ml of dichloromethane. At 0° C., 0.13 ml of thionyl chloride (1.79 mmol, 3 equivalents) was added dropwise, and the mixture was stirred at 0° C. for 1 h and then at RT overnight. The mixture was then concentrated under reduced pressure, three times, dichloromethane was added and removed again under reduced pressure, and the product was then dried under reduced pressure. This gave 295 mg (97% of theory) of the title compound.

LC-MS (Method 1): $R_t$=1.33 min

MS (ESpos): m/z=470.3 (M+H)$^+$

Example 48A

3-[(4R)-4-Butyl-4,5-dihydro-1,3-oxazol-2-yl]-6-chloro-8-[(2,6-difluorobenzyl)oxy]-2-methylimidazo[1,2-a]pyridine

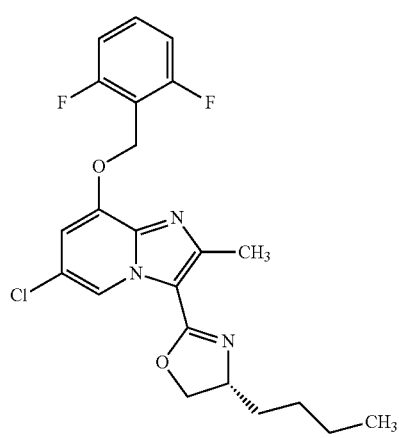 [SMILES: CCCC[C@@H]1COC(c2c(C)nc3c(OCc4c(F)cccc4F)cc(Cl)cn23)=N1]

393 mg of 6-chloro-N-[(2R)-1-chlorohexan-2-yl]-8-[(2,6-difluorobenzyl)oxy]-2-methylimidazo[1,2-a]pyridine-3-carboxamide hydrochloride (Example 47A, 0.78 mmol, 1 equivalent) were initially charged in 79 ml of DMF, 1 g of sodium azide (15.5 mmol, 20 equivalents) was added and the mixture was stirred at 60° C. for 6 h. 65 ml of water were then added to the reaction mixture, and the mixture was extracted three times with ethyl acetate. The combined organic phases were dried over sodium sulphate, filtered and concentrated under reduced pressure. The residue was purified by silica gel chromatography (cyclohexane/ethyl acetate=9:1, 7:3). This gave 167 mg (50% of theory) of the title compound.

LC-MS (Method 1): $R_t$=1.52 min

MS (ESpos): m/z=434.3 (M+H)$^+$ $^1$H-NMR (400 MHz, DMSO-$d_6$): δ=0.91 (t, 3 H), 1.21-1.50 (m, 5 H), 1.52-1.70 (m, 2 H), 4.01 (m, 7.90 Hz, 1 H), 4.21-4.36 (m, 1 H), 4.43-4.57 (m, 1 H), 5.36 (s, 2 H), 7.16-7.35 (m, 3 H), 7.52-7.70 (m, 1 H), 9.29 (s, 1 H); [further signals hidden under the solvent peaks].

Example 49A

8-[(2,6-Difluorobenzyl)oxy]-2,6-dimethyl-3-[(trimethylsilyl)ethynyl]imidazo[1,2-a]pyridine

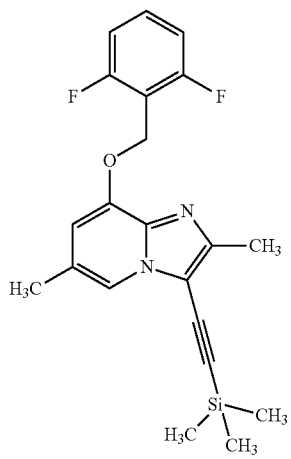

2.0 g (5.27 mmol) of 3-bromo-8-[(2,6-difluorobenzyl)oxy]-2,6-dimethylimidazo[1,2-a]pyridine from Example 30A were initially charged in 16 ml of acetonitrile, 1.04 g (10.55 mmol) of ethynyl(trimethyl)silane, 152 mg (0.13 mmol) of bis(triphenylphosphine)palladium(II) chloride, 36 mg (0.19 mmol) of copper(I) iodide and 1.04 ml (7.38 mmol) of diisopropylamine were added and the mixture was stirred under reflux overnight. The mixture was concentrated under reduced pressure and the residue was taken up in ethyl acetate and extracted with water. There was no phase separation. The mixture was filtered off through Celite, and a little saturated aqueous sodium chloride solution was added to the filtrate. The two phases were then separated. The organic phase was dried over sodium sulphate, filtered and concentrated under reduced pressure. The crude product was purified by silica gel chromatography (mobile phase: cyclohexane/ethyl acetate 5/1 to 7/3). This gave 1.1 mg of the target compound (35% of theory, purity about 64%).

LC-MS (Method 1): $R_t$=1.25 min

MS (ESpos): m/z=385 (M+H)$^+$

Example 50A

8-[(2,6-Difluorobenzyl)oxy]-3-ethynyl-2,6-dimethylimidazo[1,2-a]pyridine

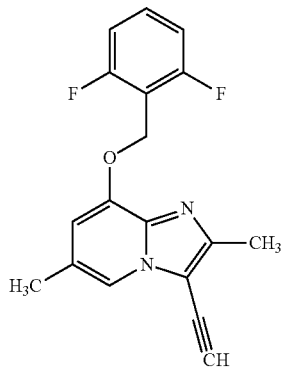

1.1 g (1.83 mmol; purity 64%) of 8-[(2,6-difluorobenzyl)oxy]-2,6-dimethyl-3-[(trimethylsilyl)ethynyl]imidazo[1,2-a]pyridine from Example 49A were initially charged in 9.3 ml of methanol, 25 mg (0.18 mmol) of potassium carbonate were added and the mixture was stirred at RT for 1 h. The residue was filtered off and washed with methanol. The filtrate was concentrated under reduced pressure and the residue was dried under high vacuum. This gave 0.97 mg of the target compound (99% of theory, purity about 60%).

LC-MS (Method 1): $R_t$=0.91 minpo
MS (ESpos): m/z=313 (M+H)$^+$

Example 51A

2-Methyl-2-nitropropyl trifluoromethanesulphonate

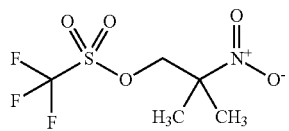

1.0 g (8.40 mmol) of 2-methyl-2-nitropropan-1-ol was initially charged in 20 ml of dichloromethane, 1.0 ml (12.59 mmol) of pyridine was added, the mixture was cooled to 0° C. and 1.85 ml (10.91 mmol) of trifluoromethanesulphonic anhydride was added slowly. The mixture was then stirred at 0° C. for 1 h. The course of the reaction was monitored by TLC (cyclohexane/ethyl acetate 7/3, staining reagent: potassium permanganate stain). The reaction solution was washed in each case once with water and saturated aqueous sodium chloride solution. The organic phase was dried over sodium sulphate and filtered and the filtrate was concentrated. 2.18 g of the target compound were obtained (99% of theory). The target compound was stored at −18° C. and used without further purification.

MS (Method 13):
MS (ESpos): m/z=269 (M+NH$_4$)$^+$
$^1$H NMR (400 MHz, DMSO-d$_6$) δ=1.64 (s, 6 H), 5.13 (s, 2 H).

Example 52A

8-[(2,6-Difluorobenzyl)oxy]-2-methyl-3-[1-(2-methyl-2-nitropropyl)-1H-pyrazol-4-yl]imidazo[1,2-a]pyridine

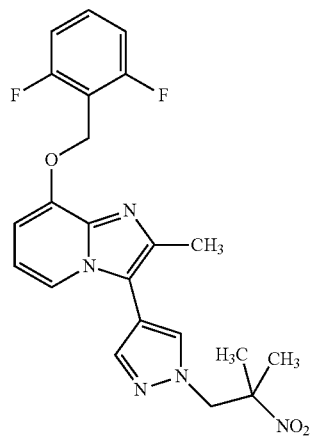 [SMILES: Cc1nc2c(OCc3c(F)cccc3F)cccn2c1-c1cnn(CC(C)(C)[N+](=O)[O-])c1]

479 mg (1.47 mmol) of caesium carbonate and 435 mg (1.73 mmol) of 2-methyl-2-nitropropyl trifluoromethanesulphonate Example 51A were added to 417 mg (1.23 mmol) of 8-[(2,6-difluorobenzyl)oxy]-2-methyl-3-(1H-pyrazol-4-yl)imidazo[1,2-a]pyridine from Example 45 in 7.5 ml of DMF, and the mixture was stirred at 100° C. overnight. 242 mg (0.96 mmol) of 2-methyl-2-nitropropyl trifluoromethanesulphonate Example 51A were then added, and the mixture was stirred at 100° C. for 6 h. The reaction solution was filtered, the solid was washed with ethyl acetate and the filtrate was concentrated under reduced pressure. The residue was purified by preparative HPLC (RP18 column; mobile phase: acetonitrile/water gradient with addition of 0.1% TFA). Saturated aqueous sodium bicarbonate solution was added to the crude product, and the mixture was extracted three times with dichloromethane. The combined organic phases were dried over sodium sulphate and filtered. The filtrate was concentrated and the residue was dried under high vacuum and purified by silica gel chromatography (mobile phase: first cyclohexane/ethyl acetate 1/1, then dichloromethane/2 N methanolic ammonia solution 20/1). This gave 193 mg of the target compound (33% of theory, purity 93%).

LC-MS (Method 1): $R_t$=0.79 min
MS (ESpos): m/z=442 (M+H)$^+$
$^1$H NMR (400 MHz, DMSO-d$_6$) δ=1.58 (s, 6 H), 2.31 (s, 3 H), 4.79 (s, 2 H), 5.31 (s, 2 H), 6.80-6.89 (m, 2 H), 7.23 (t, 2 H), 7.55-7.64 (m, 1 H), 7.82-7.86 (m, 2 H), 8.08 (s, 1 H).

Example 53A

8-[(2,6-Difluorobenzyl)oxy]-2,6-dimethyl-3-[1-(2-methyl-2-nitropropyl)-1H-pyrazol-4-yl]imidazo[1,2-a]pyridine

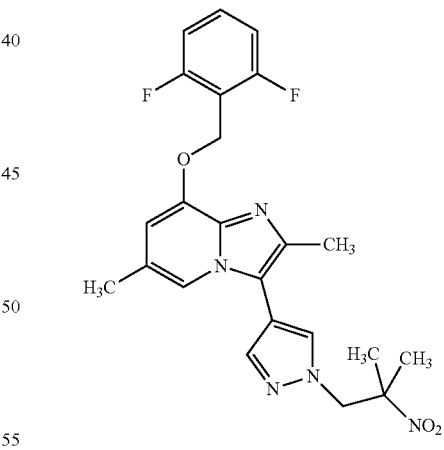

1.30 g (3.67 mmol) of 8-[(2,6-difluorobenzyl)oxy]-2,6-dimethyl-3-(1H-pyrazol-4-yl)imidazo[1,2-a]pyridine from Example 88 were initially charged in 22.5 ml of DMF, 1.43 g (4.40 mmol) of caesium carbonate and 2.53 g (10.07 mmol) of 2-methyl-2-nitropropyl trifluoromethanesulphonate Example 51A were added and the mixture was stirred at 100° C. overnight. The reaction mixture was filtered, the precipitate was washed with ethyl acetate and the filtrate was concentrated under reduced pressure. Water and ethyl acetate were added to the residue, the aqueous phase was extracted twice with ethyl acetate and the combined organic phases were dried over sodium sulphate. After filtration, the filtrate was concentrated under reduced pressure and the residue was purified by silica gel chromatography (mobile phase: dichloromethane/methanol 60/1). The crude product was purified once more by silica gel chromatography (mobile phase: dichloromethane/methanol 80/1). This gave 412 mg of the target compound (24% of theory).

LC-MS (Method 1): $R_t$=0.82 min

MS (ESpos): m/z=456 (M+H)$^+$ $^1$H NMR (400 MHz, DMSO-d$_6$) δ=1.57 (s, 6 H), 2.25-2.32 (m, 6 H), 4.78 (s, 2 H), 5.28 (s, 2 H), 6.73 (s, 1 H), 7.22 (t, 2 H), 7.54-7.64 (m, 1 H), 7.68 (s, 1 H), 7.82 (s, 1 H), 8.06 (s, 1 H).

Example 54A 2,6-Dimethyl-3-[1-(2-methyl-2-nitropropyl)-1H-pyrazol-4-yl]-8-[(2,3,6-trifluorobenzyl)oxy]imidazo[1,2-a]pyridine

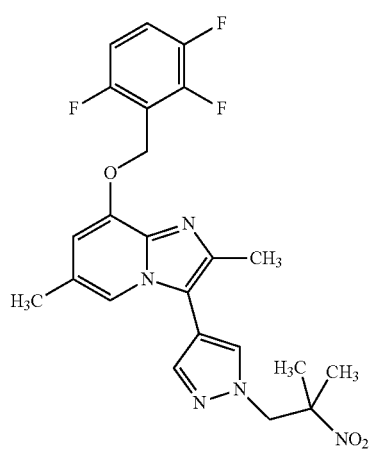 [SMILES: Cc1cc(OCc2c(F)ccc(F)c2F)c2nc(C)c(-c3cnn(CC(C)(C)[N+](=O)[O-])c3)n2c1]

100 mg (0.27 mmol) of 2,6-dimethyl-3-(1H-pyrazol-4-yl)-8-[(2,3,6-trifluorobenzyl)oxy]imidazo[1,2-a]pyridine from Example 86 were initially charged in 3.8 ml of THF, 12 mg (0.32 mmol) of sodium hydride (65%) were added, the mixture was stirred at room temperature for 5 min and 213 mg (0.81 mmol) of 2-methyl-2-nitropropyl trifluoromethanesulphonate Example 51A in 0.3 ml of DMF were then added. The reaction mixture was stirred at room temperature for 1 h. The mixture was then diluted with ethyl acetate and washed twice with water. The organic phase was dried over sodium sulphate and filtered, the filtrate was concentrated and the residue was purified by silica gel chromatography (mobile phase dichloromethane/methanol 80/1 to 40/1). This gave 94 mg of the target compound (65% of theory, purity 89%).

LC-MS (Method 1): $R_t$=0.87 min

MS (ESpos): m/z=474 (M+H)$^+$ $^1$H NMR (400 MHz, DMSO-d$_6$) δ=1.58 (s, 6 H), 2.39 (s, 3 H), 2.43 (s, 3 H), 4.82 (s, 2 H), 5.49 (s, 2 H), 6.78-6.87 (m, 1 H), 7.59 (br. s, 1 H), 7.65-7.76 (m, 1 H), 7.93 (s, 1 H), 8.02 (s, 1 H), 8.22 (s, 1 H).

Example 55A

8-[(3-Fluoropyridin-2-yl)methoxy]-2,6-dimethyl-3-[1-(2-methyl-2-nitropropyl)-1H-pyrazol-4-yl]imidazo[1,2-a]pyridine

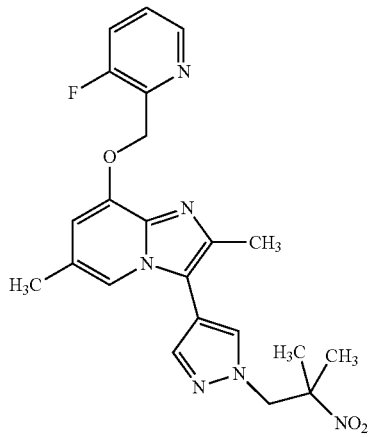 [SMILES: Cc1cc(OCc2ncccc2F)c2nc(C)c(-c3cnn(CC(C)(C)[N+](=O)[O-])c3)n2c1]

95 mg (0.28 mmol) of 8-[(3-fluoropyridin-2-yl)methoxy]-2,6-dimethyl-3-(1H-pyrazol-4-yl)imidazo[1,2-a]pyridine from Example 84 were initially charged in 1.73 ml of THF, 8.5 mg (0.34 mmol) of sodium hydride (95%) were added, the mixture was stirred at room temperature for 5 min and 185 mg (0.70 mmol) of 2-methyl-2-nitropropyl trifluoromethanesulphonate Example 51A were then added. The reaction mixture was stirred at room temperature for 1 h. Another 2 mg (0.09 mmol) of sodium hydride (95%) were then added and the mixture was stirred at room temperature for 15 min. 74 mg (0.28 mmol) of 2-methyl-2-nitropropyl trifluoromethanesulphonate were added, and the mixture was stirred at room temperature overnight. The reaction mixture was diluted with ethyl acetate and washed twice with water. The organic phase was dried over sodium sulphate and filtered, the filtrate was concentrated and the residue was purified by silica gel chromatography (mobile phase dichloromethane/2 N methanolic ammonia solution (60/1)). This gave 66 mg of the target compound (50% of theory, purity 93%).

LC-MS (Method 1): $R_t$=0.75 min

MS (ESpos): m/z=439 (M+H)$^+$

Example 56A

8-[(2,6-Difluorobenzyl)oxy]-2,6-dimethyl-3-[2-(2-methyl-2-nitropropyl)-2H-1,2,3-triazol-4-yl]imidazo[1,2-a]pyridine trifluoroacetate

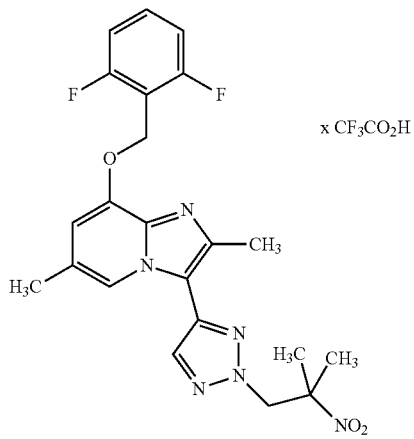 [SMILES: Cc1cc(OCc2c(F)cccc2F)c2nc(C)c(-c3cnn(CC(C)(C)[N+](=O)[O-])n3)n2c1]

6.1 mg (0.15 mmol) of sodium hydride (60%) were added to 70 mg (0.13 mmol; purity about 84%) of 8-[(2,6-difluorobenzyl)oxy]-2,6-dimethyl-3-(2H-1,2,3-triazol-4-yl)imidazo[1,2-a]pyridine from Example 82 in 1.8 ml of THF and 0.45 ml DMF, and the mixture was stirred at room temperature for 10 min. 95 mg (0.38 mmol) of 2-methyl-2-nitropropyl trifluoromethanesulphonate from Example 51A were then added, and the mixture was stirred at room temperature for 1.5 h. A little water/TFA was added and the mixture was purified by preparative HPLC (RP18 column, mobile phase: acetonitrile/water gradient with addition of 0.1% TFA). This gave 46 mg of the target compound (48% of theory, purity about 75%) which were converted further without further purification.

LC-MS (Method 1): $R_t$=0.93 min
MS (ESpos): m/z=457 (M+H)$^+$

Example 57A 2-(4-{8-[(2,6-Difluorobenzyl)oxy]-2,6-dimethylimidazo[1,2-a]pyridin-3-yl}-1H-pyrazol-1-yl)ethyl methanesulphonate

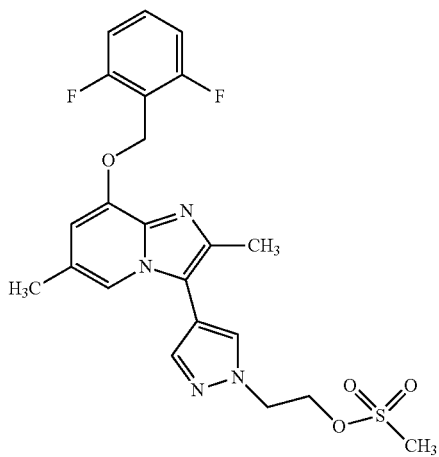 [SMILES: Cc1cc(OCc2c(F)cccc2F)c2nc(C)c(-c3cnn(CCOS(C)(=O)=O)c3)n2c1]

Under argon, 780 mg (1.72 mmol; purity about 90%) of 2-(4-{8-[(2,6-difluorobenzyl)oxy]-2,6-dimethylimidazo[1,2-a]pyridin-3-yl}-1H-pyrazol-1-yl)ethanol from Example 91 were dissolved in 4.0 ml of dichloromethane, and 0.72 ml (5.17 mmol) of triethylamine was added. With ice-cooling, 0.16 ml (2.08 mmol) of methansulphonyl chloride was added dropwise and the reaction mixture was stirred for 30 min while slowly warming to room temperature. 0.08 ml (1.04 mmol) of methanesulphonyl chloride was added at RT, and the mixture was then stirred for 30 min. The reaction mixture was diluted with dichloromethane and washed once with saturated aqueous sodium chloride solution. The organic phase was dried over sodium sulphate and filtered and the filtrate was concentrated and purified by silica gel chromatography (solvent: ethyl acetate/cyclohexane=2/1). This gave 608 mg (74% of theory) of the target compound.

LC-MS (Method 1): $R_t$=0.78 min
MS (ESpos): m/z=477 (M+H)$^+$
$^1$H NMR (400 MHz, DMSO-$d_6$) δ=2.27-2.35 (m, 6 H), 3.12 (s, 3 H), 4.52-4.69 (m, 4 H), 5.28 (s, 2 H), 6.73 (s, 1 H), 7.22 (t, 2 H), 7.53-7.65 (m, 1 H), 7.72 (s, 1 H), 7.83 (s, 1 H), 8.20 (s, 1 H).

Example 58A

8-[(2,6-Difluorobenzyl)oxy]-2,6-dimethyl-N-(prop-2-yn-1-yl)imidazo[1,2-a]pyridine-3-carboxamide

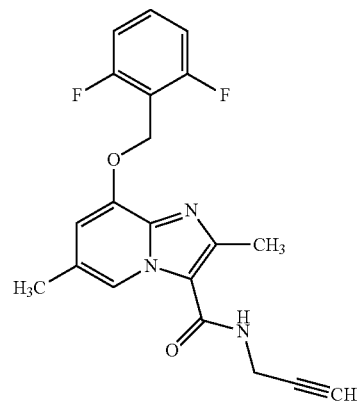 [SMILES: C#CCNC(=O)c1c(C)nc2c(OCc3c(F)cccc3F)cc(C)cn12]

1.49 g of HATU (3.91 mmol) were added to a mixture of 1.00 g of 8-[(2,6-difluorobenzyl)oxy]-2,6-dimethylimidazo[1,2-a]pyridine-3-carboxylic acid (3.01 mmol) from Example 16A, 0.29 ml of propargylamine (4.5 mmol) and 2.6 ml of N,N-diisopropylethylamine (15.0 mmol) in 6.0 ml of DMF, and the mixture was stirred at room temperature for 1 h. 70 ml of water were then added and the precipitated solid was stirred, filtered off, washed with water and dried under high vacuum. This gave 933 mg (81% of theory) of the title compound.

LC-MS (Method 1): $R_t$=0.79 min
MS (ESpos): m/z=370 (M+H)$^+$
$^1$H-NMR (400 MHz, DMSO-$d_6$): δ [ppm]=2.32 (s, 3 H), 2.49 (s, 3 H), 3.13-3.17 (m, 1 H), 4.08 (dd, 2 H), 5.28 (s, 2 H), 6.94 (s, 1 H), 7.20-7.28 (m, 2 H), 7.53-7.65 (m, 1 H), 8.21-8.28 (m, 1 H), 8.48 (s, 1 H).

Example 59A

8-[(2,6-Difluorobenzyl)oxy]-N-methoxy-N,2,6-trimethylimidazo[1,2-a]pyridine-3-carboxamide

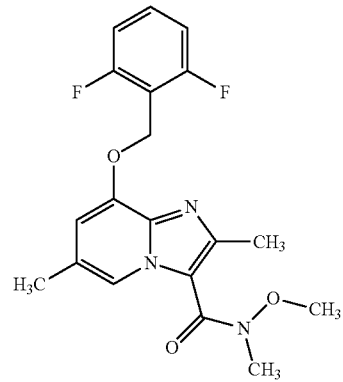

2.16 g of EDCI (11.3 mmol) and 1.73 g of HOBT (11.3 mmol) were added to a solution of 2.50 g of 8-[(2,6-difluorobenzyl)oxy]-2,6-dimethylimidazo[1,2-a]pyridine-3- carboxylic acid (7.52 mmol) from Example 16A in 100 ml of dichloromethane, and the mixture was stirred at room temperature for 10 min. 9.2 ml of N,N-diisopropylethylamine (52.7 mmol) and 3.67 g of N,O-dimethylhydroxylamine hydrochloride (37.6 mmol) were then added and the mixture was stirred at room temperature overnight. The mixture was concentrated and the residue was stirred initially with 200 ml of water and then with 150 ml of tert-butyl methyl ether and then filtered off. The solid was taken up in ethyl acetate and washed three times with saturated aqueous sodium bicarbonate solution, and with water and saturated aqueous sodium chloride solution, dried with magnesium sulphate, filtered and concentrated. The crude product was stirred with diisopropyl ether, filtered off and dried under high vacuum. This gave 1.75 g (61% of theory) of the title compound.

LC-MS (Method 1): $R_t$=0.79 min

MS (ESpos): m/z=376 (M+H)$^+$ $^1$H-NMR (400 MHz, DMSO-d$_6$): δ [ppm]=2.31 (s, 3 H), 2.33 (s, 3 H), 3.31 (s, 3 H), 3.50 (s, 3 H), 5.28 (s, 2 H), 6.90-6.92 (m, 1 H), 7.20-7.29 (m, 2 H), 7.55-7.65 (m, 1 H), 7.96-7.99 (m, 1 H).

Example 60A

1-{8-[(2,6-Difluorobenzyl)oxy]-2,6-dimethylimidazo[1,2-a]pyridin-3-yl}ethanone

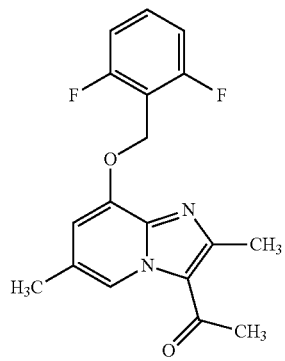

1.97 ml of 3 N methylmagnesium bromide solution in THF (5.9 mmol) were slowly added dropwise to a solution, cooled to 0° C., of 1.70 g of 8-[(2,6-difluorobenzyl)oxy]-N-methoxy-N,2,6-trimethylimidazo-[1,2-a]pyridine-3-carboxamide (4.53 mmol) from Example 59A in 45 ml of THF. The mixture was then stirred at 0° C. for 15 min and then at RT for 2 h. 150 ml of water were added dropwise and the mixture was extracted three times with ethyl acetate. The combined organic phases were washed with saturated aqueous sodium chloride solution, dried over magnesium sulphate, filtered and concentrated. The residue was triturated with n-pentane and the solid formed was filtered off and dried under high vacuum. This gave 1.24 g (78% of theory) of the title compound.

TLC (cyclohexane/ethyl acetate 1:1): $R_F$=0.32

LC-MS (Method 1): $R_t$=0.96 min

MS (ESpos): m/z=331 (M+H)$^+$ $^1$H-NMR (400 MHz, DMSO-d$_6$): δ [ppm]=2.37 (s, 3 H), 2.56 (s, 3 H), 2.65 (s, 3 H), 5.31 (s, 2 H), 7.16 (s, 1 H), 7.20-7.29 (m, 2 H), 7.54-7.65 (m, 1 H), 9.11 (s, 1 H).

Example 61A

2-Bromo-1-{8-[(2,6-difluorobenzyl)oxy]-2,6-dimethylimidazo[1,2-a]pyridin-3-yl}ethanone

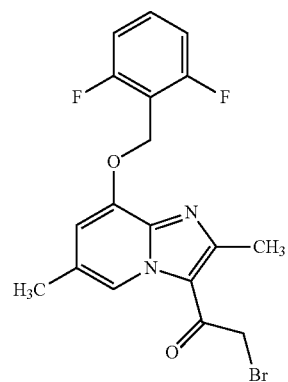

At room temperature, 170 μl of bromine (3.30 mmol) were added dropwise to a suspension of 990 mg of 1-{8-[(2,6-difluorobenzyl)oxy]-2,6-dimethylimidazo[1,2-a]pyridin-3-yl}ethanone (3.00 mmol) from Example 60A in 10 ml of hydrogen bromide (33% in acetic acid), and the mixture was stirred at room temperature for 1 h. 40 ml of diisopropyl ether were then added, the mixture was stirred and the solid was then filtered off. The solid was purified using Biotage Isolera (100 g silica gel cartridge, cyclohexane/ethyl acetate gradient followed by dichloromethane/methanol 5:1). This gave 317 mg (23% of theory, purity 90%) and 819 mg (47% of theory, purity 70%) of the title compound.

LC-MS (Method 1): $R_t$=1.13 min

MS (ESpos): m/z=409 (M+H)$^+$

Example 62A

Ethyl 4-{8-[(2,6-difluorobenzyl)oxy]-2,6-dimethylimidazo[1,2-a]pyridin-3-yl}-2,4-dioxobutanoate

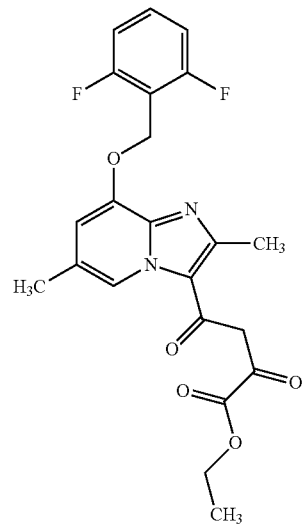 [SMILES: CCOC(=O)C(=O)CC(=O)c1c(C)nc2c(OCc3c(F)cccc3F)cc(C)cn12]

At −40° C., 2.66 ml of 1 N lithium hexamethylsilazane solution in THF (2.66 mmol) were added dropwise to a solution of 800 mg of 1-{8-[(2,6-difluorobenzyl)oxy]-2,6-dimethylimidazo[1,2-a]pyridin-3-yl}ethanone (2.42 mmol) from Example 61A and 493 µl of ethyl oxalate (3.63 mmol) in 80 ml of THF, and the mixture was stirred at −40° C. for 30 min and at room temperature for 1.5 h. 250 ml of water were then added dropwise and the mixture was extracted repeatedly with ethyl acetate. The combined organic phases were washed with saturated aqueous sodium chloride solution, dried with magnesium sulphate, filtered and concentrated. This gave 814 mg (62% of theory; purity 80%) of the title compound.

LC-MS (Method 1): $R_t$=1.25 min
MS (ESpos): m/z=431 (M+H)$^+$

Example 63A

8-[(2,6-Difluorobenzyl)oxy]-2,6-dimethylimidazo[1,2-a]pyridine-3-carbohydrazide

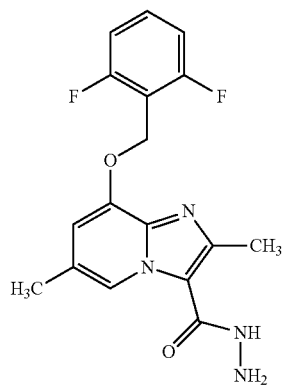

1.474 g (4.09 mmol) of ethyl 8-[(2,6-difluorobenzyl)oxy]-2,6-dimethylimidazo[1,2-a]pyridine-3-carboxylate from Example 15A were initially charged in ethanol (30 ml), and 7.60 ml (195.11 mmol) of hydrazine hydrate (80%) were added. The mixture was stirred at reflux for 2 days, 3.80 ml (97.5 mmol) of hydrazine hydrate (80%) were then added and the mixture was stirred under reflux for 6 h. Water was added and the reaction mixture was cooled in an ice bath. The solid was filtered off, washed thoroughly with water and dried under high vacuum overnight. This gave 998 mg (70% of theory) of the title compound.

LC-MS (Method 1): $R_t$=0.60 min
MS (ESpos): m/z=347 (M+H)$^+$ $^1$H NMR (400 MHz, DMSO-d$_6$) δ=2.31 (s, 3 H), 2.44 (s, 3 H), 4.50-4.54 (m, 2 H), 5.28 (s, 2 H), 6.91 (s, 1 H), 7.23 (t, 2 H), 7.54-7.64 (m, 1 H), 8.38 (s, 1 H), 9.18 (br. s, 1 H).

Example 64A tert-Butyl {4-[2-({8-[(2,6-difluorobenzyl)oxy]-2,6-dimethylimidazo[1,2-a]pyridin-3-yl}carbonyl)hydrazino]-2-methyl-4-oxobutan-2-yl}carbamate

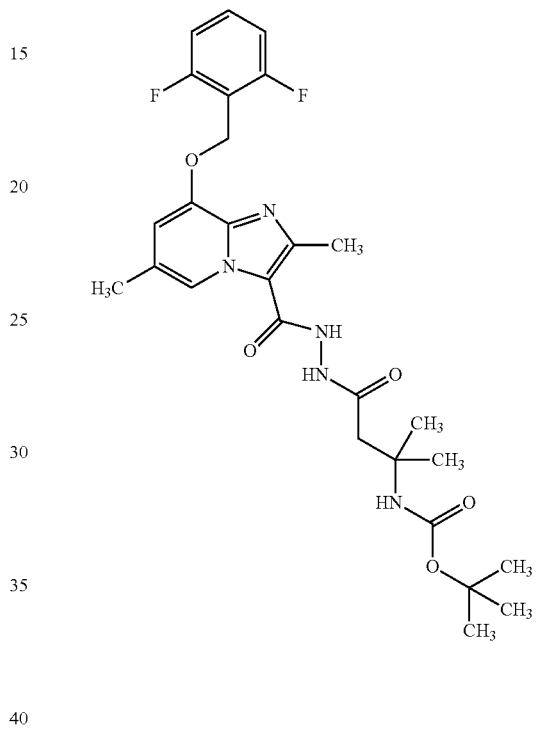

125.5 mg (0.58 mmol) of 3-[(tert-butoxycarbonyl)amino]-3-methylbutanoic acid from Example 63A were initially charged in 4 ml of DMF, 266 mg (1.39 mmol) of EDCI and 212 mg (1.39 mmol) of HOBT were added and the mixture was stirred at RT for 30 min. 200 mg (0.58 mmol) of 8-[(2,6-difluorobenzyl)oxy]-2,6-dimethylimidazo[1,2-a]pyridine-3-carbohydrazide from Example 63A and 0.24 ml (1.39 mmol) of N,N-diisopropylethylamine were then added and the mixture was stirred at RT overnight. The reaction mixture was purified by preparative HPLC (RP18 column; mobile phase: acetonitrile/water gradient with addition of 0.05% formic acid). This gave 128 mg (40% of theory) of the title compound.

LC-MS (Method 1): $R_t$=0.95 min
MS (ESpos): m/z=546 (M+H)$^+$ $^1$H NMR (400 MHz, DMSO-d$_6$) δ=1.34 (s, 6 H), 1.38 (s, 9 H), 2.32 (s, 3 H), 5.29 (s, 2 H), 5.76 (s, 1 H), 6.57 (br. s, 1 H), 6.97 (s, 1 H), 7.24 (t, 2 H), 7.54-7.64 (m, 1 H), 8.37 (br. s, 1 H), 9.74 (br. s, 1 H), 10.00 (br. s, 1 H) [further signals under solvent signals].

Example 65A tert-Butyl[1-(5-{8-[(2,6-difluorobenzyl)oxy]-2,6-dimethylimidazo[1,2-a]pyridin-3-yl}-1,3,4-thiadiazol-2-yl)-2-methylpropan-2-yl]carbamate

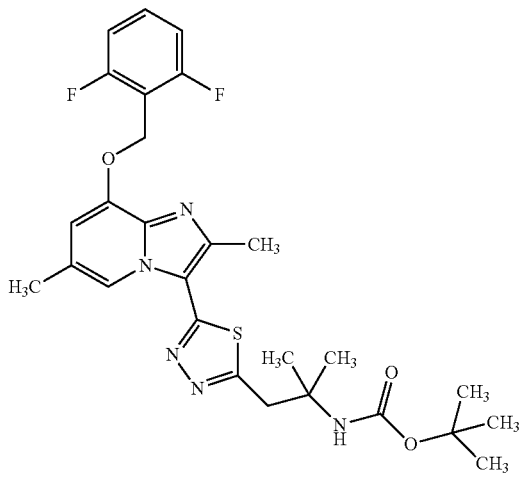 [SMILES: Cc1cc(OCc2c(F)cccc2F)c2nc(C)c(-c3nnc(CC(C)(C)NC(=O)OC(C)(C)C)s3)n2c1]

77 mg (0.19 mmol) of 2,4-bis(4-methoxyphenyl)-1,3,2,4-dithiadiphosphetane-2,4-disulphide [Lawesson's reagent] were added to 126 mg (0.13 mmol; purity 55%) of tert-butyl {4-[2-({8-[(2,6-difluorobenzyl)oxy]-2,6-dimethylimidazo[1,2-a]pyridin-3-yl}carbonyl)hydrazino]-2-methyl-4-oxobutan-2-yl}carbamate from Example 64A in 3 ml of THF, and the mixture was stirred in a microwave oven at 100° C. for 2 h. 77 mg (0.19 mmol) of 2,4-bis(4-methoxyphenyl)-1,3,2,4-dithiadiphosphetane-2,4-disulphide [Lawesson's reagent] were added and the mixture was stirred initially in the microwave at 100° C. for 8 h and then in the microwave at 120° C. for 11 h. The reaction mixture was purified by preparative HPLC (RP18 column; mobile phase: acetonitrile/water gradient with addition of 0.05% formic acid). This gave 12 mg (18% of theory) of the title compound.

LC-MS (Method 1): $R_t$=1.28 min
MS (ESpos): m/z=544 (M+H)$^+$

Example 66A tert-Butyl[1-(5-{8-[(2,6-difluorobenzyl)oxy]-2,6-dimethylimidazo[1,2-a]pyridin-3-yl}-1,3,4-oxadiazol-2-yl)-2-methylpropan-2-yl]carbamate

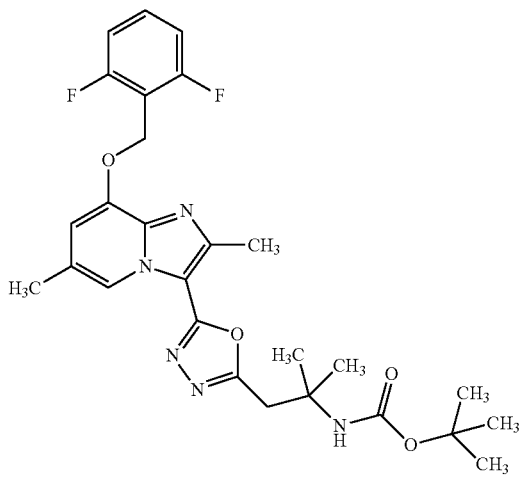 [SMILES: Cc1cc(OCc2c(F)cccc2F)c2nc(C)c(-c3nnc(CC(C)(C)NC(=O)OC(C)(C)C)o3)n2c1]

129 mg (0.24 mmol) of tert-butyl {4-[2-({8-[(2,6-difluorobenzyl)oxy]-2,6-dimethylimidazo[1,2-a]pyridin-3-yl}carbonyl)hydrazino]-2-methyl-4-oxobutan-2-yl}carbamate from Example 64A were initially charged in 4 ml of THF, 169 mg (0.71 mmol) of 3,3,3-triethyl-1-(methoxycarbonyl)diazathian-3-ium-1-ide 2,2-dioxide (Burgess reagent) were added and the reaction mixture was stirred in a microwave oven at 80° C. for 15 min. Concentration under reduced pressure gave 125 mg of the target compound (quantitative yield).

LC-MS (Method 1): $R_t$=1.23 min
MS (ESpos): m/z=528 (M+H)$^+$

Example 67A

8-[(2,6-Difluorobenzyl)oxy]-N-hydroxy-2,6-dimethylimidazo[1,2-a]pyridine-3-carboximidamide

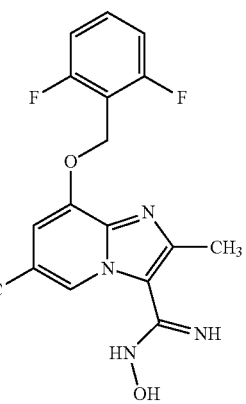

500 mg (1.43 mmol) of 8-[(2,6-difluorobenzyl)oxy]-2,6-dimethylimidazo[1,2-a]pyridine-3-carbonitrile from Example 41A were initially charged in 15 ml of ethanol, 0.43 ml (7.15 mmol) of 50% strength hydroxylamine solution in water was added and the mixture was stirred at RT for 16 h. The reaction mixture was concentrated under reduced pressure and 20 ml of water and 1 ml of ethanol were added to the residue. The solid formed was filtered off, washed with 10 ml of water and dried under high vacuum overnight. This gave 512 mg of the target compound (90% of theory, purity 87%).

LC-MS (Method 1): $R_t$=0.58 min
MS (ESpos): m/z=347 (M+H)$^+$
$^1$H-NMR (400 MHz, DMSO-$d_6$): δ=2.28 (s, 3 H), 2.36 (s, 3 H), 5.27 (s, 2 H), 5.87 (s, 2 H), 6.78 (s, 1 H), 7.19-7.28 (m, 2 H), 7.54-7.64 (m, 1 H), 8.15 (s, 1 H), 9.77 (s, 1 H).

Example 68A tert-Butyl[4-({[(Z)-amino{8-[(2,6-difluorobenzyl)oxy]-2,6-dimethylimidazo[1,2-a]pyridin-3-yl}methylene]amino}oxy)-2-methyl-4-oxobutan-2-yl]carbamate

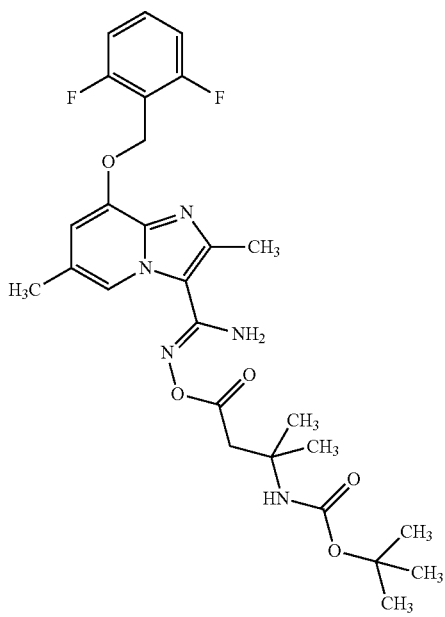 [SMILES: Cc1cc(OCc2c(F)cccc2F)c2nc(C)c(/C(N)=N/OC(=O)CC(C)(C)NC(=O)OC(C)(C)C)n2c1]

121 mg (0.63 mmol) of 1-(3-dimethylaminopropyl)-3-ethylcarbodiimide hydrochloride and 96.4 mg (0.63 mmol) of 1-hydroxy-1H-benzotriazole hydrate were added to 137 mg (0.63 mmol) of Boc-3-amino-3-methylbutyric acid, initially charged in 5 ml DMF, and the mixture was stirred at RT for 30 min. 250 mg (0.63 mmol, 87%) of 8-[(2,6-difluorobenzyl)oxy]-N'-hydroxy-2,6-dimethylimidazo[1,2-a]pyridine-3-carboximidamide from Example 67A were suspended in 3 ml of DMF and added to the reaction mixture, and the mixture was stirred at RT for 48 hours. The mixture was then purified by preparative HPLC (RP18 column, mobile phase: acetonitrile/water gradient with addition of 0.05% formic acid), and the product fractions were concentrated on a rotary evaporator. This gave 168 mg of the target compound (49% of theory).

LC-MS (Method 1): $R_t$=0.99 min

MS (ESpos): m/z=546 (M+H)$^+$ $^1$H-NMR (400 MHz, DMSO-d$_6$): δ=1.32 (s, 6 H), 1.39 (s, 9 H), 2.29 (s, 3 H), 2.39 (s, 3 H), 2.83-2.89 (m, 2 H), 5.26-5.31 (m, 2 H), 6.76-6.81 (m, 2 H), 6.84-6.88 (m, 1 H), 7.19-7.28 (m, 2 H), 7.54-7.64 (m, 1 H), 8.25-8.30 (m, 1 H).

Example 69A tert-Butyl[1-(3-{8-[(2,6-difluorobenzyl)oxy]-2,6-dimethylimidazo[1,2-a]pyridin-3-yl}-1,2,4-oxadiazol-5-yl)-2-methylpropan-2-yl]carbamate

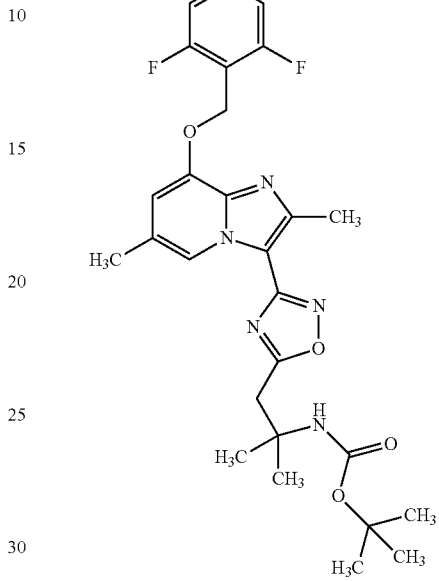

0.092 ml (0.09 mmol) of tetra-n-butylammonium fluoride solution (1 M in THF) were added to 50 mg (0.09 mmol) of tert-butyl[4-({[(Z)-amino{8-[(2,6-difluorobenzyl)oxy]-2,6-dimethylimidazo[1,2-a]pyridin-3-yl}methylene]amino}oxy)-2-methyl-4-oxobutan-2-yl]carbamate from Example 68A in 3 ml of THF, and the mixture was stirred at RT overnight. The reaction mixture was concentrated to dryness and dried under high vacuum. 54 mg of the target compound were obtained. The product was used further without further purification.

LC-MS (Method 1): $R_t$=1.26 min

MS (ESpos): m/z=528 (M+H)$^+$

Example 70A

Benzyl [4-(hydroxyamino)-2-methylpentan-2-yl]carbamate

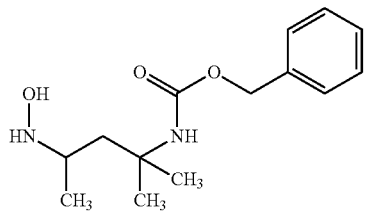 [SMILES: CC(CC(C)(C)NC(=O)OCc1ccccc1)NO]

1.58 ml (25.83 mmol) of 50% strength aqueous hydroxylamine solution were added to 1.20 g (5.17 mmol) of benzyl (1-cyano-2-methylpropan-2-yl)carbamate in 10 ml of ethanol, and the mixture was stirred at RT overnight. Another 1.58 ml (25.83 mmol) of 50% strength aqueous hydroxylamine solution were added and the mixture was stirred for 5 days. The reaction mixture was concentrated and the residue was taken up in 20 ml of ethyl acetate and washed three times with saturated aqueous sodium chloride solution. The organic phase was dried over sodium sulphate, filtered off and concentrated under reduced pressure. This gave 1.39 g of the target compound (quantitative). The product was used further without further purification.

LC-MS (Method 1): $R_t$=0.60 min

MS (ESpos): m/z=266 (M+H)$^+$ $^1$H-NMR (400 MHz, DMSO-d$_6$): δ=1.27 (s, 6 H), 2.24 (s, 2 H), 4.97 (s, 2 H), 5.36 (s, 2 H), 6.89-6.95 (m, 1 H), 7.28-7.40 (m, 5 H), 8.96 (s, 1 H).

Example 71A

Benzyl [(4Z)-4-amino-4-{[({8-[(2,6-difluorobenzyl)oxy]-2,6-dimethylimidazo[1,2-a]pyridin-3-yl}carbonyl)oxy]imino}-2-methylbutan-2-yl]carbamate

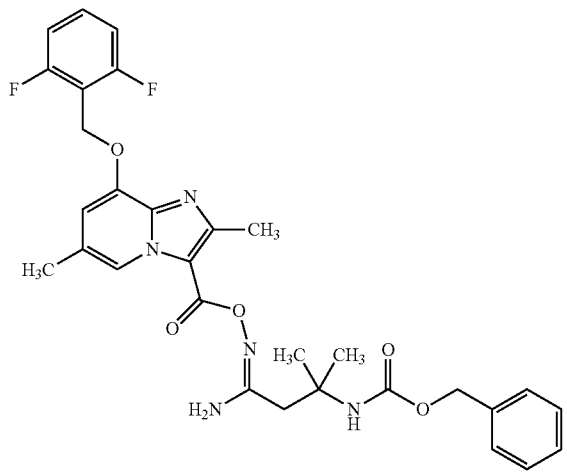 [SMILES: Cc1cc(OCc2c(F)cccc2F)c2nc(C)c(C(=O)O/N=C(\N)CC(C)(C)NC(=O)OCc3ccccc3)n2c1]

180.6 mg (0.9 mmol) of 1-(3-dimethylaminopropyl)-3-ethylcarbodiimide hydrochloride and 144 mg (0.94 mmol) of 1-hydroxy-1H-benzotriazole hydrate were added to 313 mg (0.94 mmol) of 8-[(2,6-difluorobenzyl)oxy]-2,6-dimethylimidazo[1,2-a]pyridine-3-carboxylic acid from Example 16A in 5 ml of DMF, and the reaction mixture was stirred at RT for 30 min. 250 mg (0.94 mmol) of benzyl [4-(hydroxyamino)-2-methylpentan-2-yl]carbamate from Example 70A were suspended in 3 ml of DMF and added dropwise, and the reaction mixture was stirred at RT overnight. The reaction solution was then purified by preparative HPLC (RP18 column, mobile phase: acetonitrile/water gradient with addition of 0.05% formic acid), and the product fractions were concentrated on a rotary evaporator. This gave 317 mg of the target compound (58% of theory).

LC-MS (Method 1): $R_t$=1.15 min

MS (ESpos): m/z=580 (M+H)$^+$ $^1$H-NMR (400 MHz, DMSO-d$_6$): δ=1.37 (s, 6 H), 2.36 (s, 3 H), 2.58 (s, 3 H), 5.01 (s, 2 H), 5.31 (s, 2 H), 6.33 (s, 2 H), 7.06-7.13 (m, 2 H), 7.21-7.27 (m, 2 H), 7.28-7.40 (m, 5 H), 7.55-7.65 (m, 1 H), 8.71 (s, 1 H).

Example 72A

Benzyl [1-(5-{8-[(2,6-difluorobenzyl)oxy]-2,6-dimethylimidazo[1,2-a]pyridin-3-yl}-1,2,4-oxadiazol-3-yl)-2-methylpropan-2-yl]carbamate

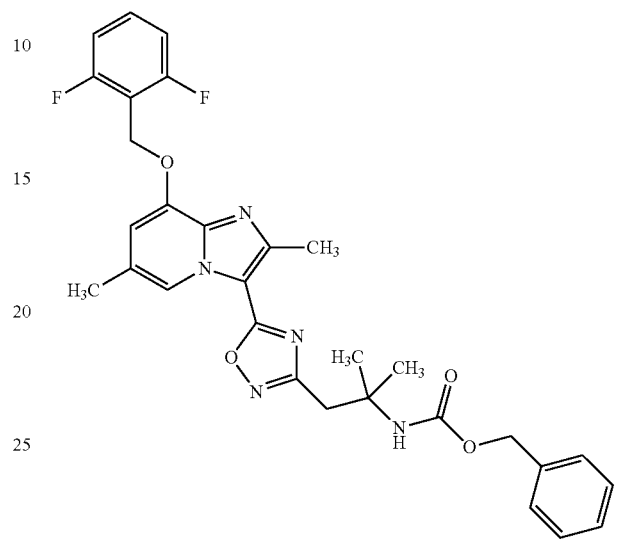

0.09 ml (0.09 mmol) of tetra-n-butylammonium fluoride solution (1 M in THF) were added to 50 mg (0.09 mmol) of benzyl [(4Z)-4-amino-4-{[({8-[(2,6-difluorobenzyl)oxy]-2,6-dimethylimidazo[1,2-a]pyridin-3-yl}carbonyl)oxy]imino}-2-methylbutan-2-yl]carbamate from Example 71A in 3 ml of THF, and the mixture was stirred at RT overnight. The reaction mixture was concentrated under reduced pressure and dried under high vacuum. This gave 58 mg of the target compound (quantitative). The product was used further without further purification.

LC-MS (Method 1): Rt=1.36 min

MS (ESpos): m/z=562 (M+H)$^+$

Example 73A

5-Methyl-1-(2-methyl-2-nitropropyl)-4-(4,4,5,5-tetramethyl-1,3,2-dioxaborolan-2-yl)-1H-pyrazole

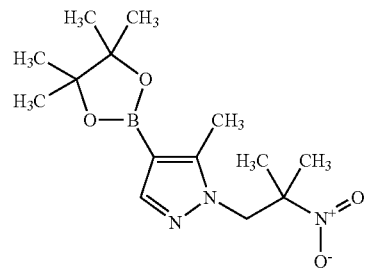 [SMILES: Cc1c(B2OC(C)(C)C(C)(C)O2)cnn1CC(C)(C)[N+](=O)[O-]]

69 mg (1.72 mmol) of 60% sodium hydride were added to 300 mg (1.44 mmol) of 5-methyl-4-(4,4,5,5-tetramethyl-1,3,2-dioxaborolan-2-yl)-1H-pyrazole in 4 ml of THF and 2 ml of DMF, the mixture was stirred at RT for 10 min and 435 mg (1.73 mmol) of 2-methyl-2-nitropropyl trifluoromethanesulphonate from Example 51A were added. The reaction mixture was then stirred at RT for 5 days. 29 mg (0.72 mmol) of 60% sodium hydride were then added, the mixture was stirred at RT for 5 min and 181 mg (0.72 mmol) of 2-methyl-2-nitropropyl trifluoromethanesulphonate from Example 51A were then added. The mixture was stirred at RT overnight. 1 ml of saturated aqueous ammonium chloride solution was added to the reaction mixture. Acetonitrile and water were added and the mixture was purified by preparative HPLC (RP18 column, mobile phase: acetonitrile/water gradient with addition of 0.05% formic acid). The product fractions were concentrated and dried under high vacuum. This gave 174 mg of the target compound (39% of theory).

LC-MS (Method 1): $R_t$=1.10 min
MS (ESpos): m/z=310 (M+H)$^+$
$^1$H-NMR (400 MHz, DMSO-d$_6$): δ=1.24 (s, 18 H), 2.18 (s, 3 H), 4.58 (s, 2 H), 7.70 (s, 1 H).

Example 74A

8-[(2,6-Difluorobenzyl)oxy]-2,6-dimethyl-3-[3-methyl-1-(2-methyl-2-nitropropyl)-1H-pyrazol-4-yl]imidazo[1,2-a]pyridine

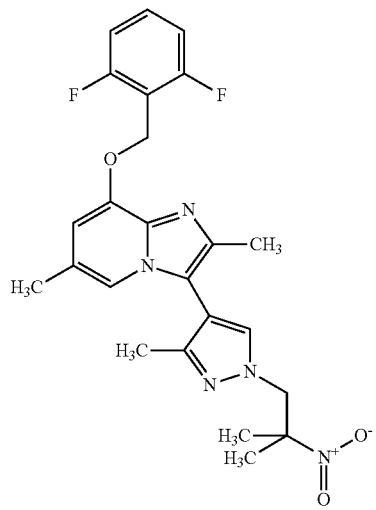 [SMILES: Cc1cc(OCc2c(F)cccc2F)c2nc(C)c(-c3cn(CC(C)(C)[N+](=O)[O-])nc3C)n2c1]

Under argon, 30 mg (0.04 mmol) of bis(diphenylphosphino)ferrocenepalladium(II) chloride/dichloromethane complex and 2 ml (2.0 mmol) of aqueous 1 M potassium carbonate solution were added to 186 mg (0.51 mmol) of 3-bromo-8-[(2,6-difluorobenzyl)oxy]-2,6-dimethylimidazo[1,2-a]pyridine from Example 30A and 172 mg (0.56 mmol) of 5-methyl-1-(2-methyl-2-nitropropyl)-4-(4,4,5,5-tetramethyl-1,3,2-dioxaborolan-2-yl)-1H-pyrazole from Example 73A in 10 ml of acetonitrile, and the mixture was heated at 90° C. overnight. The mixture was filtered, 3 drops of water were added to the filtrate and the filtrate was purified by preparative HPLC (RP18 column, mobile phase: acetonitrile/water gradient with addition of 0.05% formic acid). The product fractions were concentrated on a rotary evaporator. This gave 74 mg of the target compound (31% of theory).

LC-MS (Method 1): $R_t$=0.92 min
MS (ESpos): m/z=470 (M+H)$^+$
$^1$H-NMR (400 MHz, DMSO-d$_6$): δ=1.54-1.61 (m, 6 H), 1.96 (s, 3 H), 2.11-2.16 (m, 3 H), 2.25 (s, 3 H), 4.66-4.71 (m, 2 H), 5.28 (s, 2 H), 6.74 (s, 1 H), 7.24 (m, 2 H), 7.29-7.33 (m, 1 H), 7.55-7.64 (m, 1 H), 7.82 (s, 1 H).

Example 75A

8-[(2,6-Difluorobenzyl)oxy]-2,6-dimethyl-3-[1-(2-methyl-2-nitropropyl)-1H-1,2,4-triazol-3-yl]imidazo[1,2-a]pyridine

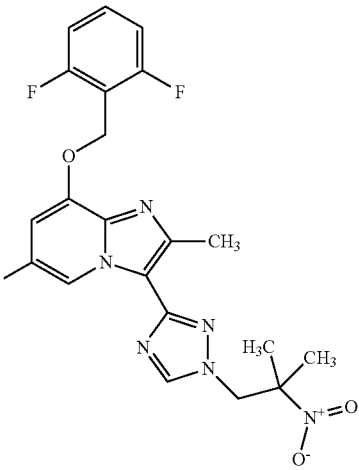

27 mg of 60% sodium hydride (0.68 mmol) were added to 200 mg (0.56 mmol) of 8-[(2,6-difluorobenzyl)oxy]-2,6-dimethyl-3-(1H-1,2,4-triazol-3-yl)imidazo[1,2-a]pyridine from Example 128 in 8 ml of THF and 2 ml of DMF. The reaction mixture was stirred at RT for 10 min. 424 mg (1.69 mmol) of 2-methyl-2-nitropropyl trifluoromethanesulphonate from Example 51A were then added, and the reaction was stirred at RT for 30 min. Saturated aqueous ammonium chloride solution and 2 ml of water were added to the reaction mixture and the THF was distilled off on a rotary evaporator. 5 ml of acetonitrile were added and the solid formed was filtered off, washed with acetonitrile and dried under high vacuum. The filtrate was concentrated and stirred in 10 ml of water and 2 ml of acetonitrile, and the residue was filtered off, washed with acetonitrile and dried under high vacuum. This gave 287 mg of the target compound (quantitative).

LC-MS (Method 1): $R_t$=0.86 min
MS (ESpos): m/z=457 (M+H)$^+$
$^1$H-NMR (400 MHz, DMSO-d$_6$): δ=1.59 (s, 6 H), 2.43 (s, 3 H), 2.64 (s, 3 H), 4.95 (s, 2 H), 5.38 (s, 2 H), 7.21-7.30 (m, 3 H), 7.61 (quin, 1 H), 8.75-8.86 (m, 2 H).

Example 76A

8-[(2,6-Difluorobenzyl)oxy]-2-methyl-3-[(trimethylsilyl)ethinyl]imidazo[1,2-a]pyridine

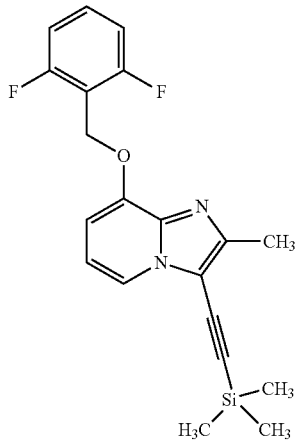 [SMILES: Cc1nc2c(OCc3c(F)cccc3F)cccn2c1C#C[Si](C)(C)C]

2 ml (14.15 mmol) of trimethylsilylacetylene were slowly added dropwise to 2.60 g (7.08 mmol, purity 96%) of 3-bromo-8-[(2,6-difluorobenzyl)oxy]-2-methylimidazo[1,2-a]pyridine from Example 28A, 202 mg (1.06 mmol) of copper(I) iodide, 0.50 g (0.71 mmol) of bis(triphenylphosphine)palladium(II) chloride and 3.12 ml (22.41 mmol) of triethylamine in 3.1 ml of THF, and the reaction mixture was stirred under argon at reflux for 8 hours. The mixture was concentrated and the residue was taken up in dichloromethane and purified by silica gel chromatography (mobile phase: dichloromethane). The product fractions were concentrated and dried under high vacuum. 1.46 g of the target compound were obtained (56% of theory).

LC-MS (Method 1): $R_t$=1.23 min
MS (ESpos): m/z=371 (M+H)$^+$
$^1$H-NMR (400 MHz, DMSO-d$_6$): δ=0.29 (s, 9 H), 2.34 (s, 3 H), 5.30 (s, 2 H), 6.93-7.03 (m, 2 H), 7.23 (quin, 2 H), 7.54-7.63 (m, 1 H), 7.90-7.97 (m, 1 H).

Example 77A

8-[(2,6-Difluorobenzyl)oxy]-3-ethynyl-2-methylimidazo[1,2-a]pyridine

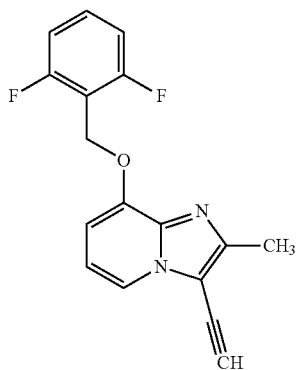 [SMILES: C#Cc1c(C)nc2c(OCc3c(F)cccc3F)cccn12]

1.46 g (3.93 mmol) of 8-[(2,6-difluorobenzyl)oxy]-2-methyl-3-[(trimethylsilyl)ethinyl]imidazo[1,2-a]pyridine from Example 76A and 54 mg (0.39 mmol) of potassium carbonate in 20 ml of methanol were stirred under argon at RT for 30 min. The reaction mixture was then filtered, the residue was washed with methanol, and the filtrate was concentrated and dried under high vacuum. 1.31 g of the target compound were obtained (84% of theory, 76% purity).

LC-MS (Method 1): $R_t$=0.86 min
MS (ESpos): m/z=299 (M+H)$^+$
$^1$H-NMR (400 MHz, DMSO-d$_6$): δ=2.30 (s, 1 H), 2.35 (s, 3 H), 5.30 (s, 2 H), 6.93-7.02 (m, 2 H), 7.23 (quin, 2 H), 7.54-7.64 (m, 1 H), 8.00 (dd, 1 H).

Example 78A

Pyrimidine-2-carbohydrazide

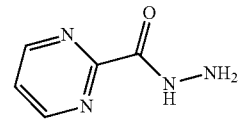

The title compound can be prepared using the following procedures: 1.) WOCKHARDT RESEARCH CENTRE; TRIVEDI, Bharat Kalidas; PATEL, Mahesh Vithalbhai, WO2010/136971 A1, 2010 or 2.) GLAXO GROUP LIMITED; DEAN, David Kenneth; MUNOZ-MURIEDAS, Jorge; SIME, Mairi; STEADMAN, Jon Graham Anthony; THEWLIS, Rachel Elizabeth Anne; TRANI, Giancarlo; WALTER, Daryl Simon, WO2010/125102 A1, 2010.

Example 79A tert-Butyl (6-{8-[(2,6-difluorobenzyl)oxy]-2,6-dimethylimidazo[1,2-a]pyridin-3-yl}-2-methyl-4,6-dioxohexan-2-yl)carbamate

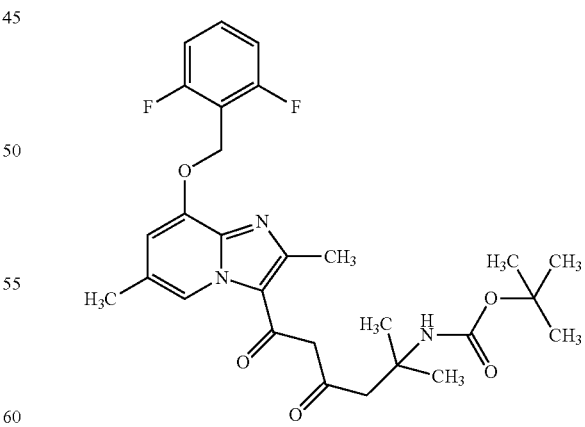

A mixture of 98.6 mg (0.454 mmol) of 3-[(tert-butoxycarbonyl)amino]-3-methylbutanoic acid (CAS 129765-95-

3) and 73.6 mg (0.454 mmol) of 1,1'-carbonyldiimidazole in 2 ml of dry THF was stirred at room temperature for 3 h. The solution obtained was added dropwise to a freshly prepared solution of 150 mg (0.454 mmol) of 1-{8-[(2,6-difluorobenzyl)oxy]-2,6-dimethylimidazo[1,2-a]pyridin-3-yl}ethanone Example 60A and 0.454 ml (0.454 mmol) of lithium hexamethyldisilazide (1M in tetrahydrofuran) in 5 ml of dry tetrahydrofuran which was stirred under argon at −40° C. After 30 min at −40° C. and 30 min at room temperature, the reaction mixture was partitioned between water (20 ml) and ethyl acetate (30 ml). The phases were separated and the aqueous phase was additionally extracted with ethyl acetate (2×15 ml). The combined organic phases were concentrated under reduced pressure, giving 200 mg of crude material comprising the target product in a yield of 8.4% as by-product in a mixture with starting material. Used in the next step without further purification.

LC-MS (Method 23): $R_t$=1.39 min; m/z=530.36 (M+H)$^+$

Example 80A tert-Butyl[1-(3-{8-[(2,6-difluorobenzyl)oxy]-2,6-dimethylimidazo[1,2-a]pyridin-3-yl}-1H-pyrazol-5-yl)-2-methylpropan-2-yl]carbamate

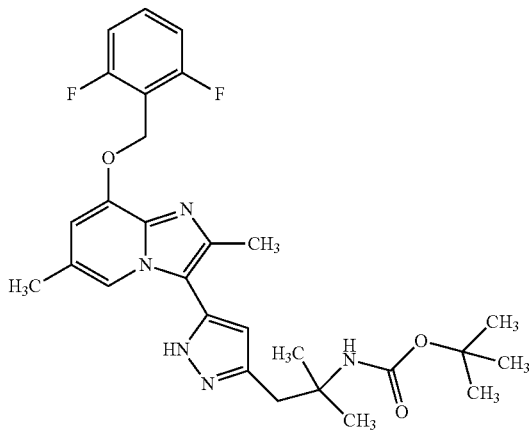 [SMILES: Cc1cc(OCc2c(F)cccc2F)c2nc(C)c(-c3cc(CC(C)(C)NC(=O)OC(C)(C)C)n[nH]3)n2c1]

Under microwave irradiation, a mixture of 200 mg (0.032 mmol, 8.4% yield in a mixture) of tert-butyl (6-{8-[(2,6-difluorobenzyl)oxy]-2,6-dimethylimidazo[1,2-a]pyridin-3-yl}-2-methyl-4,6-dioxohexan-2-yl)carbamate Example 79A and 21.7 mg (0.317 mmol) of hydrazine monohydrochloride in 5 ml of ethanol was heated at 120° C. for 30 min. The reaction mixture was cooled to room temperature, the solvent was evaporated under reduced pressure and the residue was partitioned between ethyl acetate (15 ml) and water (10 ml). The phases were separated and the organic phases were concentrated under reduced pressure, giving 120 mg of crude material comprising the target product in a yield of 8% as by-product in a mixture with starting material from the previous step. The crude mixture was used without further purification.

LC-MS (Method 23): $R_t$=1.00 min; m/z=526.38 (M+H)$^+$

Working Examples

Example 1

3-(1-Benzyl-1H-pyrazol-4-yl)-8-[(2,6-difluorobenzyl)oxy]-2-methylimidazo[1,2-a]pyridine

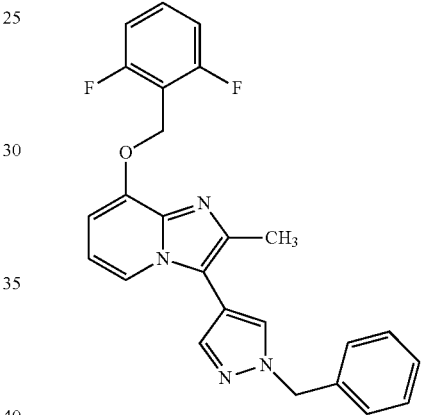

35 mg of 3-bromo-8-[(2,6-difluorobenzyl)oxy]-2-methylimidazo[1,2-a]pyridine (Example 28A), 5.8 mg of tetrakis(triphenylphosphine)palladium(0) (0.005 mmol, 0.05 equivalent), 21 mg of sodium carbonate (0.2 mmol, 2 equivalents) and 0.2 ml of water were added to 28 mg of 1-benzyl-4-(4,4,5,5-tetramethyl-1,3,2-dioxaborolan-2-yl)-1H-pyrazole (0.1 mmol, 1 equivalent) in 0.6 ml of 1,4-dioxane, and the mixture was shaken at 85° C. overnight. After the reaction had ended, the reaction solution was filtered, the 1,4-dioxane was removed under reduced pressure and the residue was dissolved in a little DMSO and purified by preparative HPLC (Method 11). This gave 0.6 mg (1.4% of theory) of the title compound.

LC-MS (Method 12): $R_t$=0.90 min

MS (ESpos): m/z=431 (M+H)$^+$

Analogously to Example 1, the example compounds shown in Table 1 were prepared by reacting 3-bromo-8-[(2,6-difluorobenzyl)oxy]-2-methylimidazo[1,2-a]pyridine (Example 28A) with the appropriate boronic acids or boronic esters.

TABLE 1

| Example No. | IUPAC name Structure (Yield) | Analytical data |
|---|---|---|
| 2 | 1-(3-{8-[(2,6-difluorobenzyl)oxy]-2-methylimidazo[1,2-a]pyridin-3-yl}phenyl)ethanone<br><br>(35% of theory, purity 82%) | LC-MS (Method 12): $R_t$ = 0.87 min<br>MS (ESpos): m/z = 393.2 (M + H)$^+$ |
| 3 | 8-[(2,6-difluorobenzyl)oxy]-2-methyl-3-(2-methylpyridin-4-yl)imidazo[1,2-a]pyridine<br><br>(21% of theory, purity 77%) | LC-MS (Method 12): $R_t$ = 0.77 min<br>MS (ESpos): m/z = 366.1 (M + H)$^+$ |
| 4 | N-(3-{8-[(2,6-difluorobenzyl)oxy]-2-methylimidazo[1,2-a]pyridin-3-yl}phenyl)acetamide<br><br>(5% of theory) | LC-MS (Method 12): $R_t$ = 0.83 min<br>MS (ESpos): m/z = 408.1 (M + H)$^+$ |

TABLE 1-continued
| Example No. | IUPAC name Structure (Yield) | Analytical data |
|---|---|---|
| 5 | N-(3-{8-[(2,6-difluorobenzyl)oxy]-2-methylimidazo[1,2-a]pyridin-3-yl}benzyl)-N-methylethanamine<br>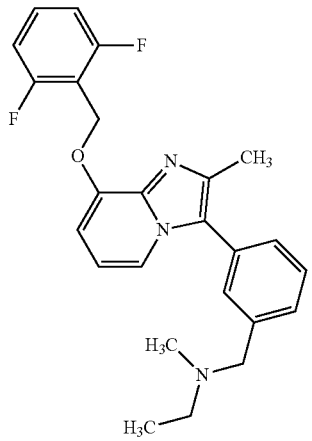<br>(31% of theory) [1] | LC-MS (Method 12): $R_t$ = 0.64 min<br>MS (ESpos): m/z = 422.3 (M + H)$^+$ |
| 6 | 8-[(2,6-difluorobenzyl)oxy]-3-[3-(ethylsulphonyl)phenyl]-2-methylimidazo[1,2-a]pyridine<br>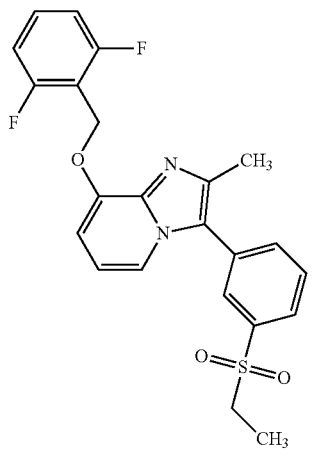<br>(32% of theory, purity 83%) | LC-MS (Method 12): $R_t$ = 0.85 min<br>MS (ESpos): m/z = 443.1 (M + H)$^+$ |

TABLE 1-continued

| Example No. | IUPAC name Structure (Yield) | Analytical data |
|---|---|---|
|  | 3-{8-[(2,6-difluorobenzyl)oxy]-2-methylimidazo[1,2-a]pyridin-3-yl}benzamide 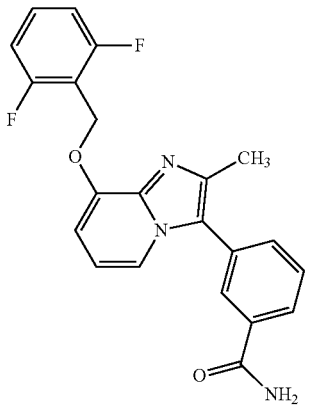 The boronic acid pinacol ester was used. (27% of theory) | LC-MS (Method 12): $R_t$ = 0.78 min<br>MS (ESpos): m/z = 394.1 (M + H)$^+$ |
| 8 | 3-{8-[(2,6-difluorobenzyl)oxy]-2-methylimidazo[1,2-a]pyridin-3-yl}phenol 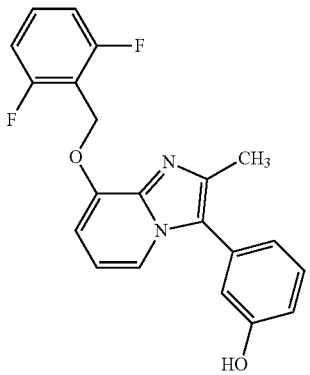 (33% of theory, purity 89%) | LC-MS (Method 12): $R_t$ = 0.83 min<br>MS (ESpos): m/z = 367.1 (M + H)$^+$ |
| 9 | N-cyclopropyl-4-{8-[(2,6-difluorobenzyl)oxy]-2-methylimidazo[1,2-a]pyridin-3-yl}benzamide 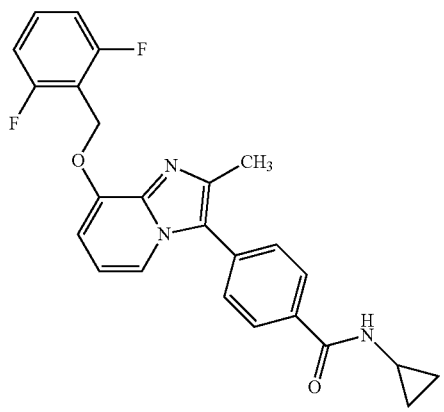 (12% of theory) | LC-MS (Method 12): $R_t$ = 0.84 min<br>MS (ESpos): m/z = 434.2 (M + H)$^+$ |

TABLE 1-continued

| Example No. | IUPAC name Structure (Yield) | Analytical data |
|---|---|---|
| 10 | 8-[(2,6-difluorobenzyl)oxy]-3-(4-ethoxyphenyl)-2-methylimidazo[1,2-a]pyridine<br>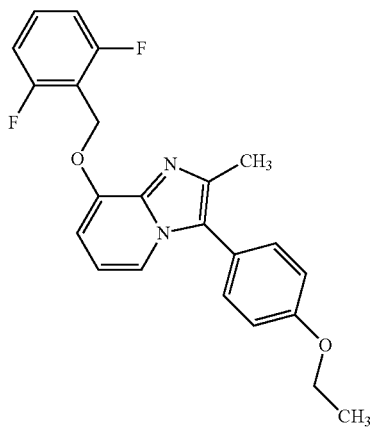<br>(45% of theory, purity 80%) | LC-MS (Method 12): $R_t$ = 0.93 min<br>MS (ESpos): m/z = 395.2 (M + H)$^+$ |
| 11 | 8-[(2,6-difluorobenzyl)oxy]-2-methyl-3-(1-methyl-1H-pyrazol-5-yl)imidazo[1,2-a]pyridine<br>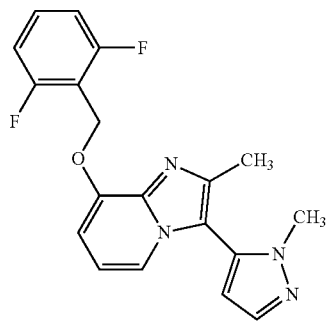<br>(18% of theory) | LC-MS (Method 12): $R_t$ = 0.94 min<br>MS (ESpos): m/z = 355.0 (M + H)$^+$ |
| 12 | 3-(6-chloro-5-methylpyridin-3-yl)-8-[(2,6-difluorobenzyl)oxy]-2-methylimidazo[1,2-a]pyridine<br>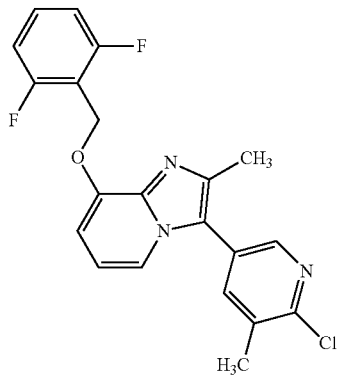<br>(4% of theory, purity 84%) | LC-MS (Method 12): $R_t$ = 0.94 min<br>MS (ESpos): m/z = 400.1 (M + H)$^+$ |

TABLE 1-continued

| Example No. | IUPAC name Structure (Yield) | Analytical data |
|---|---|---|
| 13 | 3-(3-bromophenyl)-8-[(2,6-difluorobenzyl)oxy]-2-methylimidazo[1,2-a]pyridine<br>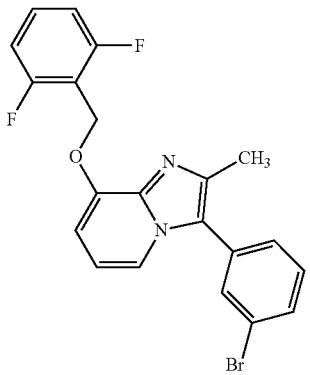<br>(12% of theory) | LC-MS (Method 12): $R_t$ = 0.86 min<br>MS (ESpos): m/z = 430.0 (M + H)$^+$ |
| 14 | 8-[(2,6-difluorobenzyl)oxy]-2-methyl-3-(3-thienyl)imidazo[1,2-a]pyridine<br>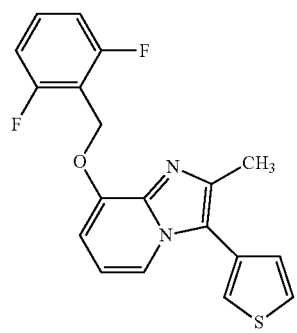<br>The boronic acid pinacol ester was used.<br>(26% of theory, purity 80%) | LC-MS (Method 12): $R_t$ = 0.87 min<br>MS (ESpos): m/z = 357.0 (M + H)$^+$ |
| 15 | 8-[(2,6-difluorobenzyl)oxy]-2-methyl-3-[3-(pyrrolidin-1-ylmethyl)phenyl]imidazo[1,2-a]pyridine<br>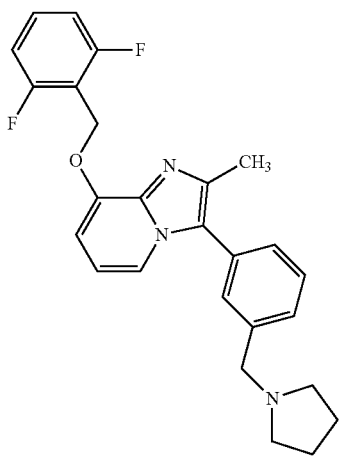<br>(11% of theory) [2] | LC-MS (Method 12): $R_t$ = 0.65 min<br>MS (ESpos): m/z = 434.3 (M + H)$^+$ |

TABLE 1-continued

| Example No. | IUPAC name Structure (Yield) | Analytical data |
|---|---|---|
| 16 | 8-[(2,6-difluorobenzyl)oxy]-3-(4-fluorophenyl)-2-methylimidazo[1,2-a]pyridine<br>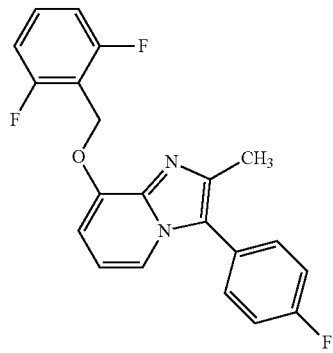<br>(31% of theory) | LC-MS (Method 12): $R_t$ = 0.89 min<br>MS (ESpos): m/z = 369.1 (M + H)$^+$ |
| 17 | 4-{8-[(2,6-difluorobenzyl)oxy]-2-methylimidazo[1,2-a]pyridin-3-yl}benzonitrile<br>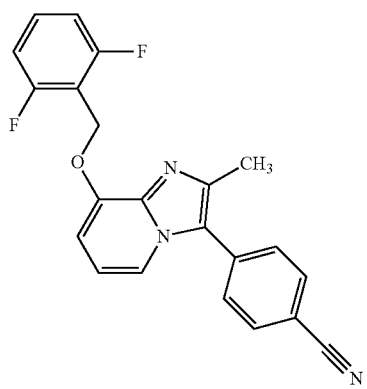<br>The boronic acid pinacol ester was used.<br>(6% of theory, purity 87%) | LC-MS (Method 12): $R_t$ = 0.89 min<br>MS (ESpos): m/z = 376.1 (M + H)$^+$ |
| 18 | Ethyl 3-{8-[(2,6-difluorobenzyl)oxy]-2-methylimidazo[1,2-a]pyridin-3-yl}benzoate<br>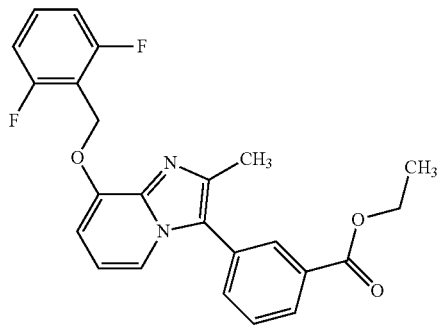<br>(39% of theory, purity 82%) | LC-MS (Method 12): $R_t$ = 0.93 min<br>MS (ESpos): m/z = 423.2 (M + H)$^+$ |

TABLE 1-continued

| Example No. | IUPAC name Structure (Yield) | Analytical data |
|---|---|---|
| 19 | 3-{8-[(2,6-difluorobenzyl)oxy]-2-methylimidazo[1,2-a]pyridin-3-yl}quinoline<br>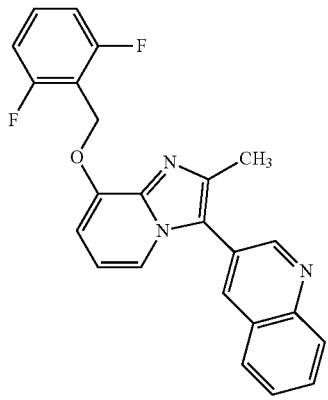<br>(16% of theory, purity 77%) | LC-MS (Method 12): $R_t$ = 0.93 min<br>MS (ESpos): m/z = 423.2 (M + H)$^+$ |
| 20 | 8-[(2,6-difluorobenzyl)oxy]-2-methyl-3-(5-methyl-2-furyl)imidazo[1,2-a]pyridine<br>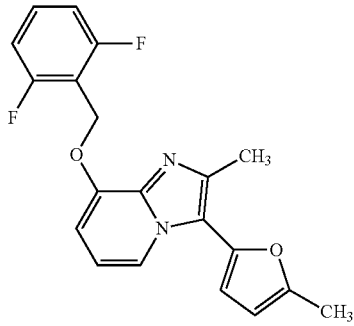<br>(26% of theory, purity 84%) [3] | LC-MS (Method 12): $R_t$ = 0.94 min<br>MS (ESpos): m/z = 353.0/356.0 (M + H)$^+$ |
| 21 | 8-[(2,6-difluorobenzyl)oxy]-2-methyl-3-[3-(morpholin-4-ylmethyl)phenyl]imidazo[1,2-a]pyridine<br>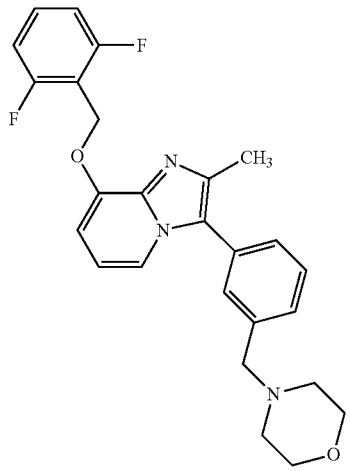<br>(32% of theory) | LC-MS (Method 12): $R_t$ = 0.96 min<br>MS (ESpos): m/z = 419.1 (M + H)$^+$ |

TABLE 1-continued
| Example No. | IUPAC name<br>Structure<br>(Yield) | Analytical data |
|---|---|---|
| 22 | 8-[(2,6-difluorobenzyl)oxy]-2-methyl-3-(6-propoxypyridin-3-yl)imidazo[1,2-a]pyridine | LC-MS (Method 12): $R_t$ = 0.94 min<br>MS (ESpos): m/z = 410.1(M + H)⁺ |
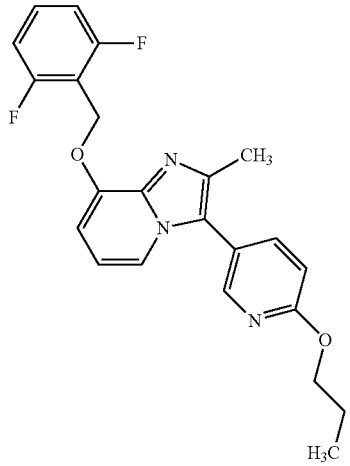
(4% of theory)
| 23 | 5-{8-[(2,6-difluorobenzyl)oxy]-2-methylimidazo[1,2-a]pyridin-3-yl}-2-benzofuran-1(3H)-one | LC-MS (Method 12): $R_t$ = 0.85 min<br>MS (ESpos): m/z = 407.0 (M + H)⁺ |
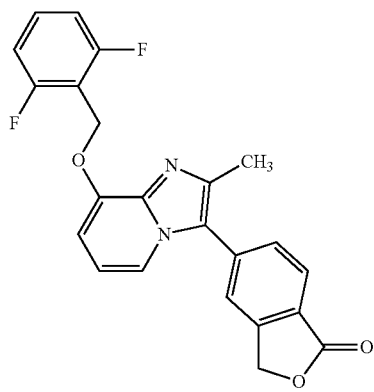
The boronic acid pinacol ester was used.
(8% of theory) [4]

TABLE 1-continued
| Example No. | IUPAC name Structure (Yield) | Analytical data |
|---|---|---|
| 24 | 8-[(2,6-difluorobenzyl)oxy]-2-methyl-3-[3-(trifluoromethoxy)phenyl]imidazo[1,2-a]pyridine<br>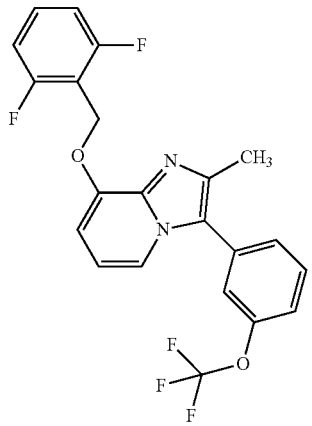<br>(20% of theory, purity 78%) | LC-MS (Method 12): $R_t$ = 0.97 min<br>MS (ESpos): m/z = 435.0 (M + H)$^+$ |
| 25 | 8-[(2,6-difluorobenzyl)oxy]-3-(4-methoxyphenyl)-2-methylimidazo[1,2-a]pyridine<br>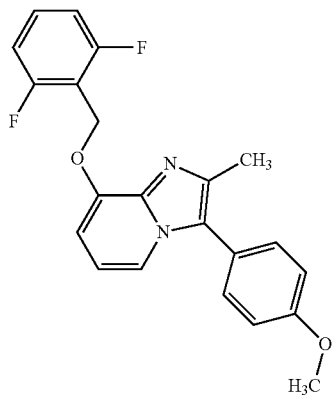<br>(4% of theory, purity 84%) | LC-MS (Method 12): $R_t$ = 0.89 min<br>MS (ESpos): m/z = 400.1 (M + H)$^+$ |

TABLE 1-continued

| Example No. | IUPAC name Structure (Yield) | Analytical data |
|---|---|---|
| 26 | 1-(4-{8-[(2,6-difluorobenzyl)oxy]-2-methylimidazo[1,2-a]pyridin-3-yl}phenyl)-N,N-dimethylmethanamine 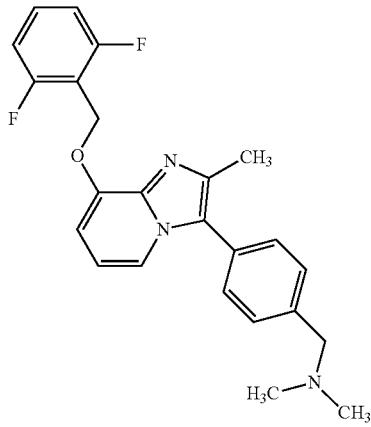 (39% of theory, purity 82%) [5] | LC-MS (Method 12): $R_t$ = 0.90 min<br>MS (ESpos): m/z = 381.2 (M + H)$^+$ |
| 27 | N-(5-{8-[(2,6-difluorobenzyl)oxy]-2-methylimidazo[1,2-a]pyridin-3-yl}-2-methoxybenzyl)-2-methoxy-N-methylethanamine 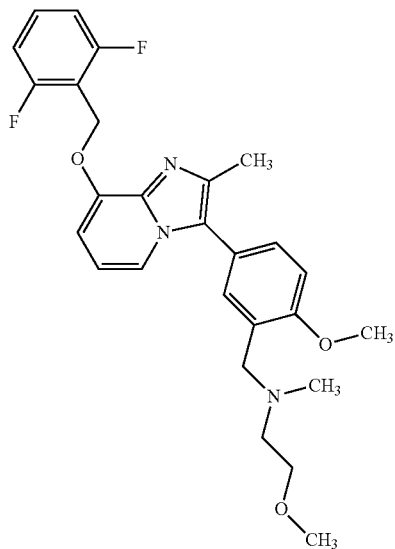 (33% of theory) [6] | LC-MS (Method 12): $R_t$ = 0.67 min<br>MS (ESpos): m/z = 482.3 (M + H)$^+$ |

TABLE 1-continued

| Example No. | IUPAC name Structure (Yield) | Analytical data |
|---|---|---|
| 28 | N-(3-{8-[(2,6-difluorobenzyl)oxy]-2-methylimidazo[1,2-a]pyridin-3-yl}-4-methoxybenzyl)-N-methylethanamine<br>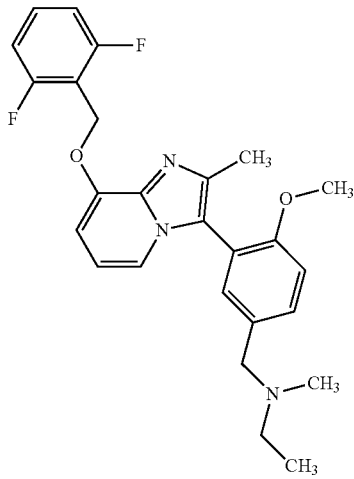<br>(25% of theory) [7] | LC-MS (Method 12): $R_t$ = 0.65 min<br>MS (ESpos): m/z = 452.2 $(M + H)^+$ |
| 29 | 8-[(2,6-difluorobenzyl)oxy]-2-methyl-3-(pyridin-4-yl)imidazo[1,2-a]pyridine<br>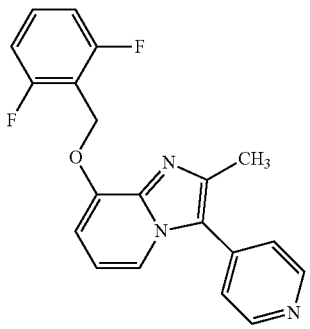<br>(13% of theory, purity 81%) | LC-MS (Method 12): $R_t$ = 0.79 min<br>MS (ESpos): m/z = 352.2 $(M + H)^+$ |
| 30 | 8-[(2,6-difluorobenzyl)oxy]-2-methyl-3-(4-methylphenyl)imidazo[1,2-a]pyridine<br>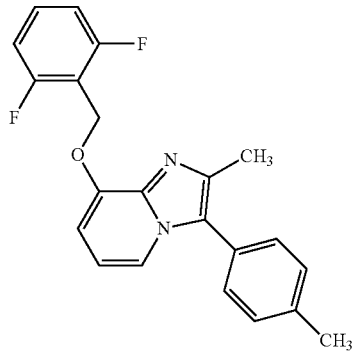<br>(27% of theory) | LC-MS (Method 12): $R_t$ = 0.92 min<br>MS (ESpos): m/z = 365.1 $(M + H)^+$ |

TABLE 1-continued

| Example No. | IUPAC name Structure (Yield) | Analytical data |
|---|---|---|
| 31 | 8-[(2,6-difluorobenzyl)oxy]-2-methyl-3-(4-phenoxyphenyl)imidazo[1,2-a]pyridine 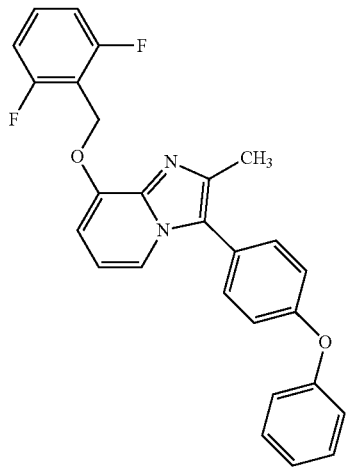 (7% of theory) | LC-MS (Method 12): $R_t$ = 1.01 min MS (ESpos): m/z = 443.2 (M + H)$^+$ |
| 32 | 8-[(2,6-difluorobenzyl)oxy]-2-methyl-3-(4-vinylphenyl)imidazo[1,2-a]pyridine 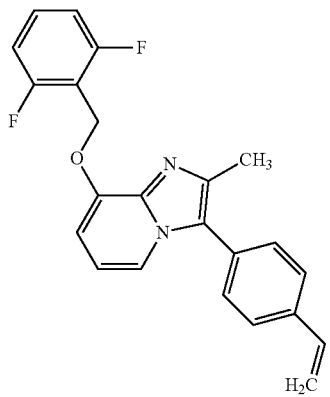 (3% of theory) | LC-MS (Method 12): $R_t$ = 0.95 min MS (ESpos): m/z = 377.1 (M + H)$^+$ |
| 33 | 8-[(2,6-difluorobenzyl)oxy]-2-methyl-3-[3-(methylsulphanyl)phenyl]imidazo[1,2-a]pyridine 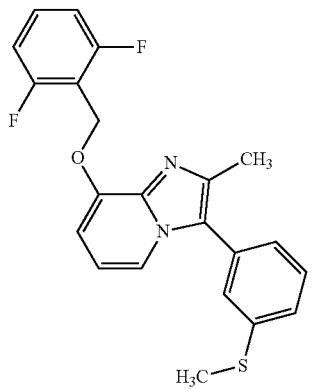 (45% of theory) | LC-MS (Method 12): $R_t$ = 0.93 min MS (ESpos): m/z = 397.1 (M + H)$^+$ |

TABLE 1-continued

| Example No. | IUPAC name Structure (Yield) | Analytical data |
|---|---|---|
| 34 | 3-(3-chlorophenyl)-8-[(2,6-difluorobenzyl)oxy]-2-methylimidazo[1,2-a]pyridine 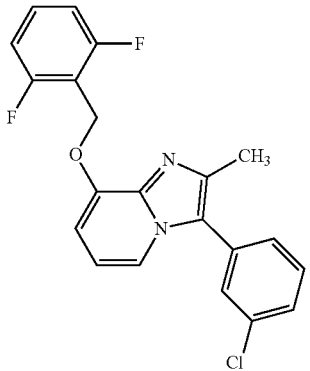 (29% of theory, purity 77%) | LC-MS (Method 12): $R_t$ = 0.93 min<br>MS (ESpos): m/z = 385.1 (M + H)$^+$ |
| 35 | 3-(1-benzothiophen-3-yl)-8-[(2,6-difluorobenzyl)oxy]-2-methylimidazo[1,2-a]pyridine 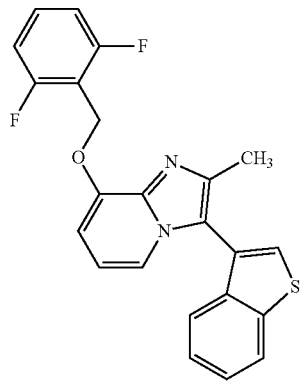 (10% of theory) | LC-MS (Method 12): $R_t$ = 0.94 min<br>MS (ESpos): m/z = 407.1 (M + H)$^+$ |
| 36 | 8-[(2,6-difluorobenzyl)oxy]-2-methyl-3-(1-methyl-1H-indol-5-yl)imidazo[1,2-a]pyridine 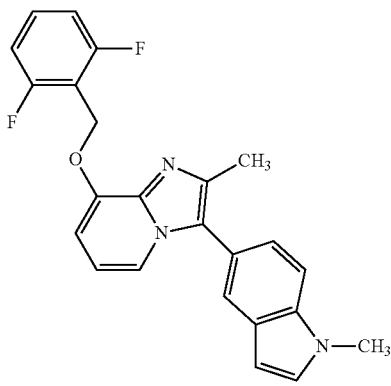 The boronic acid pinacol ester was used.<br>(30% of theory) | LC-MS (Method 12): $R_t$ = 0.94 min<br>MS (ESpos): m/z = 404.1 (M + H)$^+$ |

TABLE 1-continued

| Example No. | IUPAC name Structure (Yield) | Analytical data |
|---|---|---|
| 37 | 8-[(2,6-difluorobenzyl)oxy]-3-(2,3-dihydro-1,4-benzodioxin-6-yl)-2-methylimidazo[1,2-a]pyridine<br>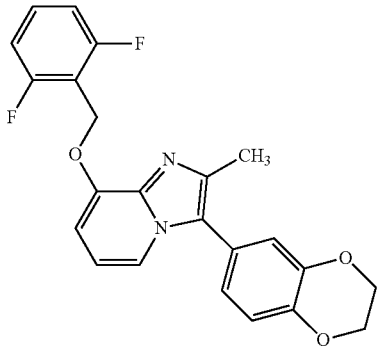<br>(28% of theory, purity 86%) | LC-MS (Method 12): $R_t$ = 0.90 min<br>MS (ESpos): m/z = 409.1 (M + H)$^+$ |
| 38 | 8-[(2,6-difluorobenzyl)oxy]-2-methyl-3-[3-(piperidin-1-yl)phenyl]imidazo[1,2-a]pyridine<br>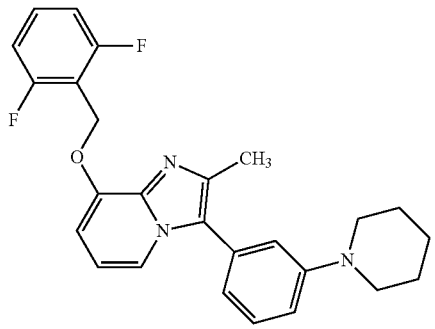<br>(31% of theory, purity 93%) [8] | LC-MS (Method 12): $R_t$ = 0.92 min<br>MS (ESpos): m/z = 434.2 (M + H)$^+$ |
| 39 | 8-[(2,6-difluorobenzyl)oxy]-3-[3-fluoro-4-(morpholin-4-ylmethyl)phenyl]-2-methylimidazo[1,2-a]pyridine<br>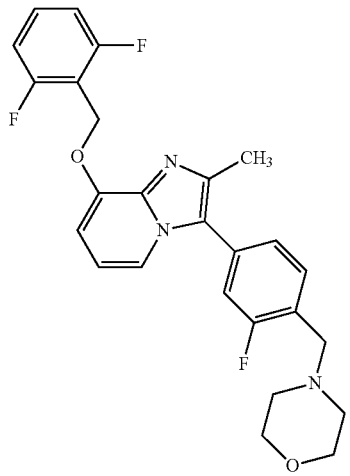<br>(42% of theory) [9] | LC-MS (Method 12): $R_t$ = 0.65 min<br>MS (ESpos): m/z = 468.2 (M + H)$^+$ |

TABLE 1-continued
| Example No. | IUPAC name Structure (Yield) | Analytical data |
|---|---|---|
| 40 | 4-{8-[(2,6-difluorobenzyl)oxy]-2-methylimidazo[1,2-a]pyridin-3-yl}benzamide<br />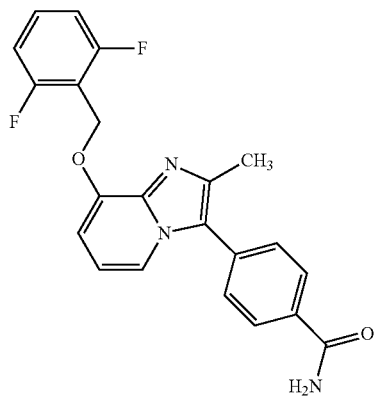<br />(35% of theory) | LC-MS (Method 12): $R_t$ = 0.77 min<br />MS (ESpos): m/z = 394.2 (M + H)$^+$ |
| 41 | 8-[(2,6-difluorobenzyl)oxy]-3-[4-methoxy-3-(morpholin-4-ylmethyl)phenyl]-2-methylimidazo[1,2-a]pyridine<br />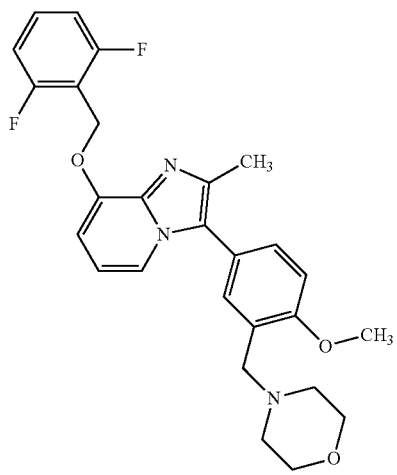<br />(39% of theory) [10] | LC-MS (Method 12): $R_t$ = 0.66 min<br />MS (ESpos): m/z = 480.4 (M + H)$^+$ |

TABLE 1-continued

| Example No. | IUPAC name Structure (Yield) | Analytical data |
|---|---|---|
| 42 | 8-[(2,6-difluorobenzyl)oxy]-2-methyl-3-[3-(piperidin-1-ylmethyl)phenyl]imidazo[1,2-a]pyridine<br />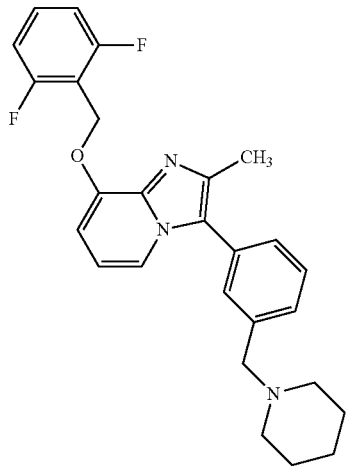<br />(18% of theory) | LC-MS (Method 12): $R_t$ = 0.69 min<br />MS (ESpos): m/z = 448.2 (M + H)$^+$ |
| 43 | N-(4-{8-[(2,6-difluorobenzyl)oxy]-2-methylimidazo[1,2-a]pyridin-3-yl}-2-fluorobenzyl)-N-ethylethanamine<br />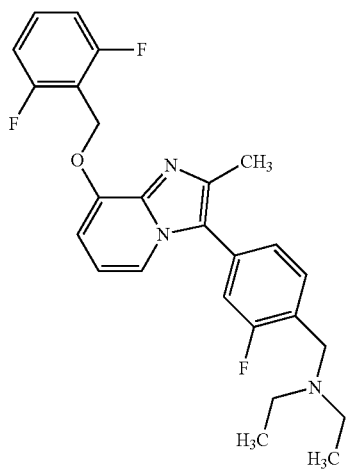<br />(23% of theory) [11] | LC-MS (Method 12): $R_t$ = 0.66 min<br />MS (ESpos): m/z = 454.3 (M + H)$^+$ |

TABLE 1-continued

| Example No. | IUPAC name Structure (Yield) | Analytical data |
|---|---|---|
| 44 | 8-[(2,6-difluorobenzyl)oxy]-3-[4-fluoro-3-(morpholin-4-ylmethyl)phenyl]-2-methylimidazo[1,2-a]pyridine 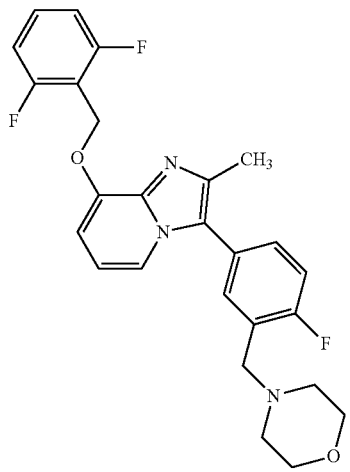 (50% of theory) [12] | LC-MS (Method 12): $R_t$ = 0.65 min MS (ESpos): m/z = 468.2 (M + H)$^+$ |

Boronic acids and boronic esters not commercially available can be prepared according to the following literature procedures:

[1] Preparation analogously to Leblanc, Catherine; Pulz, Robert Alexander; Stiefl, Nikolaus Johannes patent: US2009/181941 A1, 2009 from N-(3-bromobenzyl)-N-methylethanamine.

[2] SIRTRIS PHARMACEUTICALS, INC.; Rebecca, L.; patent: WO2010/101949 A1, 2010.

[3] Florentin et al., *Journal of Heterocyclic Chemistry*, 1976, Vol. 13, p. 1265, 12664268, 1271.

[4] ELI LILLY AND COMPANY; Patent: WO2005/73205 A1, 2005.

[5] Leblanc, Catherine; Pulz, Robert Alexander; Stiefl, Nikolaus Johannes; Patent: US2009/181941 A1, 2009.

[6] Preparation analogously to Leblanc, Catherine; Pulz, Robert Alexander; Stiefl, Nikolaus Johannes patent: US2009/181941 A1, 2009 from N-(5-bromo-2-methoxybenzyl)-2-methoxy-N-methylethanamine.

[7] Preparation analogously to Leblanc, Catherine; Pulz, Robert Alexander; Stiefl, Nikolaus Johannes patent: US2009/181941 A1, 2009 from N-(3-bromo-4-methoxybenzyl)-2-methoxy-N-methylethanamine.

[8] Preparation analogously to Leblanc, Catherine; Pulz, Robert Alexander; Stiefl, Nikolaus Johannes patent: US2009/181941 A1, 2009 from 1-(3-bromophenyl)piperidine.

[9] Preparation analogously to NOVARTIS AG; patent: WO2008/148867 A2, 2008 from 4-(4-bromo-2-fluorobenzyl)morpholine.

[10] Preparation analogously to NOVARTIS AG; patent. WO2008/148867 A2, 2008 from 4-(5-bromo-2-methoxybenzyl)morpholine.

[11] Preparation analogously to ASTRAZENECA AB; patent: WO2008/32191 A2, 2008 from N-(4-bromo-2-fluorobenzyl)-N-ethylethanamine.

[12] Preparation analogously to NOVARTIS AG; patent: WO2008/148867 A2, 2008 from 4-(5-bromo-2-fluorobenzyl)morpholine.

Example 45

8-[(2,6-Difluorobenzyl)oxy]-2-methyl-3-(1H-pyrazol-4-yl)imidazo[1,2-a]pyridine

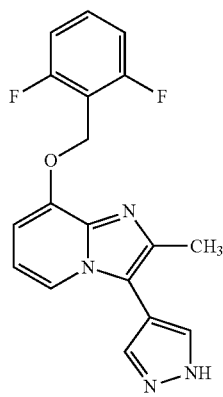 [SMILES: Cc1nc2c(OCc3c(F)cccc3F)cccn2c1-c1cn[nH]c1]

Under argon, 95 mg of 1H-pyrazol-4-ylboronic acid (0.85 mmol, 3 equivalents), 180 mg of potassium phosphate and 15 mg of bis(tri-tert-butylphosphine)palladium(0) (0.85 mmol, 3 equivalents) were added to 100 mg of 3-bromo-8-[(2,6-difluorobenzyl)oxy]-2-methylimidazo[1,2-a]pyridine (Example 28A, 0.28 mmol, 1 equivalent) in a mixture of 2 ml of ethanol, 1 ml of water and 1 ml of toluene. The suspension was degassed with argon and stirred for 30 seconds and then stirred in a CEM Discover microwave at 120° C. for 15 min. After the reaction had ended, the reaction mixture was applied to diatomaceous earth and purified using Isolera (column: Biotage SNAP Cartridge KP-Sil 10 g, mobile phase: gradient: 100% cyclohexane to ethyl acetate 100%). This gave 23 mg (24% of theory) of the title compound.

LC-MS (Method 1): $R_t$=0.65 min

MS (ESpos): m/z=341 (M+H)$^+$ $^1$H NMR (400 MHz, DMSO-d$_6$) δ=2.32 (s, 3 H), 5.31 (s, 2 H), 6.75-6.87 (m, 3 H), 7.18-7.29 (m, 3 H), 7.53-7.65 (m, 2 H), 7.80 (s, 1 H), 7.87-7.92 (m, 2 H), 8.10-8.19 (m, 1 H), 13.25 (s, 1 H).

Analogously to Example 45, the example compounds shown in Table 2 were prepared by reacting 3-bromo-8-[(2,6-difluorobenzyl)oxy]-2-methylimidazo[1,2-a]pyridine (Example 28A) with the appropriate commercially available boronic acids or boronic esters.

TABLE 2

| 46 | 8-[(2,6-Difluorobenzyl)oxy]-2-methyl-3-[3-(methylsulphonyl)phenyl]imidazo[1,2-a]pyridine | LC-MS (Method 2): $R_t$ = 0.86 min<br>MS (ESpos): m/z = 429.0 (M + H)$^+$<br>$^1$H NMR (400 MHz, DMSO-d$_6$) δ = 2.35 (s, 3 H), 5.33 (s, 2 H), 6.83-6.89 (m, 1 H), 6.91-6.96 (m, 1 H), 7.21-7.29 (m, 2 H), 7.55-7.65 (m, 1 H), 7.80-7.92 (m, 2 H), 7.93-8.04 (m, 3 H) [further signal hidden under solvent peaks]. |
|---|---|---|
|  | The resulting crude product was, after silica gel chromatography, triturated with acetonitrile, filtered off and dried under reduced pressure.<br>(66% of theory) |  |
| 47 | 8-[(2,6-Difluorobenzyl)oxy]-2-methyl-3-(1H-pyrazol-5-yl)imidazo[1,2-a]pyridine | LC-MS (Method 1): $R_t$ = 0.69 min<br>MS (ESpos): m/z = 341.1 (M + H)$^+$<br>$^1$H NMR (400 MHz, DMSO-d$_6$) δ = 5.32 (s, 2 H), 6.63 (s, 1 H), 6.81-6.96 (m, 2 H), 7.24 (t, 2 H), 7.50-7.69 (m, 1 H), 7.95 (d, 1 H), 8.85 (dd, 2.13 Hz, 1 H), 13.17 (br. s., 1 H) [further signal hidden under solvent peaks]. |
|  | The resulting crude product was, after silica gel chromatography, triturated with acetonitrile, filtered off and dired under reduced pressure.<br>(66% of theory) |  |

| | | |
|---|---|---|
| 48 | N-(3-{8-[(2,6-Difluorobenzyl)oxy]-2-methylimidazo[1,2-a]pyridin-3-yl}phenyl)methanesulphonamide<br />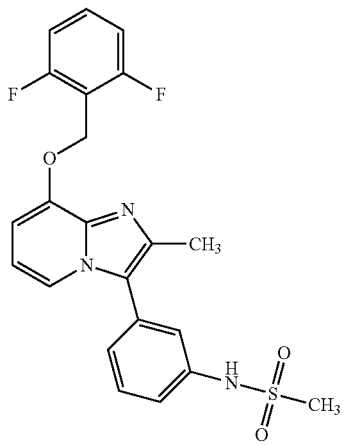The boronic acid pinacol ester was used. The resulting crude product was, after silica gel chromatography, re-purified by preparative HPLC (Method 10) using Isolera.<br />(49% of theory) | LC-MS (Method 1): $R_t$ = 0.76 min<br />MS (ESpos): m/z = 444.2 $(M + H)^+$<br />$^1$H NMR (400 MHz, DMSO-$d_6$) δ = 2.33 (s, 3 H), 3.06 (s, 3 H), 5.32 (s, 2 H), 6.79-6.86 (m, 1 H), 6.87-6.92 (m, 1 H), 7.20-7.35 (m, 5 H), 7.49-7.64 (m, 2 H), 7.93 (d, 1 H), 9.92 (s, 1 H). |
| 49 | 8-[(2,6-Difluorobenzyl)oxy]-3-(1-ethyl-1H-pyrazol-4-yl)-2-methylimidazo[1,2-a]pyridine<br />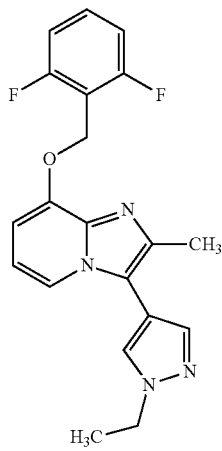(43% of theory)<br />The boronic acid pinacol ester was used. | LC-MS (Method 2): $R_t$ = 0.85 min<br />MS (ESpos): m/z = 369.1 $(M + H)^+$<br />$^1$H NMR (400 MHz, DMSO-$d_6$) δ = 1.45 (t, 3 H), 2.32 (s, 3 H), 4.23 (m, 2 H), 5.30 (s, 2 H), 6.74-6.89 (m, 2 H), 7.24 (s, 2 H), 7.50-7.66 (m, 1 H), 7.76 (d, 1 H), 7.89-7.97 (m, 1 H), 8.16 (s, 1 H). |

TABLE 2-continued

| | | |
|---|---|---|
| 50 | 8-[(2,6-Difluorobenzyl)oxy]-2-methyl-3-(1-methyl-1H-pyrazol-4-yl)imidazo[1,2-a]pyridine 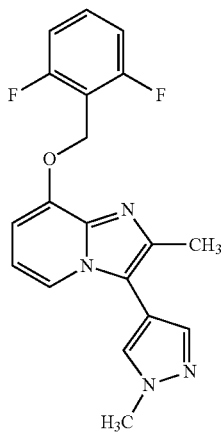 The boronic acid pinacol ester was used. (22% of theory) | LC-MS (Method 1): $R_t$ = 0.63 min<br>MS (ESpos): m/z = 355.1 $(M + H)^+$<br>$^1$H NMR (400 MHz, DMSO-$d_6$) δ = 2.31 (s, 3 H), 3.94 (s, 3 H), 5.29 (s, 2 H), 6.73-6.89 (m, 2 H), 7.14-7.29 (m, 2 H), 7.54-7.64 (m, 1 H), 7.74 (s, 1 H), 7.87-7.97 (m, 1 H), 8.10 (s, 1 H). |
| 51 | 6-{8-[(2,6-Difluorobenzyl)oxy]-2-methylimidazo[1,2-a]pyridin-3-yl}-1H-indazole 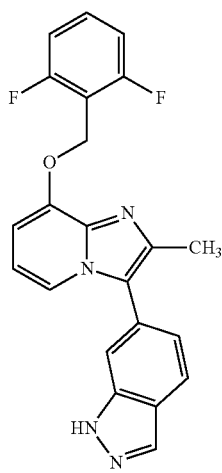 (22% of theory) | LC-MS (Method 1): $R_t$ = 0.72 min<br>MS (ESpos): m/z = 391.1 $(M + H)^+$<br>$^1$H NMR (400 MHz, DMSO-$d_6$) δ = 2.35 (s, 3 H), 5.29 (s, 2 H), 6.74-6.97 (m, 2 H), 7.14-7.36 (m, 3 H), 7.53-7.69 (m, 2 H), 7.86-8.03 (m, 2 H), 8.16 (s, 1 H), 13.18 (s, 1 H). |

| | | |
|---|---|---|
| 52 | 8-[(2,6-Difluorobenzyl)oxy]-3-(1-isopropyl-1H-pyrazol-4-yl)-2-methylimidazo[1,2-a]pyridine 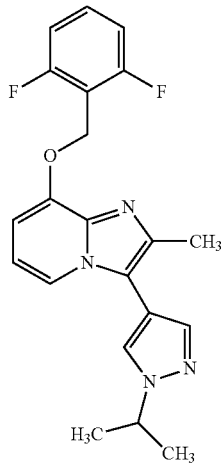  The boronic acid pinacol ester was used. The resulting crude product was, after silica gel chromatography, re-purified by preparative HPLC (Method 10) using Isolera. (41% of theory) | LC-MS (Method 1): $R_t$ = 0.74 min MS (ESpos): m/z = 383.1 (M + H)$^+$ $^1$H NMR (400 MHz, DMSO-$d_6$) δ = 1.49 (d, 6 H), 2.33 (s, 3 H), 4.54-4.65 (m, 1 H), 5.30 (s, 2 H), 6.78-6.86 (m, 2 H), 7.19-7.28 (m, 2 H), 7.54-7.64 (m, 1 H), 7.76 (s, 1 H), 7.91-7.96 (m, 1 H), 8.18 (s, 1 H). |
| 53 | 4-{8-[(2,6-Difluorobenzyl)oxy]-2-methylimidazo[1,2-a]pyridin-3-yl}-1H-indazole 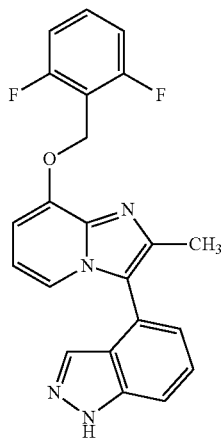  The resulting crude product was, after silica gel chromatography, re-purified by preparative HPLC (Method 10) using Isolera. (9% of theory) | LC-MS (Method 1): $R_t$ = 0.72 min MS (ESpos): m/z = 391.1 (M + H)$^+$ $^1$H NMR (400 MHz, DMSO-$d_6$) δ = 2.29 (s, 3 H), 5.32 (s, 2 H) 6.73-6.83 (m, 1 H), 6.88-6.96 (m, 1 H), 7.21-7.35 (m, 3 H), 7.47-7.75 (m, 5 H), 13.34 (s, 1 H). |

| | | |
|---|---|---|
| 54 | 5-{8-[(2,6-Difluorobenzyl)oxy]-2-methylimidazo[1,2-a]pyridin-3-yl}-1H-indazole 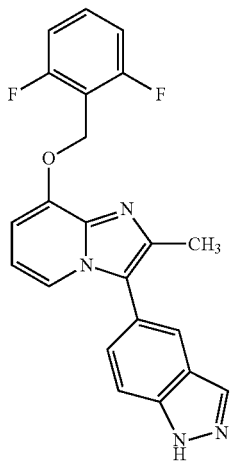 The resulting crude product was, after silica gel chromatography, re-purified by preparative HPLC (Method 10) using Isolera. (30% of theory) | LC-MS (Method 2): $R_t$ = 0.87 min<br>MS (ESpos): m/z = 391.0 (M + H)$^+$<br>$^1$H NMR (400 MHz, DMSO-$d_6$) δ = 2.31 (s, 3 H), 5.32 (s, 2 H), 6.78 (t, 1 H), 6.87 (d, 1 H), 7.21-7.29 (m, 2 H), 7.41-7.46 (m, 1 H), 7.55-7.65 (m, 1 H), 7.72 (d, 1 H), 7.85 (d, 1 H), 7.89-7.92 (m, 1 H), 8.16 (s, 1 H), 13.24 (s, 1 H). |
| 55 | 8-[(2,6-Difluorobenzyl)oxy]-3-(1,3-dimethyl-1H-pyrazol-4-yl)-2-methylimidazo[1,2-a]pyridine 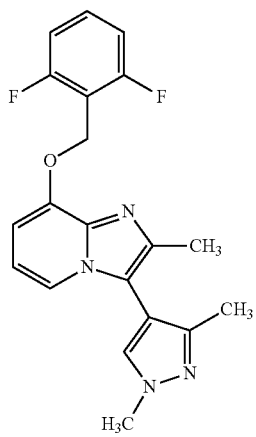 The boronic acid pinacol ester was used. (25% of theory) | LC-MS (Method 1): $R_t$ = 0.70 min<br>MS (ESpos): m/z = 369.1 (M + H)$^+$<br>$^1$H NMR (400 MHz, DMSO-$d_6$) δ = 1.98 (s, 3 H), 2.19 (s, 3 H), 3.85 (s, 3 H), 5.28 (s, 2 H), 6.70-6.88 (m, 2 H), 7.18-7.29 (m, 2 H), 7.51-7.66 (m, 2 H), 7.87 (s, 1 H). |

TABLE 2-continued

| | | |
|---|---|---|
| 56 | 8-[(2,6-Difluorobenzyl)oxy]-3-(1,5-dimethyl-1H-pyrazol-4-yl)-2-methylimidazo[1,2-a]pyridine 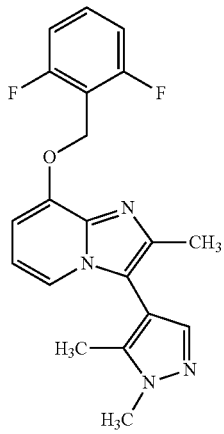 The boronic acid pinacol ester was used. (13% of theory) | LC-MS (Method 1): R$_t$ = 0.71 min<br>MS (ESpos): m/z = 369.2 (M + H)$^+$<br>$^1$H NMR (400 MHz, DMSO-d$_6$) δ = 2.10 (s, 3 H), 2.19 (s, 3 H), 3.84 (s, 3 H), 5.29 (s, 2 H), 6.73-6.78 (m, 1 H), 6.84 (d, 1 H), 7.17-7.31 (m, 2 H), 7.53 (s, 1 H), 7.55-7.64 (m, 2 H). |

Example 57

5-{8-[(2,6-Difluorobenzyl)oxy]-2-methylimidazo[1,2-a]pyridin-3-yl}-N-ethyl-1,3,4-oxadiazole-2-amine

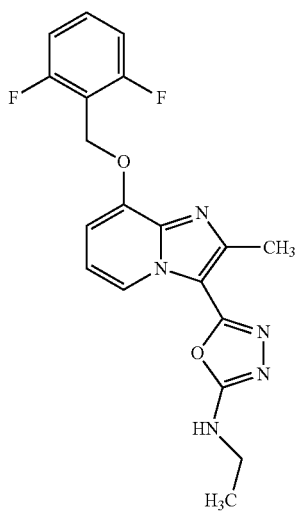 [SMILES: CCNc1nnc(-c2c(C)nc3c(OCc4c(F)cccc4F)cccn23)o1]

At RT, 50 mg of 5-{8-[(2,6-difluorobenzyl)oxy]-2-methylimidazo[1,2-a]pyridin-3-yl}-1,3,4-oxadiazol-2(3 H)-one (Example 45A, 0.13 mmol, 1 equivalent) were suspended in 1.3 ml of ethanol, 0.19 ml of 2 M ethylamine in THF (0.4 mmol, 3 equivalents) were added and the mixture was stirred in a CEM Discover microwave at 80° C. for 2.5 h. The mixture was then concentrated under reduced pressure, the residue was subsequently dissolved in a mixture of 1 ml of acetonitrile and 3 ml of dichloromethane, and 0.09 ml of triethylamine (0.6 mmol, 5 equivalents) and 0.04 ml of carbon tetrachloride (0.4 mmol, 3 equivalents) were added in succession. The reaction mixture was stirred at 50° C. for 1.5 h and then concentrated under reduced pressure. The crude product was separated via Biotage using a mobile phase mixture of cyclohexane/ethyl acetate. The resulting product was re-purified by preparative HPLC (column: Sunfire C 18, 5 μm, 250×20 mm, mobile phase: 45% methanol+TFA). This gave 18 mg (36% of theory) of the title compound.

LC-MS (Method 1): R$_t$=0.82 min
MS (ESpos): m/z=386.2 (M+H)$^+$
$^1$H-NMR (400 MHz, DMSO-d$_6$): δ=1.21 (t, 3 H), 2.59 (s, 3 H), 3.22-3.36 (m, 2 H), 5.30-5.45 (s, 2 H), 7.19-7.34 (m, 4 H), 7.54-7.65 (m, 1 H), 7.83-7.96 (m, 1 H), 8.85-8.97 (d, 1 H).

Example 58

5-{8-[(2,6-Difluorobenzyl)oxy]-2-methylimidazo[1,2-a]pyridin-3-yl}-1,3,4-oxadiazole-2-amine

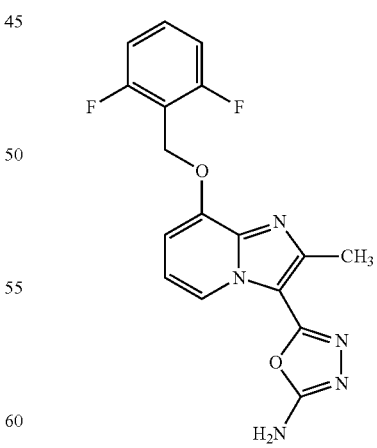

2.3 ml of 0.1 M aqueous sodium carbonate solution (0.23 mmol, 1.1 equivalents) were added to 85 mg of 8-[(2,6-difluorobenzyl)oxy]-2-methylimidazo[1,2-a]pyridine-3-carbohydrazide (Example 44A, 0.2 mmol, 1 equivalent) and 43 mg of cyanogen bromide (0.4 mmol, 2 equivalents) in 2.25 ml of 1,4-dioxane. The mixture was stirred at RT overnight and then extracted with ethyl acetate and water. The organic phase was dried over magnesium sulfate, filtered and concentrated by rotary evaporation. The residue was purified by preparative HPLC (Method 10). This gave 32 mg (44% of theory) of the title compound.

LC-MS (Method 1): $R_t$=0.70 min

MS (ESpos): m/z=358.1 (M+H)$^+$ $^1$H-NMR (400 MHz, DMSO-d$_6$): δ=2.57 (s, 3 H), 5.34 (s, 2 H), 7.07-7.13 (m, 2 H), 7.25 (t, 2 H), 7.31 (s, 2 H), 7.52-7.66 (m, 1 H), 8.85 (dd, 2.36 Hz, 1 H).

Example 59

8-[(2,6-Difluorobenzyl)oxy]-3-[2-(4-fluorophenyl) pyridin-4-yl]-2-methylimidazo[1,2-a]pyridine

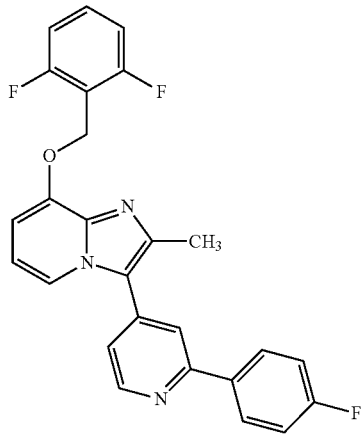 [SMILES: Cc1nc2c(OCc3c(F)cccc3F)cccn2c1-c1ccnc(-c2ccc(F)cc2)c1]

2.2 mg of palladium(II) acetate (0.01 mmol, 0.05 equivalent) and 8 mg of 2-dicyclohexylphosphino-2',6'-dimethoxybiphenyl (S-Phos, 0.02 mmol, 0.1 equivalent) in 0.35 ml of acetonitrile were stirred at RT for 15 min. First a solution of 82 mg of potassium carbonate (0.6 mmol, 3 equivalents) in 0.5 ml of water, then a solution of 77 mg of 2-(4-fluorophenyl)-4-(4,4,5,5-tetramethyl-1,3,2-dioxaborolan-2-yl) pyridine (0.3 mmol, 1.3 equivalents) in 0.35 ml of acetonitrile and subsequently 70 mg of 3-bromo-8[(2,6-difluorobenzyl)oxy]-2-methylimidazo[1,2-a]pyridine (Example 28A, 0.2 mmol, 1 equivalent) were then added. The reaction mixture was stirred under reflux for 8 h. After cooling, the reaction mixture was filtered through a Millipore filter and the filtrate was purified by preparative HPLC (RP18 column, mobile phase: acetonitrile/water gradient with addition of 0.1% TFA). The product-containing fractions were concentrated, the residue was taken up in ethyl acetate and washed twice with aqueous saturated sodium bicarbonate solution and the organic phase was dried over sodium sulphate, filtered, concentrated and lyophilized. This gave 56 mg (63% of theory) of the title compound.

LC-MS (Method 1): $R_t$=0.95 min

MS (ESpos): m/z=446.3 (M+H)$^+$ $^1$H-NMR (400 MHz, DMSO-d$_6$): δ=2.43 (s, 3 H), 5.34 (s, 2 H), 6.88 (t, 1 H), 6.97 (d, 1 H), 7.25 (t, 2 H), 7.34 (t, 2 H), 7.50-7.54 (m, 1 H), 7.56-7.65 (m, 1 H), 8.08 (s, 1 H), 8.15 (d, 1 H), 8.19-8.26 (m, 2 H), 8.73-8.86 (m, 1 H).

Example 60

8-[(2,6-Difluorobenzyl)oxy]-2-methyl-3-(pyrazin-2-yl)imidazo[1,2-a]pyridine

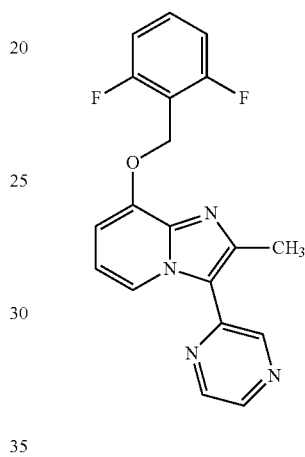

600 mg of 2-(tributylstannyl)pyrazine (1.6 mmol, 1.7 equivalents) and 60 mg of dichloropalladiumditriphenylphosphane (0.09 mmol, 0.125 equivalent) were added to 350 mg of 3-bromo-8-[(2,6-difluorobenzyl)oxy]-2-methylimidazo[1,2-a]pyridine (Example 28A, 0.99 mmol, 1 equivalent) in 10.5 ml of DMF. The batch was divided into 4 batches and each was stirred at 120° C. in a CEM Discover microwave for 1 h. Then water was added, and the reaction mixture was extracted three times with ethyl acetate. The organic phase was washed with saturated aqueous sodium chloride solution, dried over magnesium sulphate and concentrated using a rotary evaporator. The residue was absorbed on diatomaceous earth and purified using Isolera (column: Biotage SNAP Cartridge KP-Sil 50 g, mobile phase: gradient cyclohexane 100% to ethyl acetate 100%). The solid obtained was triturated with methanol, filtered off and dried under high vacuum. The filtrate was concentrated on a rotary evaporator and purified by preparative HPLC (Method 10). This gave 56 mg (16% of theory) of the title compound.

LC-MS (Method 2): $R_t$=0.93 min

MS (ESpos): m/z=353.1 (M+H)$^+$ $^1$H-NMR (400 MHz, DMSO-d$_6$): δ=2.58 (s, 3 H), 5.34 (s, 2 H), 6.95 (t, 1 H), 7.04 (d, 1 H), 7.25 (m, 2 H), 7.55-7.65 (m, 1 H), 8.59 (d, 1 H), 8.77-8.80 (m, 1 H), 8.85-8.90 (m, 1 H), 8.97 (d, Hz, 1 H).

Example 61

3-(4-Butyl-1,3-oxazol-2-yl)-6-chloro-8-[(2,6-difluorobenzyl)oxy]-2-methylimidazo[1,2-a]pyridine trifluoroacetate

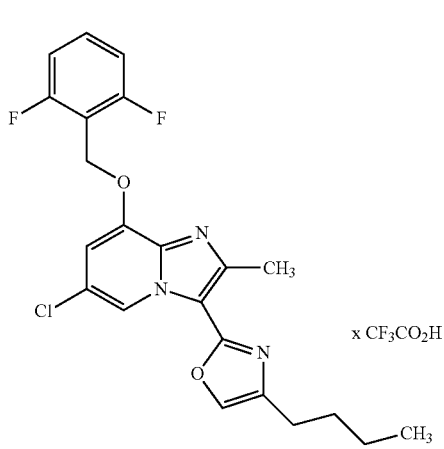 [SMILES: CCCCc1coc(-c2c(C)nc3c(OCc4c(F)cccc4F)cc(Cl)cn23)n1]

44 mg of 2,3-dichloro-5,6-dicyano-1,4-benzoquinone (DDQ, 0.2 mmol, 1.8 equivalents) were added to 47 mg of 3-[(4S)-4-butyl-4,5-dihydro-1,3-oxazol-2-yl]-6-chloro-8-[(2,6-difluorobenzyl)oxy]-2-methylimidazo[1,2-a]pyridine (Example 48A, 0.1 mmol, 1 equivalent) in 2.35 ml of toluene, and the mixture was stirred at 150° C. in a microwave oven for 45 min. This was followed by concentration under reduced pressure, and the residue was purified by preparative thin-layer chromatography (mobile phase: cyclohexane/ethyl acetate=7:3). The product obtained was re-purified by preparative HPLC (column: Nucleodur C 18, 5 μm, Gravity 21×100, mobile phase: acetonitrile/water+ TFA 50% to 70%). This gave 6 mg (10% of theory) of the title compound.

$^1$H-NMR (400 MHz, DMSO-$d_6$): δ=0.94 (s, 3 H), 1.32-1.48 (m, 2 H), 1.57-1.71 (m, 2 H), 2.58-2.65 (m, 5 H), 5.38 (s, 2 H), 7.16-7.37 (m, 3 H), 7.54-7.68 (m, 1 H), 7.95-8.06 (m, 1 H), 9.14-9.26 (m, 1 H).

Example 62

8-(Cyclohexylmethoxy)-2-methyl-3-[5-(pyrimidin-2-yl)-1,3,4-oxadiazol-2-yl]imidazo[1,2-a]pyridine

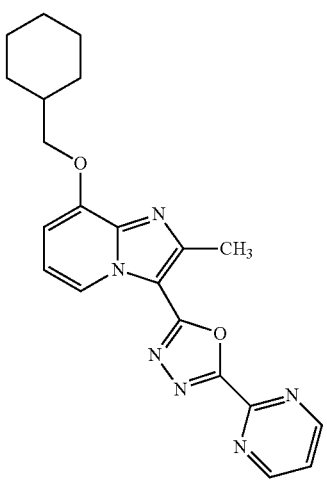 [SMILES: Cc1nc2c(OCC3CCCCC3)cccn2c1-c1nnc(-c2ncccn2)o1]

15 mg of pyrimidine-2-carbohydrazide (Example 78A, 0.11 mmol, 1.1 equivalents) were initially charged, and 8-(cyclohexylmethoxy)-2-methylimidazo[1,2-a]pyridine-3-carbonyl chloride (Example 26A, 0.1 mmol, 1 equivalent), dissolved in 0.6 ml of methylene chloride, were added. 0.02 mg of pyridine (0.3 mmol, 3 equivalents) was then added, and this mixture was shaken at RT overnight. After this time the reaction was diluted with 0.6 ml of methylene chloride and, with ice bath cooling, 0.05 mg of pyridine (0.6 mmol, 6 equivalents) and 0.112 mg of trifluoromethanesulphonic acid (0.4 mmol, 4 equivalents) were added in succession and the mixture was shaken first at 0° C. for 1 h and then at RT overnight. The product formed was purified by preparative HPLC (Method 11). This gave 13 mg (30% of theory; purity 92%) of the title compound.

LC-MS (Method 12): $R_t$=1.15 min

MS (ESpos): m/z=391.2 (M+H)$^+$

Analogously to Example 62, the example compounds shown in Table 3 were prepared by reacting 8-(cyclohexylmethoxy)-2-methylimidazo[1,2-a]pyridine-3-carbonyl chloride (Example 26A) with the appropriate hydrazides.

TABLE 3
| Example No. | IUPAC name Structure (Yield) | Analytical methods |
|---|---|---|
| 63 | {5-[8-(cyclohexylmethoxy)-2-methylimidazo[1.2-a]pyridin-3-yl]-1,3,4-oxadiazol-2-yl}(phenyl)methanol 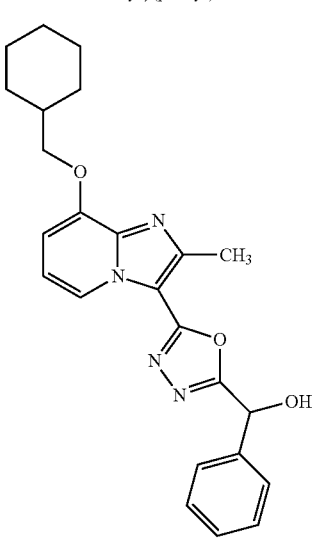 (3% of theory) | LC-MS (Method 12): $R_t$ = 1.16 min MS (ESpos): m/z = 319.2 (M + H)$^+$ |
| 64 | 8-(cyclohexylmethoxy)-2-methyl-3-[5-(pyridin-3-yl)-1,3,4-oxadiazol-2-yl]imidazo[1,2-a]pyridine 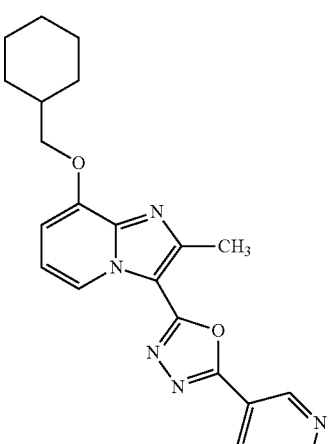 (23% of theory) | LC-MS (Method 12): $R_t$ = 1.25 min MS (ESpos): m/z = 390.2 (M + H)$^+$ |

TABLE 3-continued
| Example No. | IUPAC name<br>Structure<br>(Yield) | Analytical methods |
|---|---|---|
| 65 | 1-{5-[8-(cyclohexylmethoxy)-2-methylimidazol[1,2-a]pyridin-3-yl]-1,3,4-oxadiazol-2-yl}ethanol<br>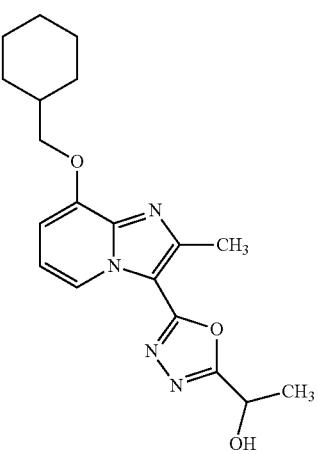<br>(4% of theory) | LC-MS (Method 12): $R_t$ = 1.03 min<br>MS (ESpos): m/z = 357.2 (M + H)$^+$ |
| 66 | 8-(cyclohexylmethoxy)-3-[5-(ethoxymethyl)-1,3,4-oxadiazol-2-yl]-2-methylimidazol[1,2-a]pyridine<br>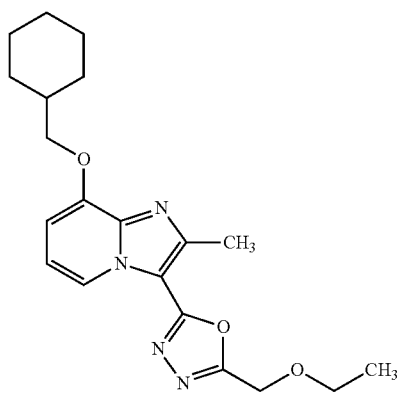<br>(18% of theory) | LC-MS (Method 12): $R_t$ = 1.18 min<br>MS (ESpos): m/z = 371.2 (M + H)$^+$ |

TABLE 3-continued
| Example No. | IUPAC name Structure (Yield) | Analytical methods |
|---|---|---|
| 67 | 8-(cyclohexylmethoxy)-3-[5-(methoxymethyl)-1,3,4-oxadiazol-2-yl]-2-methylimidazo[1,2-a]pyridine 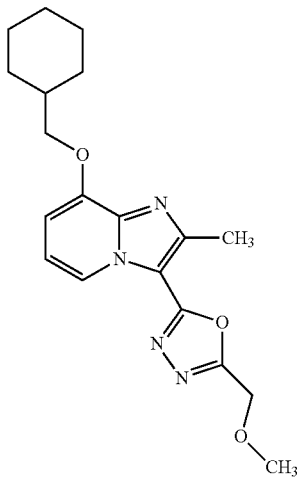 (23% of theory; purity 91%) | LC-MS (Method 12): $R_t$ = 1.14 min<br>MS (ESpos): m/z = 357.2 $(M + H)^+$ |
| 68 | 8-(cyclohexylmethoxy)-3-[5-(2-methoxyethyl)-1,3,4-oxadiazol-2-yl]-2-methylimidazo[1,2-a]pyridine 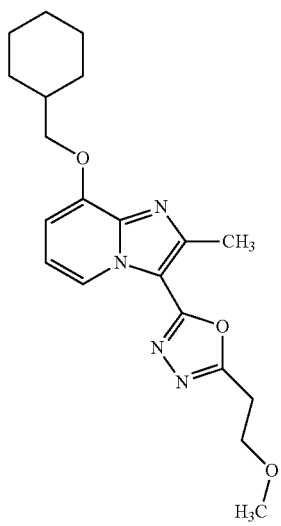 (25% of theory) | LC-MS (Method 12): $R_t$ = 1.12 min<br>MS (ESpos): m/z = 371.2 $(M + H)^+$ |

TABLE 3-continued
| Example No. | IUPAC name<br>Structure<br>(Yield) | Analytical methods |
|---|---|---|
| 69 | 8-(cyclohexylmethoxy)-3-[5-(2-methoxyethyl)-1,3,4-oxadiazol-2-yl]-2-methylimidazo[1,2-a]pyridine<br>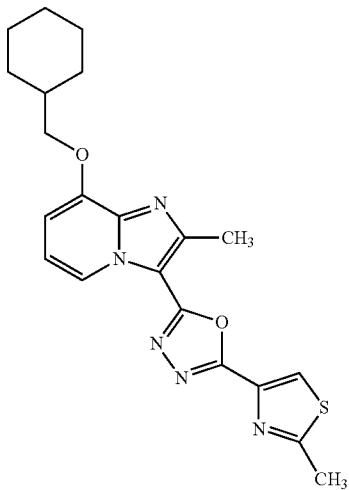<br>(13% of theory) | LC-MS (Method 12): $R_t$ = 1.23 min<br>MS (ESpos): m/z = 410.2 (M + H)$^+$ |
| 70 | 3-(5-sec-butyl-1,3,4-oxadiazol-2-yl)-8-(cyclohexylmethoxy)-2-methylimidazo[1,2-a]pyridine<br>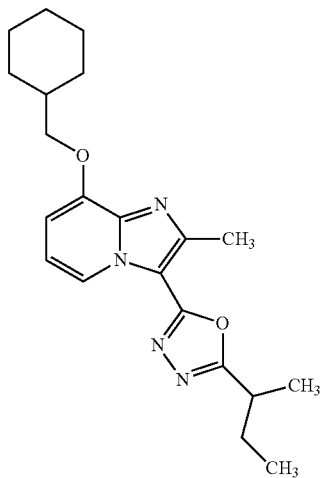<br>(32% of theory) | LC-MS (Method 12): $R_t$ = 1.25 min<br>MS (ESpos): m/z = 369.2 (M + H)$^+$ |

TABLE 3-continued

| Example No. | IUPAC name Structure (Yield) | Analytical methods |
|---|---|---|
| 71 | 1-({5-[8-(cyclohexylmethoxy)-2-methylimidazo[1,2-a]pyridin-3-yl]-1,3,4-oxadiazol-2-yl}methyl)pyrrolidin-2-one 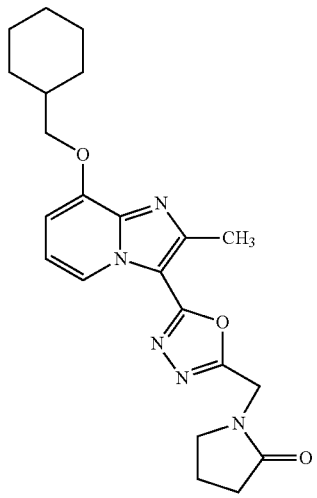 (12% of theory) | LC-MS (Method 12): $R_t$ = 1.07 min<br>MS (ESpos): m/z = 410.2 (M + H)$^+$ |
| 72 | 8-(cyclohexylmethoxy)-3-{5-[(3,5-dimethyl-1H-1,2,4-triazol-1-yl)methyl]-1,3,4-oxadiazol-2-yl}-2-methylimidazo[1,2-a]pyridine 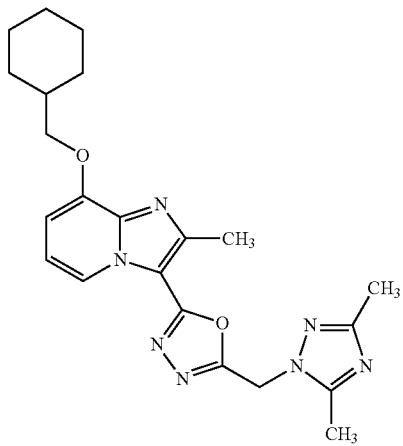 (1% of theory) | LC-MS (Method 12): $R_t$ = 1.12 min<br>MS (ESpos): m/z = 422.2 (M + H)$^+$ |

TABLE 3-continued

| Example No. | IUPAC name Structure (Yield) | Analytical methods |
|---|---|---|
| 73 | rac-8-(cyclohexylmethoxy)-3-[5-(1,1-dioxidotetrahydrothiophen-3-yl)-1,3,4-oxadiazol-2-yl]-2-methylimidazo[1,2-a]pyridine<br>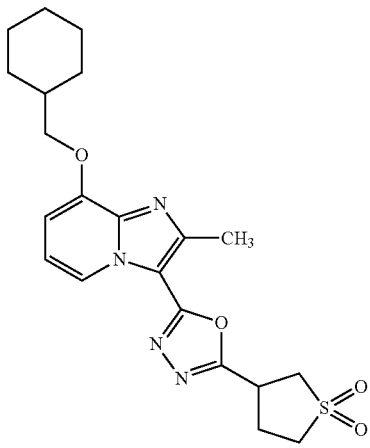<br>(21% of theory) | LC-MS (Method 12): $R_t$ = 1.08 min<br>MS (ESpos): m/z = 431.2 (M + H)$^+$ |
| 74 | 8-(cyclohexylmethoxy)-3-(5-cyclopropyl-1,3,4-oxadiazol-2-yl)-2-methylimidazo[1,2-a]pyridine<br>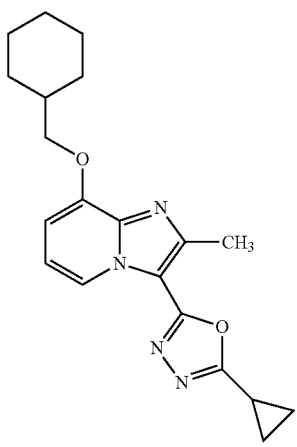<br>(36% of theory; purity 90%) | LC-MS (Method 12): $R_t$ = 1.18 min<br>MS (ESpos): m/z = 353.2 (M + H)$^+$ |

Example 75

Ethyl 5-{8-[(2,6-difluorobenzyl)oxy]-2,6-dimethyl-imidazo[1,2-a]pyridin-3-yl}nicotinate trifluoroacetate

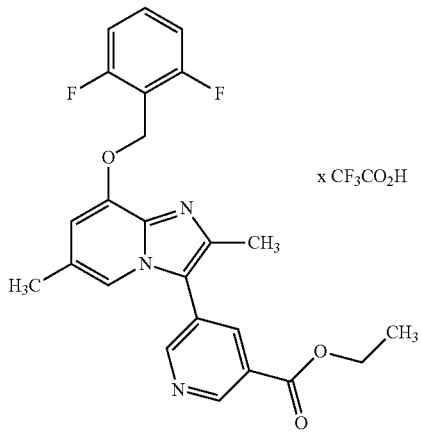 [SMILES: CCOC(=O)c1cncc(-c2c(C)nc3c(OCc4c(F)cccc4F)cc(C)cn23)c1]

Under argon, 2.16 ml of 1 M aqueous potassium carbonate solution were added to 200 mg (0.55 mmol) of 3-bromo-8-[(2,6-difluorobenzyl)oxy]-2,6-dimethylimidazo[1,2-a]pyridine from Example 30A, 166 mg (0.60 mmol) of ethyl 5-(4,4,5,5-tetramethyl-1,3,2-dioxaborolan-2-yl)nicotinate and 33 mg (0.04 mmol) of bis(diphenylphosphino)ferrocenepalladium(II) chloride dichloromethane complex in 10.8 ml of acetonitrile, and the mixture was stirred at 90° C. overnight. Water and TFA were added and the reaction solution was purified in two portions by preparative HPLC (RP18 column, mobile phase: acetonitrile/water gradient with addition of 0.1% TFA). This gave 134 mg of the target compound (42% of theory, purity 94%).

LC-MS (Method 1): $R_t$=0.85 min
MS (ESpos): m/z=438 (M-TFA+H)$^+$
$^1$H-NMR (400 MHz, DMSO-d$_6$): δ=2.28 (s, 3 H), 2.33 (s, 3 H); 5.30 (s, 2 H); 6.89 (s, 1 H); 7.22 (t, 2 H); 7.53-7.63 (m, 1 H); 7.75 (s, 1 H).

Example 76

5-{8-[(2,6-Difluorobenzyl)oxy]-2,6-dimethylimidazo[1,2-a]pyridin-3-yl}nicotinic acid trifluoroacetate

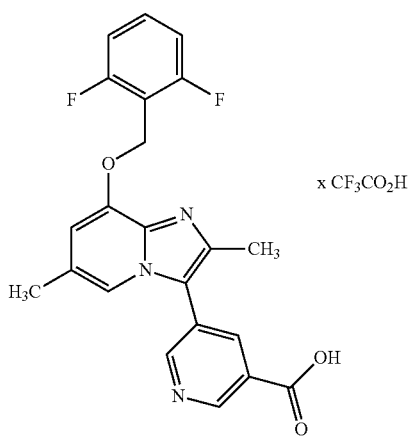 [SMILES: Cc1cc(OCc2c(F)cccc2F)c2nc(C)c(-c3cncc(C(=O)O)c3)n2c1]

1.38 ml of 1N aqueous lithium hydroxide solution were added to 152 mg (0.28 mmol) ethyl 5-{8-[(2,6-difluorobenzyl)oxy]-2,6-dimethylimidazo[1,2-a]pyridin-3-yl}nicotinate trifluoroacetate from Example 75 in 5.9 ml of THF/ethanol (5/1), and the mixture was stirred at room temperature for 4 h. With ice cooling, the mixture was adjusted to pH=4 using 1 N aqueous hydrochloric acid solution, and the solvent was then removed on a rotary evaporator. This gave 189 mg of the crude product. 80 mg of this crude product were taken up in acetonitrile/water/TFA and purified by preparative HPLC (RP18 column, mobile phase: acetonitrile/water gradient with addition of 0.1% TFA). This gave 55 mg of the title compound.

LC-MS (Method 1): $R_t$=0.73 min
MS (ESpos): m/z=410 (M-TFA+H)$^+$
$^1$H NMR (400 MHz, DMSO-d$_6$) δ=2.38 (s, 3 H), 2.40 (s, 3 H), 5.48 (s, 2 H), 7.29 (t, 2 H), 7.52-7.69 (m, 2 H), 8.09 (s, 1 H), 8.48 (s, 1 H), 8.98 (d, 1 H), 9.27 (d, 1 H), 13.78 (br. s, 1H).

Example 77

5-{8-[(2,6-Difluorobenzyl)oxy]-2,6-dimethylimidazo[1,2-a]pyridin-3-yl}nicotinamide

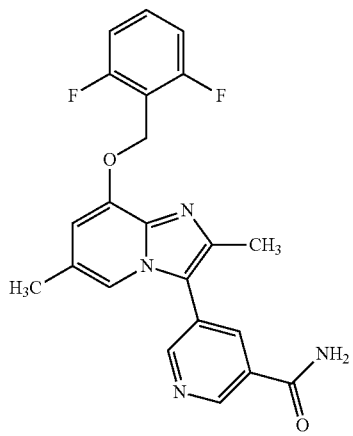 [SMILES: Cc1cc(OCc2c(F)cccc2F)c2nc(C)c(-c3cncc(C(N)=O)c3)n2c1]

54 mg (0.28 mmol) of 1-(3-dimethylaminopropyl)-3-ethylcarbodiimide hydrochloride and 38 mg (0.28 mmol) of 1-hydroxy-1H-benzotriazole hydrate were added to 50 mg (0.09 mmol) of 5-{8-[(2,6-difluorobenzyl)oxy]-2,6-dimethylimidazo[1,2-a]pyridin-3-yl}nicotinic acid trifluoroacetate from Example 76 in 1.8 ml of dichloromethane, and the mixture was stirred at room temperature for 10 min. Subsequently, 50 mg (0.94 mmol) of ammonium chloride and 158 mg (1.22 mmol) of N,N-diisopropylethylamine were added and the mixture was stirred at room temperature overnight. The reaction mixture was concentrated and the residue was applied to silica gel and purified by silica gel chromatography (mobile phase: dichloromethane/2 N ammonia in methanol 50/1, 20/1). This gave 25 mg (66% of theory) of the title compound.

LC-MS (Method 1): $R_t$=0.69 min
MS (ESpos): m/z=409 (M+H)$^+$
$^1$H NMR (400 MHz, DMSO-d$_6$) δ=2.29 (s, 3 H), 2.31 (s, 3 H), 5.30 (s, 2 H), 6.83 (s, 1 H), 7.23 (t, 2 H), 7.55-7.64 (m, 1 H), 7.72 (br. s, 1 H), 7.78 (s, 1 H), 8.26 (br. s, 1 H), 8.29-8.33 (m, 1 H), 8.82 (d, 1 H), 9.08 (d, 1 H).

Example 78

N-Cyclopropyl-5-{8-[(2,6-difluorobenzyl)oxy]-2,6-dimethylimidazo[1,2-a]pyridin-3-yl}nicotinamide trifluoroacetate

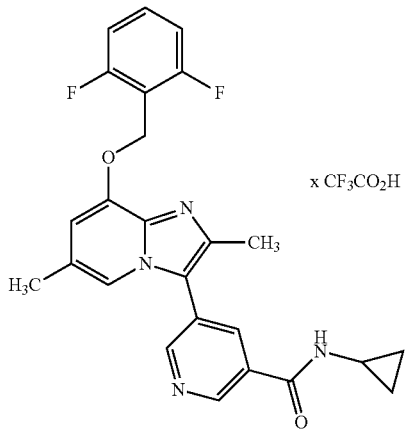 [SMILES: Cc1cc(OCc2c(F)cccc2F)c2nc(C)c(-c3cncc(C(=O)NC4CC4)c3)n2c1]

x CF$_3$CO$_2$H 0.012 m (0.12 mmol) of cyclopropylamine was added to 54 mg (0.10 mmol) of 5-{-[(2,6-difluorobenzyl)oxy]-2,6-dimethylimidazo[1,2-a]pyridin-3-yl}nicotinic acid trifluoroacetate from Example 76, 49 mg (0.15 mmol) of (benzotriazol-1-yloxy)bisdimethylaminomethylium fluoroborate and 0.056 ml (0.51 mmol) of 4-methylmorpholine in 0.65 ml of DMF, and the mixture was stirred at room temperature overnight. The reaction solution was diluted with water and TFA and purified by preparative HPLC (RP18 column, mobile phase: acetonitrile/water gradient with addition of 0.1% TFA). This gave 35 mg (60% of theory) of the title compound.

LC-MS (Method 1): R$_t$=0.75 min
MS (ESpos): m/z=449 (M-TFA+H)$^+$
$^1$H NMR (400 MHz, DMSO-d$_6$) δ=0.58-0.62 (m, 2 H), 0.72-0.79 (m, 2 H), 2.37 (s, 3 H), 2.39 (s, 3 H), 2.85-2.93 (m, 1 H), 5.48 (s, 2 H), 7.29 (t, 2 H), 7.40-7.68 (m, 2 H), 8.04 (br. s, 1 H), 8.38 (s, 1 H), 8.79 (d, 1 H), 8.88 (d, 1 H), 9.17 (s, 1 H).

Example 79

Methyl 2-{8-[(2,6-difluorobenzyl)oxy]-2,6-dimethylimidazo[1,2-a]pyridin-3-yl}pyrimidine-4-carboxylate

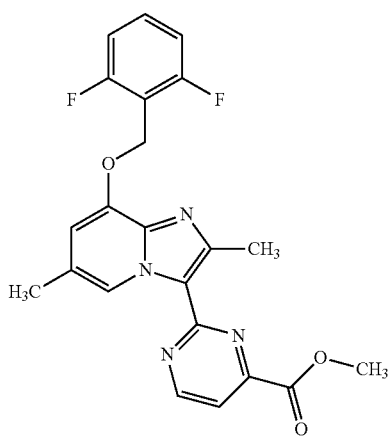

Under reflux, 200 mg (0.61 mmol) of 8-[(2,6-difluorobenzyl)oxy]-2,6-dimethylimidazo[1,2-a]pyridine-3-carboximidamide from Example 42A were dissolved in 7 ml of ethanol. The mixture was then cooled to 50° C., and 51 mg (0.76 mmol) of sodium ethoxide were added. 207 mg (1.21 mmol) of ethyl 4-(dimethylamino)-2-oxobut-3-enoate, dissolved in 0.26 ml of ethanol, were then added, and the reaction solution was stirred at 50° C. for 4 days. Another 52 mg (0.24 mmol) of ethyl 3-(dimethylamino)-2-oxobut-3-enoate and 10 mg (0.15 mmol) of sodium ethoxide were then added, and the reaction solution was stirred at 50° C. for 3 days. The reaction mixture was filtered through molecular sieve, the molecular sieve was washed with ethanol and the filtrate was concentrated under reduced pressure. The filtrate was purified by preparative HPLC (RP18 column; mobile phase: acetonitrile/water gradient with addition of 0.1% TFA). This gave 19 mg of the target compound (6% of theory, purity 80%).

LC-MS (Method 17): R$_t$=2.12 min
MS (ESpos): m/z=425 (M+H)$^+$

Example 80

2-{8-[(2,6-Difluorobenzyl)oxy]-2,6-dimethylimidazo[1,2-a]pyridin-3-yl}pyrimidine-4-carboxamide trifluoroacetate

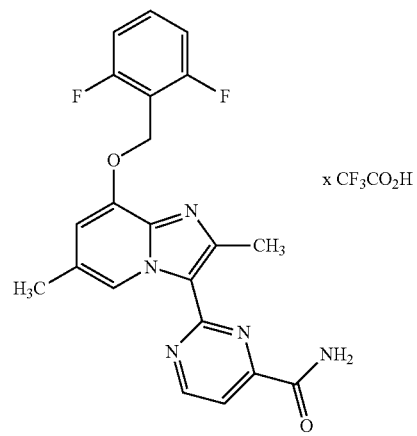 [SMILES: Cc1cc(OCc2c(F)cccc2F)c2nc(C)c(-c3nccc(C(N)=O)n3)n2c1]

x CF$_3$CO$_2$H 0.29 ml (2.05 mmol) of 7 N ammonia solution in methanol was added to 6.7 mg (0.016 mmol) of methyl 2-{8-[(2,6-difluorobenzyl)oxy]-2,6-dimethylimidazo[1,2-a]pyridin-3-yl}pyrimidine-4-carboxylate from Example 79, and the mixture was stirred at 50° C. overnight. The reaction mixture was concentrated under reduced pressure and the residue was purified by thick-layer chromatography (mobile phase: dichloromethane/methanol=20/1). The product-containing fractions were re-purified [column: Sunfire C18, 5 μm, 250×20 mm; mobile phase: 52% water, 35% acetonitrile+ 13% 1% strength aqueous TFA; flow rate: 25 ml/min; 40° C.; detection: 210 nm], concentrated and lyophilized. This gave 1.2 mg of the target compound (14% of theory).

LC-MS (Method 1): R$_t$=0.80 min
MS (ESpos): m/z=410 (M+H)$^+$
$^1$H NMR (400 MHz, DMSO-d$_6$) δ=2.40 (s, 3 H), 2.74 (s, 3 H), 5.32 (s, 2 H), 7.03 (s, 1 H), 7.23 (t, 2 H), 7.53-7.65 (m, 1 H), 7.73 (d, 1 H), 7.98-8.10 (m, 2 H), 9.13 (d, 1 H), 9.30 (s, 1 H).

Example 81

N-Cyclopropyl-2-{8-[(2,6-difluorobenzyl)oxy]-2,6-dimethylimidazo[1,2-a]pyridin-3-yl}pyrimidine-4-carboxamide trifluoroacetate

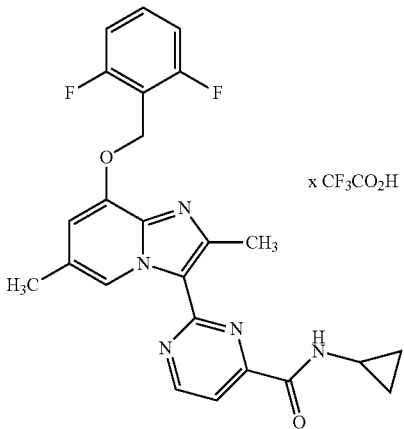 [SMILES: Cc1cc(OCc2c(F)cccc2F)c2nc(C)c(-c3nccc(C(=O)NC4CC4)n3)n2c1]

x CF₃CO₂H 0.256 ml (3.70 mmol) of cyclopropylamine was added to 15 mg (0.028 mmol) of methyl 2-{8-[(2,6-difluorobenzyl)oxy]-2,6-dimethylimidazo[1,2-a]pyridin-3-yl}pyrimidine-4-carboxylate Example 79, and the mixture was stirred at 50° C. overnight. The reaction mixture was concentrated under reduced pressure and the residue was purified by thick-layer chromatography (mobile phase: dichloromethane/methanol=20/1). The product-containing fractions were re-purified [column: Shield RP18, 5 µm, 19×100 mm; mobile phase (gradient): water/acetonitrile/1% strength aqueous TFA; flow rate: 40 ml/min; 25° C.; detection: 210 nm], concentrated and lyophilized. This gave 1 mg of the target compound (6% of theory, purity 90%).

LC-MS (Method 1): $R_t$=0.89 min
MS (ESpos): m/z=450 (M+H)⁺
¹H NMR (400 MHz, DMSO-d₆) δ=0.59-0.65 (m, 2 H), 0.69-0.74 (2 H), 2.33 (s, 3 H), 2.70 (s, 3 H), 2.82-2.94 (m, 1 H), 5.30 (s, 2 H), 7.05-7.22 (m, 3 H), 7.51-7.62 (m, 1 H), 7.67-7.72 (m, 1 H), 8.53-8.62 (m, 1 H), 9.08 (d, 1 H), 9.30 (s, 1 H).

Example 82

8-[(2,6-Difluorobenzyl)oxy]-2,6-dimethyl-3-(2H-1,2,3-triazol-4-yl)imidazo[1,2-a]pyridine

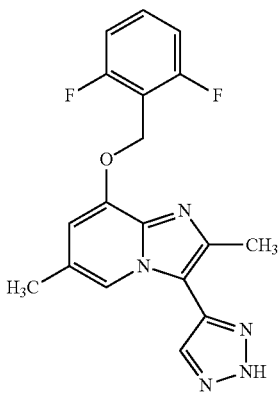

762 mg (1.44 mmol; purity about 60%) of 8-[(2,6-difluorobenzyl)oxy]-3-ethynyl-2,6-dimethylimidazo[1,2-a]pyridine from Example 77A were initially charged in a dry reaction flask in 1.44 ml of DMF/methanol (4/1), 14 mg (0.07 mmol) of copper(I) iodide and 249 mg (2.16 mmol) of azido(trimethyl)silane were added and the mixture was stirred under argon at 100° C. overnight. The reaction solution was diluted with water/acetonitrile/TFA and purified by preparative HPLC (RP18 column, mobile phase: acetonitrile/water gradient with addition of 0.1% TFA). This gave 471 mg of the target compound as TFA salt (59% of theory, purity 84%). 20 mg of this fraction were purified by thick-layer chromatography (mobile phase: dichloromethane/2N ammonia in methanol 20/1). This gave 6.4 mg of the target compound.

LC-MS (Method 1): $R_t$=0.74 min
MS (ESpos): m/z=356 (M+H)⁺
¹H NMR (400 MHz, DMSO-d₆) δ=2.33 (s, 3 H), 2.43 (s, 3 H), 5.30 (s, 2 H), 6.83 (s, 1 H), 7.23 (t, 2 H), 7.54-7.66 (m, 1 H), 8.29 (br. s, 1 H), 8.45 (s, 1 H), 15.38 (br. s, 1 H).

Example 83

1-(4-{8-[(2,6-Difluorobenzyl)oxy]-2,6-dimethylimidazo[1,2-a]pyridin-3-yl}-2H-1,2,3-triazol-2-yl)-2-methylpropan-2-amine

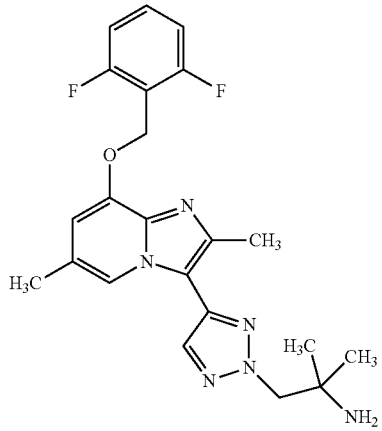 [SMILES: Cc1cc(OCc2c(F)cccc2F)c2nc(C)c(-c3cnn(CC(C)(C)N)n3)n2c1]

About 80 mg of Raney nickel (50% aqueous suspension) were added to 46 mg (0.06 mmol; purity about 75%) of 8-[(2,6-difluorobenzyl)oxy]-2,6-dimethyl-3-[2-(2-methyl-2-nitropropyl)-2H-1,2,3-triazol-4-yl]imidazo[1,2-a]pyridine trifluoroacetate from Example 56A in 0.25 ml of ethanol, and the mixture was hydrogenated under atmospheric pressure at room temperature overnight. The reaction mixture was filtered through Celite and the filter cake was washed thoroughly with ethanol and a mixture of dichloromethane/2 N ammonia solution in methanol (20/1). The filtrate was concentrated under reduced pressure. The residue was purified by thick-layer chromatography (mobile phase: dichloromethane/2N ammonia in methanol 20/1). This gave 19 mg of the target compound (73% of theory).

LC-MS (Method 1): $R_t$=0.61 min
MS (ESpos): m/z=427 (M+H)⁺
¹H NMR (400 MHz, DMSO-d₆) δ=1.08 (s, 6 H), 1.68 (br. s, 2 H), 2.32 (s, 3 H), 2.45 (s, 3 H), 4.41 (s, 2 H), 5.31 (s, 2 H), 6.87 (s, 1 H), 7.22 (t, 2 H), 7.54-7.64 (m, 1 H), 8.18 (s, 1 H), 8.39 (s, 1 H).

Example 84

8-[(3-Fluoropyridin-2-yl)methoxy]-2,6-dimethyl-3-(1H-pyrazol-4-yl)imidazo[1,2-a]pyridine

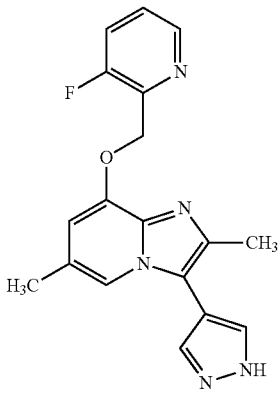

Under argon, 1.08 g (5.08 mmol) of [1-(tert-butoxycarbonyl)-1H-pyrazol-4-yl]boronic acid [can be prepared from the corresponding pinacol boronic acid ester by methods known from the literature, e.g. WO2009/155527; WO2012/6760], 1.29 g (6.09 mmol) of potassium phosphate and 104 mg (0.20 mmol) of bis(tri-tert-butyl-phosphine)palladium (0) were added to 0.943 g (2.03 mmol) of 3-bromo-8-[(3-fluoropyridin-2-yl)methoxy]-2,6-dimethylimidazo[1,2-a]pyridine trifluoroacetate from Example 34A in toluene/ethanol/water (7.2 ml/14.4 ml/7.2 ml), and the mixture was stirred in an oil bath, preheated to 120° C., for 30 min. The reaction mixture was concentrated and the residue was taken up in ethyl acetate/water. An insoluble solid formed. The solvent was decanted off from the solid and the solid was stirred in acetonitrile/water. The acetonitrile was then distilled off and the aqueous mixture was cooled. The precipitate was filtered off and dried under high vacuum. This gave 581 mg of the target compound (84% of theory).

LC-MS (Method 1): $R_t$=0.66 min
MS (ESpos): m/z=338 (M+H)$^+$
$^1$H NMR (400 MHz, DMSO-$d_6$) δ=2.27 (s, 3 H), 2.30 (s, 3 H), 5.38 (s, 2 H), 6.72 (s, 1 H), 7.55-7.63 (m, 1 H), 7.70 (s, 1 H), 7.75-7.89 (m, 2 H), 8.12 (br. s, 1 H), 8.50 (d, 1 H), 13.28 (br. s, 1 H).

Example 85

1-(4-{8-[(3-Fluoropyridin-2-yl)methoxy]-2,6-dimethylimidazo[1,2-a]pyridin-3-yl}-1H-pyrazol-1-yl)-2-methylpropan-2-amine

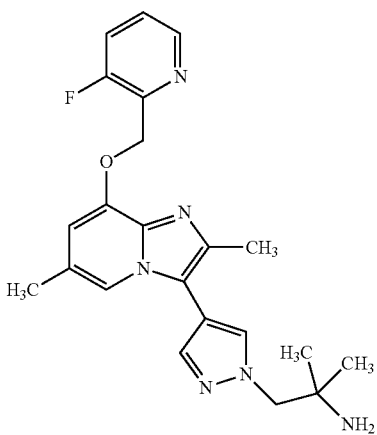 [SMILES: Cc1cc(OCc2ncccc2F)c2nc(C)c(-c3cnn(CC(C)(C)N)c3)n2c1]

About 197 mg of Raney nickel (50% aqueous suspension) were added to 65 mg (0.148 mmol) of 8-[(3-fluoropyridin-2-yl)methoxy]-2,6-dimethyl-3-[1-(2-methyl-2-nitropropyl)-1H-pyrazol-4-yl]imidazo[1,2-a]pyridine from Example 55A in 1.5 ml of ethanol, and the mixture was hydrogenated under atmospheric pressure at room temperature overnight. The reaction mixture was filtered through Celite and the filter cake was washed with dichloromethane/2 N ammonia solution in methanol (20/1). The filtrate was concentrated and the residue was purified by preparative thick-layer chromatography (mobile phase: dichloromethane/2 N ammonia solution in methanol (20/1)). This gave 42 mg of the target compound (69% of theory).

LC-MS (Method 1): $R_t$=0.46 min
MS (ESpos): m/z=409 (M+H)$^+$
$^1$H NMR (400 MHz, DMSO-$d_6$) δ=1.02 (s, 6 H), 1.61 (br. s, 2 H), 2.28 (s, 3 H), 2.31 (s, 3 H), 4.05 (s, 2 H), 5.38 (s, 2 H), 6.72 (s, 1 H), 7.55-7.62 (m, 1 H), 7.71 (s, 1 H), 7.78 (s, 1 H), 7.86 (t, 1 H), 8.10 (s, 1 H), 8.49 (d, 1 H).

Example 86

2,6-Dimethyl-3-(1H-pyrazol-4-yl)-8-[(2,3,6-trifluorobenzyl)oxy]imidazo[1,2-a]pyridine

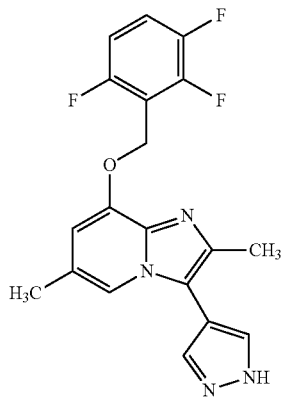

Under argon, 3.40 g (16.04 mmol) of [1-(tert-butoxycarbonyl)-1H-pyrazol-4-yl]boronic acid [can be prepared from the corresponding pinacol boronic acid ester by methods known from the literature, e.g. WO2009/155527; WO2012/6760], 4.09 g (19.25 mmol) of potassium phosphate and 328 mg (0.64 mmol) of bis(tri-tert-butyl-phosphine)palladium (0) were added to 2.47 g (6.42 mmol) of 3-bromo-2,6-dimethyl-8-[(2,3,6-trifluorobenzyl)oxy]imidazo[1,2-a]pyridine from Example 32A in toluene/ethanol/water (22.7 ml/45.3 ml/22.7 ml), and the mixture was stirred in an oil bath, preheated to 120° C., for 45 min. The reaction mixture was concentrated and the residue was taken up in dichloromethane/water. The insoluble solid was filtered off and dried under high vacuum. The aqueous phase was extracted twice with dichloromethane and the combined organic phases were dried over sodium sulphate and filtered. The filtrate was concentrated and the residue was, together with the solid, purified by silica gel chromatography (mobile phase: dichloromethane/methanol 50/1). 1.61 g of the target compound were obtained (66% of theory).

LC-MS (Method 1): $R_t$=0.67 min
MS (ESpos): m/z=373 (M+H)$^+$
$^1$H NMR (400 MHz, DMSO-$d_6$) δ=2.29 (s, 3 H), 2.30 (s, 3 H), 5.32 (s, 2 H), 6.72 (s, 1 H), 7.27-7.34 (m, 1 H), 7.61-7.73 (m, 2 H), 7.80 (s, 1 H), 8.14 (s, 1 H), 13.28 (br. s, 1 H).

Example 87

1-(4-{2,6-Dimethyl-8-[(2,3,6-trifluorobenzyl)oxy]imidazo pyridin-3-yl}-1H-pyrazol-1-yl)-2-methyl-propan-2-amine

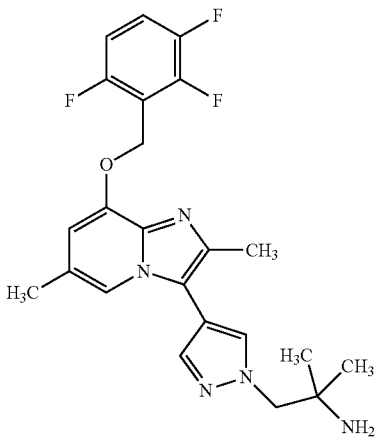 [SMILES: Cc1cc(OCc2c(F)ccc(F)c2F)c2nc(C)c(-c3cnn(CC(C)(C)N)c3)n2c1]

About 349 mg of Raney nickel (50% aqueous suspension) were added to 140 mg (0.26 mmol) of 2,6-dimethyl-3-[1-(2-methyl-2-nitropropyl)-1H-pyrazol-4-yl]-8-[(2,3,6-trifluorobenzyl)oxy]imidazo[1,2-a]pyridine from Example 54A in 1.1 ml of ethanol, and the mixture was hydrogenated under atmospheric pressure at room temperature overnight. The reaction mixture was filtered through Celite and the filter cake was washed with dichloromethane/2 N ammonia solution in methanol (20/1). The filtrate was concentrated and the residue was purified by silica gel chromatography (mobile phase: dichloromethane/2 N ammonia solution in methanol (60/1)). This gave 73 mg of the target compound (61% of theory).

LC-MS (Method 1): $R_t$=0.59 min
MS (ESpos): m/z=444 (M+H)$^+$
$^1$H NMR (400 MHz, DMSO-d$_6$) δ=1.02 (s, 6 H), 1.61 (br. s, 2 H), 2.25-2.35 (m, 6 H), 4.05 (s, 2 H), 5.32 (s, 2 H), 6.72 (s, 1 H), 7.25-7.33 (m, 1 H), 7.62-7.72 (m, 1 H), 7.73 (s, 1 H), 7.78 (s, 1 H), 8.11 (s, 1 H).

Example 88

8-[(2,6-Difluorobenzyl)oxy]-2,6-dimethyl-3-(1H-pyrazol-4-yl)imidazo[1,2-a]pyridine

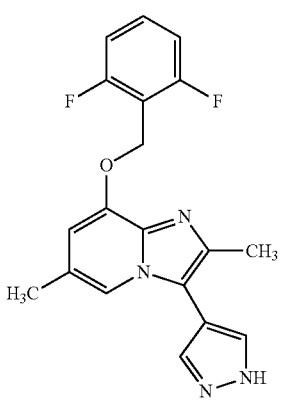

Under argon, 1.44 g (6.81 mmol) of [1-(tert-butoxycarbonyl)-1H-pyrazol-4-yl]boronic acid [can be prepared from the corresponding pinacol boronic acid ester by methods known from the literature, e.g. WO2009/155527; WO2012/6760], 1.73 g (8.17 mmol) of potassium phosphate and 139 mg (0.27 mmol) of bis(tri-tert-butyl-phosphine)palladium(0) were added to 1.0 g (2.72 mmol) of 3-bromo-8-[(2,6-difluorobenzyl)oxy]-2,6-dimethylimidazo[1,2-a]pyridine from Example 30A in toluene/ethanol/water (9.6 ml/19.2 ml/9.6 ml), and the mixture was stirred in an oil bath, preheated to 120° C., for 30 min. The reaction mixture was concentrated, the residue was taken up in ethyl acetate/water and the aqueous phase was extracted twice with ethyl acetate. The combined organic phases were dried over sodium sulphate and filtered. The filtrate was concentrated and the residue was purified by silica gel chromatography (mobile phase: dichloromethane/methanol 50/1 to 20/1). This gave 889 mg of the target compound (89% of theory).

LC-MS (Method 1): $R_t$=0.73 min
MS (ESpos): m/z=355 (M+H)$^+$
$^1$H NMR (400 MHz, DMSO-d$_6$) δ=2.26-2.30 (m, 6 H), 5.28 (s, 2 H), 6.72 (s, 1 H), 7.22 (t, 2 H), 7.54-7.63 (m, 1 H), 7.70 (s, 1 H), 7.80 (s, 1 H), 8.14 (s, 1 H), 13.28 (br. s, 1 H).

Example 89

1-(4-{8-[(2,6-Difluorobenzyl)oxy]-2,6-dimethylimidazo[1,2-a]pyridin-3-yl}-1H-pyrazol-1-yl)-2-methyl-propan-2-amine

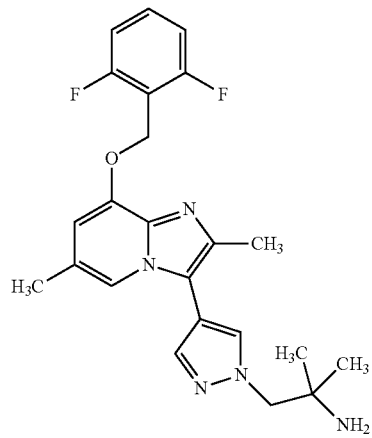 [SMILES: Cc1cc(OCc2c(F)cccc2F)c2nc(C)c(-c3cnn(CC(C)(C)N)c3)n2c1]

About 1200 mg of Raney nickel (50% aqueous suspension) were added to 412 mg (0.91 mmol) of 8-[(2,6-difluorobenzyl)oxy]-2,6-dimethyl-3-[1-(2-methyl-2-nitropropyl)-1H-pyrazol-4-yl]imidazo[1,2-a]pyridine from Example 53A in 3.75 ml of ethanol, and the mixture was hydrogenated under atmospheric pressure at room temperature overnight. The reaction mixture was filtered through Celite and the filter cake was washed with ethanol, dichloromethane, ethanol and THF. The filtrate was concentrated and the residue was purified by silica gel chromatography (mobile phase: dichloromethane/2 N ammonia solution in methanol (60/1)). This gave 263 mg of the target compound (68% of theory).

LC-MS (Method 1): $R_t$=0.59 min
MS (ESpos): m/z=426 (M+H)$^+$
$^1$H NMR (400 MHz, DMSO-d$_6$) δ=1.04 (s, 6 H), 1.59 (br. s, 2 H), 2.27-2.32 (m, 6 H), 4.07 (s, 2 H), 5.28 (s, 2 H), 6.72 (s, 1 H), 7.22 (t, 2 H), 7.54-7.64 (m, 1 H), 7.71 (s, 1 H), 7.78 (s, 1 H), 8.09 (s, 1 H).

Example 90

1-(4-{8-[(2,6-Difluorobenzyl)oxy]-2-methylimidazo[1,2-a]pyridin-3-yl}-1H-pyrazol-1-yl)-2-methylpropan-2-amine

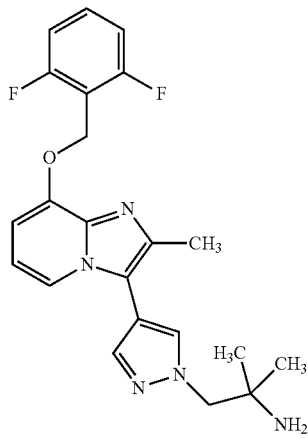 [SMILES: Cc1nc2c(OCc3c(F)cccc3F)cccn2c1-c1cnn(CC(C)(C)N)c1]

About 150 mg of Raney nickel (50% aqueous suspension) were added to 151 mg (0.32 mmol; purity 93%) of 8-[(2,6-difluorobenzyl)oxy]-2-methyl-3-[1-(2-methyl-2-nitropropyl)-1H-pyrazol-4-yl]imidazo[1,2-a]pyridine from Example 52A in 3.3 ml of DMF, and the mixture was hydrogenated under atmospheric pressure at room temperature overnight. 150 mg of Raney nickel (50% aqueous suspension) were added and the mixture was once more hydrogenated under atmospheric pressure overnight. The mixture was then filtered through Celite, the filter cake was washed with dichloromethane, the filtrate was concentrated and the residue was purified by preparative HPLC (RP18 column, mobile phase: acetonitrile/water gradient with addition of 0.1% TFA). Dichloromethane and saturated aqueous sodium bicarbonate solution were added to the product fractions and the aqueous phase was extracted three times with dichloromethane. The combined organic phases were dried over sodium sulphate and filtered and the filtrate was concentrated and lyophilized. The product was re-dissolved in dichloromethane, saturated aqueous sodium bicarbonate solution was added and the aqueous phase was extracted three times with dichloromethane. The combined organic phases were dried over sodium sulphate and filtered and the filtrate was concentrated and lyophilized. This gave 28 mg of the target compound (21% of theory).

LC-MS (Method 1): $R_t$=0.48 min
MS (ESpos): m/z=412 (M+H)$^+$
$^1$H NMR (400 MHz, DMSO-$d_6$) δ=1.04 (s, 6 H), 1.68 (br. s, 2 H), 2.31 (s, 3 H), 4.05 (s, 2 H), 5.31 (s, 2 H), 6.78-6.84 (m, 2 H), 7.22 (t, 2 H), 7.54-7.63 (m, 1 H), 7.78 (s, 1 H), 7.88-7.92 (m, 1 H), 8.11 (s, 1 H).

Example 91

2-(4-{8-[(2,6-Difluorobenzyl)oxy]-2,6-dimethylimidazo[1,2-a]pyridin-3-yl}-1H-pyrazol-1-yl)ethanol

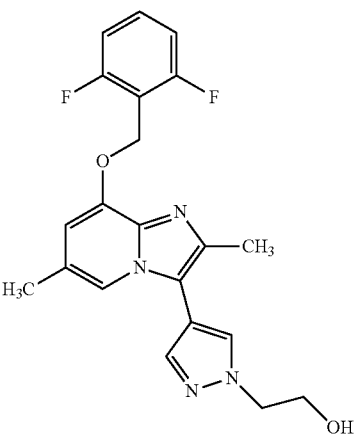 [SMILES: Cc1cc(OCc2c(F)cccc2F)c2nc(C)c(-c3cnn(CCO)c3)n2c1]

3.35 g (10.27 mmol) of caesium carbonate, 66 mg (0.40 mmol) of potassium iodide and 0.40 ml (5.14 mmol) of iodoethanol were added to 1.40 g (3.95 mmol) of 8-[(2,6-difluorobenzyl)oxy]-2,6-dimethyl-3-(1H-pyrazol-4-yl)imidazo[1,2-a]pyridine from Example 88 in 21.6 DMF, and the mixture was stirred at 70° C. overnight. After cooling, the solid was filtered off and washed with dichloromethane/methanol (20/1), the filtrate was concentrated and the residue was purified by silica gel chromatography (solvents: dichloromethane/methanol=80/1). 962 mg of the target compound were obtained (54% of theory, about 90% purity). The mixed fractions of the silica gel chromatography were concentrated and the residue was purified by preparative HPLC (RP18 column, mobile phase: acetonitrile/water gradient with addition of 0.1% TFA). The concentrated product fractions were partitioned between dichloromethane and saturated aqueous sodium bicarbonate solution and the aqueous phase was extracted twice with dichloromethane. The combined organic phases were dried over sodium sulphate and filtered and the filtrate was concentrated and lyophilized. This gave another 211 mg of the target compound (10% of theory, purity about 80%).

LC-MS (Method 1): $R_t$=0.71 min
MS (ESpos): m/z=399 (M+H)$^+$
$^1$H NMR (400 MHz, DMSO-$d_6$) δ=2.25-2.33 (m, 6 H), 3.80 (q, 2 H), 4.23 (t, 2 H), 4.96 (t, 1 H), 5.28 (s, 2 H), 6.73 (s, 1 H), 7.22 (t, 2 H), 7.54-7.65 (m, 1 H), 7.72 (s, 1 H), 7.78 (s, 1 H), 8.10 (s, 1 H).

Example 92

8-[(2,6-Difluorobenzyl)oxy]-3-{1-[2-(4,4-difluoropiperidin-1-yl)ethyl]-1H-pyrazol-4-yl}-2,6-dimethylimidazo[1,2-a]pyridine

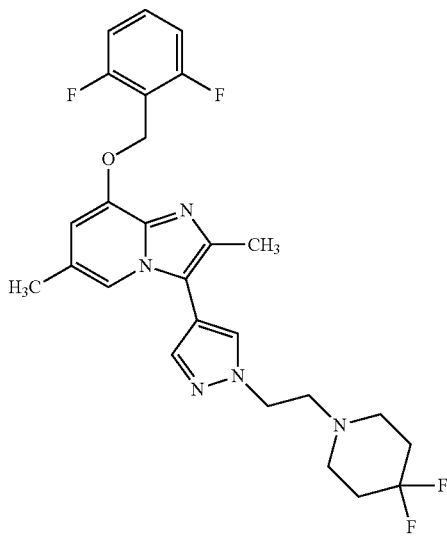 [SMILES: Cc1cc(OCc2c(F)cccc2F)c2nc(C)c(-c3cnn(CCN4CCC(F)(F)CC4)c3)n2c1]

0.07 ml (0.40 mmol) of N,N-diisopropylethylamine, 0.08 ml (0.60 mmol) of triethylamine, 2.4 mg (0.02 mmol) of 4-dimethylaminopyridine, 60 mg (0.40 mmol) of sodium iodide and 157 mg (1.0 mmol) of 4,4-difluoropiperidine hydrochloride in 2 ml THF were added to 106 mg (0.20 mmol; purity about 90%) of 2-(4-{8-[(2,6-difluorobenzyl)oxy]-2,6-dimethylimidazo[1,2-a]pyridin-3-yl}-1H-pyrazol-1-yl)ethyl methanesulphonate from Example 57A. The mixture was stirred at reflux overnight. After cooling, the reaction mixture was diluted with ethyl acetate and washed with water/saturated aqueous sodium chloride solution (1/1). The aqueous phase was extracted twice with ethyl acetate and the combined organic phases were dried over sodium sulphate and filtered. The filtrate was concentrated and dried under high vacuum. The residue was purified by thick-layer chromatography (solvent: ethyl acetate/cyclohexane=4/1). This gave 16 mg of the target compound (16% of theory).

LC-MS (Method 1): $R_t$=0.67 min

MS (ESpos): m/z=502 (M+H)$^+$ $^1$H NMR (400 MHz, DMSO-d$_6$) δ=1.85-2.00 (m, 4 H), 2.25-2.32 (m, 6 H), 2.50-2.64 (m, 4 H), 2.87 (t, 2 H), 4.30 (t, 2 H), 5.28 (s, 2 H), 6.73 (s, 1 H), 7.23 (t, 2 H), 7.54-7.63 (m, 1 H), 7.69 (s, 1 H), 7.76 (s, 1 H), 8.17 (s, 1 H).

Example 93

8-[(2,6-Difluorobenzyl)oxy]-3-{1-[2-(1,1-dioxidothiomorpholin-4-yl)ethyl]-1H-pyrazol-4-yl}-2,6-dimethylimidazo[1,2-a]pyridine

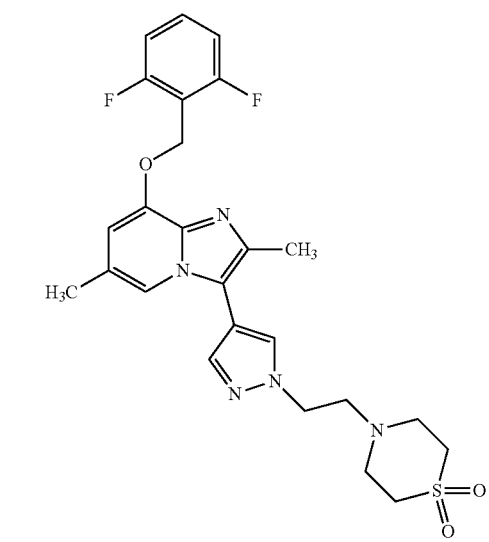 [SMILES: Cc1cc(OCc2c(F)cccc2F)c2nc(C)c(-c3cnn(CCN4CCS(=O)(=O)CC4)c3)n2c1]

135 mg (0.98 mmol) of thiomorpholine 1,1-dioxide were added to 130 mg (0.25 mmol; purity about 90%) of 2-(4-{8-[(2,6-difluorobenzyl)oxy]-2,6-dimethylimidazo[1,2-a]pyridin-3-yl}-1H-pyrazol-1-yl)ethyl methanesulphonate from Example 57A, 0.17 ml (0.98 mmol) of N,N-diisopropylethylamine, 3 mg (0.025 mmol) of 4-dimethylaminopyridine and 74 mg (0.49 mmol) of sodium iodide in 2.4 ml of THF. The mixture was stirred at reflux overnight. After cooling, the reaction mixture was diluted with ethyl acetate and washed with water/saturated aqueous sodium chloride solution (1/1). The aqueous phase was extracted twice with ethyl acetate, the combined organic phases were dried over sodium sulphate and filtered and the filtrate was concentrated. The residue was purified by silica gel chromatography (solvent: dichloromethane/methanol=80/1 to 40/1). This gave 85 mg of the target compound (64% of theory).

LC-MS (Method 1): $R_t$=0.76 min

MS (ESpos): m/z=516 (M+H)$^+$ $^1$H NMR (400 MHz, DMSO-d$_6$) δ=2.25-2.32 (m, 6 H), 2.93-3.11 (m, 10 H), 4.30 (t, 2 H), 5.29 (s, 2 H), 6.69-6.81 (m, 1 H), 7.23 (t, 2 H), 7.54-7.64 (m, 1 H), 7.70 (br. s, 1 H), 7.78 (s, 1 H), 8.18 (s, 1 H).

Example 94

8-[(2,6-Difluorobenzyl)oxy]-2,6-dimethyl-3-{1-[2-(4-methylpiperazin-1-yl)ethyl]-1H-pyrazol-4-yl}imidazo[1,2-a]pyridine

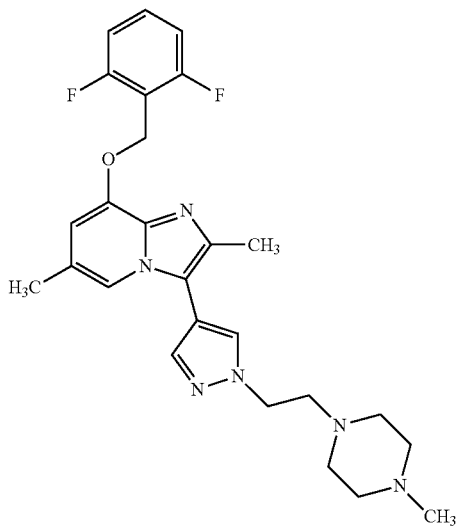

77 mg (0.77 mmol) of 1-methylpiperazine were added to 106 mg (0.20 mmol; purity about 90%) of 2-(4-{8-[(2,6-difluorobenzyl)oxy]-2,6-dimethylimidazo[1,2-a]pyridin-3-yl}-1H-pyrazol-1-yl)ethyl methanesulphonate from Example 57A, 0.13 ml (0.77 mmol) of N,N-diisopropylethylamine, 2.4 mg (0.02 mmol) of 4-dimethylaminopyridine and 58 mg (0.39 mmol) of sodium iodide in 1.9 ml of THF. The mixture was stirred at reflux overnight. After cooling, the reaction mixture was diluted with ethyl acetate and washed with water/saturated aqueous sodium chloride solution (1/1). The aqueous phase was extracted twice with ethyl acetate, the combined organic phases were dried over sodium sulphate and filtered and the filtrate was concentrated. The residue was purified by preparative HPLC (RP18 column; mobile phase: acetonitrile/water gradient with addition of 0.1% TFA). The product-containing fractions were concentrated and the residue was partitioned between dichloromethane and saturated aqueous sodium bicarbonate solution. The aqueous phase was extracted twice with dichloromethane and the combined organic phases were dried over sodium sulphate and filtered. The filtrate was concentrated and the residue was purified by thick-layer chromatography (dichloromethane/methanol 10/1) (the silica gel of the TLC plate was extracted with dichloromethane/2 N ammonia solution in methanol (10/1)). This gave 19 mg of the target compound (20% of theory).

LC-MS (Method 1): $R_t$=0.53 min
MS (ESpos): m/z=481 (M+H)$^+$
$^1$H NMR (400 MHz, DMSO-$d_6$) δ=2.18 (s, 3 H), 2.25-2.58 (m, 14 H), 2.75 (t, 2 H), 4.29 (t, 2 H), 5.28 (s, 2 H), 6.72 (m, 1 H), 7.22 (t, 2 H), 7.55-7.65 (m, 1 H), 7.70 (s, 1 H), 7.75 (s, 1 H), 8.13 (s, 1 H).

Example 95

1-[2-(4-{8-[(2,6-Difluorobenzyl)oxy]-2,6-dimethylimidazo[1,2-a]pyridin-3-yl}-1H-pyrazol-1-yl)ethyl]azetidin-3-ol trifluoroacetate

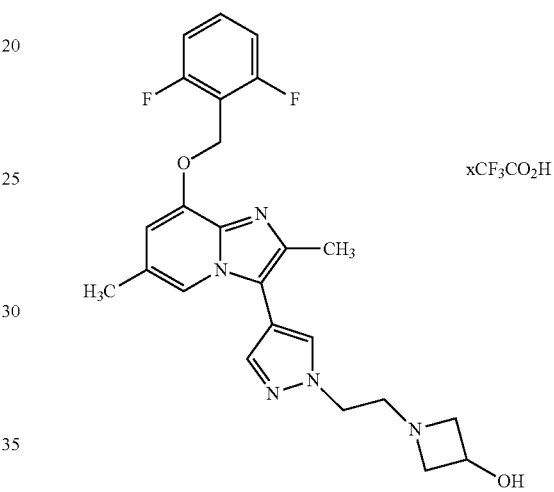

80 mg (0.15 mmol; purity about 90%) of 2-(4-{8-[(2,6-difluorobenzyl)oxy]-2,6-dimethylimidazo[1,2-a]pyridin-3-yl}-1H-pyrazol-1-yl)ethyl methanesulphonate from Example 57A, 0.13 ml (0.76 mmol) of N,N-diisopropylethylamine, 1.8 mg (0.015 mmol) of 4-dimethylaminopyridine and 45 mg (0.30 mmol) of sodium iodide were added to 56 mg (0.76 mmol) of azetidin-3-ol in 1.47 ml of abs. THF. The mixture was stirred at reflux overnight. Another 56 mg (0.76 mmol) of azetidin-3-ol were added and the mixture was stirred at reflux for 3 days. The reaction mixture was then concentrated, water/TFA was added to the residue and the mixture was purified by preparative HPLC (RP18 column, mobile phase: acetonitrile/water gradient with addition of 0.1% TFA). This gave 6.2 mg (7% of theory) of the target compound.

LC-MS (Method 1): $R_t$=0.60 min
MS (ESpos): m/z=454 (M-TFA+H)$^+$
$^1$H NMR (400 MHz, DMSO-$d_6$) δ=2.36-2.44 (m, 6 H), 3.69-3.96 (m, 4 H), 4.12-4.20 (m, 1 H), 4.28-4.38 (m, 1 H), 4.41-4.60 (m, 3 H), 5.46 (s, 2 H), 6.09-6.25 (m, 1 H), 7.27 (t, 2 H), 7.52-7.66 (m, 2 H), 7.97-8.08 (m, 2 H), 8.31 (d, 1 H).

Example 96

8-[(2,6-Difluorobenzyl)oxy]-2,6-dimethyl-3-{1-[2-(methylsulphonyl)ethyl]-1H-pyrazol-4-yl}imidazo[1,2-a]pyridine

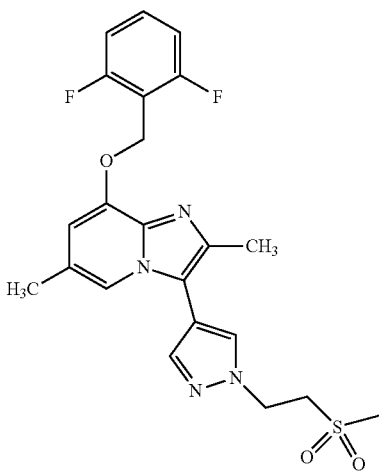

130 mg (0.25 mmol; purity about 90%) of 2-(4-{8-[(2,6-difluorobenzyl)oxy]-2,6-dimethylimidazo[1,2-a]pyridin-3-yl}-1H-pyrazol-1-yl)ethyl methanesulphonate from Example 57A and 295 mg (2.46 mmol) of sodium methanesulphinate in 2.4 ml DMF were stirred at 100° C. overnight. The reaction mixture was diluted with ethyl acetate and washed once with saturated aqueous sodium chloride solution/water (1/1). The aqueous phase was extracted twice with ethyl acetate, the combined organic phases were concentrated and the residue was purified by silica gel chromatography (dichloromethane/methanol=40/1). The product fractions were re-purified by preparative HPLC (RP18 column, mobile phase: acetonitrile/water gradient with addition of 0.1% TFA). The product-containing fractions were concentrated, the residue was partitioned between dichloromethane and saturated aqueous sodium bicarbonate solution and the aqueous phase was extracted twice with dichloromethane. The combined organic phases were dried over sodium sulphate and filtered, the filtrate was concentrated and the residue was lyophilized. The crude product was purified once more by preparative HPLC (RP18 column, mobile phase: acetonitrile/water gradient with addition of 0.1% TFA). The product-containing fractions were concentrated, the residue was partitioned between dichloromethane and saturated aqueous sodium bicarbonate solution and the aqueous phase was extracted twice with dichloromethane. The combined organic phases were dried over sodium sulphate and filtered, the filtrate was concentrated and the residue was lyophilized. This gave 51 mg of the target compound (42% of theory, purity 94%).

LC-MS (Method 1): $R_t$=0.68 min
MS (ESpos): m/z=461 (M+H)$^+$
$^1$H NMR (400 MHz, DMSO-d$_6$) δ=2.26-2.35 (m, 6 H), 2.97 (s, 3 H), 3.80 (t, 2 H), 4.68 (t, 1 H), 5.30 (s, 2 H), 6.83 (br. s, 1 H), 7.23 (t, 2 H), 7.55-7.64 (m, 1 H), 7.78 (br. s, 1 H), 7.85 (s, 1 H), 8.23 (s, 1 H).

Example 97

2-(4-{8-[(2,6-Difluorobenzyl)oxy]-2,6-dimethylimidazo[1,2-a]pyridin-3-yl}-1H-pyrazol-1-yl)ethyl carbamate

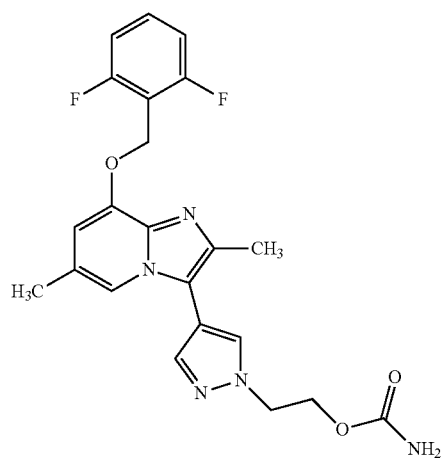 [SMILES: Cc1cc(OCc2c(F)cccc2F)c2nc(C)c(-c3cnn(CCOC(N)=O)c3)n2c1]

At −15° C., 128 mg (0.90 mmol) of isocyanatosulphuryl chloride were added to 180 mg (0.45 mmol) of 2-(4-{8-[(2,6-difluorobenzyl)oxy]-2,6-dimethylimidazo[1,2-a]pyridin-3-yl}-1H-pyrazol-1-yl)ethanol from Example 91 in 4.6 ml of dichloromethane, and the mixture was stirred for 1 h whilst slowly warming to room temperature. The reaction mixture was concentrated and the residue was purified by preparative TLC (mobile phase: dichloromethane/methanol=10/1). The crude product was purified once more by preparative TLC (mobile phase: dichloromethane/2 N methanolic ammonia solution=20/1). This gave 19 mg of the target compound (9% of theory).

LC-MS (Method 1): $R_t$=0.73 min
MS (ESpos): m/z=442 (M+H)$^+$
$^1$H NMR (400 MHz, DMSO-d$_6$) δ=2.25-2.32 (m, 6 H), 4.29-4.44 (m, 4 H), 5.27 (s, 2 H), 6.40-6.79 (m, 3 H), 7.23 (t, 2 H), 7.54-7.65 (m, 1 H), 7.73 (s, 1 H), 7.79 (s, 1 H), 8.12 (s, 1 H).

Example 98

8-[(2,6-Difluorobenzyl)oxy]-2,6-dimethyl-3-{1-[(5-methyl-1,2-oxazol-3-yl)methyl]-1H-pyrazol-4-yl}imidazo[1,2-a]pyridine

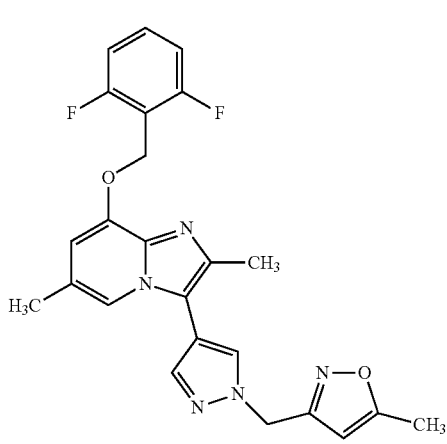

0.65 ml (0.65 mmol) of potassium tert-butoxide solution (1 N in THF) was added to 100 mg (0.28 mmol) of 8-[(2,6-difluorobenzyl)oxy]-2,6-dimethyl-3-(1H-pyrazol-4-yl)imidazo[1,2-a]pyridine from Example 88 in 1.4 ml of DMF, the mixture was stirred at room temperature for 5 min, 77 mg (0.42 mmol) of 3-(bromomethyl)-5-methyl-1,2-oxazole and 4.7 mg (0.03 mmol) of potassium iodide were then added and the mixture was stirred at 70° C. overnight. The reaction mixture was concentrated, and the residue was taken up in ethyl acetate and washed twice with water. The organic phase was dried over sodium sulphate and filtered, the filtrate was concentrated and the residue was purified by preparative HPLC (RP18 column; mobile phase: acetonitrile/water gradient with addition of 0.1% TFA).

The product-containing fractions were concentrated, and the residue was taken up in dichloromethane and washed once with saturated aqueous sodium bicarbonate solution. The aqueous phase was extracted twice with dichloromethane, the combined organic phases were dried over sodium sulphate and filtered and the filtrate was concentrated. The crude product was purified once more by silica gel chromatography (mobile phase: dichloromethane/methanol=80/1). This gave 39 mg of the target compound (30% of theory).

LC-MS (Method 1): $R_t$=0.77 min

MS (ESpos): m/z=450 (M+H)$^+$ $^1$H NMR (400 MHz, DMSO-$d_6$) δ=2.25-2.34 (m, 6 H), 2.39 (s, 3 H), 5.28 (s, 2 H), 5.48 (s, 2 H), 6.20 (s, 1 H), 6.77 (br. s, 1 H), 7.23 (t, 2 H), 7.54-7.64 (m, 1 H), 7.73 (s, 1 H), 7.85 (s, 1 H), 8.30 (s, 1 H).

Example 99

8-[(2,6-Difluorobenzyl)oxy]-3-{1-[2-(3,5-dimethyl-1H-pyrazol-4-yl)ethyl]-1H-pyrazol-4-yl}-2,6-dimethylimidazo[1,2-a]pyridine

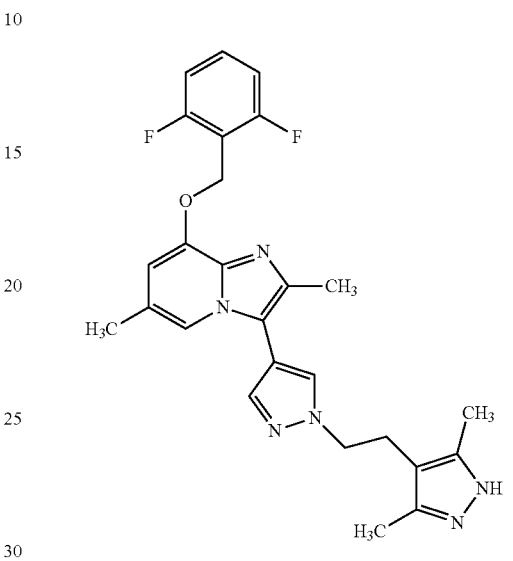

0.37 ml (0.37 mmol) of potassium tert-butoxide solution (1 N in THF) was added to 100 mg (0.28 mmol) of 8-[(2,6-difluorobenzyl)oxy]-2,6-dimethyl-3-(1H-pyrazol-4-yl)imidazo[1,2-a]pyridine from Example 88 in 1.4 ml of DMF, the mixture was stirred at room temperature for 5 min, 90 mg (0.42 mmol) of 4-(2-bromoethyl)-3,5-dimethyl-1H-pyrazole and 4.7 mg (0.03 mmol) of potassium iodide were then added and the mixture was stirred at 70° C. overnight. The reaction mixture was concentrated, and the residue was taken up in ethyl acetate and washed twice with water. The organic phase was dried over sodium sulphate and filtered, the filtrate was concentrated and the residue was purified by preparative HPLC (RP18 column; mobile phase: acetonitrile/water gradient with addition of 0.1% TFA). The product-containing fractions were concentrated, and the residue was taken up in dichloromethane and washed once with saturated aqueous sodium bicarbonate solution. The aqueous phase was extracted twice with dichloromethane, and the combined organic phases were dried over sodium sulphate and filtered, the filtrate was concentrated and the residue was lyophilized. This gave 85 mg of the target compound (62% of theory).

LC-MS (Method 1): $R_t$=0.73 min

MS (ESpos): m/z=477 (M+H)$^+$ $^1$H NMR (400 MHz, DMSO-$d_6$) δ=1.93 (s, 6 H), 2.26 (s, 3 H), 2.31 (s, 3 H), 2.82 (t, 2 H), 4.23 (t, 2 H), 5.29 (s, 2 H), 6.83 (br. s, 1 H), 7.23 (t, 2 H), 7.53-7.66 (m, 2 H), 7.74-7.83 (m, 2 H), 12.08 (br. s, 1 H).

Example 100

4-(4-{8-[(2,6-Difluorobenzyl)oxy]-2,6-dimethylimidazo[1,2-a]pyridin-3-yl}-1H-pyrazol-1-yl)butanonitrile

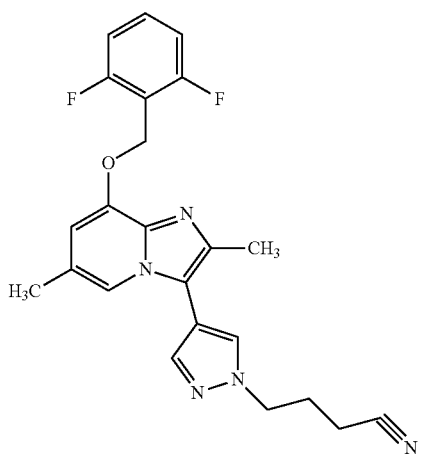 [SMILES: Cc1cc(OCc2c(F)cccc2F)c2nc(C)c(-c3cnn(CCCC#N)c3)n2c1]

0.37 ml (0.37 mmol) of potassium tert-butoxide solution (1 N in THF) was added to 100 mg (0.28 mmol) of 8-[(2,6-difluorobenzyl)oxy]-2,6-dimethyl-3-(1H-pyrazol-4-yl)imidazo[1,2-a]pyridine from Example 88 in 1.4 ml of DMF, the mixture was stirred at room temperature for 5 min, 63 mg (0.42 mmol) of 4-bromobutanonitrile and 4.7 mg (0.03 mmol) of potassium iodide were then added and the mixture was stirred at 70° C. overnight. The reaction mixture was concentrated and the residue was purified by preparative HPLC (RP18 column, mobile phase: acetonitrile/water gradient with addition of 0.1% TFA). The product-containing fractions were concentrated, and the residue was taken up in dichloromethane and washed once with saturated aqueous sodium bicarbonate solution. The aqueous phase was extracted twice with dichloromethane, the combined organic phases were dried over sodium sulphate and filtered and the filtrate was concentrated. The crude product was purified by silica gel chromatography (mobile phase: dichloromethane/methanol=20/1). This gave 47 mg of the target compound (40% of theory).

LC-MS (Method 1): $R_t$=0.77 min

MS (ESpos): m/z=422 (M+H)$^+$ $^1$H NMR (400 MHz, DMSO-d$_6$) δ=2.18 (q, 2 H), 2.25-2.32 (m, 6 H), 2.57 (t, 2 H; superimposed by DMSO signal), 4.29 (t, 2 H), 5.28 (s, 2 H), 6.73 (s, 1 H), 7.23 (t, 2 H), 7.55-7.65 (m, 1 H), 7.73 (s, 1 H), 7.79 (s, 1 H), 8.19 (s, 1 H).

Example 101

8-[(2,6-Difluorobenzyl)oxy]-2,6-dimethyl-3-{1-[3-(1H-tetrazol-5-yl)propyl]-1H-pyrazol-4-yl}imidazo[1,2-a]pyridine

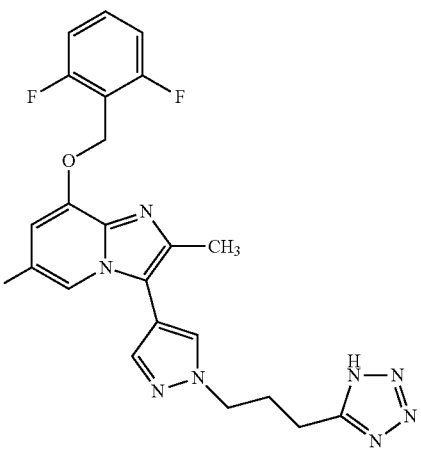

12.3 mg (0.19 mmol) of sodium azide and 41 mg (0.76 mmol) of ammonium chloride were added to 20 mg (0.05 mmol) of 4-(4-{8-[(2,6-difluorobenzyl)oxy]-2,6-dimethyl-imidazo[1,2-a]pyridin-3-yl}-1H-pyrazol-1-yl)butanonitrile from Example 100 in 0.5 ml of DMF, and the mixture was irradiated in the microwave at 150° C. for 8 h. Water/TFA was added and the reaction mixture was purified by preparative HPLC (RP18 column, mobile phase: acetonitrile/water gradient with addition of 0.1% TFA). The product-containing fractions were concentrated, concentrated three times with dichloromethane/formic acid (10/1) and three times with dichloromethane and the residue was then lyophilized. This gave 8.4 mg of the target compound (35% of theory).

LC-MS (Method 1): $R_t$=0.69 min

MS (ESpos): m/z=465 (M+H)$^+$ $^1$H NMR (400 MHz, DMSO-d$_6$) δ=2.22-2.38 (m, 8 H), 2.92 (t, 2 H), 4.30 (t, 2 H), 5.32 (s, 2 H), 6.93 (br. s, 1 H), 7.23 (t, 2 H), 7.55-7.64 (m, 1 H), 7.76-7.90 (m, 2 H), 8.18 (s, 1 H), 16.05 (br. s, 1 H).

Example 102

Methyl 3-(4-{8-[(2,6-difluorobenzyl)oxy]-2,6-dimethylimidazo[1,2-a]pyridin-3-yl}-1H-pyrazol-1-yl)propanoate

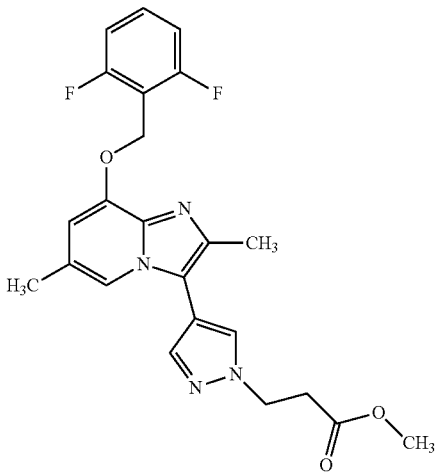

520 mg (1.60 mmol) of caesium carbonate, 10.2 mg (0.06 mmol) of potassium iodide and 133 mg (0.80 mmol) of methyl 3-bromopropanoate were added to 218 mg (0.61 mmol) of 8-[(2,6-difluorobenzyl)oxy]-2,6-dimethyl-3-(1H-pyrazol-4-yl)imidazo[1,2-a]pyridine from Example 88 in 3.3 ml of DMF, and the mixture was stirred at 70° C. for 2.5 h. After cooling, the solid was filtered off and washed with THF/methanol, the filtrate was concentrated and the residue was purified by preparative HPLC (RP18 column, mobile phase: acetonitrile/water gradient with addition of 0.1% TFA). The concentrated product fractions were partitioned between dichloromethane and saturated aqueous sodium bicarbonate solution. The aqueous phase was extracted twice with dichloromethane, the combined organic phases were dried over sodium sulphate and filtered and the filtrate was concentrated. The crude product was purified by silica gel chromatography (solvent: dichloromethane/methanol=80/1). This gave 179 mg of the target compound (65% of theory).

LC-MS (Method 1): $R_t$=0.78 min

MS (ESpos): m/z=441 (M+H)$^+$ $^1$H NMR (400 MHz, DMSO-d$_6$) δ=2.25-2.32 (m, 6 H), 2.98 (t, 2 H), 3.62 (s, 3 H), 4.44 (t, 2 H), 5.28 (s, 2 H), 6.74 (s, 1 H), 7.23 (t, 2 H), 7.55-7.65 (m, 1 H), 7.72 (s, 1 H), 7.78 (s, 1 H), 8.14 (s, 1 H).

The examples shown in Table 4 were prepared analogously to Example 102 by reacting 8-[(2,6-difluorobenzyl)oxy]-2,6-dimethyl-3-(1H-pyrazol-4-yl)imidazo[1,2-a]pyridine from Example 88 with the appropriate commercially available bromides (1.1-2.5 equivalents), caesium carbonate (2-4 equivalents) and potassium iodide (0.1-0.5 equivalent) under the reaction conditions described (reaction time: 2-24 h; temperature: 70° C.).

Illustrative Workup of the Reaction Mixture:

After cooling, the solid was filtered off and washed well with THF/methanol, the filtrate was concentrated and the residue was purified by preparative HPLC (RP18 column, mobile phase: acetonitrile/water gradient with addition of 0.1% TFA). The concentrated product fractions were partitioned between dichloromethane and saturated aqueous sodium bicarbonate solution. The aqueous phase was extracted twice with dichloromethane, the combined organic phases were dried over sodium sulphate and filtered and the filtrate was concentrated. If required, the crude product was additionally purified by silica gel chromatography (solvent: dichloromethane/methanol=80/1 to 20/1).

TABLE 4

| Example | IUPAC name/structure (Yield) | Analytical data |
| --- | --- | --- |
| 103 | Methyl (4-{8-[(2,6-difluorobenzyl)oxy]-2,6-dimethylimidazo[1,2-a]pyridin-3-yl}-1H-pyrazol-1-yl)acetate<br><br>(46% of theory) | LC-MS (Method 1): $R_t$ = 0.70 min<br>MS (ESpos): m/z = 427 (M + H)$^+$<br>$^1$H-NMR (400 MHz, DMSO-d$_6$): δ = 2.26-2.32 (m, 6 H), 3.27 (s, 3 H), 5.18 (s, 2 H), 5.28 (s, 2 H), 6.75 (s, 1 H), 7.23 (t, 2 H), 7.55-7.65 (m, 1 H), 7.71 (s, 1 H), 7.83 (s, 1 H), 8.18 (s, 1 H). |

TABLE 4-continued

| Example | IUPAC name/structure (Yield) | Analytical data |
|---|---|---|
| 104 | rac-Methyl 2-(4-{8-[(2,6-difluorobenzyl)oxy]-2,6-dimethylimidazo[1,2-a]pyridin-3-yl}-1H-pyrazol-1-yl)propanoate<br><br>(42% of theory) | LC-MS (Method 1): $R_t$ = 0.77 min<br>MS (ESpos): m/z = 441 (M + H)$^+$<br>$^1$H-NMR (400 MHz, DMSO-d$_6$): δ = 1.74 (d, 3 H), 2.25-2.32 (m, 6 H), 3.70 (s, 3 H), 5.28 (s, 2 H), 5.38 (q, 1 H), 6.75 (s, 1 H), 7.23 (t, 2 H), 7.55-7.65 (m, 1 H), 7.72 (s, 1 H), 7.83 (s, 1 H), 8.25 (s, 1 H). |
| 105 | rac-Methyl 3-(4-{8-[(2,6-difluorobenzyl)oxy]-2,6-dimethylimidazo[1,2-a]pyridin-3-yl}-1H-pyrazol-1-yl)butanoate<br><br>(47% of theory) | LC-MS (Method 1): $R_t$ = 0.80 min<br>MS (ESpos): m/z = 455 (M + H)$^+$<br>$^1$H-NMR (400 MHz, DMSO-d$_6$): δ = 1.52 (d, 3 H), 2.25-2.32 (m, 6 H), 2.88-2.97 (m, 1 H), 2.98-3.08 (m, 1 H), 3.58 (s, 3 H), 4.80-4.92 (m, 1 H), 5.28 (s, 2 H), 6.73 (s, 1 H), 7.23 (t, 2 H), 7.55-7.65 (m, 1 H), 7.72 (s, 1 H), 7.78 (s, 1 H), 8.18 (s, 1 H). |

| Example | IUPAC name/structure (Yield) | Analytical data |
|---|---|---|
| 106 | rac-Methyl 2-(4-{8-[(2,6-difluorobenzyl)oxy]-2,6-dimethylimidazo[1,2-a]pyridin-3-yl}-1H-pyrazol-1-yl)cyclopropanecarboxylate<br>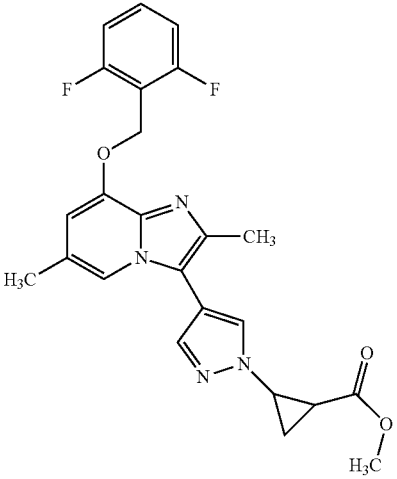<br>(% of theory) | LC-MS (Method 1): $R_t$ = 0.77 min<br>MS (ESpos): m/z = 453 (M + H)$^+$<br>$^1$H-NMR (400 MHz, DMSO-$d_6$): δ = 1.57-1.63 (m, 1 H), 1.95-2.02 (m, 1 H), 2.26-2.32 (m, 6 H), 2.33-2.40 (m, 1 H), 3.32 (s, 3 H), 4.23-4.30 (m, 1 H), 5.28 (s, 2 H), 6.73 (s, 1 H), 7.23 (t, 2 H), 7.55-7.65 (m, 1 H), 7.73 (s, 1 H), 7.79 (s, 1 H), 8.30 (s, 1 H). |

Example 107

3-(4-{8-[(2,6-Difluorobenzyl)oxy]-2,6-dimethylimidazo[1,2-a]pyridin-3-yl}-1H-pyrazol-1-yl)propanoic acid

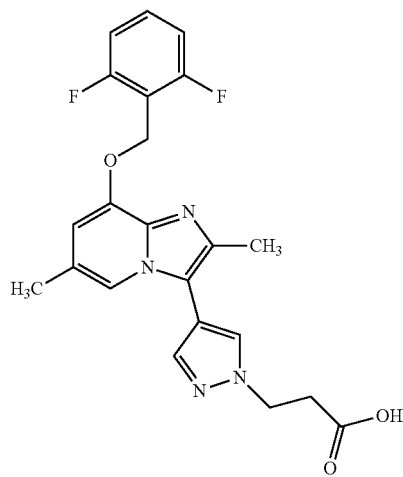 [SMILES: Cc1cc(OCc2c(F)cccc2F)c2nc(C)c(-c3cnn(CCC(=O)O)c3)n2c1]

0.23 ml (0.23 mmol) of 1 N aqueous lithium hydroxide solution was added to 50 mg (0.11 mmol) of methyl 3-(4-{8-[(2,6-difluorobenzyl)oxy]-2,6-dimethylimidazo[1,2-a]pyridin-3-yl}-1H-pyrazol-1-yl)propanoate from Example 102 in 2.45 ml of THF/methanol (5/1), and the mixture was stirred at room temperature for 2 h. The reaction solution was adjusted to pH=2 using 1 N aqueous hydrochloric acid and concentrated and the residue was purified by silica gel chromatography (mobile phase: dichloromethane/methanol=10/1). The crude product was purified by preparative HPLC (RP18 column; mobile phase: acetonitrile/water gradient with addition of 0.1% TFA). The product-containing fractions were concentrated and the residue was concentrated three times with dichloromethane/formic acid (10/1) and then three times with dichloromethane. This gave 30.5 mg of the target compound (63% of theory).

LC-MS (Method 1): $R_t$=0.72 min

MS (ESpos): m/z=427 (M+H)$^+$ $^1$H NMR (400 MHz, DMSO-$d_6$) δ=2.23-2.32 (m, 6 H), 2.88 (t, 2 H), 4.40 (t, 2 H), 5.27 (s, 2 H), 6.73 (s, 1 H), 7.23 (t, 2 H), 7.56-7.65 (m, 1 H), 7.72 (s, 1 H), 7.78 (s, 1 H), 8.13 (s, 1 H), 12.48 (br. s, 1 H).

The examples shown in Table 5 were prepared analogously to Example 107 by reacting the corresponding carboxylic esters with lithium hydroxide (2-5 equivalents) under the reaction conditions described (reaction time: 2-5 h; temperature: RT)

Illustrative Workup of the Reaction Mixture:

The reaction solution was adjusted with aqueous hydrochloric acid (1 N to 6 N) or TFA to pH=2-4 and concentrated and the residue was purified by silica gel chromatography (mobile phase: dichloromethane/methanol=10/1). Additionally or alternatively, the crude product was purified by preparative HPLC (RP18 column; mobile phase: acetonitrile/water gradient with addition of 0.1% TFA). The product-containing fractions were concentrated and the residue was concentrated three times with dichloromethane/formic acid (10/1) and then three times with dichloromethane.

TABLE 5

| Example | IUPAC name/structure (Yield) | Analytical data |
|---|---|---|
| 108 | (4-{8-[(2,6-difluorobenzyl)oxy]-2,6-dimethyloxazo[1,2-a]pyridin-3-yl}-1H-pyrazol-1-yl)acetic acid<br><br>(29% of theory) | LC-MS (Method 1): $R_t$ = 0.70 min<br>MS (ESpos): m/z = 413 (M + H)$^+$<br>$^1$H-NMR (400 MHz, DMSO-d$_6$): δ = 2.33-2.46 (m, 6 H), 5.12 (s, 2 H), 5.46 (s, 2 H), 7.27 (t, 2 H), 7.44-7.68 (m, 2 H), 7.92 (s, 1 H), 8.02 (br. s, 1 H), 8.31 (s, 1 H), 13.28 (br. s, 1 H). |
| 109 | rac-2-(4-{8-[(2,6-difluorobenzyl)oxy]-2,6-dimethylimidazo[1,2-a]pyridin-3-yl}-1H-pyrazol-1-yl)propanoic acid<br><br>(98% of theory) | LC-MS (Method 1): $R_t$ = 0.72 min<br>MS (ESpos): m/z = 427 (M + H)$^+$<br>$^1$H-NMR (400 MHz, DMSO-d$_6$): δ = 1.73 (d, 3 H), 2.25-2.32 (m, 6 H), 5.22 (q, 1 H), 5.28 (s, 2 H), 6.74 (s, 1 H), 7.23 (t, 2 H), 7.55-7.65 (m, 1 H), 7.72 (s, 1 H), 7.80 (s, 1 H), 8.12 (s, 1 H), 3.12 (br. s, 1 H). |

TABLE 5-continued

| Example | IUPAC name/structure (Yield) | Analytical data |
|---|---|---|
| 110 | rac-3-(4-{8-[(2,6-difluorobenzyl)oxy]-2,6-dimethylimidazo[1,2-a]pyridin-3-yl}-1H-pyrazol-1-yl)butanoic acid 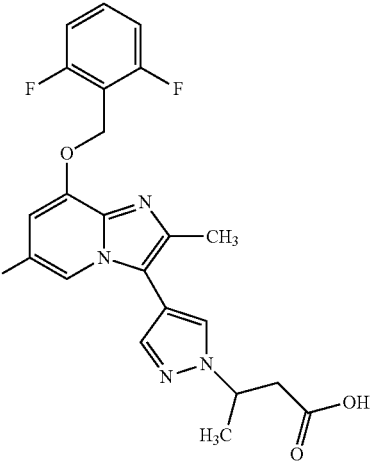 (87% of theory) | LC-MS (Method 1): $R_t$ = 0.78 min<br>MS (ESpos): m/z = 441 (M + H)$^+$<br>$^1$H-NMR (400 MHz, DMSO-d$_6$): δ = 1.50 (d, 3 H), 2.25-2.32 (m, 6 H), 2.78-2.37 (m, 1 H), 2.89-2.99 (m, 1 H), 4.78-4.88 (m, 1 H), 5.28 (s, 2 H), 6.73 (s, 1 H), 7.23 (t, 2 H), 7.55-7.65 (m, 1 H), 7.72 (s, 1 H), 7.78 (s, 1 H), 8.18 (s, 1 H), 12.40 (br. s, 1 H). |
| 111 | rac-2-(4-{8-[(2,6-difluorobenzyl)oxy]-2,6-dimethylimidazo[1,2-a]pyridin-3-yl}-1H-pyrazol-1-yl)cyclopropanecarboxylic acid 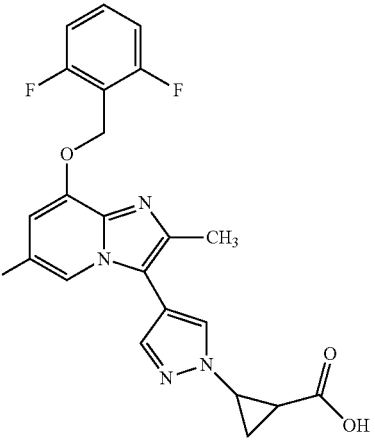 (88% of theory) | LC-MS (Method 1): $R_t$ = 0.76 min<br>MS (ESpos): m/z = 439 (M + H)$^+$<br>$^1$H-NMR (400 MHz, DMSO-d$_6$): δ = 1.53-1.60 (m, 1 H), 1.87-1.94 (m, 1 H), 2.20-2.39 (m, 7 H), 4.20-4.28 (m, 1 H), 5.33 (s, 2 H), 7.04 (br. s, 1 H), 7.22 (t, 2 H), 7.55-7.65 (m, 1 H), 7.81 (s, 1 H), 7.88 (br. s, 1 H), 8.37 (s, 1 H), 12.70 (br. s, 1 H). |

Example 112 rac-N-[2-(Diethylamino)ethyl]-3-(4-{8-[(2,6-difluorobenzyl)oxy]-2,6-dimethylimidazo[1,2-a]pyridin-3-yl}-1H-pyrazol-1-yl)butanamide

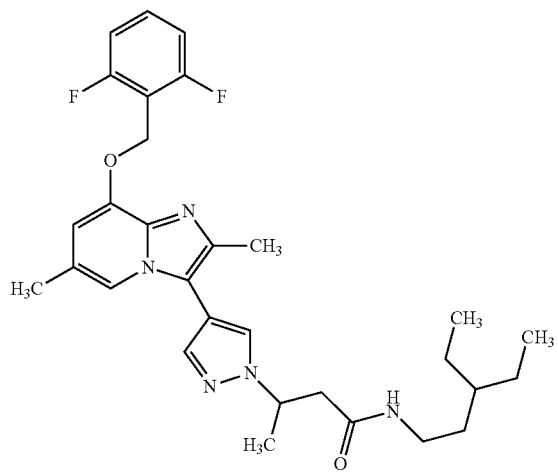 [SMILES: CCC(CC)CCNC(=O)CC(C)n1cc(-c2c(C)nc3c(OCc4c(F)cccc4F)cc(C)cn23)cn1]

44 mg (0.10 mmol) of rac-3-(4-{8-[(2,6-difluorobenzyl)oxy]-2,6-dimethylimidazo[1,2-a]pyridin-3-yl}-1H-pyrazol-1-yl)butanoic acid from Example 110, 49.4 mg (0.13 mmol) of HATU and 0.07 ml (0.40 mmol) of N,N-diisopropylethylamine in 0.33 ml of DMF were stirred at RT for 10 min, 15 mg (0.13 mmol) of N,N-diethylethane-1,2-diamine were added and the mixture was stirred at RT overnight. 19 mg (0.05 mmol) of HATU, 0.035 ml (0.20 mmol) of N,N-diisopropylethylamine and 17.4 mg (0.15 mmol) of N,N-diethylethane-1,2-diamine were then added to the reaction mixture and the mixture was stirred at RT for 30 min. TFA was added and the reaction solution was then purified by preparative HPLC (RP18 column, mobile phase: acetonitrile/water gradient with addition of 0.1% TFA). The concentrated product fractions were partitioned between dichloromethane and saturated aqueous sodium bicarbonate solution. The aqueous phase was extracted twice with dichloromethane, the combined organic phases were dried over sodium sulphate and filtered and the filtrate was concentrated and lyophilized. This gave 33 mg of the target compound (60% of theory).

LC-MS (Method 1): $R_t$=0.58 min

MS (ESpos): m/z=539 (M+H)$^+$ $^1$H NMR (400 MHz, DMSO-d$_6$) δ=0.78-0.98 (m, 6 H), 1.50 (d, 3 H), 2.23-2.47 (m, 10 H), 2.58-2.69 (m, 1 H), 2.70-2.80 (m, 1 H), 2.98-3.14 (m, 2 H), 4.79-4.89 (m, 1 H), 5.28 (s, 2 H), 6.72 (s, 1 H), 7.23 (t, 2 H), 7.55-7.65 (m, 1 H), 7.72 (s, 1 H), 7.76 (s, 1 H), 7.84 (br. s, 1 H), 8.09 (s, 1 H).

Example 113

N-Cyclopropyl-2-(4-{8-[(2,6-difluorobenzyl)oxy]-2,6-dimethylimidazo[1,2-a]pyridin-3-yl}-1H-pyrazol-1-yl)acetamide

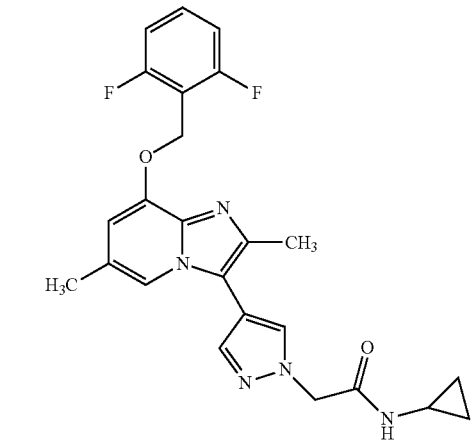 [SMILES: Cc1cc(OCc2c(F)cccc2F)c2nc(C)c(-c3cnn(CC(=O)NC4CC4)c3)n2c1]

55 mg (0.13 mmol) of (4-{8-[(2,6-difluorobenzyl)oxy]-2,6-dimethylimidazo[1,2-a]pyridin-3-yl}-1H-pyrazol-1-yl)acetic acid from Example 108, 56 mg (0.15 mmol) of HATU and 0.09 ml (0.53 mmol) of N,N-diisopropylethylamine in 0.85 ml of DMF were stirred at RT for 20 min, 9 mg (0.15 mmol) of cyclopropylamine were added and the mixture was stirred at RT overnight. The reaction solution was concentrated and then purified twice by preparative TLC (1. mobile phase: dichloromethane/methanol=10/1; 2. mobile phase: dichloromethane/2 N ammonia solution in methanol=20/1). This gave 5.1 mg of the target compound (8% of theory).

LC-MS (Method 1): $R_t$=0.76 min

MS (ESpos): m/z=452 (M+H)$^+$ $^1$H NMR (400 MHz, DMSO-d$_6$) δ=0.42-0.48 (m, 2 H), 0.62-0.69 (m, 2 H), 2.25-2.34 (m, 6 H), 2.63-2.70 (m, 1 H), 4.80 (s, 2 H), 5.28 (s, 2 H), 6.73 (s, 1 H), 7.23 (t, 2 H), 7.55-7.65 (m, 1 H), 7.72 (s, 1 H), 7.78 (s, 1 H), 8.10 (s, 1 H), 8.34 (d, 1 H).

Example 114

N-Cyclopropyl-3-(4-{8-[(2,6-difluorobenzyl)oxy]-2,6-dimethylimidazo[1,2-a]pyridin-3-yl}-1H-pyrazol-1-yl)propanamide

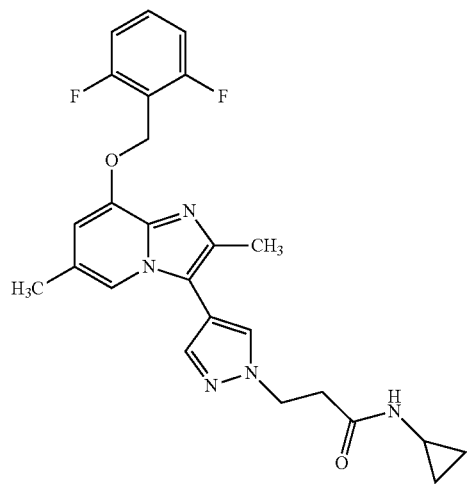 [SMILES: Cc1cc(OCc2c(F)cccc2F)c2nc(C)c(-c3cnn(CCC(=O)NC4CC4)c3)n2c1]

50 mg (0.11 mmol) of methyl 3-(4-{8-[(2,6-difluorobenzyl)oxy]-2,6-dimethylimidazo[1,2-a]pyridin-3-yl}-1H-pyrazol-1-yl)propanoate from Example 102 and 843 mg (14.76 mmol) of cyclopropylamine were stirred at 50° C. The reaction solution was concentrated and the residue was concentrated twice with dichloromethane and then purified by silica gel chromatography (solvent:

pure dichloromethane; dichloromethane/methanol 100/1 to 40/1). The concentrated product fractions were re-purified by preparative HPLC (RP18 column, mobile phase: acetonitrile/water gradient with addition of 0.1% TFA). The product-containing fractions were concentrated and the residue was concentrated three times with dichloromethane/formic acid (10/1) and then three times with dichloromethane. This gave 32 mg of the target compound (58% of theory).

LC-MS (Method 1): $R_t$=0.75 min

MS (ESpos): m/z=466 (M+H)$^+$ $^1$H NMR (400 MHz, DMSO-d$_6$) δ=0.29-0.36 (m, 2 H), 0.55-0.62 (m, 2 H), 2.24-2.39 (m, 6 H), 2.54-2.72 (m, 3 H), 4.42 (t, 2 H), 5.32 (s, 2 H), 6.99 (br. s, 1 H), 7.23 (t, 2 H), 7.55-7.65 (m, 1 H), 7.73-7.88 (m, 2 H), 8.07 (d, 1 H), 8.10 (s, 1 H).

Example 115

2-(4-{8-[(2,6-Difluorobenzyl)oxy]-2,6-dimethylimidazo[1,2-a]pyridin-3-yl}-1H-pyrazol-1-yl)acetamide

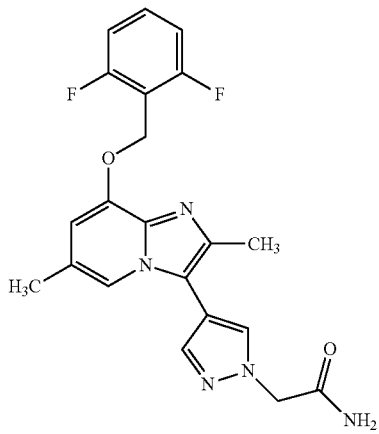 [SMILES: Cc1cc(OCc2c(F)cccc2F)c2nc(C)c(-c3cnn(CC(N)=O)c3)n2c1]

29 mg (0.26 mmol) of potassium tert-butoxide, 3.3 mg (0.02 mmol) of potassium iodide and 44 mg (0.32 mmol) of 2-bromoacetamide were added to 70 mg (0.29 mmol) of 8-[(2,6-difluorobenzyl)oxy]-2,6-dimethyl-3-(1H-pyrazol-4-yl)imidazo[1,2-a]pyridine from Example 88 in 1.1 ml of DMF, and the mixture was stirred at 70° C. overnight. After cooling, the solid was filtered off and washed well with THF, the filtrate was concentrated and the residue was purified by preparative HPLC (RP18 column, mobile phase: acetonitrile/water gradient with addition of 0.1% TFA). The concentrated product fractions were partitioned between dichloromethane and saturated aqueous sodium bicarbonate solution. The aqueous phase was extracted twice with dichloromethane, the combined organic phases were dried over sodium sulphate and filtered and the filtrate was concentrated and lyophilized. This gave 32 mg of the target compound (37% of theory).

LC-MS (Method 1): $R_t$=0.66 min

MS (ESpos): m/z=412 (M+H)$^+$ $^1$H NMR (400 MHz, DMSO-d$_6$) δ=2.25-2.32 (m, 6 H), 4.86 (s, 2 H), 5.29 (s, 2 H), 6.75 (s, 1 H), 7.23 (t, 2 H), 7.30 (br. s, 1 H), 7.48-7.65 (m, 2 H), 7.73 (s, 1 H), 7.79 (s, 1 H), 8.12 (s, 1 H).

Example 116

1-(4-{8-[(2,6-Difluorobenzyl)oxy]-2,6-dimethylimidazo[1,2-a]pyridin-3-yl}-1H-pyrazol-1-yl)-2-methylpropan-2-ol

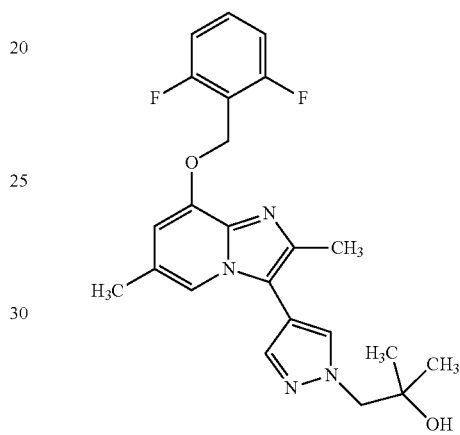

At 0° C. and under argon, 0.27 ml (0.82 mmol) of a methylmagnesium solution (3 M in diethyl ether) was added to 100 mg (0.24 mmol) of methyl (4-{8-[(2,6-difluorobenzyl)oxy]-2,6-dimethylimidazo[1,2-a]pyridin-3-yl}-1H-pyrazol-1-yl)acetate from Example 103 in 2.3 ml of dry THF, and the mixture was stirred at this temperature for 15 min. The mixture, slowly warming to RT, was then stirred at room temperature overnight. Saturated aqueous ammonium chloride solution was carefully added to the reaction mixture. Celite was added to the suspension, the solid was filtered off and washed well with THF, the filtrate was concentrated and the residue was purified by silica gel chromatography (mobile phase: dichloromethane/methanol 20/1). The product fractions were concentrated and purified by preparative TLC (mobile phase: dichloromethane/methanol=10/1). This gave 30.5 mg of the target compound (31% of theory).

LC-MS (Method 1): $R_t$=0.76 min

MS (ESpos): m/z=427 (M+H)$^+$ $^1$H NMR (400 MHz, DMSO-d$_6$) δ=1.12 (s, 6 H), 2.26-2.32 (m, 6 H), 4.12 (s, 2 H), 4.77 (s, 1 H), 5.28 (s, 2 H), 6.73 (s, 1 H), 7.23 (t, 2 H), 7.55-7.65 (m, 1 H), 7.73 (s, 1 H), 7.77 (s, 1 H), 8.04 (s, 1 H).

Example 117

1-(4-{8-[(2,6-Difluorobenzyl)oxy]-2,6-dimethylimidazo[1,2-a]pyridin-3-yl}-1H-pyrazol-1-yl)-2-methylpropan-2-amine hydrochloride

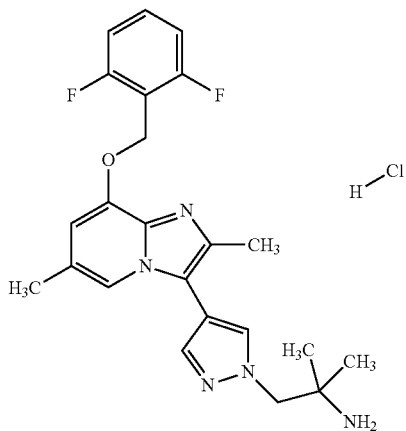 [SMILES: Cc1cc(OCc2c(F)cccc2F)c2nc(C)c(-c3cnn(CC(C)(C)N)c3)n2c1 ; Cl]

0.1 ml (0.20 mmol) of hydrogen chloride solution (2 N in diethyl ether) was added to 70 mg (0.17 mmol) of 1-(4-{8-[(2,6-difluorobenzyl)oxy]-2,6-dimethylimidazo[1,2-a]pyridin-3-yl}-1H-pyrazol-1-yl)-2-methylpropan-2-amine from Example 89 in 1.3 ml of diethyl ether, and the mixture was stirred at room temperature for 30 min. The solvent was removed on a rotary evaporator. This gave 78 mg of the target compound (98% of theory).

LC-MS (Method 1): $R_t$=0.53 min
MS (ESpos): m/z=426 (M+H)$^+$
$^1$H NMR (400 MHz, DMSO-d$_6$) δ=1.28 (s, 6 H), 2.26-2.32 (m, 6 H), 4.38 (s, 2 H), 5.28 (s, 2 H), 6.76 (s, 1 H), 7.22 (t, 2 H), 7.54-7.64 (m, 1 H), 7.80-8.12 (m, 4 H), 7.78 (s, 1 H), 8.20 (s, 1 H).

Example 118

8-[(2,6-Difluorobenzyl)oxy]-2,6-dimethyl-3-{1-[2-(morpholin-4-yl)ethyl]-1H-pyrazol-4-yl}imidazo[1,2-a]pyridine

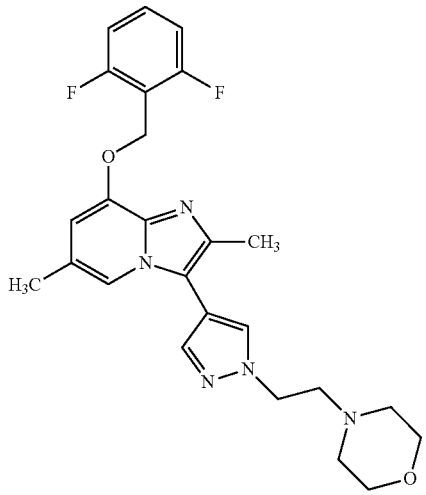 [SMILES: Cc1cc(OCc2c(F)cccc2F)c2nc(C)c(-c3cnn(CCN4CCOCC4)c3)n2c1]

Under argon, 1.9 ml of a degassed 3:1 mixture of 1,2-dimethoxyethane and water were added to 125 mg (0.33 mmol) of 3-bromo-8-[(2,6-difluorobenzyl)oxy]-2,6-dimethylimidazo[1,2-a]pyridine from Example 30A, 112 mg (0.36 mmol) of 4-{2-[4-(4,4,5,5-tetramethyl-1,3,2-dioxaborolan-2-yl)-1H-pyrazol-1-yl]ethyl}morpholine, 111 mg (1.32 mmol) of sodium bicarbonate and 13.5 mg (0.02 mmol) of bis(diphenylphosphino)ferrocenepalladium(II) chloride/dichloromethane complex. The reaction mixture was stirred at 80° C. overnight. The reaction mixture was diluted with water/TFA and purified by preparative HPLC (RP18 column, mobile phase: acetonitrile/water gradient with addition of 0.1% TFA). The product-containing fractions were concentrated, and the residue was taken up in dichloromethane and washed with saturated aqueous sodium bicarbonate solution. The aqueous phase was extracted twice with dichloromethane, and the combined organic phases were dried over sodium sulphate, filtered, concentrated and lyophilized. This gave 44 mg of the target compound (27% of theory, purity 94%).

LC-MS (Method 1): $R_t$=0.60 min
MS (ESpos): m/z=468 (M+H)$^+$
$^1$H NMR (400 MHz, DMSO-d$_6$) δ=2.26-2.32 (m, 6 H), 2.38-2.50 (m, 4 H), 2.78 (t, 2 H), 3.48-3.60 (m, 4 H), 4.32 (t, 2 H), 5.28 (s, 2 H), 6.74 (s, 1 H), 7.23 (t, 2 H), 7.54-7.65 (m, 1 H), 7.71 (s, 1 H), 7.77 (s, 1 H), 8.16 (s, 1 H).

The example compounds shown in Table 6 were prepared analogously to Example 118 by reacting 3-bromo-8-[(2,6-difluorobenzyl)oxy]-2-methylimidazo[1,2-a]pyridine from Example 28A or 3-bromo-8-[(2,6-difluorobenzyl)oxy]-2,6-dimethylimidazo[1,2-a]pyridine from Example 30A with the appropriate commercially available pinacol boronic acid esters, sodium bicarbonate or potassium carbonate (4 equivalents) and bis(diphenylphosphino)ferrocenepalladium (II) chloride/dichloromethane complex (0.02-0.1 equivalent) in 1,2-dimethoxyethane/water (3/1) or acetonitrile under the reaction conditions described (reaction time: 12-24 h; temperature: 80° C.).

Illustrative Workup of the Reaction Mixture:
The reaction mixture was diluted with water/TFA and purified by preparative HPLC (RP18 column, mobile phase: acetonitrile/water gradient with addition of 0.1% TFA). Additionally or alternatively, the crude product was purified by silica gel chromatography (mobile phase: dichloromethane/methanol=20/1 to 10/1). The product-containing fractions were concentrated, and the residue was taken up in dichloromethane and washed with saturated aqueous sodium bicarbonate solution. The aqueous phase was extracted twice with dichloromethane, and the combined organic phases were dried over sodium sulphate, filtered, concentrated and lyophilized.

TABLE 6

| Example No. | IUPAC name/structure (Yield) | Analytical methods |
|---|---|---|
| 119 | 8-[(2,6-difluorobenzyl)oxy]-2-methyl-3-{1-[2-(morpholin-4-yl)ethyl]-1H-pyrazol-4-yl}imidazo[1,2-a]pyridine<br>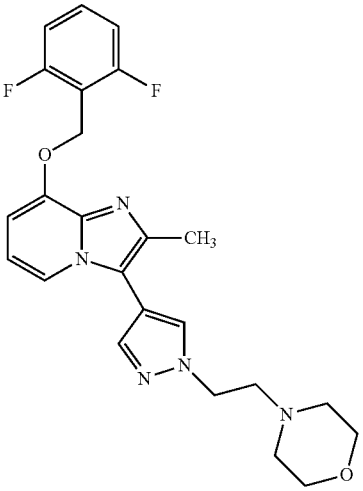<br>(33% of theory) | LC-MS (Method 1): $R_t$ = 0.53 min<br>MS (ESpos): m/z = 454 (M + H)$^+$<br>$^1$H-NMR (400 MHz, DMSO-d$_6$) δ = 2.32 (s, 3 H), 2.39-2.50 (m, 4 H), 2.78 (t, 2 H), 3.54-3.60 (m, 4 H), 4.32 (t, 2 H), 5.30 (s, 2 H), 6.79-6.85 (m, 2 H), 7.22 (t, 2 H), 7.54-7.64 (m, 1 H), 7.77 (s, 1 H), 7.90 (d, 1 H), 8.18 (s, 1 H). |
| 120 | 8-[(2,6-difluorobenzyl)oxy]-2,6-dimethyl-3-{3-[(4-methylpiperazin-1-yl)methyl]phenyl}imidazo[1,2-a]pyridine<br>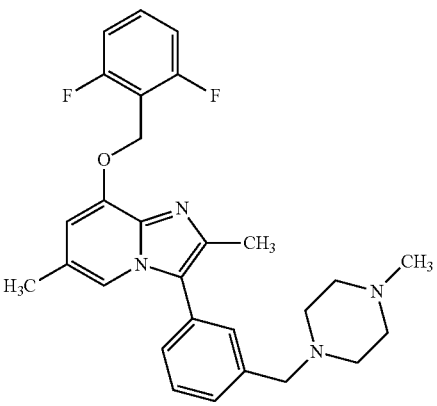<br>(10% of theory) | LC-MS (Method 1): $R_t$ = 0.61 min<br>MS (ESpos): m/z = 477 (M + H)$^+$<br>$^1$H-NMR (400 MHz, DMSO-d$_6$) δ = 2.18 (s, 3 H), 2.22-2.55 (m, 14 H), 3.57 (s, 2 H), 5.29 (s, 2 H), 6.78 (s, 1 H), 7.24 (t, 2 H), 7.32-7.43 (m, 3 H), 7.52 (t, 1 H), 7.55-7.65 (m, 1 H), 7.69 (s, 1 H). |

TABLE 6-continued

| Example No. | IUPAC name/structure (Yield) | Analytical methods |
|---|---|---|
| 121 | 8-[(2,6-difluorobenzyl)oxy]-2-methyl-3-[1-(pyridin-3-yl)-1H-pyrazol-4-yl]imidazo[1,2-a]pyridine<br>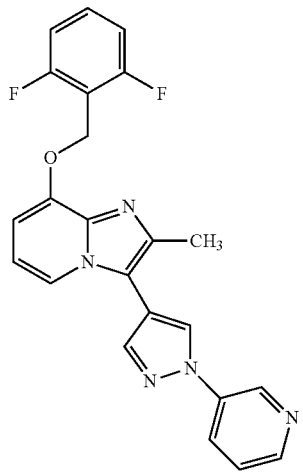<br>(13% of theory) | LC-MS (Method 1): $R_t$ = 0.70 min<br>MS (ESpos): m/z = 418 (M + H)$^+$<br>$^1$H-NMR (400 MHz, DMSO-d$_6$) δ = 2.40 (s, 3 H), 5.32 (s, 2 H), 6.83-6.91 (m, 2 H), 7.23 (t, 2 H), 7.55-7.64 (m, 2 H), 8.11 (d, 1 H), 8.20 (s, 1 H), 8.32-8.38 (m, 1 H), 8.58 (d, 1 H), 9.01 (s, 1 H), 9.24 (d, 1 H). |
| 122 | 8-[(2,6-difluorobenzyl)oxy]-3-[1-(5-fluorpyridin-3-yl)-1H-pyrazol-4-yl]-2-methylimidazo[1,2-a]pyridine<br>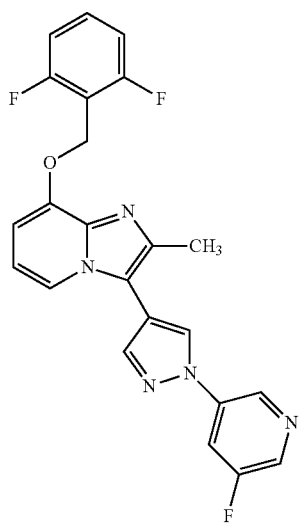<br>(23% of theory) | LC-MS (Method 1): $R_t$ = 0.77 min<br>MS (ESpos): m/z = 436 (M + H)$^+$<br>$^1$H-NMR (400 MHz, DMSO-d$_6$) δ = 2.42 (s, 3 H), 5.33 (s, 2 H), 6.84-6.91 (m, 2 H), 7.23 (t, 2 H), 7.55-7.64 (m, 1 H), 8.11 (d, 1 H), 8.23 (s, 1 H), 8.33-8.39 (m, 1 H), 8.60 (d, 1 H), 9.06 (s, 1 H), 9.18 (s, 1 H). |

Example 123

8-[(2,6-Difluorobenzyl)oxy]-3-[1-(4-fluorophenyl)-1H-pyrazol-4-yl]-2-methylimidazo[1,2-a]pyridine

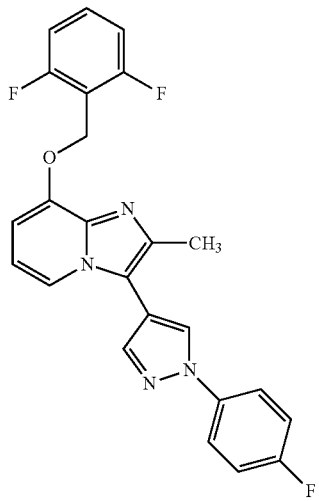 [SMILES: Cc1nc2c(OCc3c(F)cccc3F)cccn2c1-c1cnn(-c2ccc(F)cc2)c1]

Under argon, 175 mg (6.81 mmol) of [1-(4-fluorophenyl)-1H-pyrazol-4-yl]boronic acid, 180 mg (0.85 mmol) of potassium phosphate and 14.5 mg (0.03 mmol) of bis(tri-tert-butylphosphine)palladium(0) were added to 100 mg (0.28 mmol) of 3-bromo-8-[(2,6-difluorobenzyl)oxy]-2-methylimidazo[1,2-a]pyridine from Example 28A in the solvent mixture toluene/ethanol/water (1 ml/2 ml/1 ml), and the mixture was stirred in an oil bath, preheated to 120° C., for 15 min. The reaction mixture was concentrated and the crude product was purified by preparative HPLC (RP18 column, mobile phase: acetonitrile/water gradient with addition of 0.1% TFA). The product fraction was triturated with acetonitrile and the solid present was filtered off. This gave 62 mg of the target compound (50% of theory).

LC-MS (Method 1): $R_t$=0.92 min

MS (ESpos): m/z=435 (M+H)$^+$ $^1$H NMR (400 MHz, DMSO-d$_6$) δ=2.39 (s, 3 H), 5.32 (s, 2 H), 6.81-6.89 (m, 2 H), 7.23 (t, 2 H), 7.40 (t, 2 H), 7.55-7.64 (m, 1 H), 7.96-8.05 (m, 2 H), 8.08-8.13 (m, 2 H), 8.88 (s, 1 H).

Example 124

5-{8-[(2,6-Difluorobenzyl)oxy]-2-methylimidazo[1,2-a]pyridin-3-yl}-1H-1,2,4-triazol-3-amine

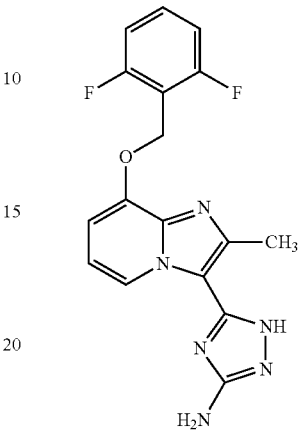

1.248 g (23.099 mmol) of sodium methoxide in 20 ml of methanol were cooled to 0° C. 2.844 g (11.549 mmol) of aminoguanidine hemisulphate were added and the mixture was stirred at RT for 10 min. 2.00 g (5.775 mmol) of ethyl 8-[(2,6-difluorobenzyl)oxy]-2-methylimidazo[1,2-a]pyridine-3-carboxylate from Example 2A were suspended in 20 ml of methanol and the mixture was heated at reflux overnight. The mixture was then concentrated and the residue was purified by preparative HPLC (methanol:water:water (+1% trifluoroacetic acid)−55:40:5-isocratic). This gave 60 mg of the target compound (2.6% of theory).

LC-MS (Method 1): $R_t$=0.64 min

MS (ESpos): m/z=357.2 (M+H)$^+$ $^1$H-NMR (400 MHz, DMSO-d$_6$): δ=2.72 (s, 3 H), 5.46 (s, 2 H), 6.45 (s br, 2H), 7.23-7.29 (m, 2 H), 7.41-7.51 (br s, 1 H), 7.59-7.66 (m, 2H), 9.33 (d, 1 H), 12.63 (br s, 1H).

Example 125

3-{8-[(2,6-Difluorobenzyl)oxy]-2-methylimidazo[1,2-a]pyridin-3-yl}-1-(2,2,2-trifluoroethyl)-1H-1,2,4-triazol-5-amine

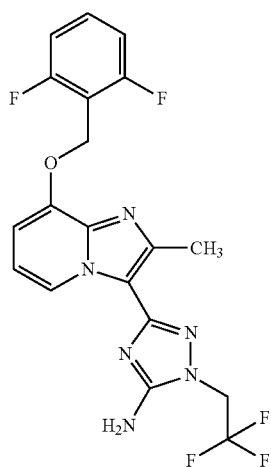 [SMILES: Cc1nc2c(OCc3c(F)cccc3F)cccn2c1-c1nc(N)n(CC(F)(F)F)n1]

25 µl (0.152 mmol) of 2,2,2-trifluoroethyl trichloromethanesulphonate were added to 45 mg (0.127 mmol) of 5-{8-[(2,6-difluorobenzyl)oxy]-2-methylimidazo[1,2-a]pyridin-3-yl}-1H-1,2,4-triazole-3-amine from Example 124 and 49.5 mg (0.152 mmol) of caesium carbonate in DMF (2 ml). The mixture was stirred at RT for 3 days and another 20.6 mg (0.063 mmol) of caesium carbonate and 10 µl (0.063 mmol) of 2,2,2-trifluoroethyl trichloromethanesulphonate were then added and the mixture was stirred at RT overnight. The reaction solution was filtered and purified by preparative HPLC (mobile phase: acetonitrile/water with 0.05% formic acid, gradient). This gave 12 mg (21% of theory) of the target compound.

LC-MS (Method 1): $R_t$=0.76 min
MS (ESpos): m/z=439.2 (M+H)$^+$
$^1$H-NMR (400 MHz, DMSO-d$_6$): δ=2.60 (s, 3 H), 4.98-5.05 (dd, 2H), 5.31 (s, 2 H), 6.88 (s br, 2H), 6.96 (d, 2H), 7.22-7.26 (m, 2 H), 7.55-7.63 (m, 1 H), 9.02 (t, 1 H).

Example 126

8-[(2,6-Difluorobenzyl)oxy]-2,6-dimethyl-3-[5-(trifluoromethyl)-1H-1,2,4-triazol-3-yl]imidazo[1,2-a]pyridine

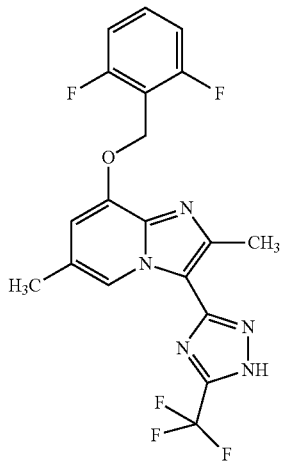

1 ml (7.080 mmol) of trifluoroacetic anhydride was added to 300 mg of 8-[(2,6-difluorobenzyl)oxy]-2,6-dimethylimidazo[1,2-a]pyridine-3-carboximidohydrazide, the crude product from Example 43A, in dichloromethane (1 ml). The mixture was stirred at RT overnight. The reaction solution was purified by preparative HPLC (mobile phase: acetonitrile/water with 0.05% formic acid, gradient). This gave 34 mg (43% of theory) of the target compound.

LC-MS (Method 1): $R_t$=1.00 min
MS (ESpos): m/z=424.2 (M+H)$^+$
$^1$H-NMR (400 MHz, DMSO-d$_6$): δ=2.36 (s, 3 H), 5.32 (s, 2 H), 7.02 (s, 1H), 7.22-7.28 (m, 2 H), 7.57-7.64 (m, 1 H), 8.47 (br s, 1 H), 15.05 (br s, 1H), 1 signal probably under DMSO signal.

Example 127

1-(4-{8-[(2,6-Difluorobenzyl)oxy]-2,6-dimethylimidazo[1,2-a]pyridin-3-yl}-3-methyl-1H-pyrazol-1-yl)-2-methylpropan-2-amine formate

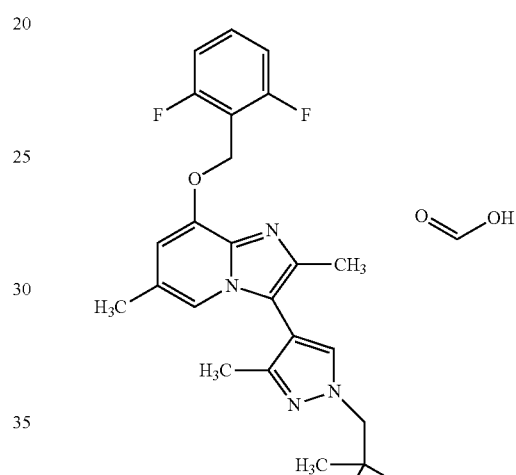

Under argon, about 203 mg of Raney nickel (50% aqueous suspension) were added to 59 mg (0.13 mmol) of 8-[(2,6-difluorobenzyl)oxy]-2,6-dimethyl-3-[3-methyl-1-(2-methyl-2-nitropropyl)-1H-pyrazol-4-yl]imidazo[1,2-a]pyridine from Example 74A in 2 ml of ethanol, and the mixture was stirred at RT and under atmospheric pressure overnight with hydrogen. The reaction mixture was filtered through kieselguhr, the filter cake was washed well with ethanol and the filtrate was concentrated to dryness. The residue was separated by preparative HPLC (RP18 column, mobile phase: acetonitrile/water gradient with addition of 0.05% formic acid) and the product fractions were concentrated on a rotary evaporator. This gave 45 mg of the target compound (74% of theory).

LC-MS (Method 17): $R_t$=1.47 min
MS (ESpos): m/z=440 (M+H)$^+$
$^1$H-NMR (400 MHz, DMSO-d$_6$): δ=1.12-1.22 (m, 6 H), 2.01 (s, 3 H), 2.14-2.19 (m, 3 H), 2.25 (s, 3 H), 4.10-4.18 (m, 2 H), 5.28 (s, 2 H), 6.75 (s, 1 H), 7.20-7.30 (m, 2 H), 7.39 (s, 1 H), 7.55-7.65 (m, 1 H), 7.91 (s, 1 H), 8.25-8.32 (m, 2 H).

Example 128

8-[(2,6-Difluorobenzyl)oxy]-2,6-dimethyl-3-(1H-1,2,4-triazol-3-yl)imidazo[1,2-a]pyridine

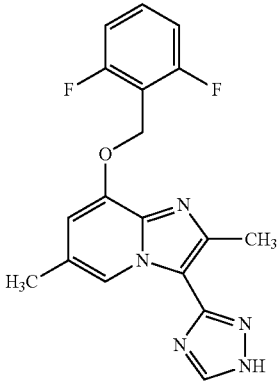

1.00 g (3.02 mmol) of 8-[(2,6-difluorobenzyl)oxy]-2,6-dimethylimidazo[1,2-a]pyridine-3-carboxamide from Example 40A in 6.30 ml (47.58 mmol) of N,N-dimethylformamide dimethyl acetal was heated at 120° C. for 2 hours. The mixture was then cooled and concentrated on a rotary evaporator. 14.5 ml (252.6 mmol) of acetic acid and 0.135 ml (3.47 mmol) of hydrazine hydrate were added to the residue and the mixture was then stirred at 90° C. overnight. After cooling, the solvent was removed on a rotary evaporator. The residue was stirred vigorously with ethyl acetate and saturated aqueous sodium bicarbonate solution. The solid formed was filtered off, washed with water and diethyl ether and then dried under high vacuum. 1.04 g of the target compound were obtained (97% of theory).

LC-MS (Method 1): $R_t$=0.71 min
MS (ESpos): m/z=356 (M+H)$^+$
$^1$H-NMR (400 MHz, DMSO-d$_6$): δ=2.36 (s, 3 H), 2.62 (s, 3 H), 5.30 (s, 2 H), 6.89 (s, 1 H), 7.20-7.29 (m, 2 H), 7.55-7.65 (m, 1 H), 8.73 (s, 1 H), 8.91 (s, 1 H).

Example 129

1-(3-{8-[(2,6-Difluorobenzyl)oxy]-2,6-dimethylimidazo[1,2-a]pyridin-3-yl}-1H-1,2,4-triazol-1-yl)-2-methylpropan-2-amine

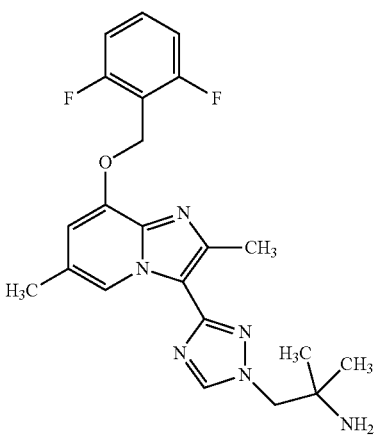

Under argon, about 500 mg of Raney nickel (50% aqueous suspension) were added to 140 mg (0.31 mmol) of 8-[(2,6-difluorobenzyl)oxy]-2,6-dimethyl-3-[1-(2-methyl-2-nitropropyl)-1H-1,2,4-triazol-3-yl]imidazo[1,2-a]pyridine from Example 75A in 5 ml of ethanol, and the mixture was stirred at RT and under atmospheric pressure with hydrogen. The reaction mixture was filtered through kieselguhr, the filter cake was washed well with ethanol and the filtrate was concentrated to dryness. The residue was separated by preparative HPLC (RP18 column, mobile phase: acetonitrile/water gradient with addition of 0.05% diethylamine) and the product fractions were concentrated on a rotary evaporator. This gave 63 mg of the target compound (48% of theory).

LC-MS (Method 1): $R_t$=0.54 min
MS (ESpos): m/z=427 (M+H)$^+$
$^1$H-NMR (400 MHz, DMSO-d$_6$): δ=1.07 (s, 6 H), 2.35 (s, 3 H), 2.61 (s, 3 H), 4.12-4.17 (m, 2 H), 5.30 (s, 2 H), 6.89 (s, 1 H), 7.21-7.29 (m, 2 H), 7.55-7.65 (m, 1 H), 8.66 (s, 1 H), 8.88 (s, 1 H).

Example 130

1-(5-{8-[(2,6-Difluorobenzyl)oxy]-2,6-dimethylimidazo[1,2-a]pyridin-3-yl}-1,3,4-oxadiazol-2-yl)-2-methylpropan-2-amine

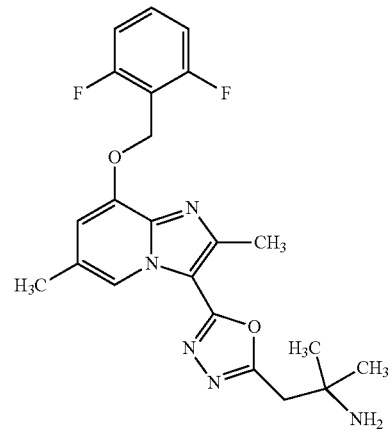 [SMILES: Cc1cc(OCc2c(F)cccc2F)c2nc(C)c(-c3nnc(CC(C)(C)N)o3)n2c1]

1.0 ml of TFA was added dropwise to 125 mg (0.24 mmol) of tert-butyl[1-(5-{8-[(2,6-difluorobenzyl)oxy]-2,6-dimethylimidazo[1,2-a]pyridin-3-yl}-1,3,4-oxadiazol-2-yl)-2-methylpropan-2-yl]carbamate from Example 66A in 4 ml of dichloromethane, and the reaction mixture was stirred at RT for 30 min. The mixture was concentrated on a rotary evaporator and the residue was purified by preparative HPLC (RP18 column, mobile phase: acetonitrile/water gradient with addition of 0.05% diethylamine). The product fractions were concentrated on a rotary evaporator. The residue was stirred with dichloromethane and saturated aqueous sodium bicarbonate solution. The phases were separated, the aqueous phase was washed twice with dichloromethane and the combined organic phases were dried over sodium sulphate. The mixture was filtered and the filtrate was concentrated on a rotary evaporator. The product-containing fractions were re-purified [column: Kromasil 100 C18, 5 μm, 250×20 mm; mobile phase: 56% water, 30% methanol+14% 1% strength aqueous TFA; flow rate: 24 ml/min; 40° C.; detection: 210 nm], concentrated and lyophilized. This gave 46 mg of the target compound (45% of theory).

LC-MS (Method 1): $R_t$=0.73 min
MS (ESpos): m/z=428 (M+H)$^+$
$^1$H-NMR (400 MHz, DMSO-$d_6$): δ=1.42 (s, 6 H), 2.43 (s, 3 H), 2.62 (s, 3 H), 5.35 (s, 2 H), 7.15 (s, 1 H), 7.21-7.30 (m, 2 H), 7.55-7.67 (m, 1 H), 8.10 (br. s., 2 H), 8.78 (s, 1 H).

Example 131

1-(3-{8-[(2,6-Difluorobenzyl)oxy]-2,6-dimethylimidazo[1,2-a]pyridin-3-yl}-1,2,4-oxadiazol-5-yl)-2-methylpropan-2-amine

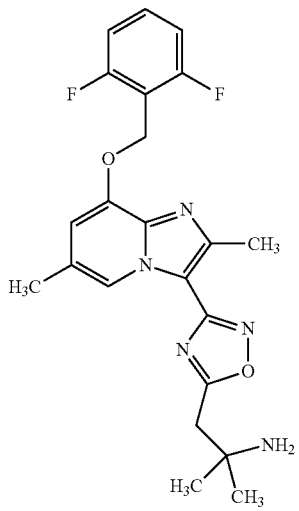 [SMILES: Cc1cc(OCc2c(F)cccc2F)c2nc(C)c(-c3noc(CC(C)(C)N)n3)n2c1]

1.0 ml of TFA was added dropwise to 160 mg (0.30 mmol) of tert-butyl[1-(3-{8-[(2,6-difluorobenzyl)oxy]-2,6-dimethylimidazo[1,2-a]pyridin-3-yl}-1,2,4-oxadiazol-5-yl)-2-methylpropan-2-yl]carbamate from Example 69A in 4 ml of dichloromethane, and the reaction mixture was stirred at RT for 1 h. The mixture was concentrated on a rotary evaporator and purified by preparative HPLC (RP18 column, mobile phase: acetonitrile/water gradient with addition of 0.05% diethylamine) and the product fractions were concentrated on a rotary evaporator. Twice, 5 ml of toluene were added to the residue and the mixture was concentrated to dryness, and 5 ml of an acetonitrile/water mixture were then added. The residual acetonitrile was removed on a rotary evaporator and the aqueous residue was frozen in a dry-ice bath and lyophilized overnight. This gave 31 mg of the target compound (23% of theory, purity 95%).

LC-MS (Method 1): $R_t$=0.79 min
MS (ESpos): m/z=428 (M+H)$^+$
$^1$H-NMR (400 MHz, DMSO-$d_6$): δ=1.25 (s, 6 H), 2.39 (s, 3 H), 2.64 (s, 3 H), 3.17 (s, 2 H), 5.33 (s, 2 H), 7.06 (s, 1 H), 7.21-7.29 (m, 2 H), 7.56-7.65 (m, 1 H), 8.64 (s, 1 H).

Example 132

1-(5-{8-[(2,6-Difluorobenzyl)oxy]-2,6-dimethylimidazo[1,2-a]pyridin-3-yl}-1,2,4-oxadiazol-3-yl)-2-methylpropan-2-amine formate

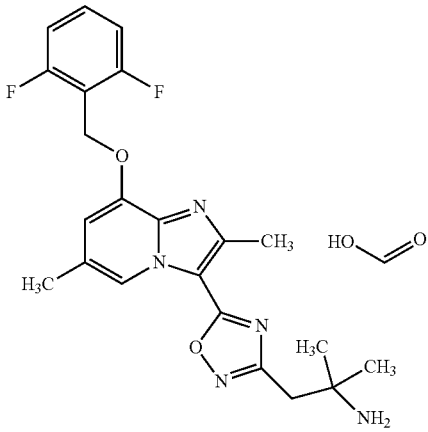 [SMILES: Cc1cc(OCc2c(F)cccc2F)c2nc(C)c(-c3nc(CC(C)(C)N)no3)n2c1 ; O=CO]

5.2 mg of 10% palladium on carbon were added to 52 mg (0.09 mmol) of benzyl [1-(5-{8-[(2,6-difluorobenzyl)oxy]-2,6-dimethylimidazo[1,2-a]pyridin-3-yl}-1,2,4-oxadiazol-3-yl)-2-methylpropan-2-yl]carbamate from Example 72A in 5 ml of ethanol, and the reaction mixture was stirred under argon and at RT for 40 min. The reaction mixture was filtered off and the solvent was removed on a rotary evaporator. The crude product was separated by preparative HPLC (RP18 column, mobile phase: acetonitrile/water gradient with addition of 0.05% formic acid) and the product fractions were concentrated on a rotary evaporator. This gave 21 mg of the target compound (44% of theory, purity 95%).

LC-MS (Method 1): $R_t$=0.78 min
MS (ESpos): m/z=428 (M+H)$^+$
$^1$H-NMR (400 MHz, DMSO-$d_6$): δ=1.22 (s, 6 H), 2.32 (s, 3 H), 2.93 (s, 2 H), 5.29 (s, 2 H), 6.94-6.99 (m, 1 H), 7.20-7.28 (m, 2 H), 7.55-7.64 (m, 1 H), 8.36-8.41 (m, 1 H), 10.18-10.23 (m, 1 H).

Example 133

1-(5-{8-[(2,6-Difluorobenzyl)oxy]-2,6-dimethylimidazo[1,2-a]pyridin-3-yl}-1,3,4-thiadiazol-2-yl)-2-methylpropan-2-amine formate

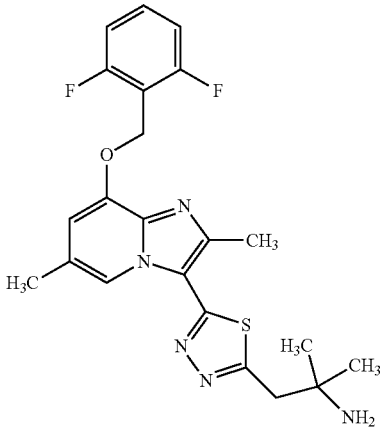

0.5 ml of TFA were added to 12 mg (0.02 mmol; crude product) of tert-butyl[1-(5-{8-[(2,6-difluorobenzyl)oxy]-2,6-dimethylimidazo[1,2-a]pyridin-3-yl}-1,3,4-thiadiazol-2-yl)-2-methylpropan-2-yl]carbamate from Example 65A in 3 ml of dichloromethane, and the mixture was stirred at RT for 0.5 h. The reaction mixture was concentrated and then purified by preparative HPLC (RP18 column, mobile phase: acetonitrile/water gradient with addition of 0.05% formic acid). The product fractions were lyophilized. This gave 6 mg (62% of theory) of the title compound.

LC-MS (Method 1): $R_t$=0.78 min

MS (ESpos): m/z=444 (M+H)$^+$ $^1$H NMR (400 MHz, DMSO-$d_6$) δ=1.15 (s, 6 H), 2.41 (s, 3 H), 2.56 (s, 3 H), 3.20 (br. s, 2 H), 5.34 (s, 2 H), 7.08 (s, 1 H), 7.24 (t, 2 H), 7.55-7.65 (m, 1 H), 9.17 (s, 1 H).

Example 134

8-[(2,6-Difluorobenzyl)oxy]-2-methyl-3-(2H-1,2,3-triazol-4-yl)imidazo[1,2-a]pyridine

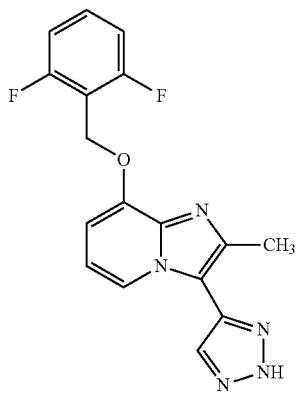 [SMILES: Cc1nc2c(OCc3c(F)cccc3F)cccn2c1-c1cn[nH]n1]

1.30 g (4.36 mmol) of 8-[(2,6-difluorobenzyl)oxy]-3-ethynyl-2-methylimidazo[1,2-a]pyridine from Example 77A, 0.57 ml (4.36 mmol) of azidotrimethylsilane, 33 ml of water/ethanol (2/1), 345 mg (1.74 mmol) of (2R)-2-[(1S)-1,2-dihydroxyethyl]-4-hydroxy-5-oxo-2H-furan-3-olate and 152 mg (0.61 mmol) of copper(II) tetraoxosulphate(VI) pentahydrate were stirred at 50° C. overnight. 173 mg (0.87 mmol) of (2R)-2-[(1S)-1,2-dihydroxyethyl]-4-hydroxy-5-oxo-2H-furan-3-olate and 76 mg (0.31 mmol) of copper(II) tetraoxosulphate(VI) pentahydrate were added and stirring was continued at reflux overnight. 173 mg (0.87 mmol) of (2R)-2-[(1S)-1,2-dihydroxyethyl]-4-hydroxy-5-oxo-2H-furan-3-olate, 76 mg (0.31 mmol) of copper(II) tetraoxosulphate(VI) pentahydrate and 0.573 ml (4.36 mmol) of azidotrimethylsilane were added and stirring was continued at 85° C. overnight. The mixture was cooled, filtered and washed with water. The solid was washed with ethyl acetate. The filtrate was filtered off, washed with water and diethyl ether and dried under high vacuum. The two solids fractions were combined and re-purified [column: Sunfire C18, 5 μm, 250×20 mm; mobile phase: 56% water, 30% acetonitrile+14% 1% strength aqueous TFA; flow rate: 25 ml/min; 25° C.; detection: 210 nm]. This gave 293 mg of the target compound (19% of theory).

LC-MS (Method 16): $R_t$=0.62 min

MS (ESpos): m/z=342 (M+H)$^+$ $^1$H-NMR (400 MHz, DMSO-$d_6$): δ=2.56 (br. s., 3 H), 5.45 (s, 2 H), 7.22-7.31 (m, 2 H), 7.32-7.44 (m, 1 H), 7.45-7.57 (m, 1 H), 7.57-7.66 (m, 1 H), 8.30-8.93 (m, 2 H).

Example 135

8-[(2,6-Difluorobenzyl)oxy]-2,6-dimethyl-3-(4-methylphenyl)imidazo[1,2-a]pyridine

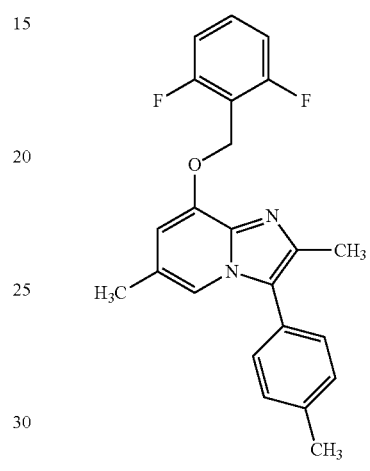

A mixture of 100 mg of 8-[(2,6-difluorobenzyl)oxy]-2,6-dimethylimidazo[1,2-a]pyridine-3-carboxylic acid (0.301 mmol, 1.0 eq.) from Example 16A, 56 μl of 4-bromotoluene (0.45 mmol, 1.5 eq.), 49.9 mg of potassium carbonate (0.361 mmol, 1.2 eq.), 11.5 mg of copper(I) iodide (0.060 mmol, 0.2 eq.) and 16.3 mg of 1,10-phenanthroline in 2.0 ml of N-methylpyrrolidone was degassed in a stream of argon, 3.4 mg of palladium(II) acetate (0.015 mmol, 0.05 eq.) were then added and the mixture was heated in a microwave oven at 200° C. for 30 min. The mixture was then filtered through kieselguhr, eluted with ethyl acetate and concentrated. Water was added, the mixture was extracted twice with ethyl acetate, and the combined organic phases were washed with saturated aqueous sodium chloride solution, dried with magnesium sulphate, filtered and concentrated. The residue was purified by Biotage Isolera (10 g silica gel cartridge, cyclohexane/ethyl acetate gradient, 10%->100% ethyl acetate). This gave 50.7 mg (44% of theory) of the title compound.

TLC (cyclohexane/ethyl acetate 1:1): $R_F$=0.66

LC-MS (Method 17): $R_t$=2.02 min

MS (ESpos): m/z=379 (M+H)$^+$ $^1$H NMR (400 MHz, DMSO-$d_6$): δ [ppm]=2.24 (s, 3 H), 2.26 (s, 3 H), 2.40 (s, 3 H), 5.29 (s, 2 H), 6.76 (br. s, 1 H), 7.25-7.30 (m, 2 H), 7.38 (s, 4 H), 7.55-7.64 (m, 1 H), 7.66 (br. s, 1 H).

Example 136

5-{[(2,6-Difluorobenzyl)oxy]-2,6-dimethylimidazo[1,2-a]pyridin-3-yl}pyridine-2-carbonitrile

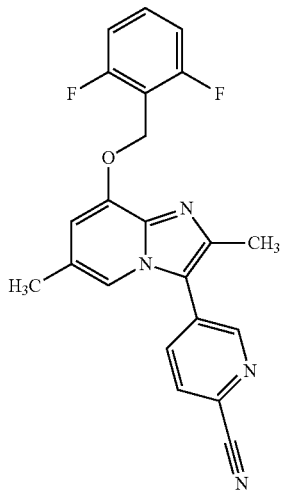

A mixture of 100 mg of 8-[(2,6-difluorobenzyl)oxy]-2,6-dimethylimidazo[1,2-a]pyridine-3-carboxylic acid (0.301 mmol, 1.0 eq.) from Example 16A, 82.6 mg of 5-bromo-2-pyridinecarbonitrile (0.45 mmol, 1.5 eq.), 49.9 mg of potassium carbonate (0.361 mmol, 1.2 eq.), 5.7 mg of copper(I) iodide (0.030 mmol, 0.1 eq.) and 8.1 mg of 1,10-phenanthroline (0.045 mmol, 0.015 eq.) in 1.0 ml of N-methylpyrrolidone was degassed in a stream of argon, 3.4 mg of palladium(II) acetate (0.015 mmol, 0.05 eq.) were then added and the mixture was heated in a microwave oven at 190° C. for 30 min. The mixture was then filtered through kieselguhr, eluted with ethyl acetate and concentrated. Water was added, the mixture was extracted twice with ethyl acetate, and the combined organic phases were washed with saturated aqueous sodium chloride solution, dried with magnesium sulphate, filtered and concentrated. The residue was purified by Biotage Isolera (10 g silica gel cartridge, cyclohexane/ethyl acetate gradient, 10%->66% ethyl acetate), giving 32.0 mg (purity: 53%) of the title compound. The impure product was purified together with the crude product of a further reaction by preparative HPLC (Method 19). The resulting crude product was recrystallized from a mixture of water, methanol and acetonitrile. This gave 20.3 mg of the title compound.

TLC (cyclohexane/ethyl acetate 2:1): $R_F$=0.17
LC-MS (Method 1): $R_t$=0.78 min
MS (ESpos): m/z=391 (M+H)$^+$
$^1$H-NMR (400 MHz, DMSO-d$_6$): δ [ppm]=2.28 (s, 3 H), 2.34 (s, 3 H), 5.30 (s, 2 H), 6.89 (s, 1 H), 7.21-7.29 (m, 2 H), 7.55-7.65 (m, 1 H), 7.91 (s, 1 H), 8.18-8.27 (m, 2 H), 8.93 (d, 1 H).

Example 137

8-[(2,6-Difluorobenzyl)oxy]-2,6-dimethyl-3-(5-methyl-1,3-oxazol-2-yl)imidazo[1,2-a]pyridine

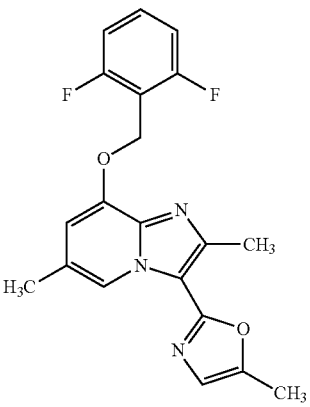

4.1 mg of gold(III) chloride (0.014 mmol, 0.05 eq.) were added to a suspension of 100 mg of 8-[(2,6-difluorobenzyl)oxy]-2,6-dimethyl-N-(prop-2-yn-1-yl)imidazo[1,2-a]pyridine-3-carboxamide (0.271 mmol, 1.0 eq.) from Example 58A in 5.0 ml of acetonitrile, and the mixture was stirred at 80° C. overnight. The mixture was then filtered through kieselguhr and eluted using a mixture of acetonitrile and dichloromethane. The filtrate was concentrated and purified using Biotage Isolera (10 g silica gel cartridge, cyclohexane/ethyl acetate gradient). This gave 59 mg (59% of theory) of the title compound.

LC-MS (Method 1): $R_t$=0.98 min
MS (ESpos): m/z=370 (M+H)$^+$
$^1$H-NMR (400 MHz, DMSO-d$_6$): δ [ppm]=2.38 (s, 3 H), 2.42 (s, 3 H), 2.60 (s, 3 H), 5.31 (s, 2 H), 6.99-7.01 (m, 1 H), 7.09-7.11 (m, 1 H), 7.20-7.30 (m, 2 H), 7.53-7.65 (m, 1 H), 8.87-8.91 (m, 1 H).

Example 138

Ethyl 5-{8-[(2,6-difluorobenzyl)oxy]-2,6-dimethylimidazo[1,2-a]pyridin-3-yl}-1,3-thiazole-2-carboxylate

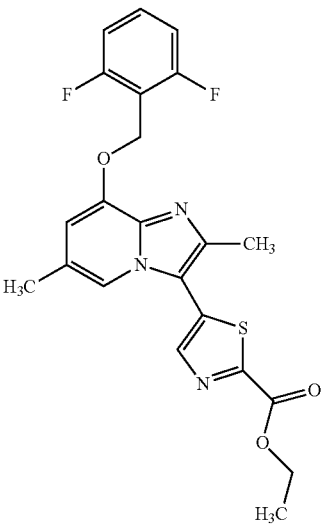 [SMILES: CCOC(=O)c1ncc(-c2c(C)nc3c(OCc4c(F)cccc4F)cc(C)cn23)s1]

A mixture of 43.0 mg of 2-bromo-1-{8-[(2,6-difluorobenzyl)oxy]-2,6-dimethylimidazo[1,2-a]pyridin-3-yl}ethanone (0.105 mmol, 1.0 eq.) from Example 61A and 28.0 mg of ethyl thiooxamidate (0.210 mmol, 2.0 eq.) in 5.0 ml of ethanol was heated at reflux for 5 h. The mixture was then concentrated and purified using Biotage Isolera (25 g silica gel cartridge, cyclohexane/ethyl acetate gradient, and dichloromethane/methanol gradient). The isolated product mixture was purified by preparative HPLC (Method 21), giving 8.9 mg (19% of theory) of the title compound.

LC-MS (Method 1): $R_t$=0.92 min

MS (ESpos): m/z=444 (M+H)$^+$ $^1$H-NMR (400 MHz, CDCl$_3$): δ [ppm]=1.48 (t, 3 H), 2.35 (s, 3 H), 2.58 (s, 3 H), 4.53 (q, 2 H), 5.32 (s, 2 H), 6.60 (s, 1 H), 6.89-6.99 (m, 2 H), 7.29-7.40 (m, 1 H), 7.61 (s, 1 H), 8.37 (s, 1 H).

Example 139

5-{8-[(2,6-Difluorobenzyl)oxy]-2,6-dimethylimidazo[1,2-a]pyridin-3-yl}-3-ethoxythiophen-2-amine

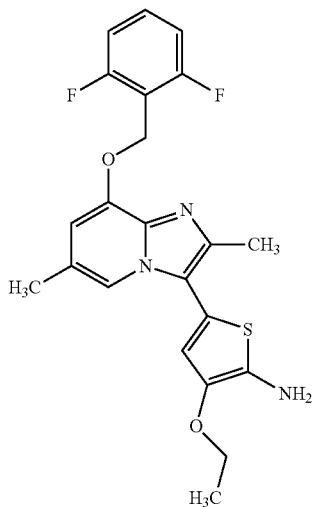 [SMILES: CCOc1cc(-c2c(C)nc3c(OCc4c(F)cccc4F)cc(C)cn23)sc1N]

The title compound was formed as a by-product in the synthesis of ethyl 5-{8-[(2,6-difluorobenzyl)oxy]-2,6-dimethylimidazo[1,2-a]pyridin-3-yl}-1,3-thiazole-2-carboxylate.

LC-MS (Method 1): $R_t$=1.01 min

MS (ESpos): m/z=430 (M+H)$^+$ $^1$H-NMR (400 MHz, CDCl$_3$): δ [ppm]=1.40 (t, 3 H), 2.38 (s, 3 H), 2.78 (s, 3 H), 4.38 (q, 2 H), 5.32 (s, 2 H), 6.53 (s, 1 H), 6.75 (s, 1 H), 6.89-6.98 (m, 2 H), 7.29-7.41 (m, 1 H), 9.18 (s, 1 H). (NH$_2$ was not observed).

Example 140

8-[(2,6-Difluorobenzyl)oxy]-2,6-dimethyl-3-(pyridin-3-yl)imidazo[1,2-a]pyridine

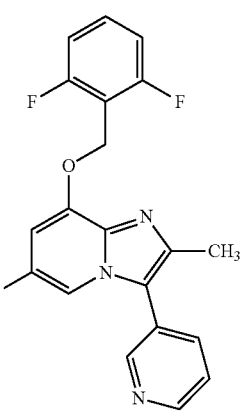

A mixture of 69.5 mg of 3-bromo-8-[(2,6-difluorobenzyl)oxy]-2,6-dimethylimidazo[1,2-a]pyridine (0.185 mmol, 1.0 eq.) from Example 30A, 34.2 mg of pyridine-3-boronic acid (0.278 mmol, 1.5 eq.) and (2-aminobiphenyl-2-yl)(chloro)palladium-dicyclohexyl[2',4',6'-tri(propan-2-yl)biphenyl-2-yl]phosphane (1:1) [CAS No: 1028206-56-5; Sigma Aldrich] (0.009 mmol, 0.05 eq.), 2.0 ml of acetonitrile and 1.1 ml of 0.5 M aqueous potassium phosphate solution (0.56 ml, 3.0 eq.) was stirred at 60° C. for 48 h. The mixture was then filtered through an Extrelute cartridge and eluted with ethyl acetate, and the filtrate was concentrated. The crude product was purified by preparative HPLC (Method 19), giving 32.7 mg (68% of theory) of the title compound.

LC-MS (Method 1): $R_t$=0.75 min

MS (ESpos): m/z=366 (M+H)$^+$ $^1$H-NMR (400 MHz, DMSO-d$_6$): δ [ppm]=2.27 (s, 3 H), 2.29 (s, 3 H), 5.30 (s, 2 H), 6.83 (br. s, 1 H), 7.22-7.29 (m, 2 H), 7.55-7.65 (m, 2 H), 7.74 (br. s, 1 H), 7.94-8.01 (m, 1 H), 8.63-8.67 (m, 1 H), 8.69-8.74 (m, 1 H)

Example 141

Ethyl 5-{8-[(2,6-difluorobenzyl)oxy]-2,6-dimethyl-imidazo[1,2-a]pyridin-3-yl}-1,2-oxazole-3-carboxylate

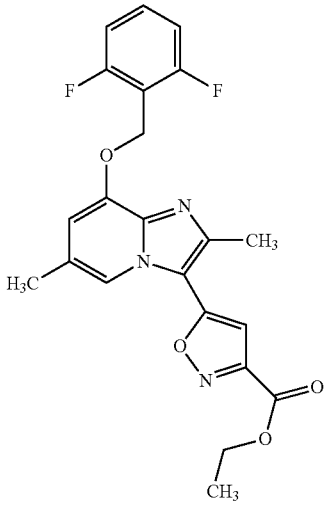 [SMILES: CCOC(=O)c1cc(-c2c(C)nc3c(OCc4c(F)cccc4F)cc(C)cn23)on1]

A mixture of 815 mg of ethyl 4-{8-[(2,6-difluorobenzyl)oxy]-2,6-dimethylimidazo[1,2-a]pyridin-3-yl}-2,4-dioxobutanoate (80%, 1.89 mmol) from Example 62A and 461 mg of hydroxylamine hydrochloride (6.63 mmol, 3.5 eq.) in 70 ml of ethanol was heated at reflux for 7 days. The reaction mixture was then concentrated and recrystallized from boiling water/acetonitrile. This gave 473 mg (51% of theory, purity 87%) of the title compound.

TLC (cyclohexane/ethyl acetate 1:1): $R_F$=0.51
LC-MS (Method 1): $R_t$=1.12 min
MS (ESpos): m/z=428 (M+H)$^+$
$^1$H-NMR (400 MHz, DMSO-d$_6$): δ [ppm]=1.32-1.41 (m, 3 H), 2.39 (s, 3 H), 4.37-4.49 (m, 2 H), 5.32 (s, 2 H), 7.05 (s, 1 H), 7.16-7.29 (m, 2 H), 7.34 (s, 1 H), 7.55-7.65 (m, 1 H), 8.24 (s, 1 H), (further peak under solvent signal).

Example 142

(5-{8-[(2,6-Difluorobenzyl)oxy]-2,6-dimethylimidazo[1,2-a]pyridin-3-yl}-1,2-oxazol-3-yl)methanol

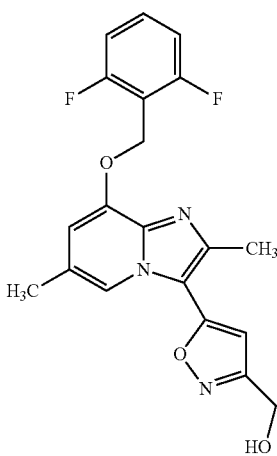 [SMILES: Cc1cc(OCc2c(F)cccc2F)c2nc(C)c(-c3cc(CO)no3)n2c1]

37.4 mg of sodium borohydride (0.990 mmol, 1.0 eq.) were added to a suspension of 470 mg of ethyl 5-{8-[(2,6-difluorobenzyl)oxy]-2,6-dimethylimidazo[1,2-a]pyridin-3-yl}-1,2-oxazole-3-carboxylate (0.990 mmol, 1.0 eq.) from Example 141 in 20 ml of ethanol, and the mixture was stirred at room temperature for 2 h and at reflux for 1 h. The mixture was then concentrated to half its original volume, water was added and the mixture was extracted repeatedly with dichloromethane. The combined organic phases were dried with magnesium sulphate, filtered and concentrated. The residue was purified using Biotage Isolera (50 g silica gel cartridge, dichloromethane/methanol gradient), giving 125 mg (32% of theory) of the title compound.

TLC (dichloromethane/methanol 100:5): $R_F$ 0.33
LC-MS (Method 1): $R_t$=0.85 min
MS (ESpos): m/z=386 (M+H)$^+$
$^1$H-NMR (400 MHz, DMSO-d$_6$): δ [ppm]=2.38 (br. s, 3 H), 2.49 (s, 3 H), 4.61 (d, 2 H), 5.31 (s, 2 H), 5.59 (t, 1 H), 6.88 (s, 1 H), 6.99 (br. s, 1 H), 7.20-7.30 (m, 2 H), 7.54-7.67 (m, 1 H), 8.18-8.21 (m, 1 H).

Example 143

1-(3-{8-[(2,6-Difluorobenzyl)oxy]-2,6-dimethylimidazo[1,2-a]pyridin-3-yl}-1H-pyrazol-5-yl)-2-methylpropan-2-amine

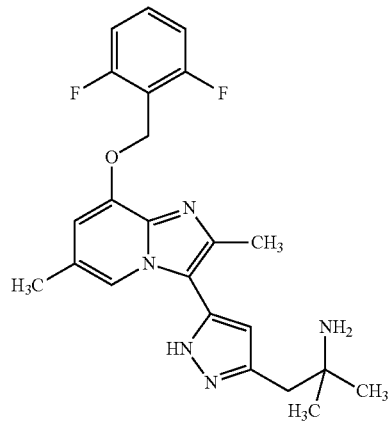 [SMILES: Cc1cc(OCc2c(F)cccc2F)c2nc(C)c(-c3cc(CC(C)(C)N)n[nH]3)n2c1]

0.028 ml (0.365 mmol) of trifluoroacetic acid was added to a solution of 120 mg (0.018 mmol) of the mixture from Example 80A [tert-butyl 1-(3-{8-[(2,6-difluorobenzyl)oxy]-2,6-dimethylimidazo[1,2-a]pyridin-3-yl}-1H-pyrazol-5-yl)-2-methylpropan-2-yl]carbamate in 2 ml dichloromethane. The resulting solution was stirred at room temperature overnight. After the reaction had ended, the solvent was removed under reduced pressure and the residue that remained was purified by preparative HPLC chromatography (Method 26), which gave 5.3 mg (60% of theory, purity 88%) of the title compound (Example 149).

LC-MS (Method 25): $R_t$=7.26 min; m/z=426.19 (M+H)$^+$
$^1$H-NMR (600 MHz, DMSO-d$_6$): δ [ppm]=1.13 (s, 6 H), 2.30 (s, 3 H), 2.42 (s, 3H), 2.79 (s, 2H), 5.28 (s. 2 H), 6.42 (s, 1 H), 6.79 (s, 1 H), 7.14-7.31 (m, 2 H), 7.53-7.66 (m, 1 H), 8.55-8.74 (m, 1H).
$^{13}$C-NMR (151 MHz, DMSO-d$_6$): δ [ppm]=14.8, 18.3, 28.0, 38.7, 50.5, 58.1, 103.7, 105.9, 111.9, 115.2, 116.9, 121.0, 132.1, 136.4, 139.5, 140.2, 145.9, 160.6.

Example 144

1-(5-{8-[(2,6-Difluorobenzyl)oxy]-2,6-dimethylimidazo[1,2-a]pyridin-3-yl}-1,2-oxazol-3-yl)-2-methylpropan-2-amine

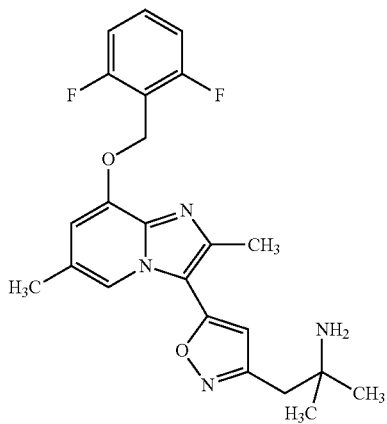 [SMILES: Cc1cc(OCc2c(F)cccc2F)c2nc(C)c(-c3cc(CC(C)(C)N)no3)n2c1]

A mixture of 200 mg (0.238 mmol, purity 63%) of tert-butyl (6-{8-[(2,6-difluorobenzyl)oxy]-2,6-dimethylimidazo[1,2-a]pyridin-3-yl}-2-methyl-4,6-dioxohexan-2-yl)carbamate (Example 79A) and 165.3 mg (2.38 mmol) of hydroxylamine hydrochloride in 10 ml of ethanol was heated in a microwave oven at 120° C. with stirring for 30 min. The reaction mixture was cooled to RT and concentrated under reduced pressure. Ethyl acetate (15 ml) and water (10 ml) were added to the residue, the mixture was shaken and the phases were then separated. The organic phase was concentrated to dryness under reduced pressure. The residue was then purified by preparative HPLC (Method 26). This gave 47 mg (46% of theory) of the title compound.

LC-MS (Method 25): $R_t$=7.71 min; m/z=427.09 (M+H)$^+$ $^1$H-NMR (600 MHz, DMSO-d$_6$): δ [ppm]=1.12 (s, 6 H), 2.38 (s, 3 H), 2.49 (s, 3 H), 2.75 (s, 2 H), 5.32 (s, 2 H), 6.80 (s, 1 H), 6.98 (s, 1 H), 7.25 (t, 2 H), 7.60 (ddd, 1 H), 8.20 (s, 1 H)

$^{13}$C-NMR (151 MHz, DMSO-d$_6$): δ [ppm]=15.0, 18.2, 30.3, 40.4, 49.4, 58.3, 102.1, 107.8, 111.3, 111.6, 111.9, 116.4, 123.2, 132.2, 138.0, 143.3, 146.0, 159.6, 161.3, 161.5.

B. Assessment of Pharmacological Efficacy

The following abbreviations are used:
ATP adenosine triphosphate
Brij35 polyoxyethylene(23) lauryl ether
BSA bovine serum albumin
DTT dithiothreitol
TEA triethanolamine The pharmacological effect of the compounds according to the invention can be shown in the following assays:

B-1. Measurement of sGC Enzyme Activity by Means of PPi Detection

Soluble guanylyl cyclase (sGC) converts GTP to cGMP and pyrophosphate (PPi) when stimulated. PPi is detected with the aid of the method described in WO 2008/061626. The signal that arises in the assay increases as the reaction progresses and serves as a measure of the sGC enzyme activity. With the aid of a PPi reference curve, the enzyme can be characterized in a known manner, for example in terms of conversion rate, stimulability or Michaelis constant.

Practice of the Test

To conduct the test, 29 μl of enzyme solution (0-10 nM soluble guanylyl cyclase (prepared according to Hönicka et al., Journal of Molecular Medicine 77(1999)14-23), in 50 mM TEA, 2 mM magnesium chloride, 0.1% BSA (fraction V), 0.005% Brij 35, pH 7.5) were initially charged in the microplate, and 1 μl of the stimulator solution (0-10 μM 3-morpholinosydnonimine, SIN-1, Merck in DMSO) was added. The microplate was incubated at RT for 10 min. Subsequently, 20 μl of detection mix (1.2 nM firefly luciferase (Photinus pyralis Luziferase, Promega), 29 μM dehydroluciferin (prepared according to Bitler & McElroy, Arch. Biochem. Biophys. 72 (1957) 358), 122 μM luciferin (Promega), 153 μM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by adding 20 μl of substrate solution (1.25 mM guanosine 5'-triphosphate (Sigma) in 50 mM TEA, 2 mM MgCl2, 0.1% BSA (fraction V), 0.005% Brij, pH 7.5) and analysed continuously in a luminometer.

B-2. Effect on a Recombinant Guanylate Cyclase Reporter Cell Line

The cellular effect of the inventive compounds is determined using a recombinant guanylate cyclase reporter cell line, as described in F. Wunder et al., Anal. Biochem. 339, 104-112 (2005).

Representative MEC values (MEC=minimum effective concentration) for the inventive compounds are shown in the table below (in some cases as mean values for individual determinations):

TABLE A

| Example No. | MEC [μM] |
|---|---|
| 1 | 0.065 |
| 2 | 0.1 |
| 3 | 0.1 |
| 4 | 0.2 |
| 5 | 0.2 |
| 6 | 0.1 |
| 7 | 0.1 |
| 8 | 0.1 |
| 9 | 0.3 |
| 10 | 1.0 |
| 11 | 3.0 |
| 12 | 0.1 |
| 13 | 0.3 |
| 14 | 0.3 |
| 15 | 0.065 |
| 16 | 1.0 |
| 17 | 1.0 |
| 18 | 1.0 |
| 19 | 1.0 |
| 20 | 1.0 |
| 21 | 1.0 |
| 22 | 1.0 |
| 23 | 1.0 |
| 24 | 1.0 |
| 25 | 1.0 |
| 26 | 1.0 |
| 27 | 1.0 |
| 28 | 1.0 |
| 29 | 1.0 |
| 30 | 3.0 |
| 31 | 3.0 |
| 32 | 3.0 |
| 33 | 3.0 |
| 34 | 3.0 |
| 35 | 3.0 |
| 36 | 3.0 |
| 37 | 3.0 |
| 38 | 3.0 |
| 39 | 3.0 |

TABLE A-continued

| Example No. | MEC [µM] |
|---|---|
| 40 | 3.0 |
| 41 | 3.0 |
| 42 | 3.0 |
| 43 | 3.0 |
| 44 | 3.0 |
| 45 | 0.1 |
| 46 | 0.2 |
| 47 | 0.3 |
| 48 | 0.2 |
| 49 | 0.3 |
| 50 | 0.3 |
| 51 | 0.3 |
| 52 | 0.3 |
| 53 | 1.0 |
| 54 | 1.0 |
| 55 | 1.0 |
| 56 | 3.0 |
| 57 | 1.0 |
| 58 | 3.0 |
| 59 | 1.0 |
| 60 | 3.0 |
| 61 | 3.0 |
| 62 | 3.0 |
| 63 | 3.0 |
| 64 | 3.0 |
| 65 | 3.0 |
| 66 | 3.0 |
| 67 | 3.0 |
| 68 | 3.0 |
| 69 | 3.0 |
| 70 | 3.0 |
| 71 | 3.0 |
| 72 | 3.0 |
| 73 | 3.0 |
| 74 | 3.0 |
| 75 | — |
| 76 | 3.0 |
| 77 | 0.1 |
| 78 | 0.1 |
| 79 | — |
| 80 | 0.3 |
| 81 | 3.0 |
| 82 | 0.1 |
| 83 | 0.3 |
| 84 | 1.0 |
| 85 | 3.0 |
| 86 | 0.03 |
| 87 | 0.1 |
| 88 | 0.01 |
| 89 | 0.03 |
| 90 | 0.3 |
| 91 | 0.1 |
| 92 | 0.03 |
| 93 | 0.1 |
| 94 | 0.3 |
| 95 | 0.3 |
| 96 | 0.065 |
| 97 | 0.3 |
| 98 | 0.03 |
| 99 | 0.03 |
| 100 | 0.03 |
| 98 | 3.0 |
| 99 | 0.1 |
| 100 | 0.03 |
| 101 | 0.1 |
| 102 | 0.1 |
| 103 | 0.03 |
| 104 | 0.3 |
| 105 | 0.01 |
| 106 | 0.3 |
| 107 | 0.065 |
| 108 | 0.3 |
| 109 | 0.3 |
| 110 | 1.0 |
| 111 | 1.0 |
| 112 | 1.0 |
| 113 | 0.03 |
| 114 | 0.3 |
| 115 | 0.1 |
| 116 | 0.01 |
| 117 | 0.1 |
| 118 | 0.03 |
| 119 | 0.1 |
| 120 | 0.3 |
| 121 | 1.0 |
| 122 | 3.0 |
| 123 | 0.3 |
| 124 | 3.0 |
| 125 | 3.0 |
| 126 | 3.0 |
| 127 | 0.3 |
| 128 | 1.0 |
| 129 | 1.0 |
| 130 | 3.0 |
| 131 | 1.0 |
| 132 | 0.3 |
| 133 | 0.3 |
| 134 | 1.0 |
| 135 | 3.0 |
| 136 | 0.3 |
| 137 | 3.0 |
| 138 | 3.0 |
| 139 | 0.1 |
| 140 | 0.1 |
| 141 | 1.0 |
| 142 | 0.1 |
| 143 | 1.0 |
| 144 | 0.3 |

B-3. Vasorelaxant Effect In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To obtain a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 µl; the DMSO content in the bath solution corresponds to 0.1%.

B-4. Blood Pressure Measurement on Anaesthetized Rats

Male Wistar rats having a body weight of 300-350 g are anaesthetized with thiopental (100 mg/kg i.p.). After tracheotomy, a catheter is introduced into the femoral artery to measure the blood pressure. The substances to be tested are administered as solutions, either orally by means of a gavage or intravenously via the femoral vein (Stasch et al. Br. J. Pharmacol. 2002; 135: 344-355).

B-5. Radiotelemetry Measurement of Blood Pressure in Conscious, Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The studies are conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6.00 am and at 7.00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vet-BonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as control.

Experimental Outline

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest TM A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (DATAQUEST TM A.R.T. TM ANALYSIS). The blank value is assumed to be the time 2 hours before administration, and so the selected data set encompasses the period from 7:00 am on the day of the experiment to 9:00 am on the following day.

The data are smoothed over a predefinable period by determination of the average (15-minute average) and transferred as a text file to a storage medium. The measured values presorted and compressed in this way are transferred to Excel templates and tabulated. For each day of the experiment, the data obtained are stored in a dedicated file bearing the number of the experiment. Results and test protocols are stored in files in paper form sorted by numbers.

LITERATURE

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994.

B-6. Determination of Pharmacokinetic Parameters Following Intravenous and Oral Administration The pharmacokinetic parameters of the inventive compounds are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the inventive compounds, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

B-7. Metabolic Study

To determine the metabolic profile of the inventive compounds, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The inventive compounds were incubated with a concentration of about 0.1-10 µM. To this end, stock solutions of the inventive compounds having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM NADP$^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15 000×g. The samples thus quenched were either analysed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable eluent mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound according to the invention in the incubation mixtures.

B-8. Caco-2 Permeability Test

The permeability of a test substance was determined with the aid of the Caco-2 cell line, an establish in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen and Zellkulturen, Braunschweig, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analysed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) is also determined in each test run as quality control.

B-9. hERG Potassium Current Assay

The hERG (human ether-a-go-go related gene) potassium current makes a significant contribution to the repolarization of the human cardiac action potential (Scheel et al., 2011). Inhibition of this current by pharmaceuticals can in rare cases cause potentially lethal cardiac arrythmia, and is therefore studied at an early stage during drug development.

The functional hERG assay used here is based on a recombinant HEK293 cell line which stably expresses the KCNH2(HERG) gene (Zhou et al., 1998). These cells are studied by means of the "whole-cell voltage-clamp" technique (Hamill et al., 1981) in an automated system (Patchliner™; Nanion, Munich, Germany), which controls the membrane voltage and measures the hERG potassium current at room temperature. The PatchControlHT™ software (Nanion) controls the Patchliner system, data capture and data analysis. The voltage is controlled by 2 EPC-10 quadro amplifiers controlled by the PatchMasterPro™ software (both: HEKA Elektronik, Lambrecht, Germany). NPC-16 chips with moderate resistance (~2 MΩ; Nanion) serve as the planar substrate for the voltage clamp experiments.

NPC-16 chips are filled with intra- and extracellular solution (cf. Himmel, 2007) and with cell suspension. After forming a gigaohm seal and establishing whole-cell mode (including several automated quality control steps), the cell membrane is clamped at the −80 mV holding potential. The subsequent voltage clamp protocol changes the command voltage to +20 mV (for 1000 ms), −120 mV (for 500 ms), and back to the −80 mV holding potential; this is repeated every 12 s. After an initial stabilization phase (about 5-6 minutes), test substance solution is introduced by pipette in rising concentrations (e.g. 0.1, 1, and 10 µl) (exposure about 5-6 minutes per concentration), followed by several washing steps.

The amplitude of the upward "tail" current which is generated by a change in potential from +20 mV to −120 mV serves to quantify the hERG potassium current, and is described as a function of time (IgorPro™ Software). The current amplitude at the end of various time intervals (for example stabilization phase before first substance, first/second/third concentration of test substance) serves to establish a concentration/effect curve, from which the half-maximum inhibiting concentration $IC_{50}$ of the test substance is calculated.

Hamill O P, Marty A, Neher E, Sakmann B, Sigworth F J. Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Pharmacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011; 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998; 74:230-241.

C. Working Examples for Pharmaceutical Compositions

The compounds according to the invention can be converted to pharmaceutical formulations as follows:

Tablet:
Composition:
100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:
The mixture of inventive compound, lactose and starch is granulated with a 5% solution (w/w) of the PVP in water. The granules are dried and then mixed with the magnesium stearate for 5 minutes. This mixture is compressed in a conventional tabletting press (see above for format of the tablet). The guide value used for the pressing is a pressing force of 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:
The Rhodigel is suspended in ethanol; the compound according to the invention is added to the suspension. The water is added while stirring. The mixture is stirred for about 6 h before swelling of the Rhodigel is complete.

Solution for Oral Administration:
Composition:
500 mg of the compound according to the invention, 2.5 g of polysorbate and 97 g of polyethylene glycol 400. 20 g of oral solution correspond to a single dose of 100 mg of the compound according to the invention.

Production:
The compound according to the invention is suspended in the mixture of polyethylene glycol and polysorbate with stirring. The stirring operation is continued until dissolution of the compound according to the invention is complete.

i.v. Solution:
The compound according to the invention is dissolved in a concentration below the saturation solubility in a physiologically acceptable solvent (e.g. isotonic saline solution, glucose solution 5% and/or PEG 400 solution 30%). The resulting solution is subjected to sterile filtration and dispensed into sterile and pyrogen-free injection vessels.

The invention claimed is:
1. A compound having the structure of formula (I)

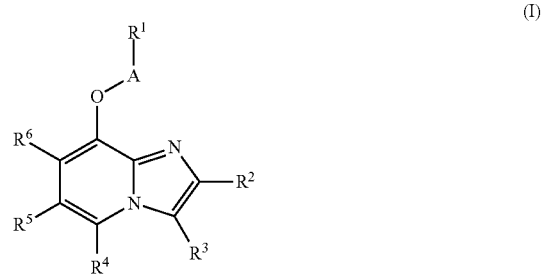

in which
A represents $CH_2$,
$R^1$ represents cyclohexyl or phenyl,
    where phenyl is substituted by 1 to 3 fluorine substituents,
    or
    represents a pyridyl group of the formula

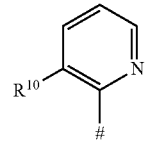

where
    # is the attachment site to A,
    and
    $R^{10}$ represents fluorine,
$R^2$ represents methyl or ethyl,
$R^3$ represents phenyl,
    where phenyl is optionally substituted by 1 or 2 substituents selected from the group consisting of fluorine, bromine, chlorine, cyano, trifluoromethyl, difluoromethyl, methyl, ethyl, —(C=O)NR$^7$R$^8$, amino, hydroxycarbonyl, methylsulphonyl, ethylsulphonyl, methoxy, ethoxy, trifluoromethoxy, difluoromethoxy and cyclobutyl,
        in which methyl and ethyl is optionally substituted by 1 or 2 substituents selected from the group consisting of trifluoromethoxy, —(C=O)NR$^7$R$^8$, methoxy, ethoxy, morpholinyl, piperidinyl, pyrrolidinyl, piperazinyl, hydroxy and amino,
            in which amino is optionally substituted by 1 or 2 substituents independently of one another selected from the group consisting of ($C_1$-$C_4$)-alkyl, methylcarbonyl, ethylcarbonyl, methylsulphonyl, ethylsulphonyl and methoxyethyl,
        in which cyclobutyl is optionally substituted by amino or hydroxy,
    in which amino is optionally substituted by 1 or 2 substituents independently of one another selected from methyl, ethyl, methylcarbonyl, ethylcarbonyl, methylsulphonyl or ethylsulphonyl,
    and in which
    $R^7$ and $R^8$ independently of one another represent hydrogen, methyl, ethyl or cyclopropyl, or represent represents a group of the formula (a-1) 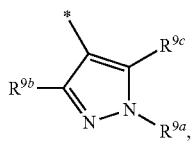

(b-1) 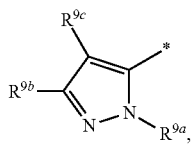

(c-1) 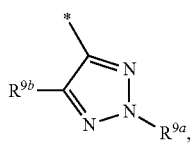

(d-1) 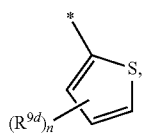

(e-1) 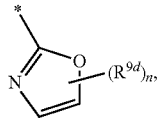

(f-1) 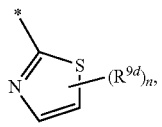

(g-1) 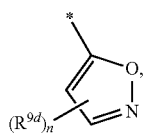

(h-1) 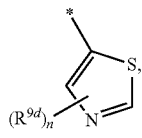

(j-1) 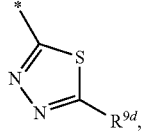

(k-1) 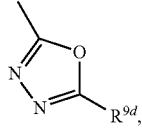

(l-1) 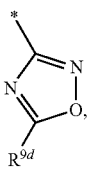

(m-1) 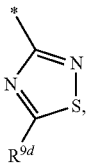

(n-1) 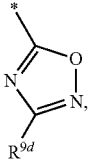

(o-1) 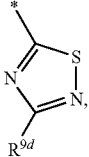

(p-1) 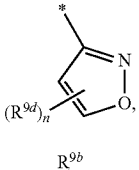

(q-1) 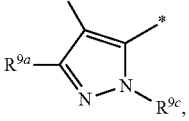

where
* represents the point of attachment to the imidazopyridine,
n represents a number 1 or 2,
$R^{9a}$ represents $(C_1\text{-}C_6)$-alkyl, phenyl, pyridyl or cyclopropyl,
where $(C_1\text{-}C_6)$-alkyl is optionally substituted by 1 or 2 substituents selected from the group consisting of fluorine, cyano, trifluoromethyl, difluoromethyl, methylcarbonyl, methoxycarbonyl, ethoxycarbonyl, hydroxycarbonyl, —(C=O)NR$^7$R$^8$, —O(C=O)NR$^7$R$^8$, methylsulphonyl, ethylsulphonyl, methoxy, phenyl, pyridyl, 1H-pyrazolyl, 1H-tetrazolyl, 1,2-oxazolyl, hydroxy, amino, $(C_3\text{-}C_5)$-cycloalkyl, morpholinyl, piperidinyl, pyrrolidinyl, piperazinyl, thiomorpholinyl 1,1-dioxide and azetidine,
in which 1H-pyrazolyl, 1H-tetrazolyl and 1,2-oxazolyl is optionally substituted by 1 or 2 methyl or ethyl substituents,
in which piperidinyl is optionally substituted by 1 to 2 fluorine substituents,
in which azetidine is optionally substituted by hydroxyl,
and in which piperazinyl is optionally substituted by methyl,
where cyclopropyl is optionally substituted by 1 to 2 substituents independently selected from the group consisting of methyl, ethyl, methoxycarbonyl, ethoxycarbonyl and hydroxycarbonyl,
where phenyl and pyridyl is optionally substituted by 1 or 2 fluorine substituents,
and in which
$R^7$ and $R^8$ independently of one another represent hydrogen, methyl, ethyl or cyclopropyl,
$R^{9b}$ represents hydrogen or $(C_1-C_4)$-alkyl,
$R^{9c}$ represents hydrogen or $(C_1-C_4)$-alkyl,
$R^{9d}$ represents hydrogen, $(C_1-C_6)$-alkyl, trifluoromethyl, methoxy, ethoxy, amino, methoxycarbonyl, ethoxycarbonyl, hydroxycarbonyl, —(C=O)NR$^7$R$^8$, phenyl, pyridyl, pyrimidyl, 1,3-thiazolyl, tetrahydrothiophenyl 1,1-dioxide or cyclopropyl,
where $(C_1-C_6)$-alkyl is optionally substituted by 1 or 2 substituents selected from the group consisting of trifluoromethyl, difluoromethyl, $(C_1-C_4)$-alkoxy, 2-oxopyrrolidin-1-yl, phenyl, pyridyl, pyrimidyl, 1H-1,2,4-triazolyl, hydroxy and amino,
in which 1H-1,2,4-triazolyl is optionally substituted by 1 or 2 methyl or ethyl substituents,
and
in which amino is optionally substituted by $(C_1-C_4)$-alkyl,
where amino is optionally substituted by $(C_1-C_4)$-alkyl,
where phenyl, pyridyl, pyrimidyl and 1,3-thiazolyl can each be substituted by 1 or 2 methyl or ethyl substituents,
and where
$R^7$ and $R^8$ each independently of one another represent hydrogen, methyl, ethyl or cyclopropyl,
$R^4$ represents hydrogen,
$R^5$ represents hydrogen, chlorine, fluorine, methyl, ethyl, difluoromethyl or cyclopropyl,
$R^6$ represents hydrogen,
and the N-oxides, salts, solvates, salts of the N-oxides and solvates of the N-oxides or salts thereof.

2. The compound according to claim 1 in which
A represents CH$_2$,
$R^1$ represents cyclohexyl,
or
represents a phenyl group of the formula

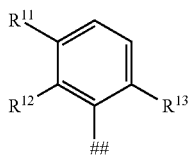

where
represents the point of attachment to A,
and
$R^{11}$, $R^{12}$ and $R^{13}$ independently of one another represent hydrogen or fluorine,
with the proviso that at least two of the radicals $R^{11}$, $R^{12}$, $R^{13}$ are different from hydrogen, or
represents a pyridyl group of the formula

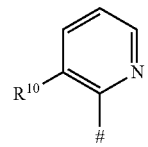

where
# represents the attachment site to A,
and
$R^{10}$ represents fluorine,
$R^2$ represents methyl or ethyl,
$R^3$ represents phenyl,
where phenyl is optionally substituted by 1 or 2 substituents selected from the group consisting of fluorine, chlorine, cyano, amino, trifluoromethyl, difluoromethyl, methyl, —(C=O)NR$^7$R$^8$, methoxy, piperidinyl and cyclobutyl,
in which methyl is optionally substituted by 1 or 2 substituents selected from the group consisting of —(C=O)NR$^7$R$^8$, methoxy, morpholinyl, piperidinyl, pyrrolidinyl, piperazinyl, hydroxy and amino,
in which amino is optionally substituted by 1 or 2 substituents independently of one another selected from methyl, ethyl and methoxyethyl,
in which amino is optionally substituted by 1 or 2 substituents independently of one another selected from methyl, ethyl, methylcarbonyl, ethylcarbonyl, methylsulphonyl or ethylsulphonyl,
in which cyclobutyl is substituted by amino,
and in which
$R^7$ and $R^8$ each independently of one another represent hydrogen, methyl, ethyl or cyclopropyl,
or
represents a group of the formula

(a-1)

(g-1)

(j-1)

where
* represents the point of attachment to the imidazopyridine,
$R^{9a}$ represents $(C_1-C_6)$-alkyl, phenyl, pyridyl or cyclopropyl, where $(C_1-C_6)$-alkyl is optionally substituted by fluorine, cyano, trifluoromethyl, difluoromethyl, methylcarbonyl, methoxycarbonyl, ethoxycarbonyl, hydroxycarbonyl, —(C=O)NR$^7$R$^8$, —O(C=O)NR$^7$R$^8$, methylsulphonyl, ethylsulphonyl, methoxy, ethoxy, trifluoromethoxy, difluoromethoxy, phenyl, pyridyl, 1H-pyrazolyl, 1H-tetrazolyl, 1,2-oxazolyl, hydroxy, amino, cyclopropyl, cyclobutyl, morpholinyl, piperidinyl, pyrrolidinyl, piperazinyl, thiomorpholinyl 1,1-dioxide or azetidine, in which 1H-pyrazolyl, 1H-tetrazolyl and 1,2-oxazolyl is optionally substituted by 1 or 2 methyl or ethyl substituents, in which piperidinyl is optionally substituted by 1 to 2 fluorine substituents, in which azetidine is optionally substituted by hydroxyl, and in which piperazinyl is optionally substituted by methyl, where cyclopropyl is optionally substituted by methoxycarbonyl, ethoxycarbonyl or hydroxycarbonyl, where phenyl and pyridyl is optionally substituted by 1 or 2 fluorine substituents, and in which R$^7$ and R$^8$ independently of one another represent hydrogen, methyl, ethyl or cyclopropyl, R$^{9b}$ represents hydrogen or methyl, R$^{9c}$ represents hydrogen or methyl, R$^{9d}$ represents hydrogen, $(C_1-C_6)$-alkyl, trifluoromethyl, methoxy, ethoxy, amino, methoxycarbonyl, ethoxycarbonyl, hydroxycarbonyl, —(C=O)NR$^7$R$^8$, phenyl, pyridyl, pyrimidyl, 1,3-thiazolyl, tetrahydrothiophenyl 1,1-dioxide or cyclopropyl, where $(C_1-C_6)$-alkyl is optionally substituted by 1 or 2 substituents selected from the group consisting of trifluoromethyl, difluoromethyl, $(C_1-C_4)$-alkoxy, 2-oxopyrrolidin-1-yl, phenyl, pyridyl, pyrimidyl, 1H-1,2,4-triazolyl, hydroxy and amino, in which 1H-1,2,4-triazolyl is optionally substituted by 1 or 2 methyl or ethyl substituents, and in which amino is optionally substituted by $(C_1-C_4)$-alkyl, where amino is optionally substituted by $(C_1-C_4)$-alkyl, where phenyl, pyridyl, pyrimidyl and 1,3-thiazolyl may each be substituted by 1 or 2 methyl or ethyl substituents, and in which R$^7$ and R$^8$ each independently of one another represent hydrogen, methyl, ethyl or cyclopropyl, R$^4$ represents hydrogen, R$^5$ represents hydrogen, chlorine, fluorine, methyl, ethyl, difluoromethyl or cyclopropyl, R$^6$ represents hydrogen, and the N-oxides, salts, solvates, salts of the N-oxides and solvates of the N-oxides or salts thereof.

3. A process for preparing the compound according to claim 1, comprising

[A] converting a compound of the formula (II)

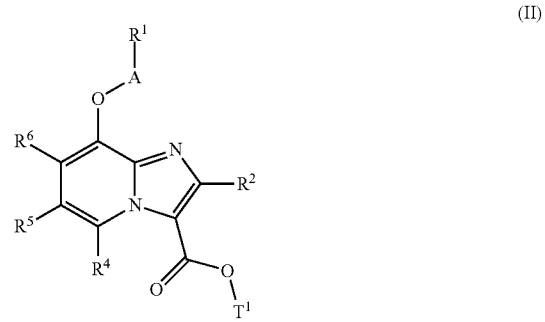

(II)

in which A, R$^1$, R$^2$, R$^4$, R$^5$ and R$^6$ are each as defined in claim 1 and T$^1$ represents $(C_1-C_4)$-alkyl or benzyl, in an inert solvent in the presence of a suitable base or acid to a carboxylic acid of the formula (III)

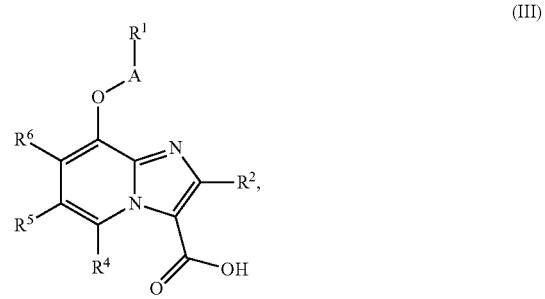

(III)

in which A, R$^1$, R$^2$, R$^4$, R$^5$ and R$^6$ each have the meanings given above, and converting the carboxylic acid of the formula (III) in the presence of a suitable acid into an imidazo[1,2-a]-pyridine of the formula (IV)

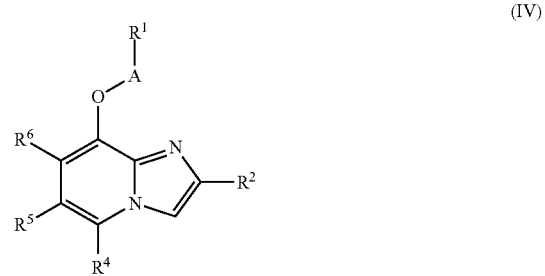

(IV)

in which A, R$^1$, R$^2$, R$^4$, R$^5$ and R$^6$ each have the meanings given above, and converting the imidazo[1,2-a]-pyridine of the formula (IV) with a halogen equivalent into a compound of the formula (V)

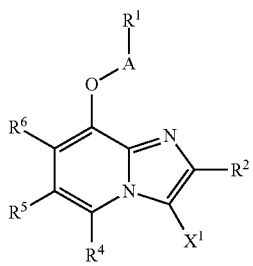
(V)

in which A, $R^1$, $R^2$, $R^4$, $R^5$ and $R^6$ are each as defined above and $X^1$ represents chlorine, bromine or iodine, and reacting the compound of the formula (V) in an inert solvent, in the presence of a suitable transition metal catalyst, with a compound of the formula (VI)

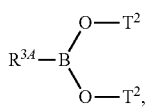
(VI)

in which $R^{3A}$ has the meanings given in claim 1 for $R^3$ and $T^2$ represents hydrogen or $(C_1-C_4)$-alkyl, or the two $T^2$ radicals together form a $—C(CH_3)_2—C(CH_3)_2—$ bridge, to give a compound of the formula (I-A)

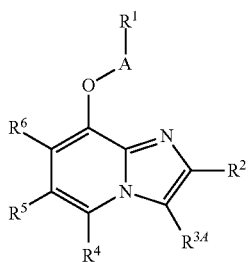
(I-A)

and if $R^{3A}$ represents

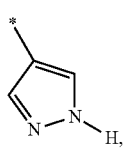
(VII)

reacting the compound of the formula (I-A) in an inert solvent in the presence of a suitable base with a compound of the formula (VIII)

$R^{14}—X^1$ (VIII), in which $X^1$ represents a suitable leaving group, and $R^{14}$ represents $(C_1-C_6)$-alkyl, where $(C_1-C_6)$-alkyl can be substituted by 1 to 3 substituents selected from the group consisting of fluorine, cyano, trifluoromethyl, difluoromethyl, $(C_1-C_4)$-alkylcarbonyl, $(C_1-C_4)$-alkoxycarbonyl, hydroxycarbonyl, $—(C=O)NR^7R^8$, $—O(C=O)NR^7R^8$, $(C_1-C_4)$-alkylsulphonyl, $(C_1-C_4)$-alkoxy, trifluoromethoxy, difluoromethoxy, phenyl, 1H-pyrazolyl, 1H-1,2,4-triazolyl, 1H-tetrazolyl, 1,2-oxazolyl, tetrahydrothiophenyl 1,1-dioxide, hydroxy, amino, $(C_3-C_7)$-cycloalkyl, morpholinyl, piperidinyl, pyrrolidinyl, 2-oxopyrrolidin-1-yl, piperazinyl, tetrahydrothiophenyl 1,1-dioxide, thiomorpholinyl 1,1-dioxide and azetidine, in which 1H-pyrazolyl, 1H-1,2,4-triazolyl, 1H-tetrazolyl and 1,2-oxazolyl is optionally substituted by 1 or 2 methyl or ethyl substituents, in which piperidinyl is optionally substituted by 1 or 2 fluorine substituents, in which phenyl is optionally substituted by 1 or 2 fluorine substituents, in which piperazinyl is optionally substituted by methyl, and in which $R^7$ and $R^8$ each independently of one another represent hydrogen, methyl or cyclopropyl, or $R^7$ and $R^8$ together with the carbon atom to which they are attached form a 3- to 5-membered carbocycle, to give a compound of the formula (I-B)

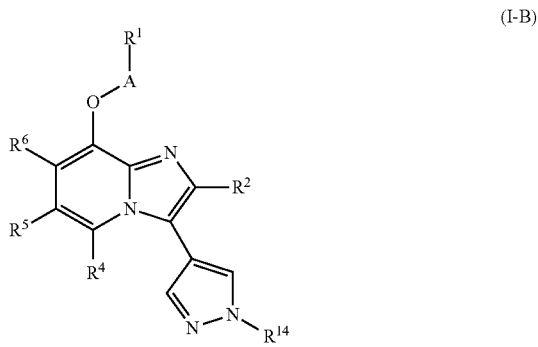
(I-B)

in which A, $R^1$, $R^2$, $R^4$, $R^5$, $R^6$ and $R^{14}$ each have the meanings given above and removing any protecting groups present, and optionally converting the resulting compounds of the formula (I-B) with the appropriate (i) solvents and/or (ii) acids or bases into the solvates, salts and/or solvates of the salts thereof, or

[B] converting the compound of the formula (II) in the presence of hydrazine hydrate into a compound of the formula (IX)

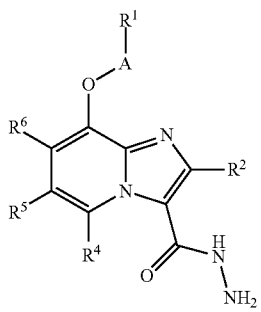

(IX)

in which A, $R^1$, $R^2$, $R^4$, $R^5$ and $R^6$ each have the meanings given above, and subsequently reacting the compound of the formula (IX) in an inert solvent under amide coupling conditions with a carboxylic acid of the formula (X)

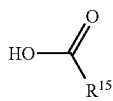

(X)

in which $R^{15}$ represents $(C_1-C_6)$-alkyl, where $(C_1-C_6)$-alkyl is optionally substituted by 1 to 3 substituents selected from the group consisting of trifluoromethyl, difluoromethyl, hydroxy and amino, to give a compound of the formula (XI)

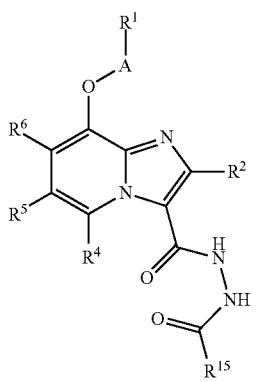

(XI)

in which A, $R^1$, $R^2$, $R^4$, $R^5$, $R^6$ and $R^{15}$ each have the meanings given above, and converting the compound of the formula XI with 2,4-bis(4-methoxyphenyl)-1,3,2,4-dithiadiphosphetane-2,4-disulphide [Lawesson's reagent] into a compound of the formula (I-C)

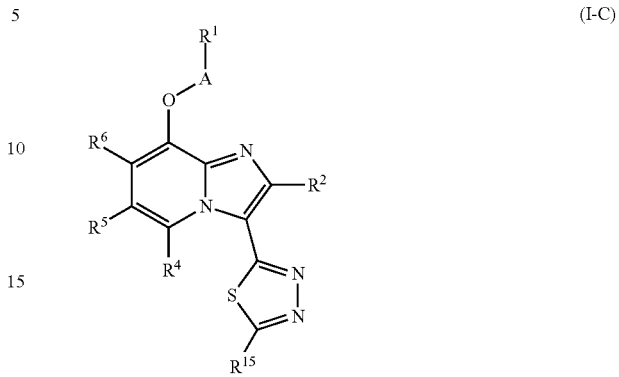

(I-C)

in which A, $R^1$, $R^2$, $R^4$, $R^5$, $R^6$ and $R^{15}$ each have the meanings given above, then detaching any protecting groups present, and optionally converting the resulting compounds of the formula (I) with the appropriate (i) solvents and/or (ii) acids or bases to the solvates, salts and/or solvates of the salts thereof.

4. A medicament comprising the compound according to claim 1 in combination with an inert, non-toxic, pharmaceutically suitable excipient.

5. A medicament comprising the compound according to claim 1 in combination with a further active ingredient selected from the group consisting of organic nitrates, NO donors, cGMP-PDE inhibitors, antithrombotic agents, hypotensive agents and lipid metabolism modifiers.

6. A method for treatment of heart failure, angina pectoris, hypertension, pulmonary hypertension, ischaemias, vascular disorders, renal insufficiency, thromboembolic disorders and arteriosclerosis in humans and animals comprising administering an effective amount of at least one compound according to claim 1 to a patient in need thereof.

7. A method for treatment of heart failure, angina pectoris, hypertension, pulmonary hypertension, ischaemias, vascular disorders, renal insufficiency, thromboembolic disorders and arteriosclerosis in humans and animals comprising administering an effective amount of the medicament according to claim 4 to a patient in need thereof.

8. A method for treatment of heart failure, angina pectoris, hypertension, pulmonary hypertension, ischaemias, vascular disorders, renal insufficiency, thromboembolic disorders and arteriosclerosis in humans and animals comprising administering an effective amount of the medicament according to claim 5 to a patient in need thereof.

* * * * *